(12) United States Patent
Zhuang et al.

(10) Patent No.: US 10,240,146 B2
(45) Date of Patent: Mar. 26, 2019

(54) PROBE LIBRARY CONSTRUCTION

(71) Applicant: President and Fellows Harvard College, Cambridge, MA (US)

(72) Inventors: Xiaowei Zhuang, Lexington, MA (US); Jeffrey R. Moffitt, Somerville, MA (US); Alistair Boettiger, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/329,651

(22) PCT Filed: Jul. 29, 2015

(86) PCT No.: PCT/US2015/042559
§ 371 (c)(1),
(2) Date: Jan. 27, 2017

(87) PCT Pub. No.: WO2016/018963
PCT Pub. Date: Feb. 4, 2016

(65) Prior Publication Data
US 2017/0212986 A1  Jul. 27, 2017

Related U.S. Application Data

(60) Provisional application No. 62/142,653, filed on Apr. 3, 2015, provisional application No. 62/050,636, filed
(Continued)

(51) Int. Cl.
*C12N 15/10* (2006.01)
*C07H 21/02* (2006.01)
(Continued)

(52) U.S. Cl.
CPC ......... *C12N 15/1065* (2013.01); *C07H 21/02* (2013.01); *C07H 21/04* (2013.01);
(Continued)

(58) Field of Classification Search
CPC .......... G06F 19/24; G06F 19/22; G06F 19/20; C12Q 1/686; C12Q 1/6844; C12Q 1/6806;
(Continued)

(56) References Cited

U.S. PATENT DOCUMENTS 7,368,265 B2 *  5/2008  Brenner ................. C12P 19/34
                                                  435/91.2
7,838,302 B2  11/2010  Zhuang et al.
(Continued)

FOREIGN PATENT DOCUMENTS

| WO | WO 03/003810 A2 | 1/2003 |
|---|---|---|
| WO | WO 2008/108843 A2 | 9/2008 |
| WO | WO 2013/090360 A2 | 6/2013 |

OTHER PUBLICATIONS

Invitation to Pay Additional Fees dated Oct. 6, 2015 for Application No. PCT/US2015/042556.
(Continued)

*Primary Examiner* — Jeremy C Flinders
(74) *Attorney, Agent, or Firm* — Wolf, Greenfield & Sacks, P.C.

(57) ABSTRACT

The present invention generally relates to systems and methods for producing nucleic acids. In some aspects, relatively large quantities of oligonucleotides can be produced, and in some cases, the oligonucleotides may have a variety of different sequences and/or lengths. For instance, a relatively small quantity of oligonucleotides may be amplified to produce a large amount of nucleotides. In one set of embodiments, oligonucleotides may be amplified using PCR, then transcribed to produce RNA. The RNA may then be reverse transcribed to produce DNA, and optionally, the RNA may be selectively degraded or removed, relative to the DNA. In one set of embodiments, the oligonucleotides
(Continued)

may be chemically modified. These modifications may include, but are not limited, to the adding of fluorescent dyes or other signaling entities.

21 Claims, 79 Drawing Sheets

Specification includes a Sequence Listing.

Related U.S. Application Data on Sep. 15, 2014, provisional application No. 62/031,062, filed on Jul. 30, 2014.

(51) Int. Cl.
| | | |
|---|---|---|
| C07H 21/04 | (2006.01) | |
| G06F 19/20 | (2011.01) | |
| C12Q 1/6806 | (2018.01) | |
| C12Q 1/6837 | (2018.01) | |
| G06F 19/22 | (2011.01) | |
| G06F 19/24 | (2011.01) | |
| G06N 7/00 | (2006.01) | |
| C12Q 1/6816 | (2018.01) | |
| C12Q 1/6841 | (2018.01) | |
| C12Q 1/6869 | (2018.01) | |

(52) U.S. Cl.
CPC ......... *C12N 15/10* (2013.01); *C12N 15/1093* (2013.01); *C12Q 1/6806* (2013.01); *G06F 19/20* (2013.01); *C12Q 1/6816* (2013.01); *C12Q 1/6837* (2013.01); *C12Q 1/6841* (2013.01); *C12Q 1/6869* (2013.01); *G06F 19/22* (2013.01); *G06F 19/24* (2013.01); *G06N 7/005* (2013.01)

(58) Field of Classification Search
CPC .......................... C12N 15/10; C12N 15/1065; C12N 15/1093; C07H 21/00; C07H 21/02; C07H 21/04
See application file for complete search history.

(56) References Cited

U.S. PATENT DOCUMENTS

| | | | |
|---|---|---|---|
| 8,564,792 B2 | 10/2013 | Zhuang et al. | |
| 2004/0053300 A1 | 3/2004 | Soderlund et al. | |
| 2010/0323348 A1 | 1/2010 | Hamady et al. | |
| 2010/0291557 A1 | 11/2010 | Livak et al. | |
| 2010/0304994 A1 | 12/2010 | Wu et al. | |
| 2012/0035065 A1* | 2/2012 | Smolke | C12N 15/111 506/9 |
| 2012/0129165 A1 | 5/2012 | Raj et al. | |
| 2013/0096014 A1* | 4/2013 | Andersen | C12Q 1/6827 506/2 |
| 2013/0261019 A1 | 10/2013 | Lin et al. | |
| 2014/0031243 A1 | 1/2014 | Cai et al. | |
| 2017/0220733 A1 | 8/2017 | Zhuang et al. | |

OTHER PUBLICATIONS

International Search Report and Written Opinion dated Dec. 18, 2015 for Application No. PCT/US2015/042556.
International Preliminary Report on Patentability dated Feb. 9, 2017 for Application No. PCT/US2015/042556.
International Search Report and Written Opinion dated Oct. 9, 2015 for Application No. PCT/US2015/042559.
International Preliminary Report on Patentability dated Feb. 9, 2017 for Application No. PCT/US2015/042559.
Chen et al., Spatially resolved, highly multiplexed RNA profiling in single cells. Science. Apr. 24, 2015;348(6233):aaa6090. doi: 10.1126/science.aaa6090. Epub Apr. 9, 2015.
Fakruddin et al., Nucleic acid sequence based amplification (NASBA)-prospects and applications. Int. J. Life Sci. Pharm. Res. Mar. 2012; 2(1): L106-L121.
Lubeck et al., Single-cell in situ RNA profiling by sequential hybridization. Nature Methods. Apr. 2014; 11(4): 360-1.
Lubeck et al., Single-cell in situ RNA profiling by sequential hybridization. Nature Methods. Apr. 2014; 11(4): 360-1. Supplementary Information.
Moffitt et al., High-performance multiplexed fluorescence in situ hybridization in culture and tissue with matrix imprinting and clearing. Proc Natl Acad Sci U S A. Dec. 13, 2016;113(50):14456-14461. Epub Nov. 22, 2016.
Moffitt et al., High-throughput single-cell gene-expression profiling with multiplexed error-robust fluorescence in situ hybridization. Proc Natl Acad Sci U S A. Sep. 27, 2016;113(39):11046-51. doi: 10.1073/pnas.1612826113. Epub Sep. 13, 2016.
Moffitt et al., RNA Imaging with Multiplexed Error-Robust Fluorescence in Situ Hybridization (MERFISH). Methods Enzymol. 2016;572:1-49. doi: 10.1016/bs.mie.2016.03.020. Epub Apr. 27, 2016.
Shiels et al., Rna-Dna hybrids containing damaged DNA are substrates for RNase H. Bioorg Med Chem Lett. Oct. 8, 2001;11(19):2623-6.
Extended European Search Report dated Feb. 6, 2018 for Application No. 15827358.1.
Extended European Search Report dated Feb. 5, 2018 for Application No. 15828133.7.
Binladen et al., The use of coded PCR primers enables high-throughput sequencing of multiple homolog amplification products by 454 parallel sequencing. PLoS One. Feb. 14, 2007;2(2):e197.
Darouich et al., Use of DOP-PCR for amplification and labeling of BAC DNA for FISH. Biotech Histochem. Feb. 2012;87(2):117-21. doi: 10.3109/10520295.2011.559175.
U.S. Appl. No. 15/329,683, filed Jan. 27, 2017, Zhuang et al.
EP 15827358.1, Feb. 6, 2018, Extended European Search Report.
EP 15828133.7, Feb. 5, 2018, Extended European Search Report.

* cited by examiner

ACAACCGCGTGTTACAAGGCCAGGCATCCGAGAGGTCTGGGAATGCC
AGCAGCTCTACAAGTGCGGCCATTTGGTTCATTGCGCTTCTCCGGAAAC
ATTAGC (SEQ ID NO: 3)

\>bc25mer_8982-20
CGGTAGGACCCTACACATCC

\>bc25mer_37497-20
TGTGGCGCCTAACCATACAC

\>bc25mer_48272-20
GACACCGAGCTAGAATTCGG

\>bc25mer_96434-20
TGTCTTGGGTCCTCTTACGG

\>bc25mer_135960-20
TATCACGTGAGGCTCCGTGT

\>bc25mer_217459-20
GTCTACGGATCCTTGCGTGT

\>bc25mer_5177-20
ACGGGTACATTGGATCCACT

\>bc25mer_7835-20
AAGACGTGGTCCACCCTGAT

\>bc25mer_13747-20
TGCCAGGTCCACTACTTGGG

\>bc25mer_14156-20
GACCCGAAGGAGAATGCAAA

\>bc25mer_14649-20
ATGTCGTCTCTCAGGGCTTT

\>bc25mer_16849-20
AAGGGCGGAAGCACTCTCTT

\>bc25mer_25227-20
TGGTCCCGCATTTGTACCTT

\>bc25mer_45585-20
AAGTCCGTCTGCTAAGCCAT

\>bc25mer_46295-20
CTTCCAGAGTCCTGGCATGA

\>bc25mer_46396-20
TCTAACGAGCTCCGTGGTTG

\>bc25mer_55377-20
CCTGGGCAGGAAACAACACT

\>bc25mer_57092-20
GCGCACACCTTAGTCATAGC

\>bc25mer_69827-20
GTGCGATTGTCACATGTGCT

\>bc25mer_85616-20
GGCTTGTCCTCAATTATCCG

\>bc25mer_90788-20
CCCACGTGACTTGACTTCTC

\>bc25mer_108211-20
CCTCTACATGCTCCGGATCC

\>bc25mer_113656-20
GAATAGTAACCCGGTCGCAA

\>bc25mer_121326-20
TGGGCCACTAGTCTTCGCTA

\>bc25mer_123881-20
CGGCACGTACCCTTTACAGG

\>bc25mer_138428-20
GATCAGTGAGCCTCACCAAG

\>bc25mer_140203-20
TGGTATGTGAGCTCTTTGGG

\>bc25mer_159878-20
AGAGTCACGCATACTTGGGA

\>bc25mer_163235-20
GGGTCAGGCGTCATAGATTG

\>bc25mer_184954-20
AGAATGTGGAGGACATGTGG

\>bc25mer_188166-20
TCGGACTGTGAGACATTTCC

\>bc25mer_192833-20
ATCAAATGCCTCGGTCGTTG

\>bc25mer_193757-20
GCAATGCTATGCTGGGACAA

\>bc25mer_199694-20
ATGGAGGCCGTTCTCTGACA

\>bc25mer_200273-20
GCAGATGGGTGCATTCATTC

\>bc25mer_208214-20
TATGCACTCTGCGGATGACC

\>bc25mer_218789-20
GACCCGGGAGTTATGATACG

\>bc25mer_235702-20
CTCGGGTAGGCTATCTCCAA

\>bc25mer_239358-20
CTGCAGGTGCTCTAGATGGA

\>bc25mer_5878-20
GTCCAGGCTCGTCTTCTCGA

\>bc25mer_9018-20
CTTACCTGAGCGCAGTTCGA

\>bc25mer_9904-20
GTTGTTCGATCCCTCCACCA

\>bc25mer_10475-20
CGGCAGAGGATAATCCTAGC

\>bc25mer_11594-20
GGGAGTCCGGATGTTAGTGC

\>bc25mer_12189-20
CGCATCTATGCTCCGCTTAC

\>bc25mer_14363-20
AACGCGCTACCCAATTCTAG

\>bc25mer_16178-20
TACTGGACGATTCCCGACTG

\>bc25mer_17067-20
AGCGTCGTACCCAGTTAAGC

\>bc25mer_18548-20
GAGATTCACGCCCTCATGAG

\>bc25mer_20080-20
CCGCTAGCGTTACCTCTACC

\>bc25mer_20601-20
CCACACCGTATGCATTTCTG

\>bc25mer_26252-20
CCTTAGCGCACAAAGAGACG

\>bc25mer_28353-20
GTCCTGATGGCTTTCTCACG

\>bc25mer_30927-20
GGTCGTCGGTAGATCATTGC

FIG. 3A

>bc25mer_32240-20
AGAGCCGGTATGATCCATCG

>bc25mer_32875-20
CCGGACGAAGGTTGATATCC

>bc25mer_39270-20
ACCCGGTACCTGTTATCACG

>bc25mer_40398-20
ATCCCGTCTCGTTCTATGGG

>bc25mer_41429-20
CAGGTGAGGGTCTCTCCTTC

>bc25mer_42283-20
CCTTATGGAAACGTGATGCC

>bc25mer_43506-20
GGCTGGGCATACATAGACCT

>bc25mer_45853-20
AGTGGCGGCTATTACCGGAT

>bc25mer_47706-20
TGATAACGTCCGCTCGTTGA

>bc25mer_54028-20
TACATCGTTGAGGCCCGTTT

>bc25mer_54772-20
CGTTGTGGCATCAGCTAGAG

>bc25mer_55112-20
ACTGGCCCACACACTTACCT

>bc25mer_57695-20
ATCGGGTCACGGAATATGAC

>bc25mer_58256-20
CGTAGGTTCACAGATTTGCG

>bc25mer_59008-20
TAGGGCACGAGAAGGTATCC

>bc25mer_61977-20
ACTAGCTTGTATCGCCGGAT

>bc25mer_63426-20
CGGCGGTTTGATATTCGAAG

>bc25mer_63840-20
GCCGAGTGTTTATGAGCAAG

>bc25mer_65782-20
TCTCCGAAGATCCGATATCG

>bc25mer_66426-20
GATGCAGGGCCTAATTAACG

>bc25mer_68963-20
TGACGCGGCTAAATACTGAC

>bc25mer_70828-20
GCAATGCACGCTCTCCTAGT

>bc25mer_71011-20
TGGCGTCAGATGGATTAGGA

>bc25mer_71626-20
GTTGGCGGGAGACTAAGAAG

>bc25mer_72701-20
TCGCGTCTCGTCCTTCTACC

>bc25mer_79345-20
CGGTCACGTCGGAAATAACC

>bc25mer_79641-20
ATTAACGGGCCAGGTTACTG

>bc25mer_81698-20
ATTGTATGGAGGCGCCCTAT

>bc25mer_82313-20
GCCAGCTTTCCAAGATTCAG

>bc25mer_83004-20
ACAACCGCGTGTTACAAGGC

>bc25mer_83517-20
GCTAATGTTTCCGGAGAAGC

>bc25mer_83687-20
GAAGTATCCGGCATCACAGC

>bc25mer_85062-20
TCGTTACGGACTTTCACGAC

>bc25mer_87436-20
GCCATTCTGACATACCCAGA

>bc25mer_90109-20
GTATTTGAACCGGCCAGCTG

>bc25mer_95782-20
GGTTGTGGGCCATATCCAAT

>bc25mer_96522-20
GGCGTTCCATCGAAACTCTA

>bc25mer_96896-20
GGCCATCGACTTAGATTCCA

>bc25mer_97519-20
GGTGCTCCTGCCATTATAGG

>bc25mer_100107-20
TGTCGACGTGCGGAAAGTAG

>bc25mer_100109-20
GCCGCACGAGTATGCTACTG

>bc25mer_100502-20
TGCTGCCGCTTACTACTGCT

>bc25mer_102626-20
TAGCACTCTTCTGGCCATCG

>bc25mer_103544-20
CGGTAATCGGTTCACCAGTG

>bc25mer_108258-20
TTTAGTGCCTGGCTCCGTTG

>bc25mer_109838-20
GGAGTTACAGCCACTTTCGG

>bc25mer_114408-20
GTGTGGACGGAACCTGACAA

>bc25mer_115589-20
CACACGTGGAATTGTTCTGC

>bc25mer_116534-20
CTTGTACATGGAGGGCGACT

>bc25mer_116605-20
AATCCGGTGTACAGGTTCCC

>bc25mer_121894-20
AGGTGCGACGATATACACCA

>bc25mer_123748-20
ACTGCATATGACCGCTGCAA

>bc25mer_125347-20
CCTTCCATTAGCCGAGATCA

>bc25mer_125541-20
GACGCGAGGAGTGATCGACT

FIG. 3B

>bc25mer_126017-20
CGACCCTCACACATTTGGGT

>bc25mer_126439-20
CGCTCCCGTATTCTTCTGTG

>bc25mer_128324-20
CAGGGATAGTCAGGCCAGTG

>bc25mer_130576-20
CGTAATGAGTGCTTCGCCAT

>bc25mer_132438-20
CTCGTCTCGTGGAACACATG

>bc25mer_133420-20
TATGCTGGGCAGTAATCAGG

>bc25mer_133575-20
GCATCTCGTAGCATCCTGCT

>bc25mer_134218-20
AGTATGGTACCGGGAACAGC

>bc25mer_136989-20
ACCATTCTCGCAACTCGCTA

>bc25mer_137798-20
CGTGGGCGAAGTACTTGGTC

>bc25mer_138338-20
CCGGACGTCTTCGATAATGC

>bc25mer_139329-20
TGATGCTCTTTGCAGTTCGG

>bc25mer_139807-20
ATGCCGGTCATAACAGTGTC

>bc25mer_140760-20
TGGTGGCTCGTTATCACAAG

>bc25mer_141708-20
TCTGAAGCGTGGCCATTACC

>bc25mer_141799-20
CATATGCCGGACATTCAGCT

>bc25mer_142929-20
ACTAATGGTCCTGCGGCATA

>bc25mer_146048-20
GGTGCCGTGTTGCATGTAAG

>bc25mer_149885-20
AAGCGGTCGTGGTTTATACC

>bc25mer_150249-20
GCCACCTTGTATGGTATCGA

>bc25mer_150996-20
TAATGCTTAGGCCCGTCGGT

>bc25mer_153952-20
GACGCGACGGATTATTTAGG

>bc25mer_156264-20
GGTCGCGCCCATATATAAGG

>bc25mer_156364-20
TGACTACGGTTGGGTGCATC

>bc25mer_157007-20
TCAGGCGCTCATTGTATGTC

>bc25mer_160860-20
GTAGATACTCCCGGCCCGAA

>bc25mer_161471-20
GCAGCACTTAGGGCAGCATC

>bc25mer_163904-20
CGCGGGAACCATATTAGGAA

>bc25mer_164195-20
GATCCATGGCCAGTTCGTAT

>bc25mer_164787-20
GTGCGCCAAAGGACTTAGTG

>bc25mer_166664-20
GATCCCGCTATTCACCGATT

>bc25mer_167568-20
GCATAGATGGTTCACCCGTA

>bc25mer_169085-20
GTCTATAAGCCGCGCTGCAA

>bc25mer_170764-20
GCGGAGTATGCCATCATGAG

>bc25mer_171455-20
TGCCGCGATCATCTACTATG

>bc25mer_174112-20
GACCGGGTATTCGACGTCAT

>bc25mer_175501-20
GCAGTGCGGGTAGATACGCT

>bc25mer_180358-20
AGGCGTGGGTAGCAACGTAT

>bc25mer_180797-20
GCTCATTGGACTTTCTCCCA

>bc25mer_181432-20
AAGGACCACGTATCTGCATG

>bc25mer_181702-20
ATCTGATAGTGCCGCGACGT

>bc25mer_182418-20
TGACCTGCACGGATAGTAGG

>bc25mer_182774-20
GTTATTCGCAGTCCTTGGGT

>bc25mer_183321-20
GTGCAGTGTGCTTAAATCCG

>bc25mer_188636-20
CGCGGGTGTTAAATAAGGAC

>bc25mer_189039-20
GCGAGGCGTGGTAATAGTCA

>bc25mer_190422-20
CAAGGCGCAAACATAGACAG

>bc25mer_191525-20
GGAACAAGGGCGTCTATGTC

>bc25mer_193359-20
GCAGTGCGGATAAGCTACAC

>bc25mer_193734-20
AGAGATGCGTGTAGGCGATT

>bc25mer_194512-20
CCCTTTCGAGCTAAGTTTGG

>bc25mer_196660-20
CCTTAAGCAACCCGTCGATG

>bc25mer_197001-20
TTGCTCGTGACTGAACAACG

>bc25mer_197794-20
GGTCGTGCGTATAAGCCTCA

FIG. 3C

>bc25mer_198508-20
CGGATGGTCTTCGTTTAACC

>bc25mer_198891-20
GGCACGGTGGCTAGTAACGA

>bc25mer_200581-20
GCCGGCCCAACTGATAGTAG

>bc25mer_200721-20
TCGACTTCGGTCACCTTTCC

>bc25mer_206382-20
CGGGTCGATACTTTCCTCGT

>bc25mer_207645-20
GTGCCGTGTGTAATATCCGA

>bc25mer_210956-20
CGCGCCTGGAATAACTCCTA

>bc25mer_210958-20
GTCAGGGAACCGTTTCTTCA

>bc25mer_210961-20
CTTGTCATGTACCCGAATGG

>bc25mer_211638-20
CGACCTGGCTACGTAGAACC

>bc25mer_211770-20
CTAGCTAAAGGGCCGTGCGT

>bc25mer_213351-20
AAGTATTAGCGCGGCAACGT

>bc25mer_213506-20
GGTTGCGTGCCACTTAAAGC

>bc25mer_216161-20
GGAGGTTCGGTTGTACTGCA

>bc25mer_216486-20
GTTGTCGTCCTCCATCGGTT

>bc25mer_218887-20
GGGACGGAACTACACATGTG

>bc25mer_221408-20
GATCCATCCTGATTGAGGGT

>bc25mer_222754-20
CTTCATGGTACCGGTTGAGA

>bc25mer_223329-20
TCGGTCGGCTGTAAGGATAC

>bc25mer_224422-20
ATTGCACGAGGTCAGAGTCG

>bc25mer_225143-20
GCTTAGATCCGCTCGCTACG

>bc25mer_227128-20
CGGCTGGCCTACTGTAGAGA

>bc25mer_227360-20
GCAACATGACCTGTCATCGC

>bc25mer_228435-20
GGCCGCACGATATATTTGAC

>bc25mer_229488-20
CAGCCGGGCCATAATAGTTG

>bc25mer_229709-20
TGCGGTGGACCTATTATCCT

>bc25mer_229929-20
CCTGCGTTAGGCAATCCATC

>bc25mer_230898-20
GTGGGCTCTTCGAAGTAACC

>bc25mer_233755-20
GCCGTGGACCACTAAAGTTC

>bc25mer_234401-20
GCTTAAGTCATGGGCGCATC

>bc25mer_236515-20
ACAGGTTAGTTCCGCGCACT

>bc25mer_237582-20
GGCGTGGCATTTAGACTACC

>bc25mer_238816-20
ACTACGGCCAACAACCAACA

>bc25mer_238839-20
GTTGACAAGGCTCTGTACGG

>bc25mer_239304-20
TTGTTCTCTTGCCGGTCGAT

>bc25mer_239849-20
GTTGATCGTAGCCAATTCGG

FIG. 3D

Exp-1_acnB-73_I1-bc25mer_83004-20_I2-bc25mer_83517-20
ACAACCGCGTGTTACAAGGC CAGGCATCCGAGAGGTCTGG
GAATGC CAGCAGCTCTACAAGTGCGGC CATTTGGTT
CATTGC GCTTCTCCGGAAACATTAGC Exp-1_acnB-191_I1-bc25mer_83004-20_I2-bc25mer_83517-20
ACAACCGCGTGTTACAAGGC CAGGCATCCGAGAGGTCTGG
GAATGC CTTTCGCGATAGCAGCCAGGA AGCCTGCTT
CATTGC GCTTCTCCGGAAACATTAGC Exp-1_acnB-671_I1-bc25mer_83004-20_I2-bc25mer_83517-20
ACAACCGCGTGTTACAAGGC CAGGCATCCGAGAGGTCTGG
GAATGC CCAGCGGGAAACCTTTCTGTT GCAGAGCTT
CATTGC GCTTCTCCGGAAACATTAGC Exp-1_acnB-2404_I1-bc25mer_83004-20_I2-bc25mer_83517-20
ACAACCGCGTGTTACAAGGC CAGGCATCCGAGAGGTCTGG
GAATGC CGCCAGTTCCGCAGAAGCCAG GAAGACATT
CATTGC GCTTCTCCGGAAACATTAGC Exp-1_acnB-1307_I1-bc25mer_83004-20_I2-bc25mer_83517-20
ACAACCGCGTGTTACAAGGC CAGGCATCCGAGAGGTCTGG
GAATGC CGGTGTGGCAGAAAGACTGCA TCACCAGGT
CATTGC GCTTCTCCGGAAACATTAGC Exp-1_acnB-779_I1-bc25mer_83004-20_I2-bc25mer_83517-20
ACAACCGCGTGTTACAAGGC CAGGCATCCGAGAGGTCTGG
GAATGC CGCCGCGTTTGTTCGGCACAT GTGGAATAT
CATTGC GCTTCTCCGGAAACATTAGC Exp-1_acnB-1343_I1-bc25mer_83004-20_I2-bc25mer_83517-20
ACAACCGCGTGTTACAAGGC CAGGCATCCGAGAGGTCTGG
GAATGC GGTGCGTGTTCACGTCAACTG GCTTCGGAT
CATTGC GCTTCTCCGGAAACATTAGC Exp-1_acnB-1961_I1-bc25mer_83004-20_I2-bc25mer_83517-20
ACAACCGCGTGTTACAAGGC CAGGCATCCGAGAGGTCTGG
GAATGC CATCTGCATCGGCTTCCAGCA GCTCAGGAT
CATTGC GCTTCTCCGGAAACATTAGC Exp-1_acnB-2131_I1-bc25mer_83004-20_I2-bc25mer_83517-20
ACAACCGCGTGTTACAAGGC CAGGCATCCGAGAGGTCTGG
GAATGC CGCAGCACGGAAGTGACCGAT GTTGGTCAT
CATTGC GCTTCTCCGGAAACATTAGC Exp-1_acnB-2039_I1-bc25mer_83004-20_I2-bc25mer_83517-20
ACAACCGCGTGTTACAAGGC CAGGCATCCGAGAGGTCTGG
GAATGC CATCCGGGTCGTTCGGAGCAC ACAGGATTG
CATTGC GCTTCTCCGGAAACATTAGC

FIG. 4A

Exp-1_acnB-2262_I1-bc25mer_83004-20_I2-bc25mer_83517-20
ACAACCGCGTGTTACAAGGC CAGGCATCCGAGAGGTCTGG
GAATGC ATACGCGCACCACTCTTACCG AAGACGCTG CATTGC
GCTTCTCCGGAAACATTAGC Exp-1_acnB-2542_I1-bc25mer_83004-20_I2-bc25mer_83517-20
ACAACCGCGTGTTACAAGGC CAGGCATCCGAGAGGTCTGG
GAATGC ATCGGCTTTCTCGGTGTACTG AGAAAGCTG CATTGC
GCTTCTCCGGAAACATTAGC Exp-1_acnB-2369_I1-bc25mer_83004-20_I2-bc25mer_83517-20
ACAACCGCGTGTTACAAGGC CAGGCATCCGAGAGGTCTGG
GAATGC CAGTACCCAGACGGTTCGGGA AGTTACGGG CATTGC
GCTTCTCCGGAAACATTAGC Exp-1_acnB-1811_I1-bc25mer_83004-20_I2-bc25mer_83517-20
ACAACCGCGTGTTACAAGGC CAGGCATCCGAGAGGTCTGG
GAATGC CTTTGTTCAGCTTGATGGTAC AACCAGCGG CATTGC
GCTTCTCCGGAAACATTAGC Exp-1_acnB-428_I1-bc25mer_83004-20_I2-bc25mer_83517-20
ACAACCGCGTGTTACAAGGC CAGGCATCCGAGAGGTCTGG
GAATGC CATCCGCCCAGGACTGCATAA CCTGCTTCG CATTGC
GCTTCTCCGGAAACATTAGC Exp-1_acnB-744_I1-bc25mer_83004-20_I2-bc25mer_83517-20
ACAACCGCGTGTTACAAGGC CAGGCATCCGAGAGGTCTGG
GAATGC CCCATAAACCACAGAACGGAG TTAGTGGCG CATTGC
GCTTCTCCGGAAACATTAGC Exp-1_acnB-393_I1-bc25mer_83004-20_I2-bc25mer_83517-20
ACAACCGCGTGTTACAAGGC CAGGCATCCGAGAGGTCTGG
GAATGC TCGTTGCCTGCTTTCGCTTTC TCTTCTACG CATTGC
GCTTCTCCGGAAACATTAGC Exp-1_acnB-530_I1-bc25mer_83004-20_I2-bc25mer_83517-20
ACAACCGCGTGTTACAAGGC CAGGCATCCGAGAGGTCTGG
GAATGC CCGGTGCCGGAGAAAGGTCAT CGGTGTTAG CATTGC
GCTTCTCCGGAAACATTAGC Exp-1_acnB-1378_I1-bc25mer_83004-20_I2-bc25mer_83517-20
ACAACCGCGTGTTACAAGGC CAGGCATCCGAGAGGTCTGG
GAATGC ACCGCCACGGTTCATAATGAA GTCCGGCAG CATTGC
GCTTCTCCGGAAACATTAGC Exp-1_acnB-2170_I1-bc25mer_83004-20_I2-bc25mer_83517-20
ACAACCGCGTGTTACAAGGC CAGGCATCCGAGAGGTCTGG
GAATGC GGTCGGCAACTGACCTTTATG CGCATCCAG CATTGC
GCTTCTCCGGAAACATTAGC

FIG. 4B

Exp-1_acnB-943_I1-bc25mer_83004-20_I2-bc25mer_83517-20
ACAACCGCGTGTTACAAGGC CAGGCATCCGAGAGGTCTGG
GAATGC CAGTTCGCCGGTTTCGTGGTT ACGCACTTC CATTGC
GCTTCTCCGGAAACATTAGC Exp-1_acnB-1881_I1-bc25mer_83004-20_I2-bc25mer_83517-20
ACAACCGCGTGTTACAAGGC CAGGCATCCGAGAGGTCTGG
GAATGC TCGCCGTAACCTTCCGCGATC ATCCACTTC
CATTGC GCTTCTCCGGAAACATTAGC Exp-1_acnB-634_I1-bc25mer_83004-20_I2-bc25mer_83517-20
ACAACCGCGTGTTACAAGGC CAGGCATCCGAGAGGTCTGG
GAATGC CTTGATCGGACCAACAACACC AGGCTGGTC CATTGC
GCTTCTCCGGAAACATTAGC Exp-1_acnB-1224_I1-bc25mer_83004-20_I2-bc25mer_83517-20
ACAACCGCGTGTTACAAGGC CAGGCATCCGAGAGGTCTGG
GAATGC CCGGTGGTGTCCTGGGAACCT ACAGAAGTC CATTGC
GCTTCTCCGGAAACATTAGC Exp-1_acnB-1768_I1-bc25mer_83004-20_I2-bc25mer_83517-20
ACAACCGCGTGTTACAAGGC CAGGCATCCGAGAGGTCTGG
GAATGC GGACGCATCGGTTAGCTCAAA GGCCTGCTC CATTGC
GCTTCTCCGGAAACATTAGC Exp-1_acnB-2473_I1-bc25mer_83004-20_I2-bc25mer_83517-20
ACAACCGCGTGTTACAAGGC CAGGCATCCGAGAGGTCTGG
GAATGC ATCTACCTGCGCCACGTAGGT CTGGTACTC CATTGC
GCTTCTCCGGAAACATTAGC Exp-1_acnB-1005_I1-bc25mer_83004-20_I2-bc25mer_83517-20
ACAACCGCGTGTTACAAGGC CAGGCATCCGAGAGGTCTGG
GAATGC ATACGGCCACCAGCACGCACT TCATCAATC CATTGC
GCTTCTCCGGAAACATTAGC Exp-1_acnB-352_I1-bc25mer_83004-20_I2-bc25mer_83517-20
ACAACCGCGTGTTACAAGGC CAGGCATCCGAGAGGTCTGG
GAATGC ATCGAACATCAGCAGCGTGTG AGAAAGTGC CATTGC
GCTTCTCCGGAAACATTAGC Exp-1_acnB-2002_I1-bc25mer_83004-20_I2-bc25mer_83517-20
ACAACCGCGTGTTACAAGGC CAGGCATCCGAGAGGTCTGG
GAATGC AATATCCGCCAGATCGATGTC GATCACTGC CATTGC
GCTTCTCCGGAAACATTAGC Exp-1_acnB-2088_I1-bc25mer_83004-20_I2-bc25mer_83517-20
ACAACCGCGTGTTACAAGGC CAGGCATCCGAGAGGTCTGG
GAATGC AACACTTCGTCGATCTTCTCA CCCTGTACC CATTGC
GCTTCTCCGGAAACATTAGC

FIG. 4C

Exp-1_acnB-1681_l1-bc25mer_83004-20_l2-bc25mer_83517-20
ACAACCGCGTGTTACAAGGC CAGGCATCCGAGAGGTCTGG
GAATGC CTTGCCTTTCTTCTAACGGT CAGCAGACC CATTGC
GCTTCTCCGGAAACATTAGC Exp-1_acnB-1916_l1-bc25mer_83004-20_l2-bc25mer_83517-20
ACAACCGCGTGTTACAAGGC CAGGCATCCGAGAGGTCTGG
GAATGC CCATGCCCTGAATACGACGTT CCAGGGTAC CATTGC
GCTTCTCCGGAAACATTAGC Exp-1_acnB-1478_l1-bc25mer_83004-20_l2-bc25mer_83517-20
ACAACCGCGTGTTACAAGGC CAGGCATCCGAGAGGTCTGG
GAATGC GGAAACGGGTATGGGAGTCAC CACCGGTAC CATTGC
GCTTCTCCGGAAACATTAGC Exp-1_acnB-706_l1-bc25mer_83004-20_l2-bc25mer_83517-20
ACAACCGCGTGTTACAAGGC CAGGCATCCGAGAGGTCTGG
GAATGC CGAAGAACCCGTACCCACAAC GTCACCGAC CATTGC
GCTTCTCCGGAAACATTAGC Exp-1_acnB-897_l1-bc25mer_83004-20_l2-bc25mer_83517-20
ACAACCGCGTGTTACAAGGC CAGGCATCCGAGAGGTCTGG
GAATGC ACGTCAATCACGTCGCCCATG TTCAGGTTA CATTGC
GCTTCTCCGGAAACATTAGC Exp-1_acnB-1515_l1-bc25mer_83004-20_l2-bc25mer_83517-20
ACAACCGCGTGTTACAAGGC CAGGCATCCGAGAGGTCTGG
GAATGC ACCAGACCAGAACCCGCCGGG AAAGAGATA CATTGC
GCTTCTCCGGAAACATTAGC Exp-1_acnB-1581_l1-bc25mer_83004-20_l2-bc25mer_83517-20
ACAACCGCGTGTTACAAGGC CAGGCATCCGAGAGGTCTGG
GAATGC TTGAAGCGCACCAGAACGGAT TCCGGCATA CATTGC
GCTTCTCCGGAAACATTAGC Exp-1_acnB-2226_l1-bc25mer_83004-20_l2-bc25mer_83517-20
ACAACCGCGTGTTACAAGGC CAGGCATCCGAGAGGTCTGG
GAATGC CCTTCTTCGGTCAACTGTGCG GCGTCCATA CATTGC
GCTTCTCCGGAAACATTAGC Exp-1_acnB-2297_l1-bc25mer_83004-20_l2-bc25mer_83517-20
ACAACCGCGTGTTACAAGGC CAGGCATCCGAGAGGTCTGG
GAATGC GGTTACCCATACACAGGGAAC AGCCAGGGA CATTGC
GCTTCTCCGGAAACATTAGC Exp-1_acnB-1733_l1-bc25mer_83004-20_l2-bc25mer_83517-20
ACAACCGCGTGTTACAAGGC CAGGCATCCGAGAGGTCTGG
GAATGC TCAGATCCGGCAGACCTTCAA TTTCCAGGA CATTGC
GCTTCTCCGGAAACATTAGC

FIG. 4D

Exp-1_acnB-305_I1-bc25mer_83004-20_I2-bc25mer_83517-20
ACAACCGCGTGTTACAAGGC CAGGCATCCGAGAGGTCTGG
GAATGC CCAGTTTGGCATCATCCAGCG CGTCGATCA CATTGC
GCTTCTCCGGAAACATTAGC Exp-1_acnB-1266_I1-bc25mer_83004-20_I2-bc25mer_83517-20
ACAACCGCGTGTTACAAGGC CAGGCATCCGAGAGGTCTGG
GAATGC CCCAGGCACGCCAGGTCTTTC AGTTCATCA CATTGC
GCTTCTCCGGAAACATTAGC Exp-1_acnB-1040_I1-bc25mer_83004-20_I2-bc25mer_83517-20
ACAACCGCGTGTTACAAGGC CAGGCATCCGAGAGGTCTGG
GAATGC CTTTGGTGGTCAGGCCACGCC CGATAATCA CATTGC
GCTTCTCCGGAAACATTAGC Exp-1_acnB-1646_I1-bc25mer_83004-20_I2-bc25mer_83517-20
ACAACCGCGTGTTACAAGGC CAGGCATCCGAGAGGTCTGG
GAATGC TGATCGCATACAGCGGAATAG CGTGTACCA CATTGC
GCTTCTCCGGAAACATTAGC Exp-1_acnB-848_I1-bc25mer_83004-20_I2-bc25mer_83517-20
ACAACCGCGTGTTACAAGGC CAGGCATCCGAGAGGTCTGG
GAATGC GCAGTGCACCCGCGTCTTCCA TCGTGTTAA CATTGC
GCTTCTCCGGAAACATTAGC Exp-1_acnB-1436_I1-bc25mer_83004-20_I2-bc25mer_83517-20
ACAACCGCGTGTTACAAGGC CAGGCATCCGAGAGGTCTGG
GAATGC GCAGCAGCATACGGTTCAGCC AGGAGTGAA CATTGC
GCTTCTCCGGAAACATTAGC Exp-1_acnB-1105_I1-bc25mer_83004-20_I2-bc25mer_83517-20
ACAACCGCGTGTTACAAGGC CAGGCATCCGAGAGGTCTGG
GAATGC GCTCTCAGCGACATCTTTCGC CTGACGGAA CATTGC
GCTTCTCCGGAAACATTAGC Exp-1_bamA-646_I1-bc25mer_83004-20_I2-bc25mer_83517-20
ACAACCGCGTGTTACAAGGC CAGGCATCCGAGAGGTCTGG
GAATGC GGTTTCAAGGTCGCCCGCCAG TTTCTGTTT CATTGC
GCTTCTCCGGAAACATTAGC Exp-1_bamA-1951_I1-bc25mer_83004-20_I2-bc25mer_83517-20
ACAACCGCGTGTTACAAGGC CAGGCATCCGAGAGGTCTGG
GAATGC CACGGTGCTGGAACCACCGGC ATAGAAGTT CATTGC
GCTTCTCCGGAAACATTAGC Exp-1_bamA-1354_I1-bc25mer_83004-20_I2-bc25mer_83517-20
ACAACCGCGTGTTACAAGGC CAGGCATCCGAGAGGTCTGG
GAATGC GGTCCCGTTGATACCAACAGC ATAACCTGT CATTGC
GCTTCTCCGGAAACATTAGC

FIG. 4E

Exp-1_bamA-686_I1-bc25mer_83004-20_I2-bc25mer_83517-20
ACAACCGCGTGTTACAAGGC CAGGCATCCGAGAGGTCTGG
GAATGC TGAAACGGGCATAACCGCGAT CCAGATAGT CATTGC
GCTTCTCCGGAAACATTAGC Exp-1_bamA-1189_I1-bc25mer_83004-20_I2-bc25mer_83517-20
ACAACCGCGTGTTACAAGGC CAGGCATCCGAGAGGTCTGG
GAATGC CGGAACACGTTGGGTATCGGT ATCGACAGT CATTGC
GCTTCTCCGGAAACATTAGC Exp-1_bamA-1410_I1-bc25mer_83004-20_I2-bc25mer_83517-20
ACAACCGCGTGTTACAAGGC CAGGCATCCGAGAGGTCTGG
GAATGC ACGGTGAAGTACGGGTTGGTT ACCGACAGT CATTGC
GCTTCTCCGGAAACATTAGC Exp-1_bamA-857_I1-bc25mer_83004-20_I2-bc25mer_83517-20
ACAACCGCGTGTTACAAGGC CAGGCATCCGAGAGGTCTGG
GAATGC ACAGCTCACCCGGCTCGATCT TAGTCAGCT CATTGC
GCTTCTCCGGAAACATTAGC Exp-1_bamA-1490_I1-bc25mer_83004-20_I2-bc25mer_83517-20
ACAACCGCGTGTTACAAGGC CAGGCATCCGAGAGGTCTGG
GAATGC TGTTGGTATAGTCGGACAGGT CGGCGTCAT CATTGC
GCTTCTCCGGAAACATTAGC Exp-1_bamA-85_I1-bc25mer_83004-20_I2-bc25mer_83517-20
ACAACCGCGTGTTACAAGGC CAGGCATCCGAGAGGTCTGG
GAATGC GGCGACACGCTGAAGGCCTTC GAAATGAAT CATTGC
GCTTCTCCGGAAACATTAGC Exp-1_bamA-564_I1-bc25mer_83004-20_I2-bc25mer_83517-20
ACAACCGCGTGTTACAAGGC CAGGCATCCGAGAGGTCTGG
GAATGC TGGAAATGAGAGATCAGTTCG TCGGTGGTG CATTGC
GCTTCTCCGGAAACATTAGC Exp-1_bamA-508_I1-bc25mer_83004-20_I2-bc25mer_83517-20
ACAACCGCGTGTTACAAGGC CAGGCATCCGAGAGGTCTGG
GAATGC TTGCTGGATTTCAGCTGACAC ACCTTCCTG CATTGC
GCTTCTCCGGAAACATTAGC Exp-1_bamA-967_I1-bc25mer_83004-20_I2-bc25mer_83517-20
ACAACCGCGTGTTACAAGGC CAGGCATCCGAGAGGTCTGG
GAATGC GTCGGCATCGTTAATTTCGGG CATCGACTG CATTGC
GCTTCTCCGGAAACATTAGC Exp-1_bamA-1989_I1-bc25mer_83004-20_I2-bc25mer_83517-20
ACAACCGCGTGTTACAAGGC CAGGCATCCGAGAGGTCTGG
GAATGC ACTGCTTTCGGACCAATGGTA TTGGACTGG CATTGC
GCTTCTCCGGAAACATTAGC

FIG. 4F

Exp-1_bamA-1224_I1-bc25mer_83004-20_I2-bc25mer_83517-20
ACAACCGCGTGTTACAAGGC CAGGCATCCGAGAGGTCTGG
GAATGC ACCTTGTAGACGACATCAACC TGGTCCGGG CATTGC
GCTTCTCCGGAAACATTAGC Exp-1_bamA-1787_I1-bc25mer_83004-20_I2-bc25mer_83517-20
ACAACCGCGTGTTACAAGGC CAGGCATCCGAGAGGTCTGG
GAATGC TATCCGATCCAGGAATGGTCA CTTTACCGG CATTGC
GCTTCTCCGGAAACATTAGC Exp-1_bamA-50_I1-bc25mer_83004-20_I2-bc25mer_83517-20
ACAACCGCGTGTTACAAGGC CAGGCATCCGAGAGGTCTGG
GAATGC TCACTACGAACCCTTCAGCAC CGTATACGG CATTGC
GCTTCTCCGGAAACATTAGC Exp-1_bamA-1101_I1-bc25mer_83004-20_I2-bc25mer_83517-20
ACAACCGCGTGTTACAAGGC CAGGCATCCGAGAGGTCTGG
GAATGC AGCCATGCACCTTCCATCTGA CGCATTTCG CATTGC
GCTTCTCCGGAAACATTAGC Exp-1_bamA-1560_I1-bc25mer_83004-20_I2-bc25mer_83517-20
ACAACCGCGTGTTACAAGGC CAGGCATCCGAGAGGTCTGG
GAATGC CCCAGACCTGCACGCAGCGAG TTATATTCG CATTGC
GCTTCTCCGGAAACATTAGC Exp-1_bamA-2382_I1-bc25mer_83004-20_I2-bc25mer_83517-20
ACAACCGCGTGTTACAAGGC CAGGCATCCGAGAGGTCTGG
GAATGC AACTGGAACTGTTCTGCCTTG TCTCCATCG CATTGC
GCTTCTCCGGAAACATTAGC Exp-1_bamA-145_I1-bc25mer_83004-20_I2-bc25mer_83517-20
ACAACCGCGTGTTACAAGGC CAGGCATCCGAGAGGTCTGG
GAATGC ATCTTCATCATTAACCGTGTC GCCTGTGCG CATTGC
GCTTCTCCGGAAACATTAGC Exp-1_bamA-1700_I1-bc25mer_83004-20_I2-bc25mer_83517-20
ACAACCGCGTGTTACAAGGC CAGGCATCCGAGAGGTCTGG
GAATGC TCCAACCATAGTTGAACGTGA AGTCGTCCG CATTGC
GCTTCTCCGGAAACATTAGC Exp-1_bamA-2299_I1-bc25mer_83004-20_I2-bc25mer_83517-20
ACAACCGCGTGTTACAAGGC CAGGCATCCGAGAGGTCTGG
GAATGC CCATTGTAATGCGATACCCGC AGACATACG CATTGC
GCTTCTCCGGAAACATTAGC Exp-1_bamA-611_I1-bc25mer_83004-20_I2-bc25mer_83517-20
ACAACCGCGTGTTACAAGGC CAGGCATCCGAGAGGTCTGG
GAATGC ATTTACGATCGCCTACCACGT TCCACCACG CATTGC
GCTTCTCCGGAAACATTAGC

FIG. 4G

Exp-1_bamA-2229_I1-bc25mer_83004-20_I2-bc25mer_83517-20
ACAACCGCGTGTTACAAGGC CAGGCATCCGAGAGGTCTGG
GAATGC TGGCTGGAATCCCAGTTTGTA TCCCAAACG CATTGC
GCTTCTCCGGAAACATTAGC Exp-1_bamA-423_I1-bc25mer_83004-20_I2-bc25mer_83517-20
ACAACCGCGTGTTACAAGGC CAGGCATCCGAGAGGTCTGG
GAATGC ACGCTGGCGCTATATTTACCG ACGCTGTAG CATTGC
GCTTCTCCGGAAACATTAGC Exp-1_bamA-2095_I1-bc25mer_83004-20_I2-bc25mer_83517-20
ACAACCGCGTGTTACAAGGC CAGGCATCCGAGAGGTCTGG
GAATGC ACCGCCTACAGCATCATCCGA TTTACACAG CATTGC
GCTTCTCCGGAAACATTAGC Exp-1_bamA-721_I1-bc25mer_83004-20_I2-bc25mer_83517-20
ACAACCGCGTGTTACAAGGC CAGGCATCCGAGAGGTCTGG
GAATGC ATCTGGCGTCAGACTGACCTG GGTAGAGTC CATTGC
GCTTCTCCGGAAACATTAGC Exp-1_bamA-2059_I1-bc25mer_83004-20_I2-bc25mer_83517-20
ACAACCGCGTGTTACAAGGC CAGGCATCCGAGAGGTCTGG
GAATGC CGCGCCGTCCTGAGTCGCACA TTCGTAATC CATTGC
GCTTCTCCGGAAACATTAGC Exp-1_bamA-1857_I1-bc25mer_83004-20_I2-bc25mer_83517-20
ACAACCGCGTGTTACAAGGC CAGGCATCCGAGAGGTCTGG
GAATGC ACAACCCATTTGTGATCGTCA TCGATCGGC CATTGC
GCTTCTCCGGAAACATTAGC Exp-1_bamA-1630_I1-bc25mer_83004-20_I2-bc25mer_83517-20
ACAACCGCGTGTTACAAGGC CAGGCATCCGAGAGGTCTGG
GAATGC ACCCATAGAGTACAGATAACG CCACATCGC CATTGC
GCTTCTCCGGAAACATTAGC Exp-1_bamA-1260_I1-bc25mer_83004-20_I2-bc25mer_83517-20
ACAACCGCGTGTTACAAGGC CAGGCATCCGAGAGGTCTGG
GAATGC ATACCAAAGTTGAAGCTACCG GTGTTGCGC CATTGC
GCTTCTCCGGAAACATTAGC Exp-1_bamA-1445_I1-bc25mer_83004-20_I2-bc25mer_83517-20
ACAACCGCGTGTTACAAGGC CAGGCATCCGAGAGGTCTGG
GAATGC TATAGAAGAGACGACCACCGA GGCTTACGC CATTGC
GCTTCTCCGGAAACATTAGC Exp-1_bamA-892_I1-bc25mer_83004-20_I2-bc25mer_83517-20
ACAACCGCGTGTTACAAGGC CAGGCATCCGAGAGGTCTGG
GAATGC GTCATCTTCCATCTTGGTCAC TTTGGTGCC CATTGC
GCTTCTCCGGAAACATTAGC

FIG. 4H

Exp-1_bamA-1029_l1-bc25mer_83004-20_l2-bc25mer_83517-20
ACAACCGCGTGTTACAAGGC CAGGCATCCGAGAGGTCTGG
GAATGC CGGATCTTACGCACGTAGAAA CGGTTACCC CATTGC
GCTTCTCCGGAAACATTAGC Exp-1_bamA-1066_l1-bc25mer_83004-20_l2-bc25mer_83517-20
ACAACCGCGTGTTACAAGGC CAGGCATCCGAGAGGTCTGG
GAATGC CAGGACGGCATCTTTCGAGGT ATCGTTACC CATTGC
GCTTCTCCGGAAACATTAGC Exp-1_bamA-1154_l1-bc25mer_83004-20_l2-bc25mer_83517-20
ACAACCGCGTGTTACAAGGC CAGGCATCCGAGAGGTCTGG
GAATGC AGAAGCCCAGACGATTCAGAC GCTCCTTAC CATTGC
GCTTCTCCGGAAACATTAGC Exp-1_bamA-1751_l1-bc25mer_83004-20_l2-bc25mer_83517-20
ACAACCGCGTGTTACAAGGC CAGGCATCCGAGAGGTCTGG
GAATGC TGACACGTGAACCATCTGTCG GGAAGTAAC CATTGC
GCTTCTCCGGAAACATTAGC Exp-1_bamA-15_l1-bc25mer_83004-20_l2-bc25mer_83517-20
ACAACCGCGTGTTACAAGGC CAGGCATCCGAGAGGTCTGG
GAATGC CTGCTAAACAGCAGCGACGCT ATGAGCAAC CATTGC
GCTTCTCCGGAAACATTAGC Exp-1_bamA-1595_l1-bc25mer_83004-20_l2-bc25mer_83517-20
ACAACCGCGTGTTACAAGGC CAGGCATCCGAGAGGTCTGG
GAATGC GAGGCTGCATGTTGGACAGGG AGTTATGTA CATTGC
GCTTCTCCGGAAACATTAGC Exp-1_bamA-1525_l1-bc25mer_83004-20_l2-bc25mer_83517-20
ACAACCGCGTGTTACAAGGC CAGGCATCCGAGAGGTCTGG
GAATGC CGGGAAGCCCAACGTCACGTC TGTACCATA CATTGC
GCTTCTCCGGAAACATTAGC Exp-1_bamA-2024_l1-bc25mer_83004-20_l2-bc25mer_83517-20
ACAACCGCGTGTTACAAGGC CAGGCATCCGAGAGGTCTGG
GAATGC CCGGATCATAATTACTGGCCT GATGCGGGA CATTGC
GCTTCTCCGGAAACATTAGC Exp-1_bamA-1665_l1-bc25mer_83004-20_l2-bc25mer_83517-20
ACAACCGCGTGTTACAAGGC CAGGCATCCGAGAGGTCTGG
GAATGC AAGCTGTTATCCTGATCAGAG GTGCTCGGA CATTGC
GCTTCTCCGGAAACATTAGC Exp-1_bamA-234_l1-bc25mer_83004-20_l2-bc25mer_83517-20
ACAACCGCGTGTTACAAGGC CAGGCATCCGAGAGGTCTGG
GAATGC ACCTGAACCAGAAGGGTATCA CCATCACGA CATTGC
GCTTCTCCGGAAACATTAGC

FIG. 4I

Exp-1_bamA-1911_I1-bc25mer_83004-20_I2-bc25mer_83517-20
ACAACCGCGTGTTACAAGGC CAGGCATCCGAGAGGTCTGG
GAATGC GGCATCTCTTTGCCGCCTAAA CCATCACCA CATTGC
GCTTCTCCGGAAACATTAGC Exp-1_bamA-1318_I1-bc25mer_83004-20_I2-bc25mer_83517-20
ACAACCGCGTGTTACAAGGC CAGGCATCCGAGAGGTCTGG
GAATGC CCAGTTATCCTGCTGCACACC AGCCTGGAA CATTGC
GCTTCTCCGGAAACATTAGC Exp-1_bamA-932_I1-bc25mer_83004-20_I2-bc25mer_83517-20
ACAACCGCGTGTTACAAGGC CAGGCATCCGAGAGGTCTGG
GAATGC GCGGATAGGCATAACCATAGC GACCGAGAA CATTGC
GCTTCTCCGGAAACATTAGC Exp-1_bamA-803_I1-bc25mer_83004-20_I2-bc25mer_83517-20
ACAACCGCGTGTTACAAGGC CAGGCATCCGAGAGGTCTGG
GAATGC CAAGGTTGCCGCTCACTTCAA CGCCAGAAA CATTGC
GCTTCTCCGGAAACATTAGC Exp-1_bamA-199_I1-bc25mer_83004-20_I2-bc25mer_83517-20
ACAACCGCGTGTTACAAGGC CAGGCATCCGAGAGGTCTGG
GAATGC GCGAACATCCTCAAAGTTGCC GGTAGCAAA CATTGC
GCTTCTCCGGAAACATTAGC Exp-1_btuF-721_I1-bc25mer_83004-20_I2-bc25mer_83517-20
ACAACCGCGTGTTACAAGGC CAGGCATCCGAGAGGTCTGG
GAATGC ACGTGGGCTTGCACGTTCAAA CCAGTCACT CATTGC
GCTTCTCCGGAAACATTAGC Exp-1_btuF-764_I1-bc25mer_83004-20_I2-bc25mer_83517-20
ACAACCGCGTGTTACAAGGC CAGGCATCCGAGAGGTCTGG
GAATGC CCTGTGAAAGCGCATTACAGA GCTGTTGTG CATTGC
GCTTCTCCGGAAACATTAGC Exp-1_btuF-418_I1-bc25mer_83004-20_I2-bc25mer_83517-20
ACAACCGCGTGTTACAAGGC CAGGCATCCGAGAGGTCTGG
GAATGC TTGCGCTTTCAATTGCGCGTA CTGATCCAG CATTGC
GCTTCTCCGGAAACATTAGC Exp-1_btuF-143_I1-bc25mer_83004-20_I2-bc25mer_83517-20
ACAACCGCGTGTTACAAGGC CAGGCATCCGAGAGGTCTGG
GAATGC GCGCTTGTGGAGGATAGTCGG AATAGCTGC CATTGC
GCTTCTCCGGAAACATTAGC Exp-1_btuF-637_I1-bc25mer_83004-20_I2-bc25mer_83517-20
ACAACCGCGTGTTACAAGGC CAGGCATCCGAGAGGTCTGG
GAATGC AGGAATTTGGTCCGGTCCGCC TGTAATGAC CATTGC
GCTTCTCCGGAAACATTAGC

FIG. 4J

Exp-1_btuF-595_l1-bc25mer_83004-20_l2-bc25mer_83517-20
ACAACCGCGTGTTACAAGGC CAGGCATCCGAGAGGTCTGG
GAATGC CGAGCGTGCTAACACCTGTTC GCGGCTAAC CATTGC
GCTTCTCCGGAAACATTAGC Exp-1_btuF-240_l1-bc25mer_83004-20_l2-bc25mer_83517-20
ACAACCGCGTGTTACAAGGC CAGGCATCCGAGAGGTCTGG
GAATGC GCATTACCTCCACGCCAGGCA ATCACCAGA CATTGC
GCTTCTCCGGAAACATTAGC Exp-1_btuF-87_l1-bc25mer_83004-20_l2-bc25mer_83517-20
ACAACCGCGTGTTACAAGGC CAGGCATCCGAGAGGTCTGG
GAATGC GCAAAGGCAAGTTCAGTGTTG GCGGGAGAA CATTGC
GCTTCTCCGGAAACATTAGC Exp-1_can-349_l1-bc25mer_83004-20_l2-bc25mer_83517-20
ACAACCGCGTGTTACAAGGC CAGGCATCCGAGAGGTCTGG
GAATGC GATATCGCGGATATGCAGCAG CCAGTTGTT CATTGC
GCTTCTCCGGAAACATTAGC Exp-1_can-202_l1-bc25mer_83004-20_l2-bc25mer_83517-20
ACAACCGCGTGTTACAAGGC CAGGCATCCGAGAGGTCTGG
GAATGC GCAGTTCAGGTCAGTGTGAAT GACCAGGTT CATTGC
GCTTCTCCGGAAACATTAGC Exp-1_can-167_l1-bc25mer_83004-20_l2-bc25mer_83517-20
ACAACCGCGTGTTACAAGGC CAGGCATCCGAGAGGTCTGG
GAATGC CATTACGGTGAACAAAGAGTT CGCCCGGCT CATTGC
GCTTCTCCGGAAACATTAGC Exp-1_can-630_l1-bc25mer_83004-20_l2-bc25mer_83517-20
ACAACCGCGTGTTACAAGGC CAGGCATCCGAGAGGTCTGG
GAATGC TTGTGGTTGGCGTGTTTCAGC TTGAGGTTG CATTGC
GCTTCTCCGGAAACATTAGC Exp-1_can-132_l1-bc25mer_83004-20_l2-bc25mer_83517-20
ACAACCGCGTGTTACAAGGC CAGGCATCCGAGAGGTCTGG
GAATGC CCGGTTAAACGTTCTGCAGGA ACGCGACTG CATTGC
GCTTCTCCGGAAACATTAGC Exp-1_can-434_l1-bc25mer_83004-20_l2-bc25mer_83517-20
ACAACCGCGTGTTACAAGGC CAGGCATCCGAGAGGTCTGG
GAATGC CCTGTTCCATGACGTTCAGTT CACACAAGG CATTGC
GCTTCTCCGGAAACATTAGC Exp-1_can-237_l1-bc25mer_83004-20_l2-bc25mer_83517-20
ACAACCGCGTGTTACAAGGC CAGGCATCCGAGAGGTCTGG
GAATGC TCGAGTACATCCACTGCATAC TGAACCACG CATTGC
GCTTCTCCGGAAACATTAGC

FIG. 4K

Exp-1_can-480_l1-bc25mer_83004-20_l2-bc25mer_83517-20
ACAACCGCGTGTTACAAGGC CAGGCATCCGAGAGGTCTGG
GAATGC CGTTTCCACGCTGATTGCATA ATGGTGGAG CATTGC
GCTTCTCCGGAAACATTAGC Exp-1_can-595_l1-bc25mer_83004-20_l2-bc25mer_83517-20
ACAACCGCGTGTTACAAGGC CAGGCATCCGAGAGGTCTGG
GAATGC CCCGTGACGGTAACGTTGCTC AAGGGTTTC CATTGC
GCTTCTCCGGAAACATTAGC Exp-1_can-279_l1-bc25mer_83004-20_l2-bc25mer_83517-20
ACAACCGCGTGTTACAAGGC CAGGCATCCGAGAGGTCTGG
GAATGC CCGCCGCAACCGTAGTGGCCA CAGATAATA CATTGC
GCTTCTCCGGAAACATTAGC Exp-1_can-559_l1-bc25mer_83004-20_l2-bc25mer_83517-20
ACAACCGCGTGTTACAAGGC CAGGCATCCGAGAGGTCTGG
GAATGC GGTGGCGGTAACATCCAGATC ACGCAGCAA CATTGC
GCTTCTCCGGAAACATTAGC Exp-1_cdsA-414_l1-bc25mer_83004-20_l2-bc25mer_83517-20
ACAACCGCGTGTTACAAGGC CAGGCATCCGAGAGGTCTGG
GAATGC TAATGATTCTCGTCATAGTGC CAGGCCCGT CATTGC
GCTTCTCCGGAAACATTAGC Exp-1_cdsA-37_l1-bc25mer_83004-20_l2-bc25mer_83517-20
ACAACCGCGTGTTACAAGGC CAGGCATCCGAGAGGTCTGG
GAATGC CAGAAACAACGCCGCGATGAC GACGGGTAT CATTGC
GCTTCTCCGGAAACATTAGC Exp-1_cdsA-87_l1-bc25mer_83004-20_l2-bc25mer_83517-20
ACAACCGCGTGTTACAAGGC CAGGCATCCGAGAGGTCTGG
GAATGC GCCAGCATGCAGACCACCAGC GTTACAATG CATTGC
GCTTCTCCGGAAACATTAGC Exp-1_cdsA-319_l1-bc25mer_83004-20_l2-bc25mer_83517-20
ACAACCGCGTGTTACAAGGC CAGGCATCCGAGAGGTCTGG
GAATGC AGAGTTACGCCAGATTGCTGC GGAACCTGG CATTGC
GCTTCTCCGGAAACATTAGC Exp-1_cdsA-247_l1-bc25mer_83004-20_l2-bc25mer_83517-20
ACAACCGCGTGTTACAAGGC CAGGCATCCGAGAGGTCTGG
GAATGC CGAAGCCCAAAGTGAGATTTC AACCAGCGG CATTGC
GCTTCTCCGGAAACATTAGC Exp-1_cdsA-809_l1-bc25mer_83004-20_l2-bc25mer_83517-20
ACAACCGCGTGTTACAAGGC CAGGCATCCGAGAGGTCTGG
GAATGC GTAACAACAAGCAAGCAAAGA CCGGTACCG CATTGC
GCTTCTCCGGAAACATTAGC

FIG. 4L

Exp-1_cdsA-449_I1-bc25mer_83004-20_I2-bc25mer_83517-20
ACAACCGCGTGTTACAAGGC CAGGCATCCGAGAGGTCTGG
GAATGC GGATCATGACATAGAGCAGCC ATATTGCGC CATTGC
GCTTCTCCGGAAACATTAGC Exp-1_cdsA-749_I1-bc25mer_83004-20_I2-bc25mer_83517-20
ACAACCGCGTGTTACAAGGC CAGGCATCCGAGAGGTCTGG
GAATGC TACCACCGTGTCCTGGAATTA AATGACCGC CATTGC
GCTTCTCCGGAAACATTAGC Exp-1_cdsA-490_I1-bc25mer_83004-20_I2-bc25mer_83517-20
ACAACCGCGTGTTACAAGGC CAGGCATCCGAGAGGTCTGG
GAATGC TTTGCCAAACATATATGCGCC GGAGTCAGC CATTGC
GCTTCTCCGGAAACATTAGC Exp-1_cdsA-575_I1-bc25mer_83004-20_I2-bc25mer_83517-20
ACAACCGCGTGTTACAAGGC CAGGCATCCGAGAGGTCTGG
GAATGC CCGCTGCAGTAGCGAGTCCAC CGATAAAGC CATTGC
GCTTCTCCGGAAACATTAGC Exp-1_cdsA-700_I1-bc25mer_83004-20_I2-bc25mer_83517-20
ACAACCGCGTGTTACAAGGC CAGGCATCCGAGAGGTCTGG
GAATGC ACGCTTAAACATACTCTCGGT CAGATCGCC CATTGC
GCTTCTCCGGAAACATTAGC Exp-1_cdsA-179_I1-bc25mer_83004-20_I2-bc25mer_83517-20
ACAACCGCGTGTTACAAGGC CAGGCATCCGAGAGGTCTGG
GAATGC GCATCAGCGCCAACAATAACC CGCATAACA CATTGC
GCTTCTCCGGAAACATTAGC Exp-1_cdsA-618_I1-bc25mer_83004-20_I2-bc25mer_83517-20
ACAACCGCGTGTTACAAGGC CAGGCATCCGAGAGGTCTGG
GAATGC GCGACGTCGAGATTCGCCCAC ATGCCATAA CATTGC
GCTTCTCCGGAAACATTAGC Exp-1_cdsA-282_I1-bc25mer_83004-20_I2-bc25mer_83517-20
ACAACCGCGTGTTACAAGGC CAGGCATCCGAGAGGTCTGG
GAATGC AGCACCAGCAATAGCGCGACA ATCCACCAA CATTGC
GCTTCTCCGGAAACATTAGC Exp-1_cdsA-665_I1-bc25mer_83004-20_I2-bc25mer_83517-20
ACAACCGCGTGTTACAAGGC CAGGCATCCGAGAGGTCTGG
GAATGC CTGAGGCTAACGCTGCGACAA TAGAGCAAA CATTGC
GCTTCTCCGGAAACATTAGC Exp-1_dapD-653_I1-bc25mer_83004-20_I2-bc25mer_83517-20
ACAACCGCGTGTTACAAGGC CAGGCATCCGAGAGGTCTGG
GAATGC GAACGCGACCGTAGTGGATTT CGCCGGTTT CATTGC
GCTTCTCCGGAAACATTAGC

FIG. 4M

Exp-1_dapD-93_l1-bc25mer_83004-20_l2-bc25mer_83517-20
ACAACCGCGTGTTACAAGGC CAGGCATCCGAGAGGTCTGG
GAATGC CCGGAATCCAGCAGGGCGATC ACCTGATTT CATTGC
GCTTCTCCGGAAACATTAGC Exp-1_dapD-384_l1-bc25mer_83004-20_l2-bc25mer_83517-20
ACAACCGCGTGTTACAAGGC CAGGCATCCGAGAGGTCTGG
GAATGC GTGCCTTCATCAACATATGCG CCGATGTTG CATTGC
GCTTCTCCGGAAACATTAGC Exp-1_dapD-148_l1-bc25mer_83004-20_l2-bc25mer_83517-20
ACAACCGCGTGTTACAAGGC CAGGCATCCGAGAGGTCTGG
GAATGC CAACCACTGATGCGTCACCCA CTGACCGTC CATTGC
GCTTCTCCGGAAACATTAGC Exp-1_dapD-51_l1-bc25mer_83004-20_l2-bc25mer_83517-20
ACAACCGCGTGTTACAAGGC CAGGCATCCGAGAGGTCTGG
GAATGC GTAACGGTGTCTGCATTGGCT GGCGTGATC CATTGC
GCTTCTCCGGAAACATTAGC Exp-1_dapD-724_l1-bc25mer_83004-20_l2-bc25mer_83517-20
ACAACCGCGTGTTACAAGGC CAGGCATCCGAGAGGTCTGG
GAATGC AACCGCACAGTAGAGGCTGTA TTTGCCATC CATTGC
GCTTCTCCGGAAACATTAGC Exp-1_dapD-794_l1-bc25mer_83004-20_l2-bc25mer_83517-20
ACAACCGCGTGTTACAAGGC CAGGCATCCGAGAGGTCTGG
GAATGC AGTCGATGGTACGCAGCAGTT CGTTAATGC CATTGC
GCTTCTCCGGAAACATTAGC Exp-1_dapD-613_l1-bc25mer_83004-20_l2-bc25mer_83517-20
ACAACCGCGTGTTACAAGGC CAGGCATCCGAGAGGTCTGG
GAATGC AATACGGGTGCTCTGACCAAT GTATACGCC CATTGC
GCTTCTCCGGAAACATTAGC Exp-1_dapD-540_l1-bc25mer_83004-20_l2-bc25mer_83517-20
ACAACCGCGTGTTACAAGGC CAGGCATCCGAGAGGTCTGG
GAATGC ACTTCAGAGCGCGCGCCGATG AAGCAATTA CATTGC
GCTTCTCCGGAAACATTAGC Exp-1_dapD-348_l1-bc25mer_83004-20_l2-bc25mer_83517-20
ACAACCGCGTGTTACAAGGC CAGGCATCCGAGAGGTCTGG
GAATGC GACGGCATCAGCACGGTGTTA CGGGCAATA CATTGC
GCTTCTCCGGAAACATTAGC Exp-1_dapD-257_l1-bc25mer_83004-20_l2-bc25mer_83517-20
ACAACCGCGTGTTACAAGGC CAGGCATCCGAGAGGTCTGG
GAATGC CTTCGTCGTAGTCGGCGAATT TCATCGGCA CATTGC
GCTTCTCCGGAAACATTAGC

FIG. 4N

Exp-1_dapD-292_I1-bc25mer_83004-20_I2-bc25mer_83517-20
ACAACCGCGTGTTACAAGGC CAGGCATCCGAGAGGTCTGG
GAATGC TGGCACAACGCGGAAGCCTTC TTTCTGGAA CATTGC
GCTTCTCCGGAAACATTAGC Exp-1_dapD-419_I1-bc25mer_83004-20_I2-bc25mer_83517-20
ACAACCGCGTGTTACAAGGC CAGGCATCCGAGAGGTCTGG
GAATGC CACAAGAACCGACGGTCGCCC AGGTATCAA CATTGC
GCTTCTCCGGAAACATTAGC Exp-1_ddlB-302_I1-bc25mer_83004-20_I2-bc25mer_83517-20
ACAACCGCGTGTTACAAGGC CAGGCATCCGAGAGGTCTGG
GAATGC CCGGTAAACCGGCACCTTGCC ATAGAAGTT CATTGC
GCTTCTCCGGAAACATTAGC Exp-1_ddlB-95_I1-bc25mer_83004-20_I2-bc25mer_83517-20
ACAACCGCGTGTTACAAGGC CAGGCATCCGAGAGGTCTGG
GAATGC GGTCGACAGGATACGCGTCAA TACCGCCTT CATTGC
GCTTCTCCGGAAACATTAGC Exp-1_ddlB-814_I1-bc25mer_83004-20_I2-bc25mer_83517-20
ACAACCGCGTGTTACAAGGC CAGGCATCCGAGAGGTCTGG
GAATGC GCTGTGGCTGGTCATACCCGG TGAGGTATT CATTGC
GCTTCTCCGGAAACATTAGC Exp-1_ddlB-766_I1-bc25mer_83004-20_I2-bc25mer_83517-20
ACAACCGCGTGTTACAAGGC CAGGCATCCGAGAGGTCTGG
GAATGC CTGTCCATCGCTGTCCAGCAT AACGTCAAT CATTGC
GCTTCTCCGGAAACATTAGC Exp-1_ddlB-614_I1-bc25mer_83004-20_I2-bc25mer_83517-20
ACAACCGCGTGTTACAAGGC CAGGCATCCGAGAGGTCTGG
GAATGC TCGCCTCATAATCATAGAAGG TTCCGGACG CATTGC
GCTTCTCCGGAAACATTAGC Exp-1_ddlB-726_I1-bc25mer_83004-20_I2-bc25mer_83517-20
ACAACCGCGTGTTACAAGGC CAGGCATCCGAGAGGTCTGG
GAATGC CCTTTGCAACCTAACGTCGTC CATGCTTTC CATTGC
GCTTCTCCGGAAACATTAGC Exp-1_ddlB-168_I1-bc25mer_83004-20_I2-bc25mer_83517-20
ACAACCGCGTGTTACAAGGC CAGGCATCCGAGAGGTCTGG
GAATGC CCGCGACCGTGTAGCGCGATA AACACTTTC CATTGC
GCTTCTCCGGAAACATTAGC Exp-1_ddlB-435_I1-bc25mer_83004-20_I2-bc25mer_83517-20
ACAACCGCGTGTTACAAGGC CAGGCATCCGAGAGGTCTGG
GAATGC GACATTCCCACACTGGAACCT TCGCGGCTC CATTGC
GCTTCTCCGGAAACATTAGC

FIG. 40

Exp-1_ddlB-559_l1-bc25mer_83004-20_l2-bc25mer_83517-20
ACAACCGCGTGTTACAAGGC CAGGCATCCGAGAGGTCTGG
GAATGC TTCTTCACCGAGTATCGCAAC CGTGAACTC CATTGC
GCTTCTCCGGAAACATTAGC Exp-1_ddlB-394_l1-bc25mer_83004-20_l2-bc25mer_83517-20
ACAACCGCGTGTTACAAGGC CAGGCATCCGAGAGGTCTGG
GAATGC AACCGGCAAACCCAGAGCAGA AATTTCTGC CATTGC
GCTTCTCCGGAAACATTAGC Exp-1_ddlB-691_l1-bc25mer_83004-20_l2-bc25mer_83517-20
ACAACCGCGTGTTACAAGGC CAGGCATCCGAGAGGTCTGG
GAATGC TAATGCCTGCAAATTGGCCTC TTGTGACGC CATTGC
GCTTCTCCGGAAACATTAGC Exp-1_ddlB-259_l1-bc25mer_83004-20_l2-bc25mer_83517-20
ACAACCGCGTGTTACAAGGC CAGGCATCCGAGAGGTCTGG
GAATGC ATCCATTGAAAGCGCAGATGC CATCACTCC CATTGC
GCTTCTCCGGAAACATTAGC Exp-1_ddlB-891_l1-bc25mer_83004-20_l2-bc25mer_83517-20
ACAACCGCGTGTTACAAGGC CAGGCATCCGAGAGGTCTGG
GAATGC TAGTCCGCCAGTTCCAGAATT CGTACTACC CATTGC
GCTTCTCCGGAAACATTAGC Exp-1_ddlB-133_l1-bc25mer_83004-20_l2-bc25mer_83517-20
ACAACCGCGTGTTACAAGGC CAGGCATCCGAGAGGTCTGG
GAATGC GCCCATCGACTTCAGTTGCGT CACGTCGAC CATTGC
GCTTCTCCGGAAACATTAGC Exp-1_ddlB-55_l1-bc25mer_83004-20_l2-bc25mer_83517-20
ACAACCGCGTGTTACAAGGC CAGGCATCCGAGAGGTCTGG
GAATGC GGCTAACACCGCTGCGCCAGA ATTCAGAGA CATTGC
GCTTCTCCGGAAACATTAGC Exp-1_ddlB-224_l1-bc25mer_83004-20_l2-bc25mer_83517-20
ACAACCGCGTGTTACAAGGC CAGGCATCCGAGAGGTCTGG
GAATGC CGGTATAAGGCAAGCCCATCA GCTCGAGCA CATTGC
GCTTCTCCGGAAACATTAGC Exp-1_degP-1219_l1-bc25mer_83004-20_l2-bc25mer_83517-20
ACAACCGCGTGTTACAAGGC CAGGCATCCGAGAGGTCTGG
GAATGC CACGTTGTTCACTACCACGCC CTGATCTTT CATTGC
GCTTCTCCGGAAACATTAGC Exp-1_degP-703_l1-bc25mer_83004-20_l2-bc25mer_83517-20
ACAACCGCGTGTTACAAGGC CAGGCATCCGAGAGGTCTGG
GAATGC GTTCAGGTTAACCAGCGCACC ACCGGAGTT CATTGC
GCTTCTCCGGAAACATTAGC

FIG. 4P

Exp-1_degP-1114_I1-bc25mer_83004-20_I2-bc25mer_83517-20
ACAACCGCGTGTTACAAGGC CAGGCATCCGAGAGGTCTGG
GAATGC CTGCAGTTCCAGGTTCACGTT AACCTGCTT CATTGC
GCTTCTCCGGAAACATTAGC Exp-1_degP-948_I1-bc25mer_83004-20_I2-bc25mer_83517-20
ACAACCGCGTGTTACAAGGC CAGGCATCCGAGAGGTCTGG
GAATGC GCAGCGGAGGAATTAGGCAGA ACCTGGCTT CATTGC
GCTTCTCCGGAAACATTAGC Exp-1_degP-13_I1-bc25mer_83004-20_I2-bc25mer_83517-20
ACAACCGCGTGTTACAAGGC CAGGCATCCGAGAGGTCTGG
GAATGC ACTCAGAGCCAGTGCACTCAG TGCTAATGT CATTGC
GCTTCTCCGGAAACATTAGC Exp-1_degP-1184_I1-bc25mer_83004-20_I2-bc25mer_83517-20
ACAACCGCGTGTTACAAGGC CAGGCATCCGAGAGGTCTGG
GAATGC TGTTGCTCATCTCAGCGCCTT CAATGCCGT CATTGC
GCTTCTCCGGAAACATTAGC Exp-1_degP-1359_I1-bc25mer_83004-20_I2-bc25mer_83517-20
ACAACCGCGTGTTACAAGGC CAGGCATCCGAGAGGTCTGG
GAATGC TGAATGTTGAGTGCCAGCACA GACGGTTTG CATTGC
GCTTCTCCGGAAACATTAGC Exp-1_degP-319_I1-bc25mer_83004-20_I2-bc25mer_83517-20
ACAACCGCGTGTTACAAGGC CAGGCATCCGAGAGGTCTGG
GAATGC GCCGGAACCCAGCGCCATGAA TTTCTGTTG CATTGC
GCTTCTCCGGAAACATTAGC Exp-1_degP-1149_I1-bc25mer_83004-20_I2-bc25mer_83517-20
ACAACCGCGTGTTACAAGGC CAGGCATCCGAGAGGTCTGG
GAATGC ATGGAGCTGGAATCAACCTGA TTCTGGCTG CATTGC
GCTTCTCCGGAAACATTAGC Exp-1_degP-852_I1-bc25mer_83004-20_I2-bc25mer_83517-20
ACAACCGCGTGTTACAAGGC CAGGCATCCGAGAGGTCTGG
GAATGC ATAATACCCAGCTCACCGCGT TTCACCTGG CATTGC
GCTTCTCCGGAAACATTAGC Exp-1_degP-1015_I1-bc25mer_83004-20_I2-bc25mer_83517-20
ACAACCGCGTGTTACAAGGC CAGGCATCCGAGAGGTCTGG
GAATGC GGCAAAGCTGCTGATCGGCTT ACCGTTCAG CATTGC
GCTTCTCCGGAAACATTAGC Exp-1_degP-904_I1-bc25mer_83004-20_I2-bc25mer_83517-20
ACAACCGCGTGTTACAAGGC CAGGCATCCGAGAGGTCTGG
GAATGC CTGGGCGTCAACTTTCATCGC TTTCGCCAG CATTGC
GCTTCTCCGGAAACATTAGC

FIG. 4Q

Exp-1_degP-86_I1-bc25mer_83004-20_I2-bc25mer_83517-20
ACAACCGCGTGTTACAAGGC CAGGCATCCGAGAGGTCTGG
GAATGC GCATCTGCTGGGCTGTCGTTG CTGAAGAAG CATTGC
GCTTCTCCGGAAACATTAGC Exp-1_degP-603_I1-bc25mer_83004-20_I2-bc25mer_83517-20
ACAACCGCGTGTTACAAGGC CAGGCATCCGAGAGGTCTGG
GAATGC AGCGCAGAGACAATCCCGGAA GTTACCGTC CATTGC
GCTTCTCCGGAAACATTAGC Exp-1_degP-481_I1-bc25mer_83004-20_I2-bc25mer_83517-20
ACAACCGCGTGTTACAAGGC CAGGCATCCGAGAGGTCTGG
GAATGC CGGGTTCTGGATTTGGATCAG CGCGATATC CATTGC
GCTTCTCCGGAAACATTAGC Exp-1_degP-741_I1-bc25mer_83004-20_I2-bc25mer_83517-20
ACAACCGCGTGTTACAAGGC CAGGCATCCGAGAGGTCTGG
GAATGC GGTGCGAGGATCGCGGTGTTG ATACCGATC CATTGC
GCTTCTCCGGAAACATTAGC Exp-1_degP-1394_I1-bc25mer_83004-20_I2-bc25mer_83517-20
ACAACCGCGTGTTACAAGGC CAGGCATCCGAGAGGTCTGG
GAATGC ACTGCATTAACAGGTAGATGG TGCTGTCGC CATTGC
GCTTCTCCGGAAACATTAGC Exp-1_degP-371_I1-bc25mer_83004-20_I2-bc25mer_83517-20
ACAACCGCGTGTTACAAGGC CAGGCATCCGAGAGGTCTGG
GAATGC CAACAACGTGGTTGTTGGTGA CGACATAGC CATTGC
GCTTCTCCGGAAACATTAGC Exp-1_degP-411_I1-bc25mer_83004-20_I2-bc25mer_83517-20
ACAACCGCGTGTTACAAGGC CAGGCATCCGAGAGGTCTGG
GAATGC CGGCCATCGCTCAGTTGAACT TTAATGACC CATTGC
GCTTCTCCGGAAACATTAGC Exp-1_degP-141_I1-bc25mer_83004-20_I2-bc25mer_83517-20
ACAACCGCGTGTTACAAGGC CAGGCATCCGAGAGGTCTGG
GAATGC ACGTTAATGCTGACCACTGAA GGCATCACC CATTGC
GCTTCTCCGGAAACATTAGC Exp-1_degP-1294_I1-bc25mer_83004-20_I2-bc25mer_83517-20
ACAACCGCGTGTTACAAGGC CAGGCATCCGAGAGGTCTGG
GAATGC CACTGCCTGCTGGTTCGCGCC AATAATCAC CATTGC
GCTTCTCCGGAAACATTAGC Exp-1_degP-528_I1-bc25mer_83004-20_I2-bc25mer_83517-20
ACAACCGCGTGTTACAAGGC CAGGCATCCGAGAGGTCTGG
GAATGC ACGCAGTGCATCAGAATCC GCCATCTTA CATTGC
GCTTCTCCGGAAACATTAGC

FIG. 4R

Exp-1_degP-565_I1-bc25mer_83004-20_I2-bc25mer_83517-20
ACAACCGCGTGTTACAAGGC CAGGCATCCGAGAGGTCTGG
GAATGC ACCAAACGGGTTACCAATCGC TACGGTGTA CATTGC
GCTTCTCCGGAAACATTAGC Exp-1_degP-177_I1-bc25mer_83004-20_I2-bc25mer_83517-20
ACAACCGCGTGTTACAAGGC CAGGCATCCGAGAGGTCTGG
GAATGC GGCATACGCGGCGTATTAACG GTTGTGCTA CATTGC
GCTTCTCCGGAAACATTAGC Exp-1_degP-1076_I1-bc25mer_83004-20_I2-bc25mer_83517-20
ACAACCGCGTGTTACAAGGC CAGGCATCCGAGAGGTCTGG
GAATGC GCAGTAAGCCCAGGGTCAGTT TGCTGCCTA CATTGC
GCTTCTCCGGAAACATTAGC Exp-1_degP-446_I1-bc25mer_83004-20_I2-bc25mer_83517-20
ACAACCGCGTGTTACAAGGC CAGGCATCCGAGAGGTCTGG
GAATGC GCGGATCTTTGCCAACCATCT TCGCGTCGA CATTGC
GCTTCTCCGGAAACATTAGC Exp-1_degP-258_I1-bc25mer_83004-20_I2-bc25mer_83517-20
ACAACCGCGTGTTACAAGGC CAGGCATCCGAGAGGTCTGG
GAATGC TGGCAGAACGGAGAGCTCTGG AACGGAGAA CATTGC
GCTTCTCCGGAAACATTAGC Exp-1_degP-223_I1-bc25mer_83004-20_I2-bc25mer_83517-20
ACAACCGCGTGTTACAAGGC CAGGCATCCGAGAGGTCTGG
GAATGC CTGGCAGAACGGAGAATCATC ACCGAAGAA CATTGC
GCTTCTCCGGAAACATTAGC Exp-1_degP-48_I1-bc25mer_83004-20_I2-bc25mer_83517-20
ACAACCGCGTGTTACAAGGC CAGGCATCCGAGAGGTCTGG
GAATGC GCCGTTGCAGAGAGCGGAGAT AACGCCAAA CATTGC
GCTTCTCCGGAAACATTAGC Exp-1_erpA-158_I1-bc25mer_83004-20_I2-bc25mer_83517-20
ACAACCGCGTGTTACAAGGC CAGGCATCCGAGAGGTCTGG
GAATGC CGATGGTCATATCGCCTTCGT TCACCTGAT CATTGC
GCTTCTCCGGAAACATTAGC Exp-1_erpA-63_I1-bc25mer_83004-20_I2-bc25mer_83517-20
ACAACCGCGTGTTACAAGGC CAGGCATCCGAGAGGTCTGG
GAATGC AGATTCGGGTTATCTTCGTCA GCGATCAGG CATTGC
GCTTCTCCGGAAACATTAGC Exp-1_erpA-314_I1-bc25mer_83004-20_I2-bc25mer_83517-20
ACAACCGCGTGTTACAAGGC CAGGCATCCGAGAGGTCTGG
GAATGC AGATACTAAAGGAAGAACCGC AACCGCAGG CATTGC
GCTTCTCCGGAAACATTAGC

FIG. 4S

Exp-1_erpA-28_l1-bc25mer_83004-20_l2-bc25mer_83517-20
ACAACCGCGTGTTACAAGGC CAGGCATCCGAGAGGTCTGG
GAATGC AACTTTGTTGGCTGCTGCGTC GGTAAACTC CATTGC
GCTTCTCCGGAAACATTAGC Exp-1_erpA-238_l1-bc25mer_83004-20_l2-bc25mer_83517-20
ACAACCGCGTGTTACAAGGC CAGGCATCCGAGAGGTCTGG
GAATGC ACCTTCGGTATAATCAACGGA ACCGCCGAC CATTGC
GCTTCTCCGGAAACATTAGC Exp-1_erpA-277_l1-bc25mer_83004-20_l2-bc25mer_83517-20
ACAACCGCGTGTTACAAGGC CAGGCATCCGAGAGGTCTGG
GAATGC CGCGTTCGGGTTGGTCACGAT GAAACGAGA CATTGC
GCTTCTCCGGAAACATTAGC Exp-1_erpA-123_l1-bc25mer_83004-20_l2-bc25mer_83517-20
ACAACCGCGTGTTACAAGGC CAGGCATCCGAGAGGTCTGG
GAATGC AAGGTGAAACCATACTGGAAG CCGCTGCAA CATTGC
GCTTCTCCGGAAACATTAGC Exp-1_fhuA-409_l1-bc25mer_83004-20_l2-bc25mer_83517-20
ACAACCGCGTGTTACAAGGC CAGGCATCCGAGAGGTCTGG
GAATGC GCCCTGCAACTTCAGGCCATT CAGATAGTT CATTGC
GCTTCTCCGGAAACATTAGC Exp-1_fhuA-599_l1-bc25mer_83004-20_l2-bc25mer_83517-20
ACAACCGCGTGTTACAAGGC CAGGCATCCGAGAGGTCTGG
GAATGC CAGTCTGGAACAGGCTGTCAG TACCGGCTT CATTGC
GCTTCTCCGGAAACATTAGC Exp-1_fhuA-529_l1-bc25mer_83004-20_l2-bc25mer_83517-20
ACAACCGCGTGTTACAAGGC CAGGCATCCGAGAGGTCTGG
GAATGC GCTGACCATATTCAACAGGCC GCCAGGACT CATTGC
GCTTCTCCGGAAACATTAGC Exp-1_fhuA-1514_l1-bc25mer_83004-20_l2-bc25mer_83517-20
ACAACCGCGTGTTACAAGGC CAGGCATCCGAGAGGTCTGG
GAATGC CACCACCACGCCAGGTAAACT GTTTGTCAT CATTGC
GCTTCTCCGGAAACATTAGC Exp-1_fhuA-1253_l1-bc25mer_83004-20_l2-bc25mer_83517-20
ACAACCGCGTGTTACAAGGC CAGGCATCCGAGAGGTCTGG
GAATGC CGTCGTAACCAAACCAGGCGT TGATGTCAT CATTGC
GCTTCTCCGGAAACATTAGC Exp-1_fhuA-490_l1-bc25mer_83004-20_l2-bc25mer_83517-20
ACAACCGCGTGTTACAAGGC CAGGCATCCGAGAGGTCTGG
GAATGC GTAAAGCACGGAAACCGGGCC ACGCATAAT CATTGC
GCTTCTCCGGAAACATTAGC

FIG. 4T

Exp-1_fhuA-176_I1-bc25mer_83004-20_I2-bc25mer_83517-20
ACAACCGCGTGTTACAAGGC CAGGCATCCGAGAGGTCTGG
GAATGC CGGTAGCAGACTGTCGCGCCG CAATAGTTG CATTGC
GCTTCTCCGGAAACATTAGC Exp-1_fhuA-1471_I1-bc25mer_83004-20_I2-bc25mer_83517-20
ACAACCGCGTGTTACAAGGC CAGGCATCCGAGAGGTCTGG
GAATGC CGTCCCGGCAACGCGGTTAAG AGATTCTTG CATTGC
GCTTCTCCGGAAACATTAGC Exp-1_fhuA-1799_I1-bc25mer_83004-20_I2-bc25mer_83517-20
ACAACCGCGTGTTACAAGGC CAGGCATCCGAGAGGTCTGG
GAATGC CCGCTTTCGCTTCGATTTCTA CGCCACGTG CATTGC
GCTTCTCCGGAAACATTAGC Exp-1_fhuA-1183_I1-bc25mer_83004-20_I2-bc25mer_83517-20
ACAACCGCGTGTTACAAGGC CAGGCATCCGAGAGGTCTGG
GAATGC GTCGATATCGCCAGTGGCAAA CTTGCTCTG CATTGC
GCTTCTCCGGAAACATTAGC Exp-1_fhuA-1100_I1-bc25mer_83004-20_I2-bc25mer_83517-20
ACAACCGCGTGTTACAAGGC CAGGCATCCGAGAGGTCTGG
GAATGC TACGTGCCAGATAATGGCCTT TATCCGCTG CATTGC
GCTTCTCCGGAAACATTAGC Exp-1_fhuA-1029_I1-bc25mer_83004-20_I2-bc25mer_83517-20
ACAACCGCGTGTTACAAGGC CAGGCATCCGAGAGGTCTGG
GAATGC TCGGAGCAGACGCCGTAACCA TAAACGCTG CATTGC
GCTTCTCCGGAAACATTAGC Exp-1_fhuA-1871_I1-bc25mer_83004-20_I2-bc25mer_83517-20
ACAACCGCGTGTTACAAGGC CAGGCATCCGAGAGGTCTGG
GAATGC AGGTAGTATCGGTGGTGTATT CCGCATCGG CATTGC
GCTTCTCCGGAAACATTAGC Exp-1_fhuA-1218_I1-bc25mer_83004-20_I2-bc25mer_83517-20
ACAACCGCGTGTTACAAGGC CAGGCATCCGAGAGGTCTGG
GAATGC ATACGCATAAAGTCGACACCG GTCAGCAGG CATTGC
GCTTCTCCGGAAACATTAGC Exp-1_fhuA-264_I1-bc25mer_83004-20_I2-bc25mer_83517-20
ACAACCGCGTGTTACAAGGC CAGGCATCCGAGAGGTCTGG
GAATGC GACTTCGGCTGATGCAGCGCC ATCTCTTCG CATTGC
GCTTCTCCGGAAACATTAGC Exp-1_fhuA-1323_I1-bc25mer_83004-20_I2-bc25mer_83517-20
ACAACCGCGTGTTACAAGGC CAGGCATCCGAGAGGTCTGG
GAATGC GCCGGATCTTTGGCATTGAAG TCGAAATCG CATTGC
GCTTCTCCGGAAACATTAGC

FIG. 4U

Exp-1_fhuA-2129_I1-bc25mer_83004-20_I2-bc25mer_83517-20
ACAACCGCGTGTTACAAGGC CAGGCATCCGAGAGGTCTGG
GAATGC CACGATCGAACAGGTTGTTAA CATGCAGCG CATTGC
GCTTCTCCGGAAACATTAGC Exp-1_fhuA-873_I1-bc25mer_83004-20_I2-bc25mer_83517-20
ACAACCGCGTGTTACAAGGC CAGGCATCCGAGAGGTCTGG
GAATGC TCATTAAAGTCTGTCGGCAGA CGCTTACCG CATTGC
GCTTCTCCGGAAACATTAGC Exp-1_fhuA-455_I1-bc25mer_83004-20_I2-bc25mer_83517-20
ACAACCGCGTGTTACAAGGC CAGGCATCCGAGAGGTCTGG
GAATGC CGCGTTCCAGCATATACGGGT CAATGACCG CATTGC
GCTTCTCCGGAAACATTAGC Exp-1_fhuA-1693_I1-bc25mer_83004-20_I2-bc25mer_83517-20
ACAACCGCGTGTTACAAGGC CAGGCATCCGAGAGGTCTGG
GAATGC ATACACGGCACCAGTAACTAC AATCGGACG CATTGC
GCTTCTCCGGAAACATTAGC Exp-1_fhuA-1435_I1-bc25mer_83004-20_I2-bc25mer_83517-20
ACAACCGCGTGTTACAAGGC CAGGCATCCGAGAGGTCTGG
GAATGC CCAGTCATAACGACCGCCTAG GGTGACCAG CATTGC
GCTTCTCCGGAAACATTAGC Exp-1_fhuA-1600_I1-bc25mer_83004-20_I2-bc25mer_83517-20
ACAACCGCGTGTTACAAGGC CAGGCATCCGAGAGGTCTGG
GAATGC ACCATCCTTCCCAACTTGCGA AGAAGGTTC CATTGC
GCTTCTCCGGAAACATTAGC Exp-1_fhuA-118_I1-bc25mer_83004-20_I2-bc25mer_83517-20
ACAACCGCGTGTTACAAGGC CAGGCATCCGAGAGGTCTGG
GAATGC CGCAGGTGCAGCGGTAACGGT GATAGTGTC CATTGC
GCTTCTCCGGAAACATTAGC Exp-1_fhuA-939_I1-bc25mer_83004-20_I2-bc25mer_83517-20
ACAACCGCGTGTTACAAGGC CAGGCATCCGAGAGGTCTGG
GAATGC AATTCGTGATCGAAGCTGTAG CCGACCATC CATTGC
GCTTCTCCGGAAACATTAGC Exp-1_fhuA-2167_I1-bc25mer_83004-20_I2-bc25mer_83517-20
ACAACCGCGTGTTACAAGGC CAGGCATCCGAGAGGTCTGG
GAATGC GAAGCAGCCATAAGTGTTAAA GCAGCTGGC CATTGC
GCTTCTCCGGAAACATTAGC Exp-1_fhuA-2029_I1-bc25mer_83004-20_I2-bc25mer_83517-20
ACAACCGCGTGTTACAAGGC CAGGCATCCGAGAGGTCTGG
GAATGC TCCCACTTTAAAGGAGTTAGC CGGATCACC CATTGC
GCTTCTCCGGAAACATTAGC

FIG. 4V

Exp-1_fhuA-2215_l1-bc25mer_83004-20_l2-bc25mer_83517-20
ACAACCGCGTGTTACAAGGC CAGGCATCCGAGAGGTCTGG
GAATGC TTAGAAACGGAAGGTTGCGGT TGCAACGAC CATTGC
GCTTCTCCGGAAACATTAGC Exp-1_fhuA-1288_l1-bc25mer_83004-20_l2-bc25mer_83517-20
ACAACCGCGTGTTACAAGGC CAGGCATCCGAGAGGTCTGG
GAATGC CACCGGATTGTACAGATTGAG CAGTGGCAC CATTGC
GCTTCTCCGGAAACATTAGC Exp-1_fhuA-734_l1-bc25mer_83004-20_l2-bc25mer_83517-20
ACAACCGCGTGTTACAAGGC CAGGCATCCGAGAGGTCTGG
GAATGC GCCAGGTGAACGCCGGTGCAA TAGCATAAC CATTGC
GCTTCTCCGGAAACATTAGC Exp-1_fhuA-664_l1-bc25mer_83004-20_l2-bc25mer_83517-20
ACAACCGCGTGTTACAAGGC CAGGCATCCGAGAGGTCTGG
GAATGC CGCAAGACCGGTCAGGCGATA AGAGTAAAC CATTGC
GCTTCTCCGGAAACATTAGC Exp-1_fhuA-1399_l1-bc25mer_83004-20_l2-bc25mer_83517-20
ACAACCGCGTGTTACAAGGC CAGGCATCCGAGAGGTCTGG
GAATGC ATCCCACTGCGCCTGATCCTG AACATAAAC CATTGC
GCTTCTCCGGAAACATTAGC Exp-1_fhuA-2084_l1-bc25mer_83004-20_l2-bc25mer_83517-20
ACAACCGCGTGTTACAAGGC CAGGCATCCGAGAGGTCTGG
GAATGC CCATGCCGACTCGCGCCAGAT CATAACGTA CATTGC
GCTTCTCCGGAAACATTAGC Exp-1_fhuA-309_l1-bc25mer_83004-20_l2-bc25mer_83517-20
ACAACCGCGTGTTACAAGGC CAGGCATCCGAGAGGTCTGG
GAATGC GTACCAACAGAGACACCCGGC GTGTAGCTA CATTGC
GCTTCTCCGGAAACATTAGC Exp-1_fhuA-358_l1-bc25mer_83004-20_l2-bc25mer_83517-20
ACAACCGCGTGTTACAAGGC CAGGCATCCGAGAGGTCTGG
GAATGC CGCAAAGCCGCGAATGATCAG GTGGTCATA CATTGC
GCTTCTCCGGAAACATTAGC Exp-1_fhuA-564_l1-bc25mer_83004-20_l2-bc25mer_83517-20
ACAACCGCGTGTTACAAGGC CAGGCATCCGAGAGGTCTGG
GAATGC TGAACTTCTTTCAGCGGTTCG GTGGTCGGA CATTGC
GCTTCTCCGGAAACATTAGC Exp-1_fhuA-47_l1-bc25mer_83004-20_l2-bc25mer_83517-20
ACAACCGCGTGTTACAAGGC CAGGCATCCGAGAGGTCTGG
GAATGC CGCTAACCGCTGTGGCTACTA CAACTGCGA CATTGC
GCTTCTCCGGAAACATTAGC

FIG. 4W

Exp-1_fhuA-82_I1-bc25mer_83004-20_I2-bc25mer_83517-20
ACAACCGCGTGTTACAAGGC CAGGCATCCGAGAGGTCTGG
GAATGC CGGTTCAACCGCTGCCTGTGC ATAAACAGA CATTGC
GCTTCTCCGGAAACATTAGC Exp-1_fhuA-796_I1-bc25mer_83004-20_I2-bc25mer_83517-20
ACAACCGCGTGTTACAAGGC CAGGCATCCGAGAGGTCTGG
GAATGC ACCGGTTTCCGGCTCGTTCTG GAAGTAAGA CATTGC
GCTTCTCCGGAAACATTAGC Exp-1_fhuA-699_I1-bc25mer_83004-20_I2-bc25mer_83517-20
ACAACCGCGTGTTACAAGGC CAGGCATCCGAGAGGTCTGG
GAATGC TCTTCTGACCCTTTCTGCTGG GCATTGGCA CATTGC
GCTTCTCCGGAAACATTAGC Exp-1_fhuA-980_I1-bc25mer_83004-20_I2-bc25mer_83517-20
ACAACCGCGTGTTACAAGGC CAGGCATCCGAGAGGTCTGG
GAATGC CAGCAAAGCGCAGGTTCTGAC GCACAGTAA CATTGC
GCTTCTCCGGAAACATTAGC Exp-1_fhuA-1764_I1-bc25mer_83004-20_I2-bc25mer_83517-20
ACAACCGCGTGTTACAAGGC CAGGCATCCGAGAGGTCTGG
GAATGC ATCTCGCCACCTTCAACCGAG AAGAAGGAA CATTGC
GCTTCTCCGGAAACATTAGC Exp-1_fhuA-1966_I1-bc25mer_83004-20_I2-bc25mer_83517-20
ACAACCGCGTGTTACAAGGC CAGGCATCCGAGAGGTCTGG
GAATGC CAGCGTCAGACCTGAAAGCGG ACCGTCAAA CATTGC
GCTTCTCCGGAAACATTAGC Exp-1_fhuC-257_I1-bc25mer_83004-20_I2-bc25mer_83517-20
ACAACCGCGTGTTACAAGGC CAGGCATCCGAGAGGTCTGG
GAATGC GAGGAAGCTGCTGCGGCAAAT AAGCCACTT CATTGC
GCTTCTCCGGAAACATTAGC Exp-1_fhuC-536_I1-bc25mer_83004-20_I2-bc25mer_83517-20
ACAACCGCGTGTTACAAGGC CAGGCATCCGAGAGGTCTGG
GAATGC GCGACAGCACATCAACCTGGT GGGCGATAT CATTGC
GCTTCTCCGGAAACATTAGC Exp-1_fhuC-133_I1-bc25mer_83004-20_I2-bc25mer_83517-20
ACAACCGCGTGTTACAAGGC CAGGCATCCGAGAGGTCTGG
GAATGC GAGCAGAGTGGATTTACCAGA ACCGTTGTG CATTGC
GCTTCTCCGGAAACATTAGC Exp-1_fhuC-720_I1-bc25mer_83004-20_I2-bc25mer_83517-20
ACAACCGCGTGTTACAAGGC CAGGCATCCGAGAGGTCTGG
GAATGC CCCATCGGGATGCCATAAATC ATTTCGAGG CATTGC
GCTTCTCCGGAAACATTAGC

FIG. 4X

Exp-1_fhuC-221_I1-bc25mer_83004-20_I2-bc25mer_83517-20
ACAACCGCGTGTTACAAGGC CAGGCATCCGAGAGGTCTGG
GAATGC CAAACGCTTTGCTGCTCCAGC TTTCCAGCG CATTGC
GCTTCTCCGGAAACATTAGC Exp-1_fhuC-639_I1-bc25mer_83004-20_I2-bc25mer_83517-20
ACAACCGCGTGTTACAAGGC CAGGCATCCGAGAGGTCTGG
GAATGC CCGCGCAGGGCGACCAGATAA TCACAGTAG CATTGC
GCTTCTCCGGAAACATTAGC Exp-1_fhuC-310_I1-bc25mer_83004-20_I2-bc25mer_83517-20
ACAACCGCGTGTTACAAGGC CAGGCATCCGAGAGGTCTGG
GAATGC CCACGGGTAACGACCAATCGC CACCAGTTC CATTGC
GCTTCTCCGGAAACATTAGC Exp-1_fhuC-500_I1-bc25mer_83004-20_I2-bc25mer_83517-20
ACAACCGCGTGTTACAAGGC CAGGCATCCGAGAGGTCTGG
GAATGC CCGAGGTCGGTTCGTCGAGCA ACAGACAAC CATTGC
GCTTCTCCGGAAACATTAGC Exp-1_fhuC-95_I1-bc25mer_83004-20_I2-bc25mer_83517-20
ACAACCGCGTGTTACAAGGC CAGGCATCCGAGAGGTCTGG
GAATGC GACCGGTCACTTTCCCGGCAG GAAAGGTTA CATTGC
GCTTCTCCGGAAACATTAGC Exp-1_fhuC-578_I1-bc25mer_83004-20_I2-bc25mer_83517-20
ACAACCGCGTGTTACAAGGC CAGGCATCCGAGAGGTCTGG
GAATGC CAATGACCGTCAGGCCACGCT CCTGACTTA CATTGC
GCTTCTCCGGAAACATTAGC Exp-1_fhuC-45_I1-bc25mer_83004-20_I2-bc25mer_83517-20
ACAACCGCGTGTTACAAGGC CAGGCATCCGAGAGGTCTGG
GAATGC GTGCGCCCGGGCACACGAAAG GAGATATTA CATTGC
GCTTCTCCGGAAACATTAGC Exp-1_fhuC-431_I1-bc25mer_83004-20_I2-bc25mer_83517-20
ACAACCGCGTGTTACAAGGC CAGGCATCCGAGAGGTCTGG
GAATGC GACGTTCGCCGCCAGAGAGAC TATCGACCA CATTGC
GCTTCTCCGGAAACATTAGC Exp-1_fhuC-680_I1-bc25mer_83004-20_I2-bc25mer_83517-20
ACAACCGCGTGTTACAAGGC CAGGCATCCGAGAGGTCTGG
GAATGC GCATAATTTCCGCAGGCGTTC CCTGAGCAA CATTGC
GCTTCTCCGGAAACATTAGC Exp-1_folK-321_I1-bc25mer_83004-20_I2-bc25mer_83517-20
ACAACCGCGTGTTACAAGGC CAGGCATCCGAGAGGTCTGG
GAATGC TAGTGCGGAACGGTCAGGCGT TCAGTATTT CATTGC
GCTTCTCCGGAAACATTAGC

FIG. 4Y

Exp-1_folK-16_l1-bc25mer_83004-20_l2-bc25mer_83517-20
ACAACCGCGTGTTACAAGGC CAGGCATCCGAGAGGTCTGG
GAATGC CGGAGAGGCCAGATTGCTGCC TATGGCAAT CATTGC
GCTTCTCCGGAAACATTAGC Exp-1_folK-281_l1-bc25mer_83004-20_l2-bc25mer_83517-20
ACAACCGCGTGTTACAAGGC CAGGCATCCGAGAGGTCTGG
GAATGC TACCAAACAGCATGATGTCGA GATCCAGCG CATTGC
GCTTCTCCGGAAACATTAGC Exp-1_folK-391_l1-bc25mer_83004-20_l2-bc25mer_83517-20
ACAACCGCGTGTTACAAGGC CAGGCATCCGAGAGGTCTGG
GAATGC ATCAGGAAACACCAACTCCGG CGCGATTTC CATTGC
GCTTCTCCGGAAACATTAGC Exp-1_folK-148_l1-bc25mer_83004-20_l2-bc25mer_83517-20
ACAACCGCGTGTTACAAGGC CAGGCATCCGAGAGGTCTGG
GAATGC CACGGCTGCGTTTAAGTAATC GGGTTGATC CATTGC
GCTTCTCCGGAAACATTAGC Exp-1_folK-80_l1-bc25mer_83004-20_l2-bc25mer_83517-20
ACAACCGCGTGTTACAAGGC CAGGCATCCGAGAGGTCTGG
GAATGC CGGTAAGAATGTGGCTTTCAG GGATATCGC CATTGC
GCTTCTCCGGAAACATTAGC Exp-1_folK-183_l1-bc25mer_83004-20_l2-bc25mer_83517-20
ACAACCGCGTGTTACAAGGC CAGGCATCCGAGAGGTCTGG
GAATGC AGTAGCTCTTCAGGTGCAAGA GAGGTTTCC CATTGC
GCTTCTCCGGAAACATTAGC Exp-1_folK-356_l1-bc25mer_83004-20_l2-bc25mer_83517-20
ACAACCGCGTGTTACAAGGC CAGGCATCCGAGAGGTCTGG
GAATGC GCGGCCACAGCATAAATCCAC GATTCTTCA CATTGC
GCTTCTCCGGAAACATTAGC Exp-1_folK-230_l1-bc25mer_83004-20_l2-bc25mer_83517-20
ACAACCGCGTGTTACAAGGC CAGGCATCCGAGAGGTCTGG
GAATGC CTTTGCGGACGCGACCTTGCT GCAATTCAA CATTGC
GCTTCTCCGGAAACATTAGC Exp-1_ftsA-866_l1-bc25mer_83004-20_l2-bc25mer_83517-20
ACAACCGCGTGTTACAAGGC CAGGCATCCGAGAGGTCTGG
GAATGC GCTCGATCACCTCTGCCAGTG TCTGACGTT CATTGC
GCTTCTCCGGAAACATTAGC Exp-1_ftsA-608_l1-bc25mer_83004-20_l2-bc25mer_83517-20
ACAACCGCGTGTTACAAGGC CAGGCATCCGAGAGGTCTGG
GAATGC CACCGATATCGACGACGCAGA CACCCAGTT CATTGC
GCTTCTCCGGAAACATTAGC

FIG. 4Z

Exp-1_ftsA-721_I1-bc25mer_83004-20_I2-bc25mer_83517-20
ACAACCGCGTGTTACAAGGC CAGGCATCCGAGAGGTCTGG
GAATGC CGGCGTGCCAAAGGCGTAAGC GATATCACT CATTGC
GCTTCTCCGGAAACATTAGC Exp-1_ftsA-43_I1-bc25mer_83004-20_I2-bc25mer_83517-20
ACAACCGCGTGTTACAAGGC CAGGCATCCGAGAGGTCTGG
GAATGC TACTAAAGCGGCAACCTTCGC GGTACCAAT CATTGC
GCTTCTCCGGAAACATTAGC Exp-1_ftsA-429_I1-bc25mer_83004-20_I2-bc25mer_83517-20
ACAACCGCGTGTTACAAGGC CAGGCATCCGAGAGGTCTGG
GAATGC CGCACGCCCGAAAGTCCTACC GGATTCTTG CATTGC
GCTTCTCCGGAAACATTAGC Exp-1_ftsA-475_I1-bc25mer_83004-20_I2-bc25mer_83517-20
ACAACCGCGTGTTACAAGGC CAGGCATCCGAGAGGTCTGG
GAATGC CGCCATATCGTTGTGACATGT GATCAGGTG CATTGC
GCTTCTCCGGAAACATTAGC Exp-1_ftsA-264_I1-bc25mer_83004-20_I2-bc25mer_83517-20
ACAACCGCGTGTTACAAGGC CAGGCATCCGAGAGGTCTGG
GAATGC GGCACCATACCAATTTCATTC TGGCAGCTG CATTGC
GCTTCTCCGGAAACATTAGC Exp-1_ftsA-117_I1-bc25mer_83004-20_I2-bc25mer_83517-20
ACAACCGCGTGTTACAAGGC CAGGCATCCGAGAGGTCTGG
GAATGC CCTTTATCCATACCACGCGAC GGGCAGCTG CATTGC
GCTTCTCCGGAAACATTAGC Exp-1_ftsA-393_I1-bc25mer_83004-20_I2-bc25mer_83517-20
ACAACCGCGTGTTACAAGGC CAGGCATCCGAGAGGTCTGG
GAATGC TCCTGATAGTCAATCGCATAC TCTTGCGGG CATTGC
GCTTCTCCGGAAACATTAGC Exp-1_ftsA-679_I1-bc25mer_83004-20_I2-bc25mer_83517-20
ACAACCGCGTGTTACAAGGC CAGGCATCCGAGAGGTCTGG
GAATGC GCCAGCATAAGGAATTACCTT AGTGTGGCG CATTGC
GCTTCTCCGGAAACATTAGC Exp-1_ftsA-1136_I1-bc25mer_83004-20_I2-bc25mer_83517-20
ACAACCGCGTGTTACAAGGC CAGGCATCCGAGAGGTCTGG
GAATGC ACTCTTTCCCATAGTGAAGCA ATCCCACCG CATTGC
GCTTCTCCGGAAACATTAGC Exp-1_ftsA-1095_I1-bc25mer_83004-20_I2-bc25mer_83517-20
ACAACCGCGTGTTACAAGGC CAGGCATCCGAGAGGTCTGG
GAATGC TACGGCTCCTGAGCATAATCC GTTAAACCG CATTGC
GCTTCTCCGGAAACATTAGC

FIG. 4AA

Exp-1_ftsA-82_l1-bc25mer_83004-20_l2-bc25mer_83517-20
ACAACCGCGTGTTACAAGGC CAGGCATCCGAGAGGTCTGG
GAATGC GCCAATGATATTGACCATACC GTCGGGCAG CATTGC
GCTTCTCCGGAAACATTAGC Exp-1_ftsA-526_l1-bc25mer_83004-20_l2-bc25mer_83517-20
ACAACCGCGTGTTACAAGGC CAGGCATCCGAGAGGTCTGG
GAATGC CAGTTGGTCAACTTTCAGCCC ACAACGTTC CATTGC
GCTTCTCCGGAAACATTAGC Exp-1_ftsA-196_l1-bc25mer_83004-20_l2-bc25mer_83517-20
ACAACCGCGTGTTACAAGGC CAGGCATCCGAGAGGTCTGG
GAATGC CTGACAATCTGCCATCAATTC TGCCTGGTC CATTGC
GCTTCTCCGGAAACATTAGC Exp-1_ftsA-907_l1-bc25mer_83004-20_l2-bc25mer_83517-20
ACAACCGCGTGTTACAAGGC CAGGCATCCGAGAGGTCTGG
GAATGC TATCTCTTCGTTGACCAGGTT GAGCAGCTC CATTGC
GCTTCTCCGGAAACATTAGC Exp-1_ftsA-768_l1-bc25mer_83004-20_l2-bc25mer_83517-20
ACAACCGCGTGTTACAAGGC CAGGCATCCGAGAGGTCTGG
GAATGC CCCAGCGCACAACCGTGGCGA ACTTTAATC CATTGC
GCTTCTCCGGAAACATTAGC Exp-1_ftsA-562_l1-bc25mer_83004-20_l2-bc25mer_83517-20
ACAACCGCGTGTTACAAGGC CAGGCATCCGAGAGGTCTGG
GAATGC CAATACCGAATAACTTGATGC CAGTCCGGC CATTGC
GCTTCTCCGGAAACATTAGC Exp-1_ftsA-1040_l1-bc25mer_83004-20_l2-bc25mer_83517-20
ACAACCGCGTGTTACAAGGC CAGGCATCCGAGAGGTCTGG
GAATGC GCACTTGCGTATGAAACACGC GCTGAGCAC CATTGC
GCTTCTCCGGAAACATTAGC Exp-1_ftsA-1221_l1-bc25mer_83004-20_l2-bc25mer_83517-20
ACAACCGCGTGTTACAAGGC CAGGCATCCGAGAGGTCTGG
GAATGC CGCAGCCAACTATTGAGTCGC TTGATCCAC CATTGC
GCTTCTCCGGAAACATTAGC Exp-1_ftsA-998_l1-bc25mer_83004-20_l2-bc25mer_83517-20
ACAACCGCGTGTTACAAGGC CAGGCATCCGAGAGGTCTGG
GAATGC CTTCGATCTGCGCTGCGCCAC CGGTTAATA CATTGC
GCTTCTCCGGAAACATTAGC Exp-1_ftsA-161_l1-bc25mer_83004-20_l2-bc25mer_83517-20
ACAACCGCGTGTTACAAGGC CAGGCATCCGAGAGGTCTGG
GAATGC CGCGTTGTACGCACTTGACCA CGGATTCGA CATTGC
GCTTCTCCGGAAACATTAGC

FIG. 4BB

Exp-1_ftsQ-423_I1-bc25mer_83004-20_I2-bc25mer_83517-20
ACAACCGCGTGTTACAAGGC CAGGCATCCGAGAGGTCTGG
GAATGC CGTTCTGGCGGCACGCTGAAG GTATTTCCT CATTGC
GCTTCTCCGGAAACATTAGC Exp-1_ftsQ-464_I1-bc25mer_83004-20_I2-bc25mer_83517-20
ACAACCGCGTGTTACAAGGC CAGGCATCCGAGAGGTCTGG
GAATGC CTTCCGGGCCATACAGCATTG GAAGCACCT CATTGC
GCTTCTCCGGAAACATTAGC Exp-1_ftsQ-500_I1-bc25mer_83004-20_I2-bc25mer_83517-20
ACAACCGCGTGTTACAAGGC CAGGCATCCGAGAGGTCTGG
GAATGC TTTCGCGATAGCCCTGCAACA CTTCATTGG CATTGC
GCTTCTCCGGAAACATTAGC Exp-1_ftsQ-773_I1-bc25mer_83004-20_I2-bc25mer_83517-20
ACAACCGCGTGTTACAAGGC CAGGCATCCGAGAGGTCTGG
GAATGC GTTGCTGAGTAGATTCCTCTG GCGGCAAGG CATTGC
GCTTCTCCGGAAACATTAGC
Exp-1_ftsQ-216_I1-bc25mer_83004-20_I2-bc25mer_83517-20

ACAACCGCGTGTTACAAGGC CAGGCATCCGAGAGGTCTGG
GAATGC CCCAATGCCAGGATCGACTGC CGGATATCG CATTGC
GCTTCTCCGGAAACATTAGC

Exp-1_ftsQ-290_I1-bc25mer_83004-20_I2-bc25mer_83517-20
ACAACCGCGTGTTACAAGGC CAGGCATCCGAGAGGTCTGG
GAATGC TAATCCACGGCAGGCGTTGTT CTATTTGCG CATTGC
GCTTCTCCGGAAACATTAGC Exp-1_ftsQ-251_I1-bc25mer_83004-20_I2-bc25mer_83517-20
ACAACCGCGTGTTACAAGGC CAGGCATCCGAGAGGTCTGG
GAATGC TGTTGACATCCTGGGTCATAA AGGTACCCG CATTGC
GCTTCTCCGGAAACATTAGC Exp-1_ftsQ-589_I1-bc25mer_83004-20_I2-bc25mer_83517-20
ACAACCGCGTGTTACAAGGC CAGGCATCCGAGAGGTCTGG
GAATGC ATCGTTATTCAGCGTCAACTG CCAGGAACG CATTGC
GCTTCTCCGGAAACATTAGC Exp-1_ftsQ-47_I1-bc25mer_83004-20_I2-bc25mer_83517-20
ACAACCGCGTGTTACAAGGC CAGGCATCCGAGAGGTCTGG
GAATGC CCAGACGCGTTCCATTATTGC GGCGAGAAG CATTGC
GCTTCTCCGGAAACATTAGC Exp-1_ftsQ-554_I1-bc25mer_83004-20_I2-bc25mer_83517-20
ACAACCGCGTGTTACAAGGC CAGGCATCCGAGAGGTCTGG
GAATGC CGGTCATCGCCGCTTCCTTCA GAGTAAATC CATTGC
GCTTCTCCGGAAACATTAGC

FIG. 4CC

Exp-1_ftsQ-702_I1-bc25mer_83004-20_I2-bc25mer_83517-20
ACAACCGCGTGTTACAAGGC CAGGCATCCGAGAGGTCTGG
GAATGC ACGTAGCTAATCCGTTTGCCA TCGGTTTGC CATTGC
GCTTCTCCGGAAACATTAGC Exp-1_ftsQ-388_I1-bc25mer_83004-20_I2-bc25mer_83517-20
ACAACCGCGTGTTACAAGGC CAGGCATCCGAGAGGTCTGG
GAATGC GTCTACCATATGTTGATCATT CCACCGCGC CATTGC
GCTTCTCCGGAAACATTAGC Exp-1_ftsQ-329_I1-bc25mer_83004-20_I2-bc25mer_83517-20
ACAACCGCGTGTTACAAGGC CAGGCATCCGAGAGGTCTGG
GAATGC TCAATTCATCAGGCCACTGCT TTCTGACGC CATTGC
GCTTCTCCGGAAACATTAGC Exp-1_ftsQ-738_I1-bc25mer_83004-20_I2-bc25mer_83517-20
ACAACCGCGTGTTACAAGGC CAGGCATCCGAGAGGTCTGG
GAATGC CAGCCTACTGCCGCTCCAGAG TCATAACGC CATTGC
GCTTCTCCGGAAACATTAGC Exp-1_ftsQ-181_I1-bc25mer_83004-20_I2-bc25mer_83517-20
ACAACCGCGTGTTACAAGGC CAGGCATCCGAGAGGTCTGG
GAATGC ACGTGTGTAATGGCGTTCACC GGTCAACAC CATTGC
GCTTCTCCGGAAACATTAGC Exp-1_ftsQ-12_I1-bc25mer_83004-20_I2-bc25mer_83517-20
ACAACCGCGTGTTACAAGGC CAGGCATCCGAGAGGTCTGG
GAATGC TCTTCTTCGCTGTTTCGCGTG TTCAGAGCA CATTGC
GCTTCTCCGGAAACATTAGC Exp-1_ftsZ-829_I1-bc25mer_83004-20_I2-bc25mer_83517-20
ACAACCGCGTGTTACAAGGC CAGGCATCCGAGAGGTCTGG
GAATGC AGCAAATGCACGGATGGTGTT ACCTACCGT CATTGC
GCTTCTCCGGAAACATTAGC Exp-1_ftsZ-552_I1-bc25mer_83004-20_I2-bc25mer_83517-20
ACAACCGCGTGTTACAAGGC CAGGCATCCGAGAGGTCTGG
GAATGC TGCACAGCGCCTTTCAGTACA TCGTTCGCT CATTGC
GCTTCTCCGGAAACATTAGC Exp-1_ftsZ-864_I1-bc25mer_83004-20_I2-bc25mer_83517-20
ACAACCGCGTGTTACAAGGC CAGGCATCCGAGAGGTCTGG
GAATGC AGAGAAGTACCGATAACCACA GTCGCGTTG CATTGC
GCTTCTCCGGAAACATTAGC Exp-1_ftsZ-969_I1-bc25mer_83004-20_I2-bc25mer_83517-20
ACAACCGCGTGTTACAAGGC CAGGCATCCGAGAGGTCTGG
GAATGC TGCTGAACCTGCTTATTGGTC ACCAGAGTG CATTGC
GCTTCTCCGGAAACATTAGC

FIG. 4DD

Exp-1_ftsZ-899_l1-bc25mer_83004-20_l2-bc25mer_83517-20
ACAACCGCGTGTTACAAGGC CAGGCATCCGAGAGGTCTGG
GAATGC CGGTTACGCGCAGCTCGTCAT TCATATCCG CATTGC GCT-
TCTCCGGAAACATTAGC Exp-1_ftsZ-505_l1-bc25mer_83004-20_l2-bc25mer_83517-20
ACAACCGCGTGTTACAAGGC CAGGCATCCGAGAGGTCTGG
GAATGC CAGGGAGATACCGCGGCCCAG AACTTTCAG CATTGC
GCTTCTCCGGAAACATTAGC Exp-1_ftsZ-742_l1-bc25mer_83004-20_l2-bc25mer_83517-20
ACAACCGCGTGTTACAAGGC CAGGCATCCGAGAGGTCTGG
GAATGC CGCGCCAGACAGGTCGATATC TTCCAGCAG CATTGC
GCTTCTCCGGAAACATTAGC Exp-1_ftsZ-781_l1-bc25mer_83004-20_l2-bc25mer_83517-20
ACAACCGCGTGTTACAAGGC CAGGCATCCGAGAGGTCTGG
GAATGC CAGGTCGAAGCCCGCCGTGAT GTTAACCAG CATTGC
GCTTCTCCGGAAACATTAGC Exp-1_ftsZ-934_l1-bc25mer_83004-20_l2-bc25mer_83517-20
ACAACCGCGTGTTACAAGGC CAGGCATCCGAGAGGTCTGG
GAATGC AGGACGTTTGTCCATGCCGAT ACCTGTCGC CATTGC
GCTTCTCCGGAAACATTAGC Exp-1_ftsZ-706_l1-bc25mer_83004-20_l2-bc25mer_83517-20
ACAACCGCGTGTTACAAGGC CAGGCATCCGAGAGGTCTGG
GAATGC AGAGATAGCCATTTCAGCAGC TTCTTCCGC CATTGC
GCTTCTCCGGAAACATTAGC Exp-1_ftsZ-291_l1-bc25mer_83004-20_l2-bc25mer_83517-20
ACAACCGCGTGTTACAAGGC CAGGCATCCGAGAGGTCTGG
GAATGC CCACCACCCATACCCGCAGCA ATAAAGACC CATTGC
GCTTCTCCGGAAACATTAGC Exp-1_ftsZ-326_l1-bc25mer_83004-20_l2-bc25mer_83517-20
ACAACCGCGTGTTACAAGGC CAGGCATCCGAGAGGTCTGG
GAATGC CTTCAGCGACGACTGGTGCTG CACCTGTAC CATTGC
GCTTCTCCGGAAACATTAGC Exp-1_ftsZ-182_l1-bc25mer_83004-20_l2-bc25mer_83517-20
ACAACCGCGTGTTACAAGGC CAGGCATCCGAGAGGTCTGG
GAATGC CAGCGCCCAGTCCTTTGGTGA TACCGCTAC CATTGC
GCTTCTCCGGAAACATTAGC Exp-1_ftsZ-1069_l1-bc25mer_83004-20_l2-bc25mer_83517-20
ACAACCGCGTGTTACAAGGC CAGGCATCCGAGAGGTCTGG
GAATGC CGCAGTTTGCGGCGCATTGTC ATTCACGAC CATTGC
GCTTCTCCGGAAACATTAGC

FIG. 4EE

Exp-1_ftsZ-622_I1-bc25mer_83004-20_I2-bc25mer_83517-20
ACAACCGCGTGTTACAAGGC CAGGCATCCGAGAGGTCTGG
GAATGC CATTACGGTGCGTACGTCTGC AAAGTCCAC CATTGC
GCTTCTCCGGAAACATTAGC Exp-1_ftsZ-587_I1-bc25mer_83004-20_I2-bc25mer_83517-20
ACAACCGCGTGTTACAAGGC CAGGCATCCGAGAGGTCTGG
GAATGC TCAAACCCGGACGAGTAATCA GTTCAGCGA CATTGC
GCTTCTCCGGAAACATTAGC Exp-1_ftsZ-377_I1-bc25mer_83004-20_I2-bc25mer_83517-20
ACAACCGCGTGTTACAAGGC CAGGCATCCGAGAGGTCTGG
GAATGC TGAAAGGCTTAGTGACGACAG CAACGGTCA CATTGC
GCTTCTCCGGAAACATTAGC Exp-1_ftsZ-27_I1-bc25mer_83004-20_I2-bc25mer_83517-20
ACAACCGCGTGTTACAAGGC CAGGCATCCGAGAGGTCTGG
GAATGC CCGACGCCGATGACTTTAATC ACCGCGTCA CATTGC
GCTTCTCCGGAAACATTAGC Exp-1_ftsZ-1004_I1-bc25mer_83004-20_I2-bc25mer_83517-20
ACAACCGCGTGTTACAAGGC CAGGCATCCGAGAGGTCTGG
GAATGC CCATCCCATGCTGCTGGTAGC GATCCATCA CATTGC
GCTTCTCCGGAAACATTAGC Exp-1_ftsZ-470_I1-bc25mer_83004-20_I2-bc25mer_83517-20
ACAACCGCGTGTTACAAGGC CAGGCATCCGAGAGGTCTGG
GAATGC TGTCGTTCGGGATAGTGATCA GAGAGTCCA CATTGC
GCTTCTCCGGAAACATTAGC Exp-1_ftsZ-118_I1-bc25mer_83004-20_I2-bc25mer_83517-20
ACAACCGCGTGTTACAAGGC CAGGCATCCGAGAGGTCTGG
GAATGC CAGCGCTTGTGCATCGGTATT TACCGCGAA CATTGC
GCTTCTCCGGAAACATTAGC Exp-1_ftsZ-77_I1-bc25mer_83004-20_I2-bc25mer_83517-20
ACAACCGCGTGTTACAAGGC CAGGCATCCGAGAGGTCTGG
GAATGC CTTCAATGCGCTCGCGCACCA TGTGTTCAA CATTGC
GCTTCTCCGGAAACATTAGC Exp-1_gcd-965_I1-bc25mer_83004-20_I2-bc25mer_83517-20
ACAACCGCGTGTTACAAGGC CAGGCATCCGAGAGGTCTGG
GAATGC GACCCGGTTTGGTGTCTGGCA TATTGCTTT CATTGC
GCTTCTCCGGAAACATTAGC Exp-1_gcd-820_I1-bc25mer_83004-20_I2-bc25mer_83517-20
ACAACCGCGTGTTACAAGGC CAGGCATCCGAGAGGTCTGG
GAATGC CATCACTTCCGGCGAAGCGGT TTCTGCTTT CATTGC
GCTTCTCCGGAAACATTAGC

FIG. 4FF

Exp-1_gcd-1189_I1-bc25mer_83004-20_I2-bc25mer_83517-20
ACAACCGCGTGTTACAAGGC CAGGCATCCGAGAGGTCTGG
GAATGC TGGTGCCCAGGAGTTTGGCGA GTTAAAGGT CATTGC
GCTTCTCCGGAAACATTAGC Exp-1_gcd-785_I1-bc25mer_83004-20_I2-bc25mer_83517-20
ACAACCGCGTGTTACAAGGC CAGGCATCCGAGAGGTCTGG
GAATGC CATGATAAGAGACACCACGGC AGGTTACGT CATTGC
GCTTCTCCGGAAACATTAGC Exp-1_gcd-1154_I1-bc25mer_83004-20_I2-bc25mer_83517-20
ACAACCGCGTGTTACAAGGC CAGGCATCCGAGAGGTCTGG
GAATGC TGTGTTCGTCAGACGGGATTG CGTTCGGAT CATTGC
GCTTCTCCGGAAACATTAGC Exp-1_gcd-1502_I1-bc25mer_83004-20_I2-bc25mer_83517-20
ACAACCGCGTGTTACAAGGC CAGGCATCCGAGAGGTCTGG
GAATGC CCGGAACCACCAGTTCGCCAT TACGACGAT CATTGC
GCTTCTCCGGAAACATTAGC Exp-1_gcd-368_I1-bc25mer_83004-20_I2-bc25mer_83517-20
ACAACCGCGTGTTACAAGGC CAGGCATCCGAGAGGTCTGG
GAATGC CACCGCTAATCAGCAGTGCGA CCACCAGTG CATTGC
GCTTCTCCGGAAACATTAGC Exp-1_gcd-1447_I1-bc25mer_83004-20_I2-bc25mer_83517-20
ACAACCGCGTGTTACAAGGC CAGGCATCCGAGAGGTCTGG
GAATGC CGCCGGAGCGTAAATAACTGG CACTTTCTG CATTGC
GCTTCTCCGGAAACATTAGC Exp-1_gcd-644_I1-bc25mer_83004-20_I2-bc25mer_83517-20
ACAACCGCGTGTTACAAGGC CAGGCATCCGAGAGGTCTGG
GAATGC CGCCCACTTTAATCGGCGTCA CTTCATTGG CATTGC
GCTTCTCCGGAAACATTAGC Exp-1_gcd-1975_I1-bc25mer_83004-20_I2-bc25mer_83517-20
ACAACCGCGTGTTACAAGGC CAGGCATCCGAGAGGTCTGG
GAATGC TGCTGGCTGTTTACATGGCAG ACCAAATGG CATTGC
GCTTCTCCGGAAACATTAGC Exp-1_gcd-877_I1-bc25mer_83004-20_I2-bc25mer_83517-20
ACAACCGCGTGTTACAAGGC CAGGCATCCGAGAGGTCTGG
GAATGC AATCGCAATCAGTCGACCATC ATTGACCGG CATTGC
GCTTCTCCGGAAACATTAGC Exp-1_gcd-930_I1-bc25mer_83004-20_I2-bc25mer_83517-20
ACAACCGCGTGTTACAAGGC CAGGCATCCGAGAGGTCTGG
GAATGC TTGAGCACGCCTTTATTGGCG AAGGTTTCG CATTGC
GCTTCTCCGGAAACATTAGC

FIG. 4GG

Exp-1_gcd-1616_l1-bc25mer_83004-20_l2-bc25mer_83517-20
ACAACCGCGTGTTACAAGGC CAGGCATCCGAGAGGTCTGG
GAATGC ACATATCCGCACCGCTCAAAT CTTTCGTCG CATTGC
GCTTCTCCGGAAACATTAGC Exp-1_gcd-542_l1-bc25mer_83004-20_l2-bc25mer_83517-20
ACAACCGCGTGTTACAAGGC CAGGCATCCGAGAGGTCTGG
GAATGC CGTTATCGGCGTTAATTTGTT TCAGCGGCG CATTGC
GCTTCTCCGGAAACATTAGC Exp-1_gcd-23_l1-bc25mer_83004-20_l2-bc25mer_83517-20
ACAACCGCGTGTTACAAGGC CAGGCATCCGAGAGGTCTGG
GAATGC GGGCTGTTAGCGTGACGAGTA ATCGTCGCG CATTGC
GCTTCTCCGGAAACATTAGC Exp-1_gcd-2325_l1-bc25mer_83004-20_l2-bc25mer_83517-20
ACAACCGCGTGTTACAAGGC CAGGCATCCGAGAGGTCTGG
GAATGC TAGTCGCCCATCTTCGTACCA AATGAACCG CATTGC
GCTTCTCCGGAAACATTAGC Exp-1_gcd-126_l1-bc25mer_83004-20_l2-bc25mer_83517-20
ACAACCGCGTGTTACAAGGC CAGGCATCCGAGAGGTCTGG
GAATGC CCGAGCATCACAAGGCCAGCG ATAGGGTAG CATTGC
GCTTCTCCGGAAACATTAGC Exp-1_gcd-403_l1-bc25mer_83004-20_l2-bc25mer_83517-20
ACAACCGCGTGTTACAAGGC CAGGCATCCGAGAGGTCTGG
GAATGC CTGCGGATCGTTAAATCCGGC CCAGGTCAG CATTGC
GCTTCTCCGGAAACATTAGC Exp-1_gcd-679_l1-bc25mer_83004-20_l2-bc25mer_83517-20
ACAACCGCGTGTTACAAGGC CAGGCATCCGAGAGGTCTGG
GAATGC CAGGCGCTGGTGAGCGGTACA CAGGTAAAG CATTGC
GCTTCTCCGGAAACATTAGC Exp-1_gcd-1729_l1-bc25mer_83004-20_l2-bc25mer_83517-20
ACAACCGCGTGTTACAAGGC CAGGCATCCGAGAGGTCTGG
GAATGC GTTACCCGGGAAGACCAGCGT ACCCTGTTC CATTGC
GCTTCTCCGGAAACATTAGC Exp-1_gcd-1000_l1-bc25mer_83004-20_l2-bc25mer_83517-20
ACAACCGCGTGTTACAAGGC CAGGCATCCGAGAGGTCTGG
GAATGC ATCGGTGATAATCGGTGGCGA AGTCGGTTC CATTGC
GCTTCTCCGGAAACATTAGC Exp-1_gcd-1387_l1-bc25mer_83004-20_l2-bc25mer_83517-20
ACAACCGCGTGTTACAAGGC CAGGCATCCGAGAGGTCTGG
GAATGC CTGTGCCGGAAGATCCATGTC CCACAGGTC CATTGC
GCTTCTCCGGAAACATTAGC

FIG. 4HH

Exp-1_gcd-1240_I1-bc25mer_83004-20_I2-bc25mer_83517-20
ACAACCGCGTGTTACAAGGC CAGGCATCCGAGAGGTCTGG
GAATGC GGTCACGCCCATCGGCAGATA GACCAGATC CATTGC
GCTTCTCCGGAAACATTAGC Exp-1_gcd-728_I1-bc25mer_83004-20_I2-bc25mer_83517-20
ACAACCGCGTGTTACAAGGC CAGGCATCCGAGAGGTCTGG
GAATGC CAGGATCGTAATGCCATTTCT CTTTGCCGC CATTGC
GCTTCTCCGGAAACATTAGC Exp-1_gcd-2362_I1-bc25mer_83004-20_I2-bc25mer_83517-20
ACAACCGCGTGTTACAAGGC CAGGCATCCGAGAGGTCTGG
GAATGC TTACTTCACATCATCCGGCAG CGCATAAGC CATTGC
GCTTCTCCGGAAACATTAGC Exp-1_gcd-1352_I1-bc25mer_83004-20_I2-bc25mer_83517-20
ACAACCGCGTGTTACAAGGC CAGGCATCCGAGAGGTCTGG
GAATGC GAACGGTCTGGTAGCTCCACG CCAGTTTCC CATTGC
GCTTCTCCGGAAACATTAGC Exp-1_gcd-2290_I1-bc25mer_83004-20_I2-bc25mer_83517-20
ACAACCGCGTGTTACAAGGC CAGGCATCCGAGAGGTCTGG
GAATGC GCCTGCGGAGATCACCACATA CTGCTTACC CATTGC
GCTTCTCCGGAAACATTAGC Exp-1_gcd-2159_I1-bc25mer_83004-20_I2-bc25mer_83517-20
ACAACCGCGTGTTACAAGGC CAGGCATCCGAGAGGTCTGG
GAATGC CTGCCGTAGCGGCGATAAACA GCACGTTAC CATTGC
GCTTCTCCGGAAACATTAGC Exp-1_gcd-2255_I1-bc25mer_83004-20_I2-bc25mer_83517-20
ACAACCGCGTGTTACAAGGC CAGGCATCCGAGAGGTCTGG
GAATGC CTTCATAGGTCATTGGCGTAG CCTGACCAC CATTGC
GCTTCTCCGGAAACATTAGC Exp-1_gcd-1789_I1-bc25mer_83004-20_I2-bc25mer_83517-20
ACAACCGCGTGTTACAAGGC CAGGCATCCGAGAGGTCTGG
GAATGC GGCAATCGCCACTTCACGATT TGGATCAAC CATTGC
GCTTCTCCGGAAACATTAGC Exp-1_gcd-247_I1-bc25mer_83004-20_I2-bc25mer_83517-20
ACAACCGCGTGTTACAAGGC CAGGCATCCGAGAGGTCTGG
GAATGC CGGAGTCAGCGCCCAGAAGTC GAAACCAAC CATTGC
GCTTCTCCGGAAACATTAGC Exp-1_gcd-1940_I1-bc25mer_83004-20_I2-bc25mer_83517-20
ACAACCGCGTGTTACAAGGC CAGGCATCCGAGAGGTCTGG
GAATGC GGAACGGGTTGAGCGTGACAC CATACGGTA CATTGC
GCTTCTCCGGAAACATTAGC

FIG. 4II

Exp-1_gcd-2194_l1-bc25mer_83004-20_l2-bc25mer_83517-20
ACAACCGCGTGTTACAAGGC CAGGCATCCGAGAGGTCTGG
GAATGC ACCGTTGCTCATGTTGTAAGC GCGCAGGTA CATTGC
GCTTCTCCGGAAACATTAGC Exp-1_gcd-603_l1-bc25mer_83004-20_l2-bc25mer_83517-20
ACAACCGCGTGTTACAAGGC CAGGCATCCGAGAGGTCTGG
GAATGC GGATCGTTCGGCTGCTTCACA TCGCCAGTA CATTGC
GCTTCTCCGGAAACATTAGC Exp-1_gcd-76_l1-bc25mer_83004-20_l2-bc25mer_83517-20
ACAACCGCGTGTTACAAGGC CAGGCATCCGAGAGGTCTGG
GAATGC GACCAGCCAGCCTCCGCCAAT GAGTAGATA CATTGC
GCTTCTCCGGAAACATTAGC Exp-1_gcd-1682_l1-bc25mer_83004-20_l2-bc25mer_83517-20
ACAACCGCGTGTTACAAGGC CAGGCATCCGAGAGGTCTGG
GAATGC TGCCTTCATAGCGCATCTGGT GGAACATCA CATTGC
GCTTCTCCGGAAACATTAGC Exp-1_gcd-507_l1-bc25mer_83004-20_l2-bc25mer_83517-20
ACAACCGCGTGTTACAAGGC CAGGCATCCGAGAGGTCTGG
GAATGC CGTTGACCTTCCTGATTACGA CCATAGGCA CATTGC
GCTTCTCCGGAAACATTAGC Exp-1_gcd-2048_l1-bc25mer_83004-20_l2-bc25mer_83517-20
ACAACCGCGTGTTACAAGGC CAGGCATCCGAGAGGTCTGG
GAATGC CCTGCGGCGTACCAATACGTT TCTTCCACA CATTGC
GCTTCTCCGGAAACATTAGC Exp-1_gcd-1839_l1-bc25mer_83004-20_l2-bc25mer_83517-20
ACAACCGCGTGTTACAAGGC CAGGCATCCGAGAGGTCTGG
GAATGC CCAGGACCACGCGGGATCAGT TTCGAAACA CATTGC
GCTTCTCCGGAAACATTAGC Exp-1_gcd-2113_l1-bc25mer_83004-20_l2-bc25mer_83517-20
ACAACCGCGTGTTACAAGGC CAGGCATCCGAGAGGTCTGG
GAATGC CCCGCCCAGCATCGGCATACC CATATTGAA CATTGC
GCTTCTCCGGAAACATTAGC Exp-1_gcd-298_l1-bc25mer_83004-20_l2-bc25mer_83517-20
ACAACCGCGTGTTACAAGGC CAGGCATCCGAGAGGTCTGG
GAATGC GACAAACGGCAGGATCAGCCA GATGCCGAA CATTGC
GCTTCTCCGGAAACATTAGC Exp-1_gcd-1066_l1-bc25mer_83004-20_l2-bc25mer_83517-20
ACAACCGCGTGTTACAAGGC CAGGCATCCGAGAGGTCTGG
GAATGC GATCACGCCAGACGTTTCGCG GGTTGAGAA CATTGC
GCTTCTCCGGAAACATTAGC

FIG. 4JJ

Exp-1_guaC-112_I1-bc25mer_83004-20_I2-bc25mer_83517-20
ACAACCGCGTGTTACAAGGC CAGGCATCCGAGAGGTCTGG
GAATGC CACGCCGGACCAGCTCTGACC TGAATGTTT CATTGC
GCTTCTCCGGAAACATTAGC Exp-1_guaC-407_I1-bc25mer_83004-20_I2-bc25mer_83517-20
ACAACCGCGTGTTACAAGGC CAGGCATCCGAGAGGTCTGG
GAATGC GCGCTTTCGCAACGAACTGCA CGAAGTGTT CATTGC
GCTTCTCCGGAAACATTAGC Exp-1_guaC-148_I1-bc25mer_83004-20_I2-bc25mer_83517-20
ACAACCGCGTGTTACAAGGC CAGGCATCCGAGAGGTCTGG
GAATGC TGTGCCTACGGTGTCCATATT TGCGGCGAT CATTGC
GCTTCTCCGGAAACATTAGC Exp-1_guaC-458_I1-bc25mer_83004-20_I2-bc25mer_83517-20
ACAACCGCGTGTTACAAGGC CAGGCATCCGAGAGGTCTGG
GAATGC CACCAGTCACTACGTTACCAG CACAAATGG CATTGC
GCTTCTCCGGAAACATTAGC Exp-1_guaC-351_I1-bc25mer_83004-20_I2-bc25mer_83517-20
ACAACCGCGTGTTACAAGGC CAGGCATCCGAGAGGTCTGG
GAATGC CAAACGAAGTTTAATGCCGGG TTCAGGTCG CATTGC
GCTTCTCCGGAAACATTAGC Exp-1_guaC-760_I1-bc25mer_83004-20_I2-bc25mer_83517-20
ACAACCGCGTGTTACAAGGC CAGGCATCCGAGAGGTCTGG
GAATGC AAATTTCTCGCCGTTCTCCTC AACGATGCG CATTGC
GCTTCTCCGGAAACATTAGC Exp-1_guaC-39_I1-bc25mer_83004-20_I2-bc25mer_83517-20
ACAACCGCGTGTTACAAGGC CAGGCATCCGAGAGGTCTGG
GAATGC AGAGTGGAGCGTTTAGGGCGG ATGAGAACG CATTGC
GCTTCTCCGGAAACATTAGC Exp-1_guaC-641_I1-bc25mer_83004-20_I2-bc25mer_83517-20
ACAACCGCGTGTTACAAGGC CAGGCATCCGAGAGGTCTGG
GAATGC TGGTGCAGCCACCATCGCTGA CGATCATTC CATTGC
GCTTCTCCGGAAACATTAGC Exp-1_guaC-499_I1-bc25mer_83004-20_I2-bc25mer_83517-20
ACAACCGCGTGTTACAAGGC CAGGCATCCGAGAGGTCTGG
GAATGC AACGATATCGGCACCTGAGAG GATAAGCTC CATTGC
GCTTCTCCGGAAACATTAGC Exp-1_guaC-989_I1-bc25mer_83004-20_I2-bc25mer_83517-20
ACAACCGCGTGTTACAAGGC CAGGCATCCGAGAGGTCTGG
GAATGC CTTGTTCCTGCACACGAATAA ACGTGGTGC CATTGC
GCTTCTCCGGAAACATTAGC

FIG. 4KK

Exp-1_guaC-74_I1-bc25mer_83004-20_I2-bc25mer_83517-20
ACAACCGCGTGTTACAAGGC CAGGCATCCGAGAGGTCTGG
GAATGC ATTGACGTTCCAGTTCAACAT CGGAACGGC CATTGC
GCTTCTCCGGAAACATTAGC Exp-1_guaC-541_I1-bc25mer_83004-20_I2-bc25mer_83517-20
ACAACCGCGTGTTACAAGGC CAGGCATCCGAGAGGTCTGG
GAATGC GACGCGAGTTGTACAAACAGA ACCTGGGCC CATTGC
GCTTCTCCGGAAACATTAGC Exp-1_guaC-811_I1-bc25mer_83004-20_I2-bc25mer_83517-20
ACAACCGCGTGTTACAAGGC CAGGCATCCGAGAGGTCTGG
GAATGC GCCAACGTGACGTTTCATCGC AGACTCGGA CATTGC
GCTTCTCCGGAAACATTAGC Exp-1_guaC-598_I1-bc25mer_83004-20_I2-bc25mer_83517-20
ACAACCGCGTGTTACAAGGC CAGGCATCCGAGAGGTCTGG
GAATGC CGCAGCATCGGCACATTCGAT TACCGCAGA CATTGC
GCTTCTCCGGAAACATTAGC Exp-1_guaC-302_I1-bc25mer_83004-20_I2-bc25mer_83517-20
ACAACCGCGTGTTACAAGGC CAGGCATCCGAGAGGTCTGG
GAATGC CGAAATCCGCATCAGACGTAC CGGTAGAAA CATTGC
GCTTCTCCGGAAACATTAGC Exp-1_hemL-416_I1-bc25mer_83004-20_I2-bc25mer_83517-20
ACAACCGCGTGTTACAAGGC CAGGCATCCGAGAGGTCTGG
GAATGC GGCAGTCAGCGTGACCATGGT AACACCCTT CATTGC
GCTTCTCCGGAAACATTAGC Exp-1_hemL-298_I1-bc25mer_83004-20_I2-bc25mer_83517-20
ACAACCGCGTGTTACAAGGC CAGGCATCCGAGAGGTCTGG
GAATGC CACCATATCCATGGTCGGGAC CAGTTCGGT CATTGC
GCTTCTCCGGAAACATTAGC Exp-1_hemL-996_I1-bc25mer_83004-20_I2-bc25mer_83517-20
ACAACCGCGTGTTACAAGGC CAGGCATCCGAGAGGTCTGG
GAATGC GCTTCTTCTGCCGCTTCCAGC AGACCTTCT CATTGC
GCTTCTCCGGAAACATTAGC Exp-1_hemL-250_I1-bc25mer_83004-20_I2-bc25mer_83517-20
ACAACCGCGTGTTACAAGGC CAGGCATCCGAGAGGTCTGG
GAATGC CACTTCCATTTCGGTTGGTGC ACCAAAGCT CATTGC
GCTTCTCCGGAAACATTAGC Exp-1_hemL-628_I1-bc25mer_83004-20_I2-bc25mer_83517-20
ACAACCGCGTGTTACAAGGC CAGGCATCCGAGAGGTCTGG
GAATGC GAACTCTGGCAGCGGCGGAAC ACAGTTCAT CATTGC
GCTTCTCCGGAAACATTAGC

FIG. 4LL

Exp-1_hemL-961_l1-bc25mer_83004-20_l2-bc25mer_83517-20
ACAACCGCGTGTTACAAGGC CAGGCATCCGAGAGGTCTGG
GAATGC ACGTGTTGTCAGCTCATCCAG CGTTTCGTG CATTGC
GCTTCTCCGGAAACATTAGC Exp-1_hemL-1211_l1-bc25mer_83004-20_l2-bc25mer_83517-20
ACAACCGCGTGTTACAAGGC CAGGCATCCGAGAGGTCTGG
GAATGC TATTGATATCTTCCATGCTGT GCGCCACGG CATTGC
GCTTCTCCGGAAACATTAGC Exp-1_hemL-708_l1-bc25mer_83004-20_l2-bc25mer_83517-20
ACAACCGCGTGTTACAAGGC CAGGCATCCGAGAGGTCTGG
GAATGC GCTACGCGGAAACCGGTCATC ACTTCATCG CATTGC
GCTTCTCCGGAAACATTAGC Exp-1_hemL-120_l1-bc25mer_83004-20_l2-bc25mer_83517-20
ACAACCGCGTGTTACAAGGC CAGGCATCCGAGAGGTCTGG
GAATGC TTGCCATCAACATCGTACAGA TAAGCGCCG CATTGC
GCTTCTCCGGAAACATTAGC Exp-1_hemL-762_l1-bc25mer_83004-20_l2-bc25mer_83517-20
ACAACCGCGTGTTACAAGGC CAGGCATCCGAGAGGTCTGG
GAATGC CCGAGGCAGGTTAAATCTGGC ACTACGCCG CATTGC
GCTTCTCCGGAAACATTAGC Exp-1_hemL-547_l1-bc25mer_83004-20_l2-bc25mer_83517-20
ACAACCGCGTGTTACAAGGC CAGGCATCCGAGAGGTCTGG
GAATGC CTCAAATGCGGCGCGTACAGA AGCCAGATC CATTGC
GCTTCTCCGGAAACATTAGC Exp-1_hemL-1249_l1-bc25mer_83004-20_l2-bc25mer_83517-20
ACAACCGCGTGTTACAAGGC CAGGCATCCGAGAGGTCTGG
GAATGC CAACTTCGCAAACACCCGACG TGCAGCATC CATTGC
GCTTCTCCGGAAACATTAGC Exp-1_hemL-1113_l1-bc25mer_83004-20_l2-bc25mer_83517-20
ACAACCGCGTGTTACAAGGC CAGGCATCCGAGAGGTCTGG
GAATGC CGCTTAAAGCGTTCCACGTCA CAGGCCATC CATTGC
GCTTCTCCGGAAACATTAGC Exp-1_hemL-500_l1-bc25mer_83004-20_l2-bc25mer_83517-20
ACAACCGCGTGTTACAAGGC CAGGCATCCGAGAGGTCTGG
GAATGC AGGTATATTTGGCGAAATCTG CCGGAACGC CATTGC
GCTTCTCCGGAAACATTAGC Exp-1_hemL-333_l1-bc25mer_83004-20_l2-bc25mer_83517-20
ACAACCGCGTGTTACAAGGC CAGGCATCCGAGAGGTCTGG
GAATGC CTCATGGTCGCTTCAGTGCCG GAGTTCACC CATTGC
GCTTCTCCGGAAACATTAGC

FIG. 4MM

Exp-1_hemL-830_I1-bc25mer_83004-20_I2-bc25mer_83517-20
ACAACCGCGTGTTACAAGGC CAGGCATCCGAGAGGTCTGG
GAATGC CCAGCGCATCCATTACATCAC GACGACCAC CATTGC
GCTTCTCCGGAAACATTAGC Exp-1_hemL-1171_I1-bc25mer_83004-20_I2-bc25mer_83517-20
ACAACCGCGTGTTACAAGGC CAGGCATCCGAGAGGTCTGG
GAATGC CGCTTCAAACGCTGACGGTGC CAGGTAAAC CATTGC
GCTTCTCCGGAAACATTAGC Exp-1_hemL-923_I1-bc25mer_83004-20_I2-bc25mer_83517-20
ACAACCGCGTGTTACAAGGC CAGGCATCCGAGAGGTCTGG
GAATGC GCTGCGCGACTTCATTCAGAC AGGCGAAAC CATTGC
GCTTCTCCGGAAACATTAGC Exp-1_hemL-888_I1-bc25mer_83004-20_I2-bc25mer_83517-20
ACAACCGCGTGTTACAAGGC CAGGCATCCGAGAGGTCTGG
GAATGC GCCATCGCAATCGGGTTACCG GAAAGCGTA CATTGC
GCTTCTCCGGAAACATTAGC Exp-1_hemL-1040_I1-bc25mer_83004-20_I2-bc25mer_83517-20
ACAACCGCGTGTTACAAGGC CAGGCATCCGAGAGGTCTGG
GAATGC TACCGAACATGCCGCCAACGT GGTTAACGA CATTGC
GCTTCTCCGGAAACATTAGC Exp-1_hemL-452_I1-bc25mer_83004-20_I2-bc25mer_83517-20
ACAACCGCGTGTTACAAGGC CAGGCATCCGAGAGGTCTGG
GAATGC CTAACGTGAGTGCGCCAGAAC CGGCTTTCA CATTGC
GCTTCTCCGGAAACATTAGC Exp-1_hemL-593_I1-bc25mer_83004-20_I2-bc25mer_83517-20
ACAACCGCGTGTTACAAGGC CAGGCATCCGAGAGGTCTGG
GAATGC CTGCCACCGGCTCGACGATAA TACAGGCAA CATTGC
GCTTCTCCGGAAACATTAGC Exp-1_hpt-483_I1-bc25mer_83004-20_I2-bc25mer_83517-20
ACAACCGCGTGTTACAAGGC CAGGCATCCGAGAGGTCTGG
GAATGC CCGATATACGGCAGATGACGG TAACGCTGT CATTGC
GCTTCTCCGGAAACATTAGC Exp-1_hpt-80_I1-bc25mer_83004-20_I2-bc25mer_83517-20
ACAACCGCGTGTTACAAGGC CAGGCATCCGAGAGGTCTGG
GAATGC CCATATCGCTGCCGCTGTCTT TGTAACGCT CATTGC
GCTTCTCCGGAAACATTAGC Exp-1_hpt-330_I1-bc25mer_83004-20_I2-bc25mer_83517-20
ACAACCGCGTGTTACAAGGC CAGGCATCCGAGAGGTCTGG
GAATGC GGTTCGCGCAGGCTTAAGATC TCACGCACT CATTGC
GCTTCTCCGGAAACATTAGC

FIG. 4NN

Exp-1_hpt-153_I1-bc25mer_83004-20_I2-bc25mer_83517-20
ACAACCGCGTGTTACAAGGC CAGGCATCCGAGAGGTCTGG
GAATGC TCATGAGATACCTGAACTTCA CGGCACAGG CATTGC
GCTTCTCCGGAAACATTAGC Exp-1_hpt-365_I1-bc25mer_83004-20_I2-bc25mer_83517-20
ACAACCGCGTGTTACAAGGC CAGGCATCCGAGAGGTCTGG
GAATGC GTTTATCCAGCAGCGTACAAA TCGCCAGCG CATTGC
GCTTCTCCGGAAACATTAGC Exp-1_hpt-400_I1-bc25mer_83004-20_I2-bc25mer_83517-20
ACAACCGCGTGTTACAAGGC CAGGCATCCGAGAGGTCTGG
GAATGC AAATTCTACCGGGACGTTCAC TTCACGACG CATTGC
GCTTCTCCGGAAACATTAGC Exp-1_hpt-271_I1-bc25mer_83004-20_I2-bc25mer_83517-20
ACAACCGCGTGTTACAAGGC CAGGCATCCGAGAGGTCTGG
GAATGC ATCTTCAACAATCAGCACGTC CTTGCCACG CATTGC
GCTTCTCCGGAAACATTAGC Exp-1_hpt-189_I1-bc25mer_83004-20_I2-bc25mer_83517-20
ACAACCGCGTGTTACAAGGC CAGGCATCCGAGAGGTCTGG
GAATGC CCGCTACCGTAGCTGGAGGCG GTCATAAAG CATTGC
GCTTCTCCGGAAACATTAGC Exp-1_hpt-447_I1-bc25mer_83004-20_I2-bc25mer_83517-20
ACAACCGCGTGTTACAAGGC CAGGCATCCGAGAGGTCTGG
GAATGC TCAATGCCGTAACCCACCACA AACTCATCC CATTGC
GCTTCTCCGGAAACATTAGC Exp-1_hpt-115_I1-bc25mer_83004-20_I2-bc25mer_83517-20
ACAACCGCGTGTTACAAGGC CAGGCATCCGAGAGGTCTGG
GAATGC AAACATAAATGAGCCACGCAG CAGACCCAC CATTGC
GCTTCTCCGGAAACATTAGC Exp-1_hpt-41_I1-bc25mer_83004-20_I2-bc25mer_83517-20
ACAACCGCGTGTTACAAGGC CAGGCATCCGAGAGGTCTGG
GAATGC GACGACCCAGTTCGGCGATAC GCGCTTTAA CATTGC
GCTTCTCCGGAAACATTAGC Exp-1_ispU-376_I1-bc25mer_83004-20_I2-bc25mer_83517-20
ACAACCGCGTGTTACAAGGC CAGGCATCCGAGAGGTCTGG
GAATGC GGTATTCCCGGCTGTTAGCGC TTCAGATTT CATTGC
GCTTCTCCGGAAACATTAGC Exp-1_ispU-339_I1-bc25mer_83004-20_I2-bc25mer_83517-20
ACAACCGCGTGTTACAAGGC CAGGCATCCGAGAGGTCTGG
GAATGC CGTTCTTGCAAACGCGAGTTA AAGCGACTG CATTGC
GCTTCTCCGGAAACATTAGC

FIG. 4OO

Exp-1_ispU-304_I1-bc25mer_83004-20_I2-bc25mer_83517-20
ACAACCGCGTGTTACAAGGC CAGGCATCCGAGAGGTCTGG
GAATGC GCCAATAATACGCAGACGCAC GTTATGTCG CATTGC
GCTTCTCCGGAAACATTAGC Exp-1_ispU-180_I1-bc25mer_83004-20_I2-bc25mer_83517-20
ACAACCGCGTGTTACAAGGC CAGGCATCCGAGAGGTCTGG
GAATGC AAGGCATACAGCGTTAACGCC TCAATACCG CATTGC
GCTTCTCCGGAAACATTAGC Exp-1_ispU-411_I1-bc25mer_83004-20_I2-bc25mer_83517-20
ACAACCGCGTGTTACAAGGC CAGGCATCCGAGAGGTCTGG
GAATGC CCACCGTAGTTCGCCGCAATA TTCAGCGTC CATTGC
GCTTCTCCGGAAACATTAGC Exp-1_ispU-486_I1-bc25mer_83004-20_I2-bc25mer_83517-20
ACAACCGCGTGTTACAAGGC CAGGCATCCGAGAGGTCTGG
GAATGC ATCTGATCTGGTTGCAGGTTT CCTTGCTGC CATTGC
GCTTCTCCGGAAACATTAGC Exp-1_ispU-106_I1-bc25mer_83004-20_I2-bc25mer_83517-20
ACAACCGCGTGTTACAAGGC CAGGCATCCGAGAGGTCTGG
GAATGC GGCTTTATGCCCAAAGGCACG AATCTTCCC CATTGC
GCTTCTCCGGAAACATTAGC Exp-1_ispU-446_I1-bc25mer_83004-20_I2-bc25mer_83517-20
ACAACCGCGTGTTACAAGGC CAGGCATCCGAGAGGTCTGG
GAATGC CCAGTTGCCTGACTCCCTGGA CTATATCCC CATTGC
GCTTCTCCGGAAACATTAGC Exp-1_ispU-655_I1-bc25mer_83004-20_I2-bc25mer_83517-20
ACAACCGCGTGTTACAAGGC CAGGCATCCGAGAGGTCTGG
GAATGC GTCTTGTTCATCGAAATCGGG CCAGAGAAC CATTGC
GCTTCTCCGGAAACATTAGC Exp-1_ispU-257_I1-bc25mer_83004-20_I2-bc25mer_83517-20
ACAACCGCGTGTTACAAGGC CAGGCATCCGAGAGGTCTGG
GAATGC CGCTATCGAGCGCCCACACAA ACAGTTCCA CATTGC
GCTTCTCCGGAAACATTAGC Exp-1_ispU-706_I1-bc25mer_83004-20_I2-bc25mer_83517-20
ACAACCGCGTGTTACAAGGC CAGGCATCCGAGAGGTCTGG
GAATGC GCCGCCGAAACGACGCTCTCG ATTAGCAAA CATTGC
GCTTCTCCGGAAACATTAGC Exp-1_map-389_I1-bc25mer_83004-20_I2-bc25mer_83517-20
ACAACCGCGTGTTACAAGGC CAGGCATCCGAGAGGTCTGG
GAATGC CCATGCGTAGCGCCAGGTACA GGCTTTCTT CATTGC
GCTTCTCCGGAAACATTAGC

FIG. 4PP

Exp-1_map-151_l1-bc25mer_83004-20_l2-bc25mer_83517-20
ACAACCGCGTGTTACAAGGC CAGGCATCCGAGAGGTCTGG
GAATGC GAGGCAGGCAGAAACCGCGTG TTGTTCATT CATTGC
GCTTCTCCGGAAACATTAGC Exp-1_map-301_l1-bc25mer_83004-20_l2-bc25mer_83517-20
ACAACCGCGTGTTACAAGGC CAGGCATCCGAGAGGTCTGG
GAATGC CGAGGTATCGCCGTGGAAACC ATCTTTGAT CATTGC
GCTTCTCCGGAAACATTAGC Exp-1_map-766_l1-bc25mer_83004-20_l2-bc25mer_83517-20
ACAACCGCGTGTTACAAGGC CAGGCATCCGAGAGGTCTGG
GAATGC TTATTCGTCGTGCGAGATTAT CGCCGGGAT CATTGC
GCTTCTCCGGAAACATTAGC Exp-1_map-79_l1-bc25mer_83004-20_l2-bc25mer_83517-20
ACAACCGCGTGTTACAAGGC CAGGCATCCGAGAGGTCTGG
GAATGC GACGCCCGGTTTAACATACGG TTCGATCAT CATTGC
GCTTCTCCGGAAACATTAGC Exp-1_map-187_l1-bc25mer_83004-20_l2-bc25mer_83517-20
ACAACCGCGTGTTACAAGGC CAGGCATCCGAGAGGTCTGG
GAATGC AGAGATGCAAACGGATTTCGG ATAGCCGTG CATTGC
GCTTCTCCGGAAACATTAGC Exp-1_map-114_l1-bc25mer_83004-20_l2-bc25mer_83517-20
ACAACCGCGTGTTACAAGGC CAGGCATCCGAGAGGTCTGG
GAATGC TAATCATTACAGATGCGATCC AGCTCGCCG CATTGC
GCTTCTCCGGAAACATTAGC Exp-1_map-247_l1-bc25mer_83004-20_l2-bc25mer_83517-20
ACAACCGCGTGTTACAAGGC CAGGCATCCGAGAGGTCTGG
GAATGC ATCGCCATCTTTCAGCAGCTT AGCATCGTC CATTGC
GCTTCTCCGGAAACATTAGC Exp-1_map-597_l1-bc25mer_83004-20_l2-bc25mer_83517-20
ACAACCGCGTGTTACAAGGC CAGGCATCCGAGAGGTCTGG
GAATGC GCGTTGACCATTGGCTCGATG GTGAACGTC CATTGC
GCTTCTCCGGAAACATTAGC Exp-1_map-639_l1-bc25mer_83004-20_l2-bc25mer_83517-20
ACAACCGCGTGTTACAAGGC CAGGCATCCGAGAGGTCTGG
GAATGC ACCGTCCAGCCATCTTTCATG GTGCGGATC CATTGC
GCTTCTCCGGAAACATTAGC Exp-1_map-731_l1-bc25mer_83004-20_l2-bc25mer_83517-20
ACAACCGCGTGTTACAAGGC CAGGCATCCGAGAGGTCTGG
GAATGC CATCCTTGCGTAGCGTCAGAA TTTCGCAGC CATTGC
GCTTCTCCGGAAACATTAGC

FIG. 4QQ

Exp-1_map-481_l1-bc25mer_83004-20_l2-bc25mer_83517-20
ACAACCGCGTGTTACAAGGC CAGGCATCCGAGAGGTCTGG
GAATGC TCCGCAATATTCACGAACGAC GGAGAAGCC CATTGC
GCTTCTCCGGAAACATTAGC Exp-1_map-516_l1-bc25mer_83004-20_l2-bc25mer_83517-20
ACAACCGCGTGTTACAAGGC CAGGCATCCGAGAGGTCTGG
GAATGC TGCGGTTCTTCATGGAAGCCG CGACCAATA CATTGC
GCTTCTCCGGAAACATTAGC Exp-1_map-562_l1-bc25mer_83004-20_l2-bc25mer_83517-20
ACAACCGCGTGTTACAAGGC CAGGCATCCGAGAGGTCTGG
GAATGC AGGTTTCAGTACGACGTTGGT TTCACGGGA CATTGC
GCTTCTCCGGAAACATTAGC Exp-1_map-446_l1-bc25mer_83004-20_l2-bc25mer_83517-20
ACAACCGCGTGTTACAAGGC CAGGCATCCGAGAGGTCTGG
GAATGC CTTCGACAAATTTCTGAATCG CCGCACCGA CATTGC
GCTTCTCCGGAAACATTAGC Exp-1_map-338_l1-bc25mer_83004-20_l2-bc25mer_83517-20
ACAACCGCGTGTTACAAGGC CAGGCATCCGAGAGGTCTGG
GAATGC CGCCCATGATGGTCGGCTTAC CGACGATAA CATTGC
GCTTCTCCGGAAACATTAGC Exp-1_mrcB-1945_l1-bc25mer_83004-20_l2-bc25mer_83517-20
ACAACCGCGTGTTACAAGGC CAGGCATCCGAGAGGTCTGG
GAATGC CGCCTGCGGGAAGCTCTGATA CAGCACTTT CATTGC
GCTTCTCCGGAAACATTAGC Exp-1_mrcB-146_l1-bc25mer_83004-20_l2-bc25mer_83517-20
ACAACCGCGTGTTACAAGGC CAGGCATCCGAGAGGTCTGG
GAATGC GCTTACGCCCTTTGCCTTTGC CCTTACCTT CATTGC
GCTTCTCCGGAAACATTAGC Exp-1_mrcB-1588_l1-bc25mer_83004-20_l2-bc25mer_83517-20
ACAACCGCGTGTTACAAGGC CAGGCATCCGAGAGGTCTGG
GAATGC CGCAATTGGCGCATCCGCAAT CCACGTATT CATTGC
GCTTCTCCGGAAACATTAGC Exp-1_mrcB-1167_l1-bc25mer_83004-20_l2-bc25mer_83517-20
ACAACCGCGTGTTACAAGGC CAGGCATCCGAGAGGTCTGG
GAATGC AGCGGACGGGCACTCAACATG TCATAGAGT CATTGC
GCTTCTCCGGAAACATTAGC Exp-1_mrcB-1001_l1-bc25mer_83004-20_l2-bc25mer_83517-20
ACAACCGCGTGTTACAAGGC CAGGCATCCGAGAGGTCTGG
GAATGC GGCTTAGCTCTTCTACCGGGC GACCAAAGT CATTGC
GCTTCTCCGGAAACATTAGC

FIG. 4RR

Exp-1_mrcB-861_I1-bc25mer_83004-20_I2-bc25mer_83517-20
ACAACCGCGTGTTACAAGGC CAGGCATCCGAGAGGTCTGG
GAATGC ATGATCAGCGCCATGTAAGCT TCGTTCGCT CATTGC
GCTTCTCCGGAAACATTAGC Exp-1_mrcB-1670_I1-bc25mer_83004-20_I2-bc25mer_83517-20
ACAACCGCGTGTTACAAGGC CAGGCATCCGAGAGGTCTGG
GAATGC CCACCAGCATCACTCTGCCGC TTTCGCTAT CATTGC
GCTTCTCCGGAAACATTAGC Exp-1_mrcB-944_I1-bc25mer_83004-20_I2-bc25mer_83517-20
ACAACCGCGTGTTACAAGGC CAGGCATCCGAGAGGTCTGG
GAATGC GGATTTCGTTGTCGCCGCTCT GACCGAGAT CATTGC
GCTTCTCCGGAAACATTAGC Exp-1_mrcB-2181_I1-bc25mer_83004-20_I2-bc25mer_83517-20
ACAACCGCGTGTTACAAGGC CAGGCATCCGAGAGGTCTGG
GAATGC CTGGCACCATACAGTTTGGTC GGCTGGTTG CATTGC
GCTTCTCCGGAAACATTAGC Exp-1_mrcB-1036_I1-bc25mer_83004-20_I2-bc25mer_83517-20
ACAACCGCGTGTTACAAGGC CAGGCATCCGAGAGGTCTGG
GAATGC TTTCACCATACCGACTAACAG CGCCTGCTG CATTGC
GCTTCTCCGGAAACATTAGC Exp-1_mrcB-446_I1-bc25mer_83004-20_I2-bc25mer_83517-20
ACAACCGCGTGTTACAAGGC CAGGCATCCGAGAGGTCTGG
GAATGC ACGGACGGCGAATCATCTCAA TGCTGTTGG CATTGC
GCTTCTCCGGAAACATTAGC Exp-1_mrcB-1635_I1-bc25mer_83004-20_I2-bc25mer_83517-20
ACAACCGCGTGTTACAAGGC CAGGCATCCGAGAGGTCTGG
GAATGC CGGTCATCATTCTGCGGTGAC CAGACCTGG CATTGC
GCTTCTCCGGAAACATTAGC Exp-1_mrcB-1710_I1-bc25mer_83004-20_I2-bc25mer_83517-20
ACAACCGCGTGTTACAAGGC CAGGCATCCGAGAGGTCTGG
GAATGC AGATTTACCGTCGGCACGTTC ATCGAACGG CATTGC
GCTTCTCCGGAAACATTAGC Exp-1_mrcB-325_I1-bc25mer_83004-20_I2-bc25mer_83517-20
ACAACCGCGTGTTACAAGGC CAGGCATCCGAGAGGTCTGG
GAATGC GGTCATGTCTGGCTCAAGATT GACCATTCG CATTGC
GCTTCTCCGGAAACATTAGC Exp-1_mrcB-1457_I1-bc25mer_83004-20_I2-bc25mer_83517-20
ACAACCGCGTGTTACAAGGC CAGGCATCCGAGAGGTCTGG
GAATGC CAAACTGCGGCTCAGAACCTC CGACCATCG CATTGC
GCTTCTCCGGAAACATTAGC

FIG. 4SS

Exp-1_mrcB-896_I1-bc25mer_83004-20_I2-bc25mer_83517-20
ACAACCGCGTGTTACAAGGC CAGGCATCCGAGAGGTCTGG
GAATGC GCTCAAGAATACGGTCTTTGC TGTAACGCG CATTGC
GCTTCTCCGGAAACATTAGC Exp-1_mrcB-2493_I1-bc25mer_83004-20_I2-bc25mer_83517-20
ACAACCGCGTGTTACAAGGC CAGGCATCCGAGAGGTCTGG
GAATGC AACATATCCTTGATCCAACCG GCTACACCG CATTGC
GCTTCTCCGGAAACATTAGC Exp-1_mrcB-826_I1-bc25mer_83004-20_I2-bc25mer_83517-20
ACAACCGCGTGTTACAAGGC CAGGCATCCGAGAGGTCTGG
GAATGC CCAGTAAGAACGCTCGCTGGA GAGGAACAG CATTGC
GCTTCTCCGGAAACATTAGC Exp-1_mrcB-582_I1-bc25mer_83004-20_I2-bc25mer_83517-20
ACAACCGCGTGTTACAAGGC CAGGCATCCGAGAGGTCTGG
GAATGC ATGGTGATCAGACGCGGATCA AGACGGAAG CATTGC
GCTTCTCCGGAAACATTAGC Exp-1_mrcB-617_I1-bc25mer_83004-20_I2-bc25mer_83517-20
ACAACCGCGTGTTACAAGGC CAGGCATCCGAGAGGTCTGG
GAATGC CAAACAGACGCTGCTCACCGT TTGGCGAAG CATTGC
GCTTCTCCGGAAACATTAGC Exp-1_mrcB-363_I1-bc25mer_83004-20_I2-bc25mer_83517-20
ACAACCGCGTGTTACAAGGC CAGGCATCCGAGAGGTCTGG
GAATGC GTCGCCTCCAGCAGCTTCACC ATCTCGTTC CATTGC
GCTTCTCCGGAAACATTAGC Exp-1_mrcB-19_I1-bc25mer_83004-20_I2-bc25mer_83517-20
ACAACCGCGTGTTACAAGGC CAGGCATCCGAGAGGTCTGG
GAATGC CGTCGGTTTCCCTTTGCGTCC AATTGGCTC CATTGC
GCTTCTCCGGAAACATTAGC Exp-1_mrcB-2425_I1-bc25mer_83004-20_I2-bc25mer_83517-20
ACAACCGCGTGTTACAAGGC CAGGCATCCGAGAGGTCTGG
GAATGC CGGCTGTTGCTGCGGCTGAGA AGACTGATC CATTGC
GCTTCTCCGGAAACATTAGC Exp-1_mrcB-541_I1-bc25mer_83004-20_I2-bc25mer_83517-20
ACAACCGCGTGTTACAAGGC CAGGCATCCGAGAGGTCTGG
GAATGC ACGGTTGTTCTCCATATTGAC GATCGTCGC CATTGC
GCTTCTCCGGAAACATTAGC Exp-1_mrcB-1543_I1-bc25mer_83004-20_I2-bc25mer_83517-20
ACAACCGCGTGTTACAAGGC CAGGCATCCGAGAGGTCTGG
GAATGC CGGCTGGCTTAAGGCCGTCAG ATAAGTCGC CATTGC
GCTTCTCCGGAAACATTAGC

FIG. 4TT

Exp-1_mrcB-234_l1-bc25mer_83004-20_l2-bc25mer_83517-20
ACAACCGCGTGTTACAAGGC CAGGCATCCGAGAGGTCTGG
GAATGC TCGAGATAAACGCCGTAAATG GCGATCAGC CATTGC
GCTTCTCCGGAAACATTAGC Exp-1_mrcB-1128_l1-bc25mer_83004-20_l2-bc25mer_83517-20
ACAACCGCGTGTTACAAGGC CAGGCATCCGAGAGGTCTGG
GAATGC ATAATCTGTTGCTGTTGCAGC AGACGCAGC CATTGC
GCTTCTCCGGAAACATTAGC Exp-1_mrcB-678_l1-bc25mer_83004-20_l2-bc25mer_83517-20
ACAACCGCGTGTTACAAGGC CAGGCATCCGAGAGGTCTGG
GAATGC TGACGGTCTTCTGTCGCCAGC AAAGTATCC CATTGC
GCTTCTCCGGAAACATTAGC Exp-1_mrcB-1377_l1-bc25mer_83004-20_l2-bc25mer_83517-20
ACAACCGCGTGTTACAAGGC CAGGCATCCGAGAGGTCTGG
GAATGC TCGCTCAACTTACGCTGTTTC TTCAGTGCC CATTGC
GCTTCTCCGGAAACATTAGC Exp-1_mrcB-784_l1-bc25mer_83004-20_l2-bc25mer_83517-20
ACAACCGCGTGTTACAAGGC CAGGCATCCGAGAGGTCTGG
GAATGC CTGTTGCGTCAGCGTACTCGC ACCCTGTAC CATTGC
GCTTCTCCGGAAACATTAGC Exp-1_mrcB-2244_l1-bc25mer_83004-20_l2-bc25mer_83517-20
ACAACCGCGTGTTACAAGGC CAGGCATCCGAGAGGTCTGG
GAATGC ACAAGATTCAGCGGCGTTGGC GTCTGGTTA CATTGC
GCTTCTCCGGAAACATTAGC Exp-1_mrcB-736_l1-bc25mer_83004-20_l2-bc25mer_83517-20
ACAACCGCGTGTTACAAGGC CAGGCATCCGAGAGGTCTGG
GAATGC GTTTGCCAGCACCGCACGTCC GATTGAGTA CATTGC
GCTTCTCCGGAAACATTAGC Exp-1_mrcB-2117_l1-bc25mer_83004-20_l2-bc25mer_83517-20
ACAACCGCGTGTTACAAGGC CAGGCATCCGAGAGGTCTGG
GAATGC TGCCGTCAATGCCCGCAAACC AGGTATCTA CATTGC
GCTTCTCCGGAAACATTAGC Exp-1_mrcB-2012_l1-bc25mer_83004-20_l2-bc25mer_83517-20
ACAACCGCGTGTTACAAGGC CAGGCATCCGAGAGGTCTGG
GAATGC CGCGTTGTACCACCTGCTGCA TGGTCCATA CATTGC
GCTTCTCCGGAAACATTAGC Exp-1_mrcB-282_l1-bc25mer_83004-20_l2-bc25mer_83517-20
ACAACCGCGTGTTACAAGGC CAGGCATCCGAGAGGTCTGG
GAATGC GCAGGCAGTTGCCAGACCTTG CCATCAATA CATTGC
GCTTCTCCGGAAACATTAGC

FIG. 4UU

Exp-1_mrcB-2286_l1-bc25mer_83004-20_l2-bc25mer_83517-20
ACAACCGCGTGTTACAAGGC CAGGCATCCGAGAGGTCTGG
GAATGC CCGTCGTAGTCCACGCCCATA TCTGCAATA CATTGC
GCTTCTCCGGAAACATTAGC Exp-1_mrcB-1422_l1-bc25mer_83004-20_l2-bc25mer_83517-20
ACAACCGCGTGTTACAAGGC CAGGCATCCGAGAGGTCTGG
GAATGC ACTTCACCACTAAAGCGGTCG ACGACCACA CATTGC
GCTTCTCCGGAAACATTAGC Exp-1_mrcB-1766_l1-bc25mer_83004-20_l2-bc25mer_83517-20
ACAACCGCGTGTTACAAGGC CAGGCATCCGAGAGGTCTGG
GAATGC GTACGCCCAGTTTAATCCAGG TCTCCGTAA CATTGC
GCTTCTCCGGAAACATTAGC Exp-1_mrcB-1241_l1-bc25mer_83004-20_l2-bc25mer_83517-20
ACAACCGCGTGTTACAAGGC CAGGCATCCGAGAGGTCTGG
GAATGC CCTGCAGCTCCTGACGCACCA GTTGCATAA CATTGC
GCTTCTCCGGAAACATTAGC Exp-1_mrcB-1315_l1-bc25mer_83004-20_l2-bc25mer_83517-20
ACAACCGCGTGTTACAAGGC CAGGCATCCGAGAGGTCTGG
GAATGC GTCCTGGGCCACCGAGTCAAA GGTAGTGAA CATTGC
GCTTCTCCGGAAACATTAGC Exp-1_mrcB-481_l1-bc25mer_83004-20_l2-bc25mer_83517-20
ACAACCGCGTGTTACAAGGC CAGGCATCCGAGAGGTCTGG
GAATGC GCGCACCTGTCCTTCTTTACT GTCCGGGAA CATTGC
GCTTCTCCGGAAACATTAGC Exp-1_mrcB-2321_l1-bc25mer_83004-20_l2-bc25mer_83517-20
ACAACCGCGTGTTACAAGGC CAGGCATCCGAGAGGTCTGG
GAATGC GCAAGATACGCATGCCACCGC TGCAAACAA CATTGC
GCTTCTCCGGAAACATTAGC Exp-1_mtn-253_l1-bc25mer_83004-20_l2-bc25mer_83517-20
ACAACCGCGTGTTACAAGGC CAGGCATCCGAGAGGTCTGG
GAATGC TTCGTCCGAGACAACGATATC GCCCACTTT CATTGC
GCTTCTCCGGAAACATTAGC Exp-1_mtn-323_l1-bc25mer_83004-20_l2-bc25mer_83517-20
ACAACCGCGTGTTACAAGGC CAGGCATCCGAGAGGTCTGG
GAATGC CTGCCGGACAGCCTGGTAACT GACCGTATT CATTGC
GCTTCTCCGGAAACATTAGC Exp-1_mtn-366_l1-bc25mer_83004-20_l2-bc25mer_83517-20
ACAACCGCGTGTTACAAGGC CAGGCATCCGAGAGGTCTGG
GAATGC CAGGCCTCAGCGGCAGCGATC AGTTTATCG CATTGC
GCTTCTCCGGAAACATTAGC

FIG. 4VV

Exp-1_mtn-67_I1-bc25mer_83004-20_I2-bc25mer_83517-20
ACAACCGCGTGTTACAAGGC CAGGCATCCGAGAGGTCTGG
GAATGC TTCGCAACCGCCGAGACTGAT AGTTTGACG CATTGC
GCTTCTCCGGAAACATTAGC Exp-1_mtn-634_I1-bc25mer_83004-20_I2-bc25mer_83517-20
ACAACCGCGTGTTACAAGGC CAGGCATCCGAGAGGTCTGG
GAATGC CATCAGGCTGGACTGTTTAGC GGCAACAGC CATTGC
GCTTCTCCGGAAACATTAGC Exp-1_mtn-183_I1-bc25mer_83004-20_I2-bc25mer_83517-20
ACAACCGCGTGTTACAAGGC CAGGCATCCGAGAGGTCTGG
GAATGC ATCACATCTGGCTTGCAGTGT TCCAACAGC CATTGC
GCTTCTCCGGAAACATTAGC Exp-1_mtn-448_I1-bc25mer_83004-20_I2-bc25mer_83517-20
ACAACCGCGTGTTACAAGGC CAGGCATCCGAGAGGTCTGG
GAATGC CGCCAGACCAACAGAACCGTT GATGAAAGC CATTGC
GCTTCTCCGGAAACATTAGC Exp-1_mtn-594_I1-bc25mer_83004-20_I2-bc25mer_83517-20
ACAACCGCGTGTTACAAGGC CAGGCATCCGAGAGGTCTGG
GAATGC TCGAAGCTAAGATGAGACTGT TGATCGGCC CATTGC
GCTTCTCCGGAAACATTAGC Exp-1_mtn-669_I1-bc25mer_83004-20_I2-bc25mer_83517-20
ACAACCGCGTGTTACAAGGC CAGGCATCCGAGAGGTCTGG
GAATGC TAGCCATGTGCAAGTTTCTGC ACCAGTGAC CATTGC
GCTTCTCCGGAAACATTAGC Exp-1_mtn-559_I1-bc25mer_83004-20_I2-bc25mer_83517-20
ACAACCGCGTGTTACAAGGC CAGGCATCCGAGAGGTCTGG
GAATGC GGAGATGGCGCGTACGACAAC AAACGGGAC CATTGC
GCTTCTCCGGAAACATTAGC Exp-1_mtn-102_I1-bc25mer_83004-20_I2-bc25mer_83517-20
ACAACCGCGTGTTACAAGGC CAGGCATCCGAGAGGTCTGG
GAATGC GCAACCTCGGTTCCATTCAGT TGGCCGGTA CATTGC
GCTTCTCCGGAAACATTAGC Exp-1_mtn-512_I1-bc25mer_83004-20_I2-bc25mer_83517-20
ACAACCGCGTGTTACAAGGC CAGGCATCCGAGAGGTCTGG
GAATGC CATGGGCGATTGCCGTCGCTT CCATCTCTA CATTGC
GCTTCTCCGGAAACATTAGC Exp-1_mtn-137_I1-bc25mer_83004-20_I2-bc25mer_83517-20
ACAACCGCGTGTTACAAGGC CAGGCATCCGAGAGGTCTGG
GAATGC CCGCAGCGACTTTACCGATGC CCGATTTCA CATTGC
GCTTCTCCGGAAACATTAGC

FIG. 4WW

Exp-1_mtn-413_I1-bc25mer_83004-20_I2-bc25mer_83517-20
ACAACCGCGTGTTACAAGGC CAGGCATCCGAGAGGTCTGG
GAATGC CGCTAACAATCAGGCCACGTA CAGCGTTAA CATTGC
GCTTCTCCGGAAACATTAGC Exp-1_mtn-288_I1-bc25mer_83004-20_I2-bc25mer_83517-20
ACAACCGCGTGTTACAAGGC CAGGCATCCGAGAGGTCTGG
GAATGC CCAAATGCCGTGACATCCGCG TCGTGATAA CATTGC
GCTTCTCCGGAAACATTAGC Exp-1_murC-1430_I1-bc25mer_83004-20_I2-bc25mer_83517-20
ACAACCGCGTGTTACAAGGC CAGGCATCCGAGAGGTCTGG
GAATGC CCTCCGGAGTTTGCGGCTTCA GTTTGATTT CATTGC
GCTTCTCCGGAAACATTAGC Exp-1_murC-282_I1-bc25mer_83004-20_I2-bc25mer_83517-20
ACAACCGCGTGTTACAAGGC CAGGCATCCGAGAGGTCTGG
GAATGC GGAATACGCGCTTCATGAGCG GCGACAATT CATTGC
GCTTCTCCGGAAACATTAGC Exp-1_murC-1064_I1-bc25mer_83004-20_I2-bc25mer_83517-20
ACAACCGCGTGTTACAAGGC CAGGCATCCGAGAGGTCTGG
GAATGC CTTTAATGGTGGCGTCCACTT CCGTCGGGT CATTGC
GCTTCTCCGGAAACATTAGC Exp-1_murC-698_I1-bc25mer_83004-20_I2-bc25mer_83517-20
ACAACCGCGTGTTACAAGGC CAGGCATCCGAGAGGTCTGG
GAATGC CTCGCGGTAACAATTCGCGGA TCACCGGAT CATTGC
GCTTCTCCGGAAACATTAGC Exp-1_murC-741_I1-bc25mer_83004-20_I2-bc25mer_83517-20
ACAACCGCGTGTTACAAGGC CAGGCATCCGAGAGGTCTGG
GAATGC TCGGCATCTTCGCTGAAGCCG TAAGTCGTG CATTGC
GCTTCTCCGGAAACATTAGC Exp-1_murC-550_I1-bc25mer_83004-20_I2-bc25mer_83517-20
ACAACCGCGTGTTACAAGGC CAGGCATCCGAGAGGTCTGG
GAATGC GGTGACAATCGCCACCATCGG TTGCAGATG CATTGC
GCTTCTCCGGAAACATTAGC Exp-1_murC-597_I1-bc25mer_83004-20_I2-bc25mer_83517-20
ACAACCGCGTGTTACAAGGC CAGGCATCCGAGAGGTCTGG
GAATGC TTCTCAAAGTCGCCCTGGTAG GTATCCATG CATTGC
GCTTCTCCGGAAACATTAGC Exp-1_murC-402_I1-bc25mer_83004-20_I2-bc25mer_83517-20
ACAACCGCGTGTTACAAGGC CAGGCATCCGAGAGGTCTGG
GAATGC GCTTCTGCGTAGATGCTGGAA ACCATCGCG CATTGC
GCTTCTCCGGAAACATTAGC

FIG. 4XX

Exp-1_murC-911_l1-bc25mer_83004-20_l2-bc25mer_83517-20
ACAACCGCGTGTTACAAGGC CAGGCATCCGAGAGGTCTGG
GAATGC TAGCCTCGTCGTCAATGCCCT CTTCCGTAG CATTGC
GCTTCTCCGGAAACATTAGC Exp-1_murC-156_l1-bc25mer_83004-20_l2-bc25mer_83517-20
ACAACCGCGTGTTACAAGGC CAGGCATCCGAGAGGTCTGG
GAATGC TTCATTAACTGCTGCGTGACC GGATTTGGC CATTGC
GCTTCTCCGGAAACATTAGC Exp-1_murC-106_l1-bc25mer_83004-20_l2-bc25mer_83517-20
ACAACCGCGTGTTACAAGGC CAGGCATCCGAGAGGTCTGG
GAATGC CTGATAACCTTCATTGGCCAG AACTTCGGC CATTGC
GCTTCTCCGGAAACATTAGC Exp-1_murC-994_l1-bc25mer_83004-20_l2-bc25mer_83517-20
ACAACCGCGTGTTACAAGGC CAGGCATCCGAGAGGTCTGG
GAATGC ACCATTCACTGGCTCCAGCGG GAATTCACC CATTGC
GCTTCTCCGGAAACATTAGC Exp-1_murC-191_l1-bc25mer_83004-20_l2-bc25mer_83517-20
ACAACCGCGTGTTACAAGGC CAGGCATCCGAGAGGTCTGG
GAATGC CCGGGCGATGGTTGAAATAAA TCGTCGCAC CATTGC
GCTTCTCCGGAAACATTAGC Exp-1_murC-776_l1-bc25mer_83004-20_l2-bc25mer_83517-20
ACAACCGCGTGTTACAAGGC CAGGCATCCGAGAGGTCTGG
GAATGC GCGGGCCAATCTGCTGATAAT CTTCTACAC CATTGC
GCTTCTCCGGAAACATTAGC Exp-1_murC-1268_l1-bc25mer_83004-20_l2-bc25mer_83517-20
ACAACCGCGTGTTACAAGGC CAGGCATCCGAGAGGTCTGG
GAATGC CACGTCCACGAATTGTGCGAC ACAGCGAAC CATTGC
GCTTCTCCGGAAACATTAGC Exp-1_murC-247_l1-bc25mer_83004-20_l2-bc25mer_83517-20
ACAACCGCGTGTTACAAGGC CAGGCATCCGAGAGGTCTGG
GAATGC GTTATCGGCAGAAATCGCGCT GGAAACAAC CATTGC
GCTTCTCCGGAAACATTAGC Exp-1_murC-1337_l1-bc25mer_83004-20_l2-bc25mer_83517-20
ACAACCGCGTGTTACAAGGC CAGGCATCCGAGAGGTCTGG
GAATGC CGGTTAATACCGGTGCCAGCA TCTCGGCTA CATTGC
GCTTCTCCGGAAACATTAGC Exp-1_murC-321_l1-bc25mer_83004-20_l2-bc25mer_83517-20
ACAACCGCGTGTTACAAGGC CAGGCATCCGAGAGGTCTGG
GAATGC CGCATTAACTCAGCCAGCATT TCGGCACGA CATTGC
GCTTCTCCGGAAACATTAGC

FIG. 4YY

Exp-1_murC-1214_I1-bc25mer_83004-20_I2-bc25mer_83517-20
ACAACCGCGTGTTACAAGGC CAGGCATCCGAGAGGTCTGG
GAATGC CTTCGCCAGCCGGATACACTT CCAGCATCA CATTGC
GCTTCTCCGGAAACATTAGC Exp-1_murC-515_I1-bc25mer_83004-20_I2-bc25mer_83517-20
ACAACCGCGTGTTACAAGGC CAGGCATCCGAGAGGTCTGG
GAATGC ACGATGCATCACTCTCATCTG CTTCGGCAA CATTGC
GCTTCTCCGGAAACATTAGC Exp-1_murC-1179_I1-bc25mer_83004-20_I2-bc25mer_83517-20
ACAACCGCGTGTTACAAGGC CAGGCATCCGAGAGGTCTGG
GAATGC GTATCAACCTGCGTCAGCACA TTGGCGAAA CATTGC
GCTTCTCCGGAAACATTAGC Exp-1_panB-616_I1-bc25mer_83004-20_I2-bc25mer_83517-20
ACAACCGCGTGTTACAAGGC CAGGCATCCGAGAGGTCTGG
GAATGC CATCACGAGGATCTGCCCGTC AGTGACGTT CATTGC
GCTTCTCCGGAAACATTAGC Exp-1_panB-578_I1-bc25mer_83004-20_I2-bc25mer_83517-20
ACAACCGCGTGTTACAAGGC CAGGCATCCGAGAGGTCTGG
GAATGC CAATGCCAATAACCGGGATCG CCAGTGCTT CATTGC
GCTTCTCCGGAAACATTAGC Exp-1_panB-304_I1-bc25mer_83004-20_I2-bc25mer_83517-20
ACAACCGCGTGTTACAAGGC CAGGCATCCGAGAGGTCTGG
GAATGC GACCATGTTAGCACCGGCACG CATAACCGT CATTGC
GCTTCTCCGGAAACATTAGC Exp-1_panB-62_I1-bc25mer_83004-20_I2-bc25mer_83517-20
ACAACCGCGTGTTACAAGGC CAGGCATCCGAGAGGTCTGG
GAATGC TGGCGAAGCTATAGTCATAAG CGGTGATGG CATTGC
GCTTCTCCGGAAACATTAGC Exp-1_panB-653_I1-bc25mer_83004-20_I2-bc25mer_83517-20
ACAACCGCGTGTTACAAGGC CAGGCATCCGAGAGGTCTGG
GAATGC TAGGAATGTGACCGCCGGTAA TACCAAAGG CATTGC
GCTTCTCCGGAAACATTAGC Exp-1_panB-8_I1-bc25mer_83004-20_I2-bc25mer_83517-20
ACAACCGCGTGTTACAAGGC CAGGCATCCGAGAGGTCTGG
GAATGC TGTACTTCTGCAGTAAGGAGA TGGTGGTCG CATTGC
GCTTCTCCGGAAACATTAGC Exp-1_panB-762_I1-bc25mer_83004-20_I2-bc25mer_83517-20
ACAACCGCGTGTTACAAGGC CAGGCATCCGAGAGGTCTGG
GAATGC TGGAAACTGTGTTCTTCGCCC GGATAAACG CATTGC
GCTTCTCCGGAAACATTAGC

FIG. 4ZZ

Exp-1_panB-490_l1-bc25mer_83004-20_l2-bc25mer_83517-20
ACAACCGCGTGTTACAAGGC CAGGCATCCGAGAGGTCTGG
GAATGC AGCAGCTTCTAAGGCTAATGC ATCGCTGAG CATTGC
GCTTCTCCGGAAACATTAGC Exp-1_panB-727_l1-bc25mer_83004-20_l2-bc25mer_83517-20
ACAACCGCGTGTTACAAGGC CAGGCATCCGAGAGGTCTGG
GAATGC CTCCACTTCAGCCATATACTG CCGCACAGC CATTGC
GCTTCTCCGGAAACATTAGC Exp-1_panB-386_l1-bc25mer_83004-20_l2-bc25mer_83517-20
ACAACCGCGTGTTACAAGGC CAGGCATCCGAGAGGTCTGG
GAATGC AACCTAAGTGACCACATACAG GAACGGCAC CATTGC
GCTTCTCCGGAAACATTAGC Exp-1_panB-351_l1-bc25mer_83004-20_l2-bc25mer_83517-20
ACAACCGCGTGTTACAAGGC CAGGCATCCGAGAGGTCTGG
GAATGC GTCAGCATTTGTACGGTTTCT ACCAGCCAC CATTGC
GCTTCTCCGGAAACATTAGC Exp-1_panB-180_l1-bc25mer_83004-20_l2-bc25mer_83517-20
ACAACCGCGTGTTACAAGGC CAGGCATCCGAGAGGTCTGG
GAATGC GCAGTGTGGTAGGCGATATCG GCAACGGTA CATTGC
GCTTCTCCGGAAACATTAGC Exp-1_panB-242_l1-bc25mer_83004-20_l2-bc25mer_83517-20
ACAACCGCGTGTTACAAGGC CAGGCATCCGAGAGGTCTGG
GAATGC CATACGCCATAAACGGCAGGT CAGCCAGCA CATTGC
GCTTCTCCGGAAACATTAGC Exp-1_panB-113_l1-bc25mer_83004-20_l2-bc25mer_83517-20
ACAACCGCGTGTTACAAGGC CAGGCATCCGAGAGGTCTGG
GAATGC CCAGCGAATCGCCCACCAGCA TGACGTTAA CATTGC
GCTTCTCCGGAAACATTAGC Exp-1_panC-775_l1-bc25mer_83004-20_l2-bc25mer_83517-20
ACAACCGCGTGTTACAAGGC CAGGCATCCGAGAGGTCTGG
GAATGC CCAGGCGGCTACCAGAATTAC TGCCCGTTT CATTGC
GCTTCTCCGGAAACATTAGC Exp-1_panC-406_l1-bc25mer_83004-20_l2-bc25mer_83517-20
ACAACCGCGTGTTACAAGGC CAGGCATCCGAGAGGTCTGG
GAATGC GATGTCCGGCTGGACCAGGTT GAACAGCTT CATTGC
GCTTCTCCGGAAACATTAGC Exp-1_panC-37_l1-bc25mer_83004-20_l2-bc25mer_83517-20
ACAACCGCGTGTTACAAGGC CAGGCATCCGAGAGGTCTGG
GAATGC CTTGCCTTCCATACGCAGGCG GCGAATTTG CATTGC
GCTTCTCCGGAAACATTAGC

FIG. 4AAA

Exp-1_panC-226_I1-bc25mer_83004-20_I2-bc25mer_83517-20
ACAACCGCGTGTTACAAGGC CAGGCATCCGAGAGGTCTGG
GAATGC ACGTTTGTTTAGCTTCTCGCA GTCCTCCTG CATTGC
GCTTCTCCGGAAACATTAGC Exp-1_panC-297_I1-bc25mer_83004-20_I2-bc25mer_83517-20
ACAACCGCGTGTTACAAGGC CAGGCATCCGAGAGGTCTGG
GAATGC ACGTAAGTGTGGGTTTCAGTA CCGTTCGGG CATTGC
GCTTCTCCGGAAACATTAGC Exp-1_panC-565_I1-bc25mer_83004-20_I2-bc25mer_83517-20
ACAACCGCGTGTTACAAGGC CAGGCATCCGAGAGGTCTGG
GAATGC GCGTTGTTCCGCCGTCAGATA ACCGTTACG CATTGC
GCTTCTCCGGAAACATTAGC Exp-1_panC-76_I1-bc25mer_83004-20_I2-bc25mer_83517-20
ACAACCGCGTGTTACAAGGC CAGGCATCCGAGAGGTCTGG
GAATGC ATCGTGCAGGTTACCCATGGT AGGCACCAG CATTGC
GCTTCTCCGGAAACATTAGC Exp-1_panC-523_I1-bc25mer_83004-20_I2-bc25mer_83517-20
ACAACCGCGTGTTACAAGGC CAGGCATCCGAGAGGTCTGG
GAATGC CAGACCGTCTTTGGCGCGCAT AATTGGCAC CATTGC
GCTTCTCCGGAAACATTAGC Exp-1_panC-111_I1-bc25mer_83004-20_I2-bc25mer_83517-20
ACAACCGCGTGTTACAAGGC CAGGCATCCGAGAGGTCTGG
GAATGC CGGGCTTTGGCTTCGTCGACC AGCTTCATA CATTGC
GCTTCTCCGGAAACATTAGC Exp-1_panC-2_I1-bc25mer_83004-20_I2-bc25mer_83517-20
ACAACCGCGTGTTACAAGGC CAGGCATCCGAGAGGTCTGG
GAATGC GCAGCAGCGGCAGGGTTTCGA TAATTAACA CATTGC
GCTTCTCCGGAAACATTAGC Exp-1_panC-332_I1-bc25mer_83004-20_I2-bc25mer_83517-20
ACAACCGCGTGTTACAAGGC CAGGCATCCGAGAGGTCTGG
GAATGC CACCTTCCAGCATGGTCGAAA GGCCAGGAA CATTGC
GCTTCTCCGGAAACATTAGC Exp-1_panD-26_I1-bc25mer_83004-20_I2-bc25mer_83517-20
ACAACCGCGTGTTACAAGGC CAGGCATCCGAGAGGTCTGG
GAATGC CCGCATGAGTCACTTTCACGC GGTGGAGTT CATTGC
GCTTCTCCGGAAACATTAGC Exp-1_panD-274_I1-bc25mer_83004-20_I2-bc25mer_83517-20
ACAACCGCGTGTTACAAGGC CAGGCATCCGAGAGGTCTGG
GAATGC CCAGGTGCGAGCTTCTTCATC TGGCATGGT CATTGC
GCTTCTCCGGAAACATTAGC

FIG. 4BBB

Exp-1_panD-156_I1-bc25mer_83004-20_I2-bc25mer_83517-20
ACAACCGCGTGTTACAAGGC CAGGCATCCGAGAGGTCTGG
GAATGC GCCGCGATGGCATAAGTGGAG AAACGCTTG CATTGC
GCTTCTCCGGAAACATTAGC Exp-1_panD-63_I1-bc25mer_83004-20_I2-bc25mer_83517-20
ACAACCGCGTGTTACAAGGC CAGGCATCCGAGAGGTCTGG
GAATGC TCCTGGTCAATGGCGCAAGAA CCTTCATAG CATTGC
GCTTCTCCGGAAACATTAGC Exp-1_panD-352_I1-bc25mer_83004-20_I2-bc25mer_83517-20
ACAACCGCGTGTTACAAGGC CAGGCATCCGAGAGGTCTGG
GAATGC TCAAGCAACCTGTACCGGAAT CGCTTTCGC CATTGC
GCTTCTCCGGAAACATTAGC Exp-1_panD-239_I1-bc25mer_83004-20_I2-bc25mer_83517-20
ACAACCGCGTGTTACAAGGC CAGGCATCCGAGAGGTCTGG
GAATGC AGCTGGCGATGATGACAATAT CGCCGACAC CATTGC
GCTTCTCCGGAAACATTAGC Exp-1_panD-204_I1-bc25mer_83004-20_I2-bc25mer_83517-20
ACAACCGCGTGTTACAAGGC CAGGCATCCGAGAGGTCTGG
GAATGC CAGTGGGCCGCCGCACCGTTA ACAGAAATA CATTGC
GCTTCTCCGGAAACATTAGC Exp-1_pcnB-1007_I1-bc25mer_83004-20_I2-bc25mer_83517-20
ACAACCGCGTGTTACAAGGC CAGGCATCCGAGAGGTCTGG
GAATGC CGAAAGCGTCGTGATAGGTCA GGCCGCTTT CATTGC
GCTTCTCCGGAAACATTAGC Exp-1_pcnB-652_I1-bc25mer_83004-20_I2-bc25mer_83517-20
ACAACCGCGTGTTACAAGGC CAGGCATCCGAGAGGTCTGG
GAATGC GGTTTCCGGGCTGATGCGCAT ACCCAATTT CATTGC
GCTTCTCCGGAAACATTAGC Exp-1_pcnB-1102_I1-bc25mer_83004-20_I2-bc25mer_83517-20
ACAACCGCGTGTTACAAGGC CAGGCATCCGAGAGGTCTGG
GAATGC CTGCAACTGCCAGATATCGCG GGTTAATGT CATTGC
GCTTCTCCGGAAACATTAGC Exp-1_pcnB-920_I1-bc25mer_83004-20_I2-bc25mer_83517-20
ACAACCGCGTGTTACAAGGC CAGGCATCCGAGAGGTCTGG
GAATGC GGAACGCCGGGTTCACGCGCA TATCGTTAT CATTGC
GCTTCTCCGGAAACATTAGC Exp-1_pcnB-1314_I1-bc25mer_83004-20_I2-bc25mer_83517-20
ACAACCGCGTGTTACAAGGC CAGGCATCCGAGAGGTCTGG
GAATGC CGCGGTGACGGTTCTTCATCC AGCTCGTTG CATTGC
GCTTCTCCGGAAACATTAGC

FIG. 4CCC

Exp-1_pcnB-960_I1-bc25mer_83004-20_I2-bc25mer_83517-20
ACAACCGCGTGTTACAAGGC CAGGCATCCGAGAGGTCTGG
GAATGC GCCGTCTCCAGCAGTGGGTAC CAGAACATG CATTGC
GCTTCTCCGGAAACATTAGC Exp-1_pcnB-478_I1-bc25mer_83004-20_I2-bc25mer_83517-20
ACAACCGCGTGTTACAAGGC CAGGCATCCGAGAGGTCTGG
GAATGC ATACAGGCTGTTGATAGTGAA ATCGCGGCG CATTGC
GCTTCTCCGGAAACATTAGC Exp-1_pcnB-728_I1-bc25mer_83004-20_I2-bc25mer_83517-20
ACAACCGCGTGTTACAAGGC CAGGCATCCGAGAGGTCTGG
GAATGC GTTTAAGCGATTCTTCAAACA GGCGTGCCG CATTGC
GCTTCTCCGGAAACATTAGC Exp-1_pcnB-767_I1-bc25mer_83004-20_I2-bc25mer_83517-20
ACAACCGCGTGTTACAAGGC CAGGCATCCGAGAGGTCTGG
GAATGC ACAGCTTATAGGTTTCGTAAC CGTAGCCCG CATTGC
GCTTCTCCGGAAACATTAGC Exp-1_pcnB-268_I1-bc25mer_83004-20_I2-bc25mer_83517-20
ACAACCGCGTGTTACAAGGC CAGGCATCCGAGAGGTCTGG
GAATGC GCAGTTACGGAACAGTTTGCG CACCTGCTC CATTGC
GCTTCTCCGGAAACATTAGC Exp-1_pcnB-569_I1-bc25mer_83004-20_I2-bc25mer_83517-20
ACAACCGCGTGTTACAAGGC CAGGCATCCGAGAGGTCTGG
GAATGC TTTCCGGGTTACCAATCAGAC GGATAACGC CATTGC
GCTTCTCCGGAAACATTAGC Exp-1_pcnB-1176_I1-bc25mer_83004-20_I2-bc25mer_83517-20
ACAACCGCGTGTTACAAGGC CAGGCATCCGAGAGGTCTGG
GAATGC TCATAAGCCGCACGGAACTTA GGATGCTCC CATTGC
GCTTCTCCGGAAACATTAGC Exp-1_pcnB-533_I1-bc25mer_83004-20_I2-bc25mer_83517-20
ACAACCGCGTGTTACAAGGC CAGGCATCCGAGAGGTCTGG
GAATGC TCAGATCCTTCATGCCGCCAA CGTAATCAC CATTGC
GCTTCTCCGGAAACATTAGC Exp-1_pcnB-371_I1-bc25mer_83004-20_I2-bc25mer_83517-20
ACAACCGCGTGTTACAAGGC CAGGCATCCGAGAGGTCTGG
GAATGC GGTCGCTGACGTTACCTTCGT GGTGTCCAC CATTGC
GCTTCTCCGGAAACATTAGC Exp-1_pcnB-336_I1-bc25mer_83004-20_I2-bc25mer_83517-20
ACAACCGCGTGTTACAAGGC CAGGCATCCGAGAGGTCTGG
GAATGC GTCGCAACTTCGATAATCTCC GGGCCAAAC CATTGC
GCTTCTCCGGAAACATTAGC

FIG. 4DDD

Exp-1_pcnB-168_I1-bc25mer_83004-20_I2-bc25mer_83517-20
ACAACCGCGTGTTACAAGGC CAGGCATCCGAGAGGTCTGG
GAATGC CCAACCAGCCAGGCTTCGTAT CCCGCTTTA CATTGC
GCTTCTCCGGAAACATTAGC Exp-1_pcnB-604_I1-bc25mer_83004-20_I2-bc25mer_83517-20
ACAACCGCGTGTTACAAGGC CAGGCATCCGAGAGGTCTGG
GAATGC GCGCAGCATACGTACCGGATC TTCACGGTA CATTGC
GCTTCTCCGGAAACATTAGC Exp-1_pcnB-1137_I1-bc25mer_83004-20_I2-bc25mer_83517-20
ACAACCGCGTGTTACAAGGC CAGGCATCCGAGAGGTCTGG
GAATGC CATGCGCGTTTACCCTGACGA CGGGACATA CATTGC
GCTTCTCCGGAAACATTAGC Exp-1_pcnB-885_I1-bc25mer_83004-20_I2-bc25mer_83517-20
ACAACCGCGTGTTACAAGGC CAGGCATCCGAGAGGTCTGG
GAATGC CGCGTATCGGTATTCTTCAGC ACCTGTTCA CATTGC
GCTTCTCCGGAAACATTAGC Exp-1_pcnB-1211_I1-bc25mer_83004-20_I2-bc25mer_83517-20
ACAACCGCGTGTTACAAGGC CAGGCATCCGAGAGGTCTGG
GAATGC CGTTACGCTCAACTTCAGCTC GCAAGGCCA CATTGC
GCTTCTCCGGAAACATTAGC Exp-1_pcnB-824_I1-bc25mer_83004-20_I2-bc25mer_83517-20
ACAACCGCGTGTTACAAGGC CAGGCATCCGAGAGGTCTGG
GAATGC CCGTGAAGTAGCGGGTAATGG TCGGGAACA CATTGC
GCTTCTCCGGAAACATTAGC Exp-1_pyrH-497_I1-bc25mer_83004-20_I2-bc25mer_83517-20
ACAACCGCGTGTTACAAGGC CAGGCATCCGAGAGGTCTGG
GAATGC CCGGATCAGCGGTAAACACGC CGTCAACTT CATTGC
GCTTCTCCGGAAACATTAGC Exp-1_pyrH-350_I1-bc25mer_83004-20_I2-bc25mer_83517-20
ACAACCGCGTGTTACAAGGC CAGGCATCCGAGAGGTCTGG
GAATGC GCAACAGGCTGATAGCTTCTG CCCAGCTGT CATTGC
GCTTCTCCGGAAACATTAGC Exp-1_pyrH-551_I1-bc25mer_83004-20_I2-bc25mer_83517-20
ACAACCGCGTGTTACAAGGC CAGGCATCCGAGAGGTCTGG
GAATGC CCAGCACTTCGCTGTAAGTCA GTTGCTCGT CATTGC
GCTTCTCCGGAAACATTAGC Exp-1_pyrH-462_I1-bc25mer_83004-20_I2-bc25mer_83517-20
ACAACCGCGTGTTACAAGGC CAGGCATCCGAGAGGTCTGG
GAATGC GCTTTCAGCACCACATCGGCT TCAATTTCG CATTGC
GCTTCTCCGGAAACATTAGC

FIG. 4EEE

Exp-1_pyrH-139_l1-bc25mer_83004-20_l2-bc25mer_83517-20
ACAACCGCGTGTTACAAGGC CAGGCATCCGAGAGGTCTGG
GAATGC ACCAATCACCACACCAACCTG AATACCCAG CATTGC
GCTTCTCCGGAAACATTAGC Exp-1_pyrH-91_l1-bc25mer_83004-20_l2-bc25mer_83517-20
ACAACCGCGTGTTACAAGGC CAGGCATCCGAGAGGTCTGG
GAATGC TTCCTGAGCCATACGATCCAG TATGCTTGC CATTGC
GCTTCTCCGGAAACATTAGC Exp-1_pyrH-618_l1-bc25mer_83004-20_l2-bc25mer_83517-20
ACAACCGCGTGTTACAAGGC CAGGCATCCGAGAGGTCTGG
GAATGC CGAATCGGTAATTTATGGTCA CGAGCCAGC CATTGC
GCTTCTCCGGAAACATTAGC Exp-1_pyrH-315_l1-bc25mer_83004-20_l2-bc25mer_83517-20
ACAACCGCGTGTTACAAGGC CAGGCATCCGAGAGGTCTGG
GAATGC TCGCACACGCCATTCAATGGA ATAGCGGAC CATTGC
GCTTCTCCGGAAACATTAGC Exp-1_pyrH-42_l1-bc25mer_83004-20_l2-bc25mer_83517-20
ACAACCGCGTGTTACAAGGC CAGGCATCCGAGAGGTCTGG
GAATGC GTGCCCTGCAGAGCTTCGCCA CTCAACTTA CATTGC
GCTTCTCCGGAAACATTAGC Exp-1_pyrH-425_l1-bc25mer_83004-20_l2-bc25mer_83517-20
ACAACCGCGTGTTACAAGGC CAGGCATCCGAGAGGTCTGG
GAATGC GCAGGCAAGCTGCTGAGTCGG TGGTAAAGA CATTGC
GCTTCTCCGGAAACATTAGC Exp-1_pyrH-390_l1-bc25mer_83004-20_l2-bc25mer_83517-20
ACAACCGCGTGTTACAAGGC CAGGCATCCGAGAGGTCTGG
GAATGC TTACCTGTACCGGCGGAGAGG ATCACCACA CATTGC
GCTTCTCCGGAAACATTAGC Exp-1_rseP-723_l1-bc25mer_83004-20_l2-bc25mer_83517-20
ACAACCGCGTGTTACAAGGC CAGGCATCCGAGAGGTCTGG
GAATGC CCATCGACTTTAACGATCCTG TCGCCTGCT CATTGC
GCTTCTCCGGAAACATTAGC Exp-1_rseP-959_l1-bc25mer_83004-20_l2-bc25mer_83517-20
ACAACCGCGTGTTACAAGGC CAGGCATCCGAGAGGTCTGG
GAATGC CTTCGACGATGGCGTTGAACG GCCCATACT CATTGC
GCTTCTCCGGAAACATTAGC Exp-1_rseP-1068_l1-bc25mer_83004-20_l2-bc25mer_83517-20
ACAACCGCGTGTTACAAGGC CAGGCATCCGAGAGGTCTGG
GAATGC TTGGCGATAGAGATCGGCCCA CTGAGGTTG CATTGC
GCTTCTCCGGAAACATTAGC

FIG. 4FFF

Exp-1_rseP-565_I1-bc25mer_83004-20_I2-bc25mer_83517-20
ACAACCGCGTGTTACAAGGC CAGGCATCCGAGAGGTCTGG
GAATGC ACGTAAATCGAGCTTTACATC CCGCCGTTG CATTGC
GCTTCTCCGGAAACATTAGC Exp-1_rseP-64_I1-bc25mer_83004-20_I2-bc25mer_83517-20
ACAACCGCGTGTTACAAGGC CAGGCATCCGAGAGGTCTGG
GAATGC CCGGGCAACCCAGAAATGACC AAATTCATG CATTGC
GCTTCTCCGGAAACATTAGC Exp-1_rseP-758_I1-bc25mer_83004-20_I2-bc25mer_83517-20
ACAACCGCGTGTTACAAGGC CAGGCATCCGAGAGGTCTGG
GAATGC GCATCACAAAGGTCACCCACT GCGTTAAGG CATTGC
GCTTCTCCGGAAACATTAGC Exp-1_rseP-245_I1-bc25mer_83004-20_I2-bc25mer_83517-20
ACAACCGCGTGTTACAAGGC CAGGCATCCGAGAGGTCTGG
GAATGC TATTATTGAAGGCATGGTGGC GGAGTTCCG CATTGC
GCTTCTCCGGAAACATTAGC Exp-1_rseP-866_I1-bc25mer_83004-20_I2-bc25mer_83517-20
ACAACCGCGTGTTACAAGGC CAGGCATCCGAGAGGTCTGG
GAATGC TCGCTTTACCATTACCCGGTT TACTCTCCG CATTGC
GCTTCTCCGGAAACATTAGC Exp-1_rseP-793_I1-bc25mer_83004-20_I2-bc25mer_83517-20
ACAACCGCGTGTTACAAGGC CAGGCATCCGAGAGGTCTGG
GAATGC TAACGCTAAGGATTTACCCGG GTTATCCCG CATTGC
GCTTCTCCGGAAACATTAGC Exp-1_rseP-650_I1-bc25mer_83004-20_I2-bc25mer_83517-20
ACAACCGCGTGTTACAAGGC CAGGCATCCGAGAGGTCTGG
GAATGC CCAGTACAGGTTCAATTTGCG GCCCACGAG CATTGC
GCTTCTCCGGAAACATTAGC Exp-1_rseP-1138_I1-bc25mer_83004-20_I2-bc25mer_83517-20
ACAACCGCGTGTTACAAGGC CAGGCATCCGAGAGGTCTGG
GAATGC GTTCACGCTAATAAGCGCAAG AAACGGCAG CATTGC
GCTTCTCCGGAAACATTAGC Exp-1_rseP-172_I1-bc25mer_83004-20_I2-bc25mer_83517-20
ACAACCGCGTGTTACAAGGC CAGGCATCCGAGAGGTCTGG
GAATGC GCCCAACGGGATCAGGGCGAT AACATATTC CATTGC
GCTTCTCCGGAAACATTAGC Exp-1_rseP-913_I1-bc25mer_83004-20_I2-bc25mer_83517-20
ACAACCGCGTGTTACAAGGC CAGGCATCCGAGAGGTCTGG
GAATGC CTCATCTGGCAAAGGAATGAC TTTCGGCTC CATTGC
GCTTCTCCGGAAACATTAGC

FIG. 4GGG

Exp-1_rseP-481_I1-bc25mer_83004-20_I2-bc25mer_83517-20
ACAACCGCGTGTTACAAGGC CAGGCATCCGAGAGGTCTGG
GAATGC GACCAACTGCAAACGCACGGC ATCCCAATC CATTGC
GCTTCTCCGGAAACATTAGC Exp-1_rseP-530_I1-bc25mer_83004-20_I2-bc25mer_83517-20
ACAACCGCGTGTTACAAGGC CAGGCATCCGAGAGGTCTGG
GAATGC TGCCAAATGGCGCTACTGTAA TGGTGGTGC CATTGC
GCTTCTCCGGAAACATTAGC Exp-1_rseP-1286_I1-bc25mer_83004-20_I2-bc25mer_83517-20
ACAACCGCGTGTTACAAGGC CAGGCATCCGAGAGGTCTGG
GAATGC TTAACAGCACCAGCAGAATCG AGCCAATGC CATTGC
GCTTCTCCGGAAACATTAGC Exp-1_rseP-1008_I1-bc25mer_83004-20_I2-bc25mer_83517-20
ACAACCGCGTGTTACAAGGC CAGGCATCCGAGAGGTCTGG
GAATGC CCCAGCATACTGACCGTCAGC TTCATCAGC CATTGC
GCTTCTCCGGAAACATTAGC Exp-1_rseP-25_I1-bc25mer_83004-20_I2-bc25mer_83517-20
ACAACCGCGTGTTACAAGGC CAGGCATCCGAGAGGTCTGG
GAATGC AAGTACACCCAGTGCAACGAT GAACGAAGC CATTGC
GCTTCTCCGGAAACATTAGC Exp-1_rseP-423_I1-bc25mer_83004-20_I2-bc25mer_83517-20
ACAACCGCGTGTTACAAGGC CAGGCATCCGAGAGGTCTGG
GAATGC AGTTCCGTACCTGGTGCAATT TGTGCTTCC CATTGC
GCTTCTCCGGAAACATTAGC Exp-1_rseP-600_I1-bc25mer_83004-20_I2-bc25mer_83517-20
ACAACCGCGTGTTACAAGGC CAGGCATCCGAGAGGTCTGG
GAATGC ACCGGATCTTCTTTATCAGGC TCAAACGCC CATTGC
GCTTCTCCGGAAACATTAGC Exp-1_rseP-387_I1-bc25mer_83004-20_I2-bc25mer_83517-20
ACAACCGCGTGTTACAAGGC CAGGCATCCGAGAGGTCTGG
GAATGC ATCGAATTGGCTGCTATTTCG CCAACCACC CATTGC
GCTTCTCCGGAAACATTAGC Exp-1_rseP-134_I1-bc25mer_83004-20_I2-bc25mer_83517-20
ACAACCGCGTGTTACAAGGC CAGGCATCCGAGAGGTCTGG
GAATGC GCTTATCAGTTCGCCGCCAGA GCGCCTTAC CATTGC
GCTTCTCCGGAAACATTAGC Exp-1_rseP-99_I1-bc25mer_83004-20_I2-bc25mer_83517-20
ACAACCGCGTGTTACAAGGC CAGGCATCCGAGAGGTCTGG
GAATGC CCTATTGAGAAACGCTCAACG CGAACACCA CATTGC
GCTTCTCCGGAAACATTAGC

FIG. 4HHH

Exp-1_rseP-299_I1-bc25mer_83004-20_I2-bc25mer_83517-20
ACAACCGCGTGTTACAAGGC CAGGCATCCGAGAGGTCTGG
GAATGC TGAAGTTTGCAACCGGACCTG CGGCAATAA CATTGC
GCTTCTCCGGAAACATTAGC Exp-1_secA-907_I1-bc25mer_83004-20_I2-bc25mer_83517-20
ACAACCGCGTGTTACAAGGC CAGGCATCCGAGAGGTCTGG
GAATGC CGCCGTTACGTGGTGCATCAG CATGATGTT CATTGC
GCTTCTCCGGAAACATTAGC Exp-1_secA-1073_I1-bc25mer_83004-20_I2-bc25mer_83517-20
ACAACCGCGTGTTACAAGGC CAGGCATCCGAGAGGTCTGG
GAATGC CGTTCTGGATCTGCACACCTT CTTTCGCTT CATTGC
GCTTCTCCGGAAACATTAGC Exp-1_secA-77_I1-bc25mer_83004-20_I2-bc25mer_83517-20
ACAACCGCGTGTTACAAGGC CAGGCATCCGAGAGGTCTGG
GAATGC CCATCTCCGGTTCCATGGCAT TGATGATGT CATTGC
GCTTCTCCGGAAACATTAGC Exp-1_secA-1859_I1-bc25mer_83004-20_I2-bc25mer_83517-20
ACAACCGCGTGTTACAAGGC CAGGCATCCGAGAGGTCTGG
GAATGC CGTTGGCAATCGCTTTAGTCA CCCACGGGT CATTGC
GCTTCTCCGGAAACATTAGC Exp-1_secA-1760_I1-bc25mer_83004-20_I2-bc25mer_83517-20
ACAACCGCGTGTTACAAGGC CAGGCATCCGAGAGGTCTGG
GAATGC TACGCATCAGCGCATCTTCCA TCGACAGGT CATTGC
GCTTCTCCGGAAACATTAGC Exp-1_secA-2308_I1-bc25mer_83004-20_I2-bc25mer_83517-20
ACAACCGCGTGTTACAAGGC CAGGCATCCGAGAGGTCTGG
GAATGC CAGGTGCTCTTTCCACAGGGA GTCAAGCGT CATTGC
GCTTCTCCGGAAACATTAGC Exp-1_secA-2184_I1-bc25mer_83004-20_I2-bc25mer_83517-20
ACAACCGCGTGTTACAAGGC CAGGCATCCGAGAGGTCTGG
GAATGC CGCTCACGCAGCGTCTCTTCA TGCAGTTCT CATTGC
GCTTCTCCGGAAACATTAGC Exp-1_secA-1703_I1-bc25mer_83004-20_I2-bc25mer_83517-20
ACAACCGCGTGTTACAAGGC CAGGCATCCGAGAGGTCTGG
GAATGC GACGACCAGAACGACCGCGCA ACTGGTTAT CATTGC
GCTTCTCCGGAAACATTAGC Exp-1_secA-1535_I1-bc25mer_83004-20_I2-bc25mer_83517-20
ACAACCGCGTGTTACAAGGC CAGGCATCCGAGAGGTCTGG
GAATGC CTGCCTGCCAGCTACCACCGA GCACAATAT CATTGC
GCTTCTCCGGAAACATTAGC

FIG. 4III

Exp-1_secA-1666_l1-bc25mer_83004-20_l2-bc25mer_83517-20
ACAACCGCGTGTTACAAGGC CAGGCATCCGAGAGGTCTGG
GAATGC ACGGGATTCGTGACGCTCGGT ACCGATGAT CATTGC
GCTTCTCCGGAAACATTAGC Exp-1_secA-2631_l1-bc25mer_83004-20_l2-bc25mer_83517-20
ACAACCGCGTGTTACAAGGC CAGGCATCCGAGAGGTCTGG
GAATGC CACGGGCAAGGATCGTTACGT CCTACTTTG CATTGC
GCTTCTCCGGAAACATTAGC Exp-1_secA-2078_l1-bc25mer_83004-20_l2-bc25mer_83517-20
ACAACCGCGTGTTACAAGGC CAGGCATCCGAGAGGTCTGG
GAATGC TATCCCACATTTCTTCCAGCG ACTGTGGTG CATTGC
GCTTCTCCGGAAACATTAGC Exp-1_secA-610_l1-bc25mer_83004-20_l2-bc25mer_83517-20
ACAACCGCGTGTTACAAGGC CAGGCATCCGAGAGGTCTGG
GAATGC GGAGTCCACTTCGTCCACCAG CGCATAGTG CATTGC
GCTTCTCCGGAAACATTAGC Exp-1_secA-247_l1-bc25mer_83004-20_l2-bc25mer_83517-20
ACAACCGCGTGTTACAAGGC CAGGCATCCGAGAGGTCTGG
GAATGC CATACCGCCGAGTAACTGAAC GTCGAAGTG CATTGC
GCTTCTCCGGAAACATTAGC Exp-1_secA-1348_l1-bc25mer_83004-20_l2-bc25mer_83517-20
ACAACCGCGTGTTACAAGGC CAGGCATCCGAGAGGTCTGG
GAATGC GATGGAGATAGTACCCACCAG CACCGGCTG CATTGC
GCTTCTCCGGAAACATTAGC Exp-1_secA-2427_l1-bc25mer_83004-20_l2-bc25mer_83517-20
ACAACCGCGTGTTACAAGGC CAGGCATCCGAGAGGTCTGG
GAATGC TTCAACGACTCCAGCATCGCT GCAAACATG CATTGC
GCTTCTCCGGAAACATTAGC Exp-1_secA-681_l1-bc25mer_83004-20_l2-bc25mer_83517-20
ACAACCGCGTGTTACAAGGC CAGGCATCCGAGAGGTCTGG
GAATGC TTATACATTTCCGAGCTGTCT TCTGCCGGG CATTGC
GCTTCTCCGGAAACATTAGC Exp-1_secA-351_l1-bc25mer_83004-20_l2-bc25mer_83517-20
ACAACCGCGTGTTACAAGGC CAGGCATCCGAGAGGTCTGG
GAATGC TGCACGCCTTTACCGGTTAGT GCGTTCAGG CATTGC
GCTTCTCCGGAAACATTAGC Exp-1_secA-2500_l1-bc25mer_83004-20_l2-bc25mer_83517-20
ACAACCGCGTGTTACAAGGC CAGGCATCCGAGAGGTCTGG
GAATGC CTGTTGTTCCAGCTCCTCAAC CTCTTCAGG CATTGC
GCTTCTCCGGAAACATTAGC

FIG. 4JJJ

Exp-1_secA-540_I1-bc25mer_83004-20_I2-bc25mer_83517-20
ACAACCGCGTGTTACAAGGC CAGGCATCCGAGAGGTCTGG
GAATGC TTGTCGCGCAGGTAGTCAAAG CCGTATTCG CATTGC
GCTTCTCCGGAAACATTAGC Exp-1_secA-1121_I1-bc25mer_83004-20_I2-bc25mer_83517-20
ACAACCGCGTGTTACAAGGC CAGGCATCCGAGAGGTCTGG
GAATGC ACAGACGGAAGTAGTTCTGGA AGGTGATCG CATTGC
GCTTCTCCGGAAACATTAGC Exp-1_secA-2148_I1-bc25mer_83004-20_I2-bc25mer_83517-20
ACAACCGCGTGTTACAAGGC CAGGCATCCGAGAGGTCTGG
GAATGC TTATCCAGCCACTCGGCAATT GGCAAATCG CATTGC
GCTTCTCCGGAAACATTAGC Exp-1_secA-575_I1-bc25mer_83004-20_I2-bc25mer_83517-20
ACAACCGCGTGTTACAAGGC CAGGCATCCGAGAGGTCTGG
GAATGC TACGCTGTACACGTTCTTCAG GGCTGAACG CATTGC
GCTTCTCCGGAAACATTAGC Exp-1_secA-1435_I1-bc25mer_83004-20_I2-bc25mer_83517-20
ACAACCGCGTGTTACAAGGC CAGGCATCCGAGAGGTCTGG
GAATGC CGCTTCGTTGGCGTGGAATTT GGCGTTCAG CATTGC
GCTTCTCCGGAAACATTAGC Exp-1_secA-454_I1-bc25mer_83004-20_I2-bc25mer_83517-20
ACAACCGCGTGTTACAAGGC CAGGCATCCGAGAGGTCTGG
GAATGC CATGCCCGGCAGGTTGATACC GACAGTCAG CATTGC
GCTTCTCCGGAAACATTAGC Exp-1_secA-1267_I1-bc25mer_83004-20_I2-bc25mer_83517-20
ACAACCGCGTGTTACAAGGC CAGGCATCCGAGAGGTCTGG
GAATGC CGCTTCAGTCATGTAGACCAG GTCCGGCAG CATTGC
GCTTCTCCGGAAACATTAGC Exp-1_secA-853_I1-bc25mer_83004-20_I2-bc25mer_83517-20
ACAACCGCGTGTTACAAGGC CAGGCATCCGAGAGGTCTGG
GAATGC TTCATCCATGATGCCCTCTTT CACCAGCAG CATTGC
GCTTCTCCGGAAACATTAGC Exp-1_secA-955_I1-bc25mer_83004-20_I2-bc25mer_83517-20
ACAACCGCGTGTTACAAGGC CAGGCATCCGAGAGGTCTGG
GAATGC AACGATGTAGTCGACGTCACG GGTAAACAG CATTGC
GCTTCTCCGGAAACATTAGC Exp-1_secA-763_I1-bc25mer_83004-20_I2-bc25mer_83517-20
ACAACCGCGTGTTACAAGGC CAGGCATCCGAGAGGTCTGG
GAATGC CGAGAAGTGGCCTTCGCCCTG GAAGGTTTC CATTGC
GCTTCTCCGGAAACATTAGC

FIG. 4KKK

Exp-1_secA-1500_l1-bc25mer_83004-20_l2-bc25mer_83517-20
ACAACCGCGTGTTACAAGGC CAGGCATCCGAGAGGTCTGG
GAATGC CCACGACCCGCCATATTGGTC GCGATAGTC CATTGC
GCTTCTCCGGAAACATTAGC Exp-1_secA-2343_l1-bc25mer_83004-20_l2-bc25mer_83517-20
ACAACCGCGTGTTACAAGGC CAGGCATCCGAGAGGTCTGG
GAATGC AGGTGGATACCCTGACGCAGA TAGTCCATC CATTGC
GCTTCTCCGGAAACATTAGC Exp-1_secA-1907_l1-bc25mer_83004-20_l2-bc25mer_83517-20
ACAACCGCGTGTTACAAGGC CAGGCATCCGAGAGGTCTGG
GAATGC GCAGTTGCTTACGAATGTCGA AGTTACGGC CATTGC
GCTTCTCCGGAAACATTAGC Exp-1_secA-2221_l1-bc25mer_83004-20_l2-bc25mer_83517-20
ACAACCGCGTGTTACAAGGC CAGGCATCCGAGAGGTCTGG
GAATGC TTTACGCTGATACACTTCGAT GGACTGCGC CATTGC
GCTTCTCCGGAAACATTAGC Exp-1_secA-1970_l1-bc25mer_83004-20_l2-bc25mer_83517-20
ACAACCGCGTGTTACAAGGC CAGGCATCCGAGAGGTCTGG
GAATGC ACAGTTCGTTACGCTGGGAGT AAATGGCGC CATTGC
GCTTCTCCGGAAACATTAGC Exp-1_secA-1821_l1-bc25mer_83004-20_l2-bc25mer_83517-20
ACAACCGCGTGTTACAAGGC CAGGCATCCGAGAGGTCTGG
GAATGC GCTTCGCCTGGCTTCATACCC AGTTTACGC CATTGC
GCTTCTCCGGAAACATTAGC Exp-1_secA-505_l1-bc25mer_83004-20_l2-bc25mer_83517-20
ACAACCGCGTGTTACAAGGC CAGGCATCCGAGAGGTCTGG
GAATGC CGTACCGTAAGTGATGTCAGC TGCGTAAGC CATTGC
GCTTCTCCGGAAACATTAGC Exp-1_secA-1626_l1-bc25mer_83004-20_l2-bc25mer_83517-20
ACAACCGCGTGTTACAAGGC CAGGCATCCGAGAGGTCTGG
GAATGC CCTGCTTCCAGTACCGCATCG TGACGTACC CATTGC
GCTTCTCCGGAAACATTAGC Exp-1_secA-1392_l1-bc25mer_83004-20_l2-bc25mer_83517-20
ACAACCGCGTGTTACAAGGC CAGGCATCCGAGAGGTCTGG
GAATGC ATACCGGCTTTGGTCAGTTCG TTTGACACC CATTGC
GCTTCTCCGGAAACATTAGC Exp-1_secA-2005_l1-bc25mer_83004-20_l2-bc25mer_83517-20
ACAACCGCGTGTTACAAGGC CAGGCATCCGAGAGGTCTGG
GAATGC GCTGTTAATGGTTTCGCTCAC ATCGCTGAC CATTGC
GCTTCTCCGGAAACATTAGC

FIG. 4LLL

Exp-1_secA-1231_I1-bc25mer_83004-20_I2-bc25mer_83517-20
ACAACCGCGTGTTACAAGGC CAGGCATCCGAGAGGTCTGG
GAATGC ACGAATCATTGGACGGTTGGT CGGAACAAC CATTGC
GCTTCTCCGGAAACATTAGC Exp-1_secA-282_I1-bc25mer_83004-20_I2-bc25mer_83517-20
ACAACCGCGTGTTACAAGGC CAGGCATCCGAGAGGTCTGG
GAATGC GTACGCATTTCGGCGATGCAG CGTTCGTTA CATTGC
GCTTCTCCGGAAACATTAGC Exp-1_secA-212_I1-bc25mer_83004-20_I2-bc25mer_83517-20
ACAACCGCGTGTTACAAGGC CAGGCATCCGAGAGGTCTGG
GAATGC TACCAAAGACGCGCTTACTTG CCTCACGTA CATTGC
GCTTCTCCGGAAACATTAGC Exp-1_secA-2535_I1-bc25mer_83004-20_I2-bc25mer_83517-20
ACAACCGCGTGTTACAAGGC CAGGCATCCGAGAGGTCTGG
GAATGC TGCATTTGCGCTAAACGCTCG GCTTCCATA CATTGC
GCTTCTCCGGAAACATTAGC Exp-1_secA-2273_I1-bc25mer_83004-20_I2-bc25mer_83517-20
ACAACCGCGTGTTACAAGGC CAGGCATCCGAGAGGTCTGG
GAATGC GCATGACGCCTTTCTCGAAGT GACGCATCA CATTGC
GCTTCTCCGGAAACATTAGC Exp-1_secA-386_I1-bc25mer_83004-20_I2-bc25mer_83517-20
ACAACCGCGTGTTACAAGGC CAGGCATCCGAGAGGTCTGG
GAATGC CACGTTGCGCCAGGTAGTCGT TGACGGTAA CATTGC
GCTTCTCCGGAAACATTAGC Exp-1_secA-2570_I1-bc25mer_83004-20_I2-bc25mer_83517-20
ACAACCGCGTGTTACAAGGC CAGGCATCCGAGAGGTCTGG
GAATGC CGGCTGCAGAGTCGTCATCCT GATGGCTAA CATTGC
GCTTCTCCGGAAACATTAGC Exp-1_secA-1007_I1-bc25mer_83004-20_I2-bc25mer_83517-20
ACAACCGCGTGTTACAAGGC CAGGCATCCGAGAGGTCTGG
GAATGC CCTGCATGGTACGACCGGTGT GTTCGTCAA CATTGC
GCTTCTCCGGAAACATTAGC Exp-1_secM-45_I1-bc25mer_83004-20_I2-bc25mer_83517-20
ACAACCGCGTGTTACAAGGC CAGGCATCCGAGAGGTCTGG
GAATGC ACCATCCCTAATAAGAGATGC GGCCAGAAG CATTGC
GCTTCTCCGGAAACATTAGC Exp-1_secM-346_I1-bc25mer_83004-20_I2-bc25mer_83517-20
ACAACCGCGTGTTACAAGGC CAGGCATCCGAGAGGTCTGG
GAATGC CAGCGCGCTGAGCGTATCCAG TAATGCAAG CATTGC
GCTTCTCCGGAAACATTAGC

FIG. 4MMM

Exp-1_secM-174_I1-bc25mer_83004-20_I2-bc25mer_83517-20
ACAACCGCGTGTTACAAGGC CAGGCATCCGAGAGGTCTGG
GAATGC TTCGCTTCCAGCAAGGCCAAT TGACCAAAG CATTGC
GCTTCTCCGGAAACATTAGC Exp-1_secM-81_I1-bc25mer_83004-20_I2-bc25mer_83517-20
ACAACCGCGTGTTACAAGGC CAGGCATCCGAGAGGTCTGG
GAATGC GCGTTGCTGAGCGCAGGCAAA CCTAAACTC CATTGC
GCTTCTCCGGAAACATTAGC Exp-1_secM-209_I1-bc25mer_83004-20_I2-bc25mer_83517-20
ACAACCGCGTGTTACAAGGC CAGGCATCCGAGAGGTCTGG
GAATGC AATCAACGGAATAGTTCGAAT TCGGGCGGC CATTGC
GCTTCTCCGGAAACATTAGC Exp-1_secM-311_I1-bc25mer_83004-20_I2-bc25mer_83517-20
ACAACCGCGTGTTACAAGGC CAGGCATCCGAGAGGTCTGG
GAATGC GCGCCTGAAGAGGCAAAGATT CTTCAGCAA CATTGC
GCTTCTCCGGAAACATTAGC Exp-1_speD-215_I1-bc25mer_83004-20_I2-bc25mer_83517-20
ACAACCGCGTGTTACAAGGC CAGGCATCCGAGAGGTCTGG
GAATGC CCAGAATAGTGACGCTGGCAC CCTGTGGTT CATTGC
GCTTCTCCGGAAACATTAGC Exp-1_speD-407_I1-bc25mer_83004-20_I2-bc25mer_83517-20
ACAACCGCGTGTTACAAGGC CAGGCATCCGAGAGGTCTGG
GAATGC GCGGAGAAATCACGCCGCAGG TAGAGACTT CATTGC
GCTTCTCCGGAAACATTAGC Exp-1_speD-689_I1-bc25mer_83004-20_I2-bc25mer_83517-20
ACAACCGCGTGTTACAAGGC CAGGCATCCGAGAGGTCTGG
GAATGC CGCTGTCGGTTAAGTCTTCCG GTTTGGTGT CATTGC
GCTTCTCCGGAAACATTAGC Exp-1_speD-724_I1-bc25mer_83004-20_I2-bc25mer_83517-20
ACAACCGCGTGTTACAAGGC CAGGCATCCGAGAGGTCTGG
GAATGC TTCTTTCCACAGCGCAGCGGT AATTTCCTG CATTGC
GCTTCTCCGGAAACATTAGC Exp-1_speD-759_I1-bc25mer_83004-20_I2-bc25mer_83517-20
ACAACCGCGTGTTACAAGGC CAGGCATCCGAGAGGTCTGG
GAATGC GCTGGCATATTGCGCCCGTAA TAAATCTCG CATTGC
GCTTCTCCGGAAACATTAGC Exp-1_speD-593_I1-bc25mer_83004-20_I2-bc25mer_83517-20
ACAACCGCGTGTTACAAGGC CAGGCATCCGAGAGGTCTGG
GAATGC AGACGTTCACATCCACCATGT CATACAGCG CATTGC
GCTTCTCCGGAAACATTAGC

FIG. 4NNN

Exp-1_speD-139_I1-bc25mer_83004-20_I2-bc25mer_83517-20
ACAACCGCGTGTTACAAGGC CAGGCATCCGAGAGGTCTGG
GAATGC ACAGGTTTCTGACAGGATTTC GGTCAGACG CATTGC
GCTTCTCCGGAAACATTAGC Exp-1_speD-371_I1-bc25mer_83004-20_I2-bc25mer_83517-20
ACAACCGCGTGTTACAAGGC CAGGCATCCGAGAGGTCTGG
GAATGC CGGCGCGGAAGGTACATAAAC CGCCTTCAG CATTGC
GCTTCTCCGGAAACATTAGC Exp-1_speD-301_I1-bc25mer_83004-20_I2-bc25mer_83517-20
ACAACCGCGTGTTACAAGGC CAGGCATCCGAGAGGTCTGG
GAATGC ATCAAGATGGGCAACGACCGT TTCTGGCAG CATTGC
GCTTCTCCGGAAACATTAGC Exp-1_speD-250_I1-bc25mer_83004-20_I2-bc25mer_83517-20
ACAACCGCGTGTTACAAGGC CAGGCATCCGAGAGGTCTGG
GAATGC GTCGATGAGTTTCGGGTCAAC CGGTTCTTC CATTGC
GCTTCTCCGGAAACATTAGC Exp-1_speD-85_I1-bc25mer_83004-20_I2-bc25mer_83517-20
ACAACCGCGTGTTACAAGGC CAGGCATCCGAGAGGTCTGG
GAATGC ATAAGCAATATAACCGTCGCG CTCTTCGGC CATTGC
GCTTCTCCGGAAACATTAGC Exp-1_speD-442_I1-bc25mer_83004-20_I2-bc25mer_83517-20
ACAACCGCGTGTTACAAGGC CAGGCATCCGAGAGGTCTGG
GAATGC CTCAAGCTGGTGGATCAGGTA ATTCAGCGC CATTGC
GCTTCTCCGGAAACATTAGC Exp-1_speD-477_I1-bc25mer_83004-20_I2-bc25mer_83517-20
ACAACCGCGTGTTACAAGGC CAGGCATCCGAGAGGTCTGG
GAATGC CCGCGCACGCGATAATCAATG GTTACGATA CATTGC
GCTTCTCCGGAAACATTAGC Exp-1_speE-622_I1-bc25mer_83004-20_I2-bc25mer_83517-20
ACAACCGCGTGTTACAAGGC CAGGCATCCGAGAGGTCTGG
GAATGC GCCAACGTCGCTGAAGTAATG GCTGAGTTT CATTGC
GCTTCTCCGGAAACATTAGC Exp-1_speE-367_I1-bc25mer_83004-20_I2-bc25mer_83517-20
ACAACCGCGTGTTACAAGGC CAGGCATCCGAGAGGTCTGG
GAATGC CGGATCGTCGTAGCTACCGGC GTTATGGTT CATTGC
GCTTCTCCGGAAACATTAGC Exp-1_speE-159_I1-bc25mer_83004-20_I2-bc25mer_83517-20
ACAACCGCGTGTTACAAGGC CAGGCATCCGAGAGGTCTGG
GAATGC TAGATAAACTCGTCGCGCTCG GTGGTTTGT CATTGC
GCTTCTCCGGAAACATTAGC

FIG. 4000

Exp-1_speE-194_l1-bc25mer_83004-20_l2-bc25mer_83517-20
ACAACCGCGTGTTACAAGGC CAGGCATCCGAGAGGTCTGG
GAATGC GGGCCAGTAGCGGAACATGGG TCATCATCT CATTGC
GCTTCTCCGGAAACATTAGC Exp-1_speE-229_l1-bc25mer_83004-20_l2-bc25mer_83517-20
ACAACCGCGTGTTACAAGGC CAGGCATCCGAGAGGTCTGG
GAATGC GCCGCCGATAATCAGCACATG TTTCGCGTG CATTGC
GCTTCTCCGGAAACATTAGC Exp-1_speE-462_l1-bc25mer_83004-20_l2-bc25mer_83517-20
ACAACCGCGTGTTACAAGGC CAGGCATCCGAGAGGTCTGG
GAATGC CCGATAGGATCGGTGCAGTCG GAGATAATG CATTGC
GCTTCTCCGGAAACATTAGC Exp-1_speE-729_l1-bc25mer_83004-20_l2-bc25mer_83517-20
ACAACCGCGTGTTACAAGGC CAGGCATCCGAGAGGTCTGG
GAATGC CGCGCCTGAATAATTTCGGTT GAGAGATGG CATTGC
GCTTCTCCGGAAACATTAGC Exp-1_speE-783_l1-bc25mer_83004-20_l2-bc25mer_83517-20
ACAACCGCGTGTTACAAGGC CAGGCATCCGAGAGGTCTGG
GAATGC GCCGTATGGATTGCCGGATTG TAATAACGG CATTGC
GCTTCTCCGGAAACATTAGC Exp-1_speE-332_l1-bc25mer_83004-20_l2-bc25mer_83517-20
ACAACCGCGTGTTACAAGGC CAGGCATCCGAGAGGTCTGG
GAATGC GATACTGACGGCAGAACGATA CGACACCCG CATTGC
GCTTCTCCGGAAACATTAGC Exp-1_speE-122_l1-bc25mer_83004-20_l2-bc25mer_83517-20
ACAACCGCGTGTTACAAGGC CAGGCATCCGAGAGGTCTGG
GAATGC CATCCAGCGCCATTACGCGAC CAAATGCAG CATTGC
GCTTCTCCGGAAACATTAGC Exp-1_speE-406_l1-bc25mer_83004-20_l2-bc25mer_83517-20
ACAACCGCGTGTTACAAGGC CAGGCATCCGAGAGGTCTGG
GAATGC AACGAAATTGACGCCATCGTC GATCACCAG CATTGC
GCTTCTCCGGAAACATTAGC Exp-1_speE-37_l1-bc25mer_83004-20_l2-bc25mer_83517-20
ACAACCGCGTGTTACAAGGC CAGGCATCCGAGAGGTCTGG
GAATGC ATCTACCGCAAAGTACTGCCC AAACTGGTC CATTGC
GCTTCTCCGGAAACATTAGC Exp-1_speE-666_l1-bc25mer_83004-20_l2-bc25mer_83517-20
ACAACCGCGTGTTACAAGGC CAGGCATCCGAGAGGTCTGG
GAATGC GTCATGATACCGCCGTAATAG GTCGGGATC CATTGC
GCTTCTCCGGAAACATTAGC

FIG. 4PPP

Exp-1_speE-542_I1-bc25mer_83004-20_I2-bc25mer_83517-20
ACAACCGCGTGTTACAAGGC CAGGCATCCGAGAGGTCTGG
GAATGC GTGCGACGAAGATACCGCCAG GATTCAGGC CATTGC
GCTTCTCCGGAAACATTAGC Exp-1_speE-824_I1-bc25mer_83004-20_I2-bc25mer_83517-20
ACAACCGCGTGTTACAAGGC CAGGCATCCGAGAGGTCTGG
GAATGC AAGCCAGTGCGTCTTGCAGAT ACTGAGGTA CATTGC
GCTTCTCCGGAAACATTAGC Exp-1_yacC-248_I1-bc25mer_83004-20_I2-bc25mer_83517-20
ACAACCGCGTGTTACAAGGC CAGGCATCCGAGAGGTCTGG
GAATGC CAATGCCGCTGAGATCGCGGT AGCTGTCTT CATTGC
GCTTCTCCGGAAACATTAGC Exp-1_yacC-80_I1-bc25mer_83004-20_I2-bc25mer_83517-20
ACAACCGCGTGTTACAAGGC CAGGCATCCGAGAGGTCTGG
GAATGC CTGCCGTTAAATCGGCCATAT CTTCGGCTT CATTGC
GCTTCTCCGGAAACATTAGC Exp-1_yacC-21_I1-bc25mer_83004-20_I2-bc25mer_83517-20
ACAACCGCGTGTTACAAGGC CAGGCATCCGAGAGGTCTGG
GAATGC CAGACGGCCATCAGGCTGCCG AATAACACT CATTGC
GCTTCTCCGGAAACATTAGC Exp-1_yacC-315_I1-bc25mer_83004-20_I2-bc25mer_83517-20
ACAACCGCGTGTTACAAGGC CAGGCATCCGAGAGGTCTGG
GAATGC TTGACGTAGGCAAGCAGGCTT AAGGAATCG CATTGC
GCTTCTCCGGAAACATTAGC Exp-1_yacC-203_I1-bc25mer_83004-20_I2-bc25mer_83517-20
ACAACCGCGTGTTACAAGGC CAGGCATCCGAGAGGTCTGG
GAATGC TGTCGAAGGTGTCGTAATTAC TGAGGTCCC CATTGC
GCTTCTCCGGAAACATTAGC Exp-1_yacC-149_I1-bc25mer_83004-20_I2-bc25mer_83517-20
ACAACCGCGTGTTACAAGGC CAGGCATCCGAGAGGTCTGG
GAATGC CCAGTGCGCGACGAATTTGCC CGTTAGGTA CATTGC
GCTTCTCCGGAAACATTAGC Exp-1_yacF-506_I1-bc25mer_83004-20_I2-bc25mer_83517-20
ACAACCGCGTGTTACAAGGC CAGGCATCCGAGAGGTCTGG
GAATGC CCGACTGGCGAATTAAATCCA GCACCATGG CATTGC
GCTTCTCCGGAAACATTAGC Exp-1_yacF-117_I1-bc25mer_83004-20_I2-bc25mer_83517-20
ACAACCGCGTGTTACAAGGC CAGGCATCCGAGAGGTCTGG
GAATGC TCACTGACATTACGGAAGAAA TGCAGCGCG CATTGC
GCTTCTCCGGAAACATTAGC

FIG. 4QQQ

Exp-1_yacF-715_l1-bc25mer_83004-20_l2-bc25mer_83517-20
ACAACCGCGTGTTACAAGGC CAGGCATCCGAGAGGTCTGG
GAATGC TTAGCAACAGGCCAGTTCGAA ATCCAGACG CATTGC
GCTTCTCCGGAAACATTAGC Exp-1_yacF-613_l1-bc25mer_83004-20_l2-bc25mer_83517-20
ACAACCGCGTGTTACAAGGC CAGGCATCCGAGAGGTCTGG
GAATGC TTGCGGATAAAGCTGTGAATC GAGCGACAG CATTGC
GCTTCTCCGGAAACATTAGC Exp-1_yacF-210_l1-bc25mer_83004-20_l2-bc25mer_83517-20
ACAACCGCGTGTTACAAGGC CAGGCATCCGAGAGGTCTGG
GAATGC ACGCCAATCCAGGTCTGGAGT TTACGTTGC CATTGC
GCTTCTCCGGAAACATTAGC Exp-1_yacF-245_l1-bc25mer_83004-20_l2-bc25mer_83517-20
ACAACCGCGTGTTACAAGGC CAGGCATCCGAGAGGTCTGG
GAATGC TTAATGCTTCAATACGGCTCT GGTCCACGC CATTGC
GCTTCTCCGGAAACATTAGC Exp-1_yacF-385_l1-bc25mer_83004-20_l2-bc25mer_83517-20
ACAACCGCGTGTTACAAGGC CAGGCATCCGAGAGGTCTGG
GAATGC TGTAGGTAAATCAAAGCTGCA ACAGCCGCC CATTGC
GCTTCTCCGGAAACATTAGC Exp-1_yacF-175_l1-bc25mer_83004-20_l2-bc25mer_83517-20
ACAACCGCGTGTTACAAGGC CAGGCATCCGAGAGGTCTGG
GAATGC GTCAAGTTCTTTCAACAGCTC AGTGCGGAC CATTGC
GCTTCTCCGGAAACATTAGC Exp-1_yacF-305_l1-bc25mer_83004-20_l2-bc25mer_83517-20
ACAACCGCGTGTTACAAGGC CAGGCATCCGAGAGGTCTGG
GAATGC GAAATTGCCCGATACGCGGCG CGGAAATTA CATTGC
GCTTCTCCGGAAACATTAGC Exp-1_yacF-461_l1-bc25mer_83004-20_l2-bc25mer_83517-20
ACAACCGCGTGTTACAAGGC CAGGCATCCGAGAGGTCTGG
GAATGC GCGGGTTCAGGCTGGCAATCC AGGTTTCTA CATTGC
GCTTCTCCGGAAACATTAGC Exp-1_yacF-349_l1-bc25mer_83004-20_l2-bc25mer_83517-20
ACAACCGCGTGTTACAAGGC CAGGCATCCGAGAGGTCTGG
GAATGC GCTCAGTCGCTGACGCACCAG AGCAATCAA CATTGC
GCTTCTCCGGAAACATTAGC Exp-1_yacG-10_l1-bc25mer_83004-20_l2-bc25mer_83517-20
ACAACCGCGTGTTACAAGGC CAGGCATCCGAGAGGTCTGG
GAATGC CCCGCAGGTTGGGCAATTCAC CGTAATAGT CATTGC
GCTTCTCCGGAAACATTAGC

FIG. 4RRR

Exp-1_yacG-169_I1-bc25mer_83004-20_I2-bc25mer_83517-20
ACAACCGCGTGTTACAAGGC CAGGCATCCGAGAGGTCTGG
GAATGC TCACTGCTTTGGTTCTTCGCT CCAGTCATC CATTGC
GCTTCTCCGGAAACATTAGC Exp-1_yacG-101_I1-bc25mer_83004-20_I2-bc25mer_83517-20
ACAACCGCGTGTTACAAGGC CAGGCATCCGAGAGGTCTGG
GAATGC CTTCAGCAGCCCATTCTCCGA GGTCGATCA CATTGC
GCTTCTCCGGAAACATTAGC Exp-1_yacL-284_I1-bc25mer_83004-20_I2-bc25mer_83517-20
ACAACCGCGTGTTACAAGGC CAGGCATCCGAGAGGTCTGG
GAATGC CCTCAACGCCGCATAGCGACA GGCTTTCTT CATTGC
GCTTCTCCGGAAACATTAGC Exp-1_yacL-191_I1-bc25mer_83004-20_I2-bc25mer_83517-20
ACAACCGCGTGTTACAAGGC CAGGCATCCGAGAGGTCTGG
GAATGC CCATCACCTCTTCACCGTCCA TCCACAGGG CATTGC
GCTTCTCCGGAAACATTAGC Exp-1_yacL-110_I1-bc25mer_83004-20_I2-bc25mer_83517-20
ACAACCGCGTGTTACAAGGC CAGGCATCCGAGAGGTCTGG
GAATGC GCGCTGCTTGTTCCACTTCAT CAAGCAAGG CATTGC
GCTTCTCCGGAAACATTAGC Exp-1_yacL-145_I1-bc25mer_83004-20_I2-bc25mer_83517-20
ACAACCGCGTGTTACAAGGC CAGGCATCCGAGAGGTCTGG
GAATGC CCGTTGCCAGGACCGTTCGCT ACCTTTCAG CATTGC
GCTTCTCCGGAAACATTAGC Exp-1_yacL-226_I1-bc25mer_83004-20_I2-bc25mer_83517-20
ACAACCGCGTGTTACAAGGC CAGGCATCCGAGAGGTCTGG
GAATGC TTCATCGCCAGCGAATTCCAG TTGATTGGC CATTGC
GCTTCTCCGGAAACATTAGC Exp-1_yacL-333_I1-bc25mer_83004-20_I2-bc25mer_83517-20
ACAACCGCGTGTTACAAGGC CAGGCATCCGAGAGGTCTGG
GAATGC TACTTCTGCTGCACGAAATTG CGGTAAGCC CATTGC
GCTTCTCCGGAAACATTAGC Exp-1_yacL-69_I1-bc25mer_83004-20_I2-bc25mer_83517-20
ACAACCGCGTGTTACAAGGC CAGGCATCCGAGAGGTCTGG
GAATGC TTCACCTCTTCATTAAACCAG TGCCCGACC CATTGC
GCTTCTCCGGAAACATTAGC Exp-1_yacL-27_I1-bc25mer_83004-20_I2-bc25mer_83517-20
ACAACCGCGTGTTACAAGGC CAGGCATCCGAGAGGTCTGG
GAATGC ATGGACATACGCACCTTTACC ACTCCGGTA CATTGC
GCTTCTCCGGAAACATTAGC

FIG. 4SSS

Exp-1_yadG-726_I1-bc25mer_83004-20_I2-bc25mer_83517-20
ACAACCGCGTGTTACAAGGC CAGGCATCCGAGAGGTCTGG
GAATGC AGTCGATACTGATAGCCATCG AGCTTCGGT CATTGC
GCTTCTCCGGAAACATTAGC Exp-1_yadG-761_I1-bc25mer_83004-20_I2-bc25mer_83517-20
ACAACCGCGTGTTACAAGGC CAGGCATCCGAGAGGTCTGG
GAATGC GCAGCACTTCAACTTCCAGCG TCGCGGTAT CATTGC
GCTTCTCCGGAAACATTAGC Exp-1_yadG-575_I1-bc25mer_83004-20_I2-bc25mer_83517-20
ACAACCGCGTGTTACAAGGC CAGGCATCCGAGAGGTCTGG
GAATGC GCATTTCTGCTTCTTCCAGGT AGTGTGTGG CATTGC
GCTTCTCCGGAAACATTAGC Exp-1_yadG-870_I1-bc25mer_83004-20_I2-bc25mer_83517-20
ACAACCGCGTGTTACAAGGC CAGGCATCCGAGAGGTCTGG
GAATGC ACCAGTGAAACAAACAGCTCT TCCAGACGG CATTGC
GCTTCTCCGGAAACATTAGC Exp-1_yadG-281_I1-bc25mer_83004-20_I2-bc25mer_83517-20
ACAACCGCGTGTTACAAGGC CAGGCATCCGAGAGGTCTGG
GAATGC CTGCCTGATTCACCACAATTT GCTGCACGG CATTGC
GCTTCTCCGGAAACATTAGC Exp-1_yadG-393_I1-bc25mer_83004-20_I2-bc25mer_83517-20
ACAACCGCGTGTTACAAGGC CAGGCATCCGAGAGGTCTGG
GAATGC ATCCCGCCAGATAACATACGC GCACGTTCG CATTGC
GCTTCTCCGGAAACATTAGC Exp-1_yadG-227_I1-bc25mer_83004-20_I2-bc25mer_83517-20
ACAACCGCGTGTTACAAGGC CAGGCATCCGAGAGGTCTGG
GAATGC CCTGCGGCACCAGTCCCAACT GACGTTTAG CATTGC
GCTTCTCCGGAAACATTAGC Exp-1_yadG-428_I1-bc25mer_83004-20_I2-bc25mer_83517-20
ACAACCGCGTGTTACAAGGC CAGGCATCCGAGAGGTCTGG
GAATGC GCATTAACGCACGGGCAATCA TTAAACGGC CATTGC
GCTTCTCCGGAAACATTAGC Exp-1_yadG-497_I1-bc25mer_83004-20_I2-bc25mer_83517-20
ACAACCGCGTGTTACAAGGC CAGGCATCCGAGAGGTCTGG
GAATGC ACATTGAGCGGCGAAGTTCAA TATCCACGC CATTGC
GCTTCTCCGGAAACATTAGC Exp-1_yadG-182_I1-bc25mer_83004-20_I2-bc25mer_83517-20
ACAACCGCGTGTTACAAGGC CAGGCATCCGAGAGGTCTGG
GAATGC TCTCGAGATCGTAACCAAATA CGCTGACCC CATTGC
GCTTCTCCGGAAACATTAGC

FIG. 4TTT

Exp-1_yadG-316_I1-bc25mer_83004-20_I2-bc25mer_83517-20
ACAACCGCGTGTTACAAGGC CAGGCATCCGAGAGGTCTGG
GAATGC GATGTACGCTTCTTTGCGCTC CACGCCGTA CATTGC
GCTTCTCCGGAAACATTAGC Exp-1_yadG-685_I1-bc25mer_83004-20_I2-bc25mer_83517-20
ACAACCGCGTGTTACAAGGC CAGGCATCCGAGAGGTCTGG
GAATGC CGGTGCGAGATCGAGAATAAA GGTTTCCGA CATTGC
GCTTCTCCGGAAACATTAGC Exp-1_yadG-617_I1-bc25mer_83004-20_I2-bc25mer_83517-20
ACAACCGCGTGTTACAAGGC CAGGCATCCGAGAGGTCTGG
GAATGC CCACCAGCTCACCGTGTTGAA TAATGCCGA CATTGC
GCTTCTCCGGAAACATTAGC Exp-1_yadG-66_I1-bc25mer_83004-20_I2-bc25mer_83517-20
ACAACCGCGTGTTACAAGGC CAGGCATCCGAGAGGTCTGG
GAATGC TCACCCGCTTCGACCTGCAAA TCTATCCCA CATTGC
GCTTCTCCGGAAACATTAGC Exp-1_yadH-217_I1-bc25mer_83004-20_I2-bc25mer_83517-20
ACAACCGCGTGTTACAAGGC CAGGCATCCGAGAGGTCTGG
GAATGC TGATGACGCAACGTTGGCGTA GGCATTGGT CATTGC
GCTTCTCCGGAAACATTAGC Exp-1_yadH-742_I1-bc25mer_83004-20_I2-bc25mer_83517-20
ACAACCGCGTGTTACAAGGC CAGGCATCCGAGAGGTCTGG
GAATGC TTAGCTACGCAAACCACGTCC ACGTTGGAT CATTGC
GCTTCTCCGGAAACATTAGC Exp-1_yadH-53_I1-bc25mer_83004-20_I2-bc25mer_83517-20
ACAACCGCGTGTTACAAGGC CAGGCATCCGAGAGGTCTGG
GAATGC GCGTCTGCACCCAGATACGCA TAAAGCGAT CATTGC
GCTTCTCCGGAAACATTAGC Exp-1_yadH-88_I1-bc25mer_83004-20_I2-bc25mer_83517-20
ACAACCGCGTGTTACAAGGC CAGGCATCCGAGAGGTCTGG
GAATGC AAAGTAAAGGGTCATGGTGAT GACTGGCGG CATTGC
GCTTCTCCGGAAACATTAGC Exp-1_yadH-463_I1-bc25mer_83004-20_I2-bc25mer_83517-20
ACAACCGCGTGTTACAAGGC CAGGCATCCGAGAGGTCTGG
GAATGC GGCAAACACACCGTTCAGCAA ACCCGCAAG CATTGC
GCTTCTCCGGAAACATTAGC Exp-1_yadH-519_I1-bc25mer_83004-20_I2-bc25mer_83517-20
ACAACCGCGTGTTACAAGGC CAGGCATCCGAGAGGTCTGG
GAATGC TACGTGAGTGGCGTTAACACA AAGGTTGGC CATTGC
GCTTCTCCGGAAACATTAGC

FIG. 4UUU

Exp-1_yadH-151_I1-bc25mer_83004-20_I2-bc25mer_83517-20
ACAACCGCGTGTTACAAGGC CAGGCATCCGAGAGGTCTGG
GAATGC CTGCATATAGCTGAAGCCATG CATATCGCC CATTGC
GCTTCTCCGGAAACATTAGC Exp-1_yadH-599_I1-bc25mer_83004-20_I2-bc25mer_83517-20
ACAACCGCGTGTTACAAGGC CAGGCATCCGAGAGGTCTGG
GAATGC TATAAACGATTGGGTTCAGGT GCGACAGCC CATTGC
GCTTCTCCGGAAACATTAGC Exp-1_yadH-297_I1-bc25mer_83004-20_I2-bc25mer_83517-20
ACAACCGCGTGTTACAAGGC CAGGCATCCGAGAGGTCTGG
GAATGC TATCCGGCAATAATGACGTGA GTCGGAACC CATTGC
GCTTCTCCGGAAACATTAGC Exp-1_yadH-419_I1-bc25mer_83004-20_I2-bc25mer_83517-20
ACAACCGCGTGTTACAAGGC CAGGCATCCGAGAGGTCTGG
GAATGC CCGTGAGCACCAGCGTTAAGG CAACGAATA CATTGC
GCTTCTCCGGAAACATTAGC Exp-1_yadH-653_I1-bc25mer_83004-20_I2-bc25mer_83517-20
ACAACCGCGTGTTACAAGGC CAGGCATCCGAGAGGTCTGG
GAATGC TGACCAGCGGAACATCATTGA TACCGAGGA CATTGC
GCTTCTCCGGAAACATTAGC Exp-1_yadH-688_I1-bc25mer_83004-20_I2-bc25mer_83517-20
ACAACCGCGTGTTACAAGGC CAGGCATCCGAGAGGTCTGG
GAATGC CGCCACAATAAAGACCACCAG TACGCCAAA CATTGC
GCTTCTCCGGAAACATTAGC

FIG. 4VVV

PROBE LIBRARY CONSTRUCTION

RELATED APPLICATIONS

This application is a national stage filing of International Patent Application Serial No. PCT/US2015/042559, filed Jul. 29, 2015, which claims the benefit of U.S. Provisional Patent Application Ser. No. 62/050,636, filed Sep. 15, 2014, entitled "Probe Library Construction," by Zhuang, et al.; U.S. Provisional Patent Application Ser. No. 62/031,062, filed Jul. 30, 2014, entitled "Systems and Methods for Determining Nucleic Acids," by Zhuang, et al.; and U.S. Provisional Patent Application Ser. No. 62/142,653, filed Apr. 3, 2015, entitled "Systems and Methods for Determining Nucleic Acids," by Zhuang, et al. Each of the above is incorporated herein by reference.

GOVERNMENT FUNDING

This invention was made with government support under Grant No. GM096450 awarded by the National Institutes of Health. The government has certain rights in the invention.

FIELD

The present invention generally relates to systems and methods for producing nucleic acids.

BACKGROUND

Custom-synthesized, oligonucleotide probes have emerged as a powerful tool for the identification and isolation of specific nucleic acid targets via hybridization. Applications for such hybridization probe sets range from next generation sequencing—where such probes are used to enrich or deplete samples for specific nucleic acid targets—to imaging of fixed samples—where fluorescently labeled hybridization probes allow the direct measurement of the number and spatial organization of the targeted species.

There are now a wide range of commercial sources for such probes. Such probes are often made by synthesizing each oligonucleotide member using standard solid phase synthesis methods. Unfortunately, this limits both the number of probes within a single set and the number of unique sets, due to the requirement that each oligonucleotide member must be individually and separately synthesized.

Recent advances in array-based synthesis of oligonucleotides by several companies have reduced the cost of producing oligonucleotides. However, these approaches also result in 1000-fold less oligonucleotide probes than is required for a single hybridization reaction, thus limiting their usefulness. Accordingly, improvements in oligonucleotide production are needed.

SUMMARY

The present invention generally relates to systems and methods for producing nucleic acids. The subject matter of the present invention involves, in some cases, interrelated products, alternative solutions to a particular problem, and/or a plurality of different uses of one or more systems and/or articles.

In one aspect, the present invention is generally directed to a method. The method, in accordance with one set of embodiments, includes amplifying at least some of a plurality of oligonucleotides using real-time PCR to produce amplified oligonucleotides, transcribing in vitro at least some of the amplified oligonucleotides to produce RNA, reverse transcribing the RNA to produce transcribed DNA, and selectively degrading the RNA relative to the transcribed DNA.

In another set of embodiments, the method includes simultaneously amplifying at least some of a plurality of oligonucleotides in a common solution using PCR to produce amplified oligonucleotides, transcribing in vitro at least some of the amplified oligonucleotides to produce RNA, reverse transcribing the RNA to produce transcribed DNA, and selectively degrading the RNA relative to the transcribed DNA.

In yet another set of embodiments, the method includes acts of providing a plurality of oligonucleotides having an average length of between 10 and 200 nucleotides and including at least 100 unique oligonucleotide sequences, producing amplified oligonucleotides comprising one of the plurality of oligonucleotides and a promoter using real-time PCR, transcribing at least some of the amplified oligonucleotides to produce RNA using an RNA polymerase, reverse transcribing the RNA to produce DNA using a primer comprising a signaling entity, and chemically reducing the RNA.

The method, in still another set of embodiments, includes acts of providing a plurality of oligonucleotides having an average length of between 10 and 200 nucleotides and including at least 100 unique oligonucleotide sequences, producing amplified oligonucleotides in a common solution comprising one of the plurality of oligonucleotides and a promoter using PCR, transcribing at least some of the amplified oligonucleotides to produce RNA using an RNA polymerase, reverse transcribing the RNA to produce DNA using a primer comprising a signaling entity, and chemically reducing the RNA.

In another aspect, the present invention encompasses methods of making one or more of the embodiments described herein, such as oligonucleotides, including but not limited to modified oligonucleotides such as those described herein (e.g., labeled with a signaling entity). In still another aspect, the present invention encompasses methods of using one or more of the embodiments described herein, for example, such as oligonucleotides, including but not limited to modified oligonucleotides such as those described herein (e.g., labeled with a signaling entity).

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 3A-3D list optimized primers from the *E. coli* transcriptome, in another embodiment of the invention (the sequences, from top to bottom and left to right, by page, correspond to SEQ ID NOs: 4-57, 58-111, 112-165, and 166-201); and FIGS. 4A-4BV show various probes in accordance with yet another embodiment of the invention. The sequences in FIGS. 4A-4BV, from top to bottom and left to right, by page, correspond to SEQ ID NOs: 202-221, 222-243, 244-265, 266-287, 288-309, 310-331, 332-353, 354-375, 376-397, 398-419, 420-441, 442-463, 464-485, 486-507, 508-529, 530-551, 552-573, 574-595, 596-617, 618-639, 640-661, 662-683, 684-705, 706-727, 728-749, 750-771, 772-793, 794-815, 816-837, 838-859, 860-881, 882-903, 904-925, and 926-937.

DETAILED DESCRIPTION

Figures 1, 2:
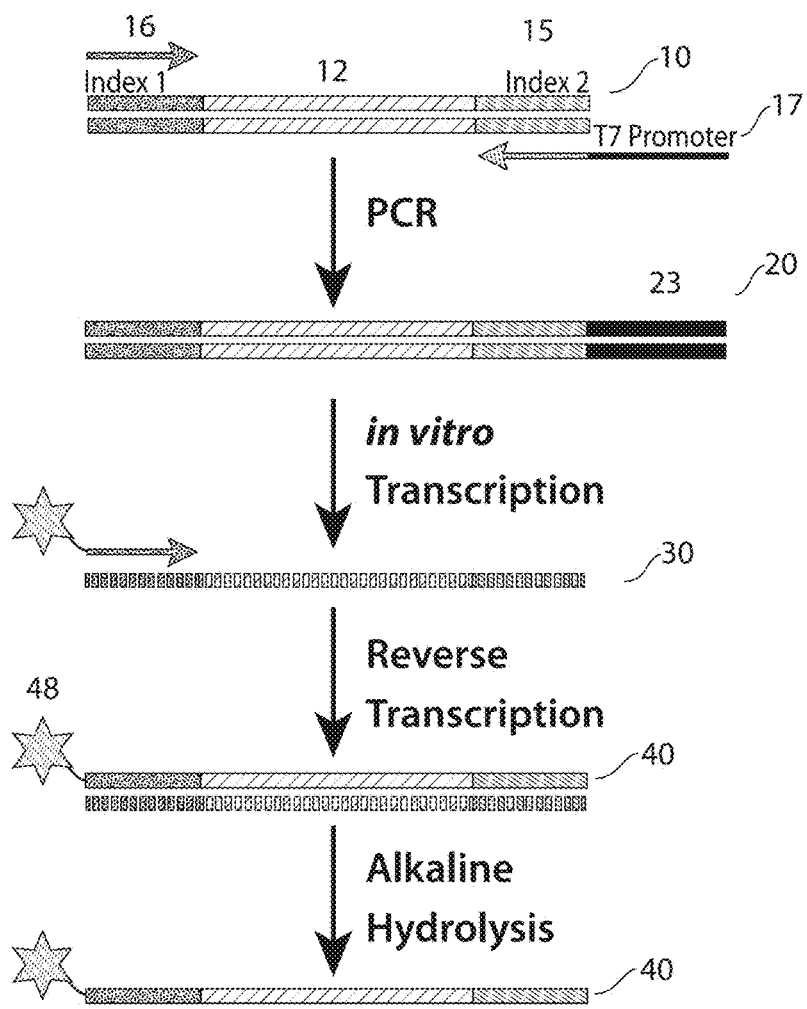
FIG. 1 illustrate the production of DNA probes, in accordance with one set of embodiments.
FIG. 2 illustrates a template molecule (SEQ ID NO: 3) produced in accordance with one embodiment of the invention.

The present invention generally relates to systems and methods for producing nucleic acids. In some aspects, relatively large quantities of oligonucleotides can be produced, and in some cases, the oligonucleotides may have a variety of different sequences and/or lengths. For instance, a relatively small quantity of oligonucleotides may be amplified to produce a large amount of nucleotides. In one set of embodiments, oligonucleotides may be amplified using PCR, then transcribed to produce RNA. The RNA may then be reverse transcribed to produce DNA, and optionally, the RNA may be selectively degraded or removed, relative to the DNA. In one set of embodiments, the oligonucleotides may be chemically modified. These modifications may include, but are not limited to, the adding of fluorescent dyes or other signaling entities.

U.S. Provisional Patent Application Ser. No. 62/031,062, filed Jul. 30, 2014, entitled "Systems and Methods for Determining Nucleic Acids," by Zhuang, et al. is incorporated herein by reference in its entirety.

In one aspect, the present invention is generally directed to in vitro methods of amplifying a plurality of oligonucleotides. In some cases, relatively large numbers of unique oligonucelotides within a plurality of oligonucleotides may be amplified. For instance, a plurality of oligonucleotides to be amplified may include 10, 100, 1,000, or more unique sequences.

In addition, in some embodiments, the oligonucleotides may be amplified without selective amplification of some oligonucleotides over others, e.g., due to competitive effects. Although some drift may occur, it is desired that the relative ratios of the oligonucleotides within a plurality of oligonucleotides stay substantially the same after amplification, at least for some applications. However, in many amplification techniques, due to differences in binding or affinity of different oligonucleotides, some oligonucleotides may be amplified to a greater degree than others, and thus, specific techniques need to be utilized to reduce or eliminate this problem, for example, by separately amplifying each of the oligonucleotides before combining them together to form the plurality of oligonucleotides. In contrast, as is discussed herein, in certain embodiments, a plurality of oligonucleotides can be amplified without causing substantial alterations or changes in the ratios of the oligonucleotides, without requiring separation of the oligonucleotides, separate growth of the oligonucleotides, or other cumbersome techniques.

Referring now to FIG. 1, one example of an embodiment of the invention is now illustrated. In this figure, a plurality of oligonucleotides 10 is provided. This may include 1, 10, 100, 1,000, 10,000, 100,000, or any other suitable number of unique oligonucleotide sequences. Of course, more than one copy of any particular unique oligonucleotide may also be present as well within the plurality of oligonucleotides. The unique oligonucleotides may have the same or different lengths. In some cases, the plurality of oligonucleotides have an overall average length (number average or arithmetic mean) of less than 200 nt (nucleotides), although longer average lengths are also possible in some embodiments.

The plurality of oligonucleotides 10 may initially be amplified, using PCR (polymerase chain reaction) or another suitable oligonucleotide amplification method, to produce a plurality of amplified oligonucleotides 20. In some cases, PCR may be used to generate thousands to millions of copies per oligonucleotide within the plurality of oligonucleotides. In some embodiments, the plurality of oligonucleotides may be amplified while still contained in a common solution, for instance, without requiring separation of the oligonucleotides prior to amplification, e.g., as is required in certain techniques such as emulsion PCR.

Within a common solution, while it is possible that different oligonucleotides of the plurality of oligonucleotides may be amplified at different rates (e.g., leading to non-uniform amplification of the plurality of oligonucleotides, and the potential loss of complexity or species within the plurality of oligonucleotides during amplification), in certain embodiments, this can be reduced or minimized through the use of various oligonucleotide structures and/or through the use of certain types of PCR techniques, as is discussed herein.

As an example, in one set of embodiments, the plurality of oligonucleotides may all be chosen to minimize competitive effects, e.g., as caused by differences in binding or affinity of the oligonucleotides to reagents within the common solution or the preferential enzymatic amplification of some sequence features. For example, in one set of embodiments, the plurality of oligonucleotides may be chosen to have similar lengths and/or sequences.

As is shown in FIG. 1, the plurality of oligonucleotides may each contain one or more index regions 15, 16 on one or both ends of the oligonucleotides that can be recognized by certain reagents. In some cases, the oligonucleotides of the plurality of oligonucleotides may have one or more index regions to which suitable primers can interact with in order to allow PCR or other amplification to occur. In some embodiments, these index regions can be used to selectively produce DNA probes only from subset of the plurality of oligonucleotides 10.

These index regions can also be used in some instances to add additional sequences to that of the plurality of oligonucleotides, e.g., as is shown in FIG. 1, oligonucleotide 11 may include an index region 15, to which a sequence 17 containing a T7 promoter can bind and be introduced into the amplified oligonucleotides (e.g., as region 23). Various sequences may thus be applied to the plurality of oligonucleotides that include a portion able to bind an index region. In some cases, if substantially all of the plurality of oligonucleotides contain similar or identical index regions, the relative affinities or binding to the index regions of the oligonucleotides by enzymes such as polymerases may be substantially similar or identical, which may allow for relatively uniform amplification to occur. The plurality of oligonucleotides may also contain other different regions that can be varied to produce a plurality of unique oligonucleotides, e.g., region 12. These regions can vary in terms of length and/or sequence, etc.

In some embodiments, the amount of amplification that occurs may be carefully controlled by monitoring the PCR amplification reaction, e.g., using techniques such as real-time PCR. This may occur, for example, using oligonucleotides having common index regions, substantially similar lengths and/or sequences, etc., including those previously discussed, or with other suitable pluralities of oligonucleotides. For instance, in some embodiments, the PCR reaction may be monitored by illuminating the solution containing the oligonucleotides with suitable light and determining the amount of fluorescence that is present, which can be related to the DNA present within the sample. Techniques for monitoring PCR reactions, such as real-time PCR methodologies, are known to those of ordinary skill in the art. The PCR reaction can also be controlled, in some embodiments, by controlling the amount and/or concentration of nucleotides and/or cofactors that are present.

After amplification, the plurality of amplified oligonucleotides 20 may be transcribed to produce a plurality of RNAs 30, as is shown in the example of FIG. 1. This may be performed, for example, by exposing the amplified oligonucleotides to a suitable RNA polymerase, such as T7 RNA polymerase, that can transcribe the oligonucleotides to produce corresponding RNA. The amount of RNA production can be controlled in some embodiments by controlling the amount and/or concentration of nucleotides and/or cofactors that are present as well as the duration of the in vitro transcription reaction.

The plurality of RNAs 30, may then be used to produce additional amounts of DNA 40, e.g., by using reverse transcription. For example a suitable enzyme, such as reverse transcriptase, may be used to perform the reverse transcription. In some cases, primers may be used to facilitate transcription, and in some embodiments, the primers may also be used to attach additional entities to the DNA. For example, signaling entities may be attached, as is shown with signaling entity 48 in FIG. 1. Alternatively, additional nucleic acid sequences can also be attached, which can serve to recruit additional oligonucleotides via Watson-Crick base-pairing. The amount of DNA that is produced can be controlled, for example, by controlling the amount and/or concentration of nucleotides and/or cofactors that are present as well as the duration and temperature of the reverse transcription reaction.

In some embodiments, multiple copies of DNA may be produced from each RNA molecule. In addition, optionally, the RNA may then be removed or selectively degraded, relative to the DNA, for example, through alkaline hydrolysis, enzymatic digestion, or other techniques.

Accordingly, in certain aspects, the present invention is generally directed to systems and methods of amplifying a plurality of oligonucleotides. In one set of embodiments, relatively large quantities or masses of oligonucleotides can be produced as is discussed herein, e.g., at least about $10^{-3}$ pmol, at least about $10^{-2}$ pmol, at least about $10^{-1}$ pmol, at least about $10^{0}$ pmol, at least about $10^{1}$ pmol, at least about $10^{2}$ pmol, at least about $10^{3}$ pmol, etc. In addition, in some embodiments, the plurality of oligonucleotides may be substantially diverse. For example, the plurality of oligonucleotides may include at least about $10^{1}$, at least about $10^{2}$, at least about $10^{3}$, at least about $10^{4}$, at least about $10^{5}$, or at least about $10^{6}$ unique sequences of oligonucleotides, even after amplification to the amounts discussed above. (It should also be noted that a plurality or population of oligonucleotides may include more than one copy of a given unique oligonucleotide sequence.) In contrast, certain prior art techniques are able to amplify large numbers of unique oligonucleotides, but to only small quantities or masses (e.g., to amounts of around $10^{-3}$ pmol or less), or are able to produce large quantities or masses of oligonucleotides, but only for 1 or a few unique sequences (e.g., less than 10 sequences).

As discussed, in certain embodiments, a plurality of oligonucleotides, which may include a plurality of unique sequences of oligonucleotides such as those described above, may be amplified without substantial selective amplification of some oligonucleotide sequences over others, e.g., due to competitive effects, unlike in many prior art techniques. Although some drift may occur during the amplification process, the drift may be relatively small. For example, in certain embodiments, the ratios or percentages of a representative unique oligonucleotide sequence, relative to the starting overall population, on the average, may change upon amplification by no more than about 10%, no more than about 8%, no more than about 6%, no more than about 5%, no more than about 4%, no more than about 3%, no more than about 2%, no more than about 1%, etc., relative to the starting ratio or percentage of the oligonucleotide sequence, prior to amplification. However, it should be noted that the oligonucleotide sequence itself, prior to any amplification, may also exhibit some variability, which is not included in the above numbers.

The unique oligonucleotides within a plurality of oligonucleotides may have the same or different lengths. If more than one unique oligonucleotide is present, then the unique oligonucleotides may independently have the same or different lengths. For example, in some cases, a plurality of oligonucleotides may have an average length (number average) of at least 5, at least 10, at least 15, at least 20, at least 25, at least 30, at least 35, at least 40, at least 50, at least 60, at least 65, at least 75, at least 100, at least 125, at least 150, at least 175, at least 200, at least 250, at least 300, at least 350, at least 400, or at least 450 nucleotides. In some cases, the average length may be no more than 500, no more than 450, no more than 400, no more than 350, no more than 300, no more than 250, no more than 200, no more than 175, no more than 150, no more than 125, no more than 100, be no more than 75, no more than 60, no more than 65, no more than 60, no more than 55, no more than 50, no more than 45, no more than 40, no more than 35, no more than 30, no more than 20, or no more than 10 nucleotides. Combinations of any of these are also possible, e.g., the average length may be between 10 and 30 nucleotides, between 20 and 40 nucleotides, between 5 and 50 nucleotides, between 10 and 200 nucleotides, or between 25 and 35 nucleotides, between 10 and 300 nucleotides, etc.

In one set of embodiments, any suitable technique may be used to amplify the plurality of oligonucleotides. In some cases, for each oligonucleotide to be amplified, at least about 100, at least about 300, at least about 500, at least about 1,000, at least about 3,000, at least about 5,000, at least about 10,000, at least about 30,000, at least about 50,000 at least about 100,000, at least about 300,000, at least about 500,000, at least about 1,000,000 copies, at least about 3,000,000 copies, at least about 5,000,000 copies, at least about 10,000,000 copies, at least about 30,000,000 copies, at least about 50,000,000 copies, or at least about 100,000,000 copies of the oligonucleotide may be produced using any of the amplification techniques discussed herein (e.g., including PCR amplification, in vitro transcription etc.). As discussed, in some cases, the amplification may occur without substantial selective amplification of some oligonucleotide sequences over others.

Any suitable technique may be used to generate the plurality of oligonucleotides. For example, the plurality of oligonucleotides may be synthetically produced, grown within a cell, grown on a substrate (e.g., in an array), or the like. Techniques for producing oligonucleotides are known to those of ordinary skill in the art. The plurality of oligonucleotides may also be computationally designed in some embodiments.

In one embodiment, the oligonucleotides may be amplified using PCR (polymerase chain reaction). In some cases, the oligonucleotides may be amplified while contained in a common liquid or solution. This is to be contrasted with certain PCR techniques, such as emulsion PCR or digital PCR, which requires separation of the oligonucleotides, e.g., into separate compartments or droplets, prior to amplification so as to prevent relatively selective amplification of certain oligonucleotides from occurring. However, surprisingly, it has been found that such separation is not required, and other techniques (such as is described herein) may be used to prevent or reduce selective amplification while keeping the oligonucleotides together within a common solution.

As mentioned, in some cases, by using certain oligonucleotide structures and/or certain types of PCR techniques, the amount of selective amplification that may occur may be reduced or eliminated. For instance, in one set of embodiments, oligonucleotides are chosen to minimize competitive effects. For instance, the oligonucleotides may have substantially the same lengths, and/or share identical or similar portions or regions.

For example, in one set of embodiments, the oligonucleotides may have a distribution of lengths such that no more than about 10%, no more than about 5%, no more than about 3%, or no more than about 1% of the oligonucleotides has a length that is less than about 80% or greater than about 120%, less than about 90% or greater than about 110%, or less than about 95% or greater than about 105% of the overall average length of the plurality of nucleotides.

In another set of embodiments the oligonucleotides may share one or more regions, such as index regions, that are identical or substantially similar. The oligonucleotides sharing index or other regions may have substantially the same lengths, as discussed above, or different lengths. In some embodiments, the oligonucleotides may comprise at least two index regions that each are identical or substantially similar, surrounding a variable region having different nucleotide sequences, and optionally, different lengths. For example, the oligonucleotides may include, in sequence, a first region that is identical or substantially similar to the other oligonucleotides, a second region that is not identical, and optionally, a third region that is identical or substantially similar to the other oligonucleotides. In some embodiments, competition of oligonucleotides may be controlled by using oligonucleotides selected to reduce amplification bias. For instance, in some cases, groups of oligonucleotides that have similar compositions may be amplified together.

In some cases, the index regions may have a length of greater than 5, 7, 10, 12, 14, 16, 18, or 20 nucleotides, and/or have a length of less than 30, 28, 25, 22, 20, 18, 16, 14, 12, or 10 nucleotides. For instance, the regions that are identical or substantially similar may have a length of between 18 and 22 nucleotides. The regions may be identical, or differ by no more than 1, 2, 3, 4, or 5 nucleotides (consecutively or non-consecutively) within the region.

In certain embodiments, primer sequences may be added to facilitate the PCR reaction. For example, the primer sequence may include sequences substantially complementary to a region within the oligonucleotides, e.g., an index region. A variety of such sequences suitable for PCR or in vitro transcription may be readily obtained commercially.

In some embodiments, the primer sequence may also include other sequences, e.g., promoter sequences or other sequences that may be added to the oligonucleotide during PCR amplification, such as is shown in FIG. 1 with a T7 promoter. Accordingly, oligonucleotides comprising the original sequence and one or more promoter sequences may be produced in certain cases. Besides the T7 promoter, other suitable promoters that may be used include, but are not limited to, T3 promoters or SP6 promoters. Such promoters may be useful, for example, to facilitate transcription to produce RNA, as is discussed in more detail below. In addition, in some embodiments, more than one promoter may be added.

In one set of embodiments, more than one sequence containing a PCR primer may be used, e.g., to amplify different subsets of the plurality of oligonucleotides. If more than one primer-containing sequence is used, the PCR primers contained on each of them may be the same or different. Examples of suitable PCR primers include those described herein. Thus, for example, in one set of embodiments, for example, the plurality of oligonucleotides may include different subpools having different index regions or other regions as discussed above, which may be selectively amplified through the use of an appropriate sequence including a PCR primer. Any suitable number of subpools may be created for a plurality of oligonucleotides. For example, at least 1, 2, 4, 10, 20, 96, 100, or 192 subpools of the plurality oligonucleotides may be selective amplified, through the use of specific PCR primers.

Thus, in some cases, the oligonucleotides may be formed into "pools" or groups or sets of oligonucleotides within the plurality of oligonucleotides that share one or more common features, such as an index region or other identical sequence. For instance, the common feature in a group or set of oligonucleotides may have an identical sequence of nucleotides of at least 5, 7, 10, 12, 14, 16, 18, or 20 nucleotides, and/or less than 30, 28, 25, 22, 20, 18, 16, 14, 12, or 10 nucleotides. For instance, the common region that is identical or substantially similar in a group of oligonucleotides may have a length of between 18 and 22 nucleotides. The common regions may be identical, or differ by no more than 1, 2, 3, 4, or 5 nucleotides (consecutively or non-consecutively) within the region. In some embodiments, each group or pool may contain two (or more) unique index regions that are not used in any other pool, e.g., to reduce the contamination of off-target amplified products from the amplification products of another.

In certain embodiments, PCR amplification may be monitored, and controlled to reduce or minimize selective amplification. For example, in one set of embodiments, real-time PCR techniques may be used. In some embodiments, the extent of the PCR reaction may be monitored or controlled, for example, by illuminating the solution containing the oligonucleotides with suitable light and determining the amount of fluorescence that is present to monitor the PCR reaction. Accordingly, for example, the reaction conditions may be controlled such that the oligonucleotides react in conditions that minimize the amount of selective amplification, for example, by providing an excess of nucleotides, ions (e.g., $Mg^{2+}$), enzyme, etc. Once the oligonucleotide concentrations have reached the point where competitive effects may start to occur, the reaction may be stopped before significant selective amplification begins.

After amplification as discussed above, the amplified oligonucleotides may then be transcribed to produce RNA. Further amplification may also occur in this step. For instance, in some cases, each oligonucleotide can be used to produce, on the average, at least about 50, at least about 100, at least about 300, at least about 500, at least about 1,000, at least about 3,000, at least about 5,000, at least about 10,000, at least about 30,000, at least about 50,000 at least about 100,000, at least about 300,000, at least about 500,000 or at least about 1,000,000 transcribed RNA molecules. In some cases, the mass of RNA that is produced may be at least about 10, at least about 20, at least about 30, at least about 50, at least about 100, at least about 200, at least about 300, or at least about 500 times the mass of the oligonucleotides. Thus, for example, one microgram of oligonucleotides may be converted into at least 10 micrograms, at least 30 micrograms, or at least 100 micrograms of RNA.

In one set of embodiments, transcription may occur in vitro by exposing the amplified oligonucleotides to a suitable RNA polymerase. A variety of RNA polymerases are available commercially, including T7, T3, or SP6 RNA polymerases. Other non-limiting examples of RNA polymerases include RNA polymerase I, RNA polymerase II, RNA polymerase III, RNA polymerase IV, or RNA polymerase V. The RNA polymerase may arise from any suitable source, e.g., bacteria, viruses, or eukaryotes. In some embodiments, more than one RNA polymerase may be used. In addition, as previously discussed, in some embodiments, the amplified oligonucleotides may include promoter sequences, such as one or more of T7, T3, or SP6 promoter sequences, that can be used to facilitate the transcription process. Those of ordinary skill in the art will be aware of suitable conditions for causing transcription in vitro using RNA polymerases.

In some embodiments, the total amplification bias may be reduced by changing the relative amount of amplification produced by the PCR and the in vitro transcription. For example, the PCR can be used to produce smaller amounts of DNA than are typically produced in a PCR, to reduce the amplification bias of this process. However, this reduced yield can be compensated in some cases by increasing the duration of the in vitro transcription reaction.

The RNA may, in turn, be reverse transcribed to produce DNA. In one set of embodiments, reverse transcription may occur by exposing the RNA to a suitable reverse transcriptase enzyme. In some cases, the reverse transcriptase may be a viral reverse transcriptase, e.g., M-MLV reverse transcriptase, AMV reverse transcriptase, or the like. A variety of reverse transcriptase enzymes are commercially available. Those of ordinary skill in the art will be aware of suitable conditions for causing reverse transcription to occur.

In certain embodiments, reverse transcription may be facilitated through the use of primer-containing sequences, e.g., containing primers for reverse transcription. In some cases, the primer-containing sequences may contain other sequences or entities as well, although this is not necessarily a requirement. The primer-containing sequences may be added at any suitable point, e.g., just before starting transcription reaction. Suitable transcription primers for conducting reverse transcription may be obtained commercially.

In one set of embodiments, the primer-containing sequence may be incorporated into the DNA during production of the DNA by the reverse transcriptase. In some cases, the primer-containing sequence may contain other entities, and/or sequences suitable for attaching other entities (e.g., on the 5' or 3' ends, internally, etc.). For instance, the primer-containing sequence may contain a non-nucleic acid moiety, such as a digoxigenin moiety, a biotin moiety, etc. located on the 5' end, the 3' end, internally, or the like. In some cases, the signaling entity that can be subsequently detected or determined may be introduced to the DNA. For instance, the signaling entity may be fluorescent, or a specific nucleotide sequence that can be determined, e.g., enzymatically. Examples of signaling entities are discussed in more detail below.

In some cases, the RNA may be purified prior to reverse transcription. However, it should be noted that purification is not required, and in other embodiments, the RNA may be reverse transcribed to form DNA without any intermediate purification steps. If the RNA is purified, it may be purified using any suitable technique, e.g., by passing the RNA over a suitable column to remove oligonucleotides.

Optionally, in some embodiments, the RNA may be separated from the DNA or the DNA may be purified in some fashion. For example, the RNA may be selectively degraded, relative to the DNA. In one set of embodiments, the RNA may be degraded relative to the DNA by alkaline hydrolysis. For instance, the pH of the solution may be raised to at least about 8, at least about 9, at least about 10, etc. Any suitable alkaline may be used to raise the pH. In some cases, after degradation of the RNA, the pH may also be lowered, e.g., to about 7, to about 7.4, to physiological conditions, or the like. In some cases, techniques such as enzymatic degradation can be used to selectively degrade RNA, relative to DNA. The DNA may also be purified using techniques such as column purification, ethanol precipitation, and/or solid-phase reversible immobilization techniques. In addition, in some cases, the DNA may be concentrated, e.g., through evaporation techniques.

In addition, techniques such as those described above may be scaled-up or "numbered-up" to produce larger quantities of material. For example, a process may be repeated using multi-well techniques or by simultaneously running multiple reactions in parallel, etc. to produce larger quantities or masses of oligonucleotides. As a non-limiting example, in one embodiment, processes such as those discussed herein may be performed using multiple wells of a microtiter plate (e.g., having 96, 384, 1536, wells, etc.) to increase output.

The DNA may be used for a variety of purposes, in different embodiments of the invention. For example, in certain embodiments, the DNA may be hybridized to nucleic acid species in liquid samples, e.g., extracted from a variety of biological sources, including human. In some cases, the DNA may be used to physically separate one set of nucleic acids from another, or as primers for PCR or reverse transcription.

In addition, as previously discussed, in certain aspects, signaling entities are incorporated into DNA in some embodiments. The signaling entities may be determined for a variety of purposes. For example, the DNA that is produced may be used as a biological probe, and the signaling entities may be determined in some fashion, e.g., quantitatively or qualitatively, to determine a characteristic or feature of the probe. Examples include, but are not limited to, the position of the probe, the activity of the probe, the concentration of the probe, or the like.

In some cases, signaling entities within a sample may be determined, e.g., spatially, using a variety of techniques. In some embodiments, the signaling entities may be fluorescent, and techniques for determining fluorescence within a sample, such as fluorescence microscopy or confocal microscopy, may be used to spatially identify the positions of signaling entities within a cell. In some cases, the positions of the entities within the sample may be determined in two or even three dimensions.

In some embodiments, the spatial positions of the signaling entities may be determined at relatively high resolutions. For instance, the positions may be determined at spatial resolutions of better than about 100 micrometers, better than about 30 micrometers, better than about 10 micrometers, better than about 3 micrometers, better than about 1 micrometer, better than about 800 nm, better than about 600 nm, better than about 500 nm, better than about 400 nm, better than about 300 nm, better than about 200 nm, better than about 100 nm, better than about 90 nm, better than about 80 nm, better than about 70 nm, better than about 60 nm, better than about 50 nm, better than about 40 nm, better than about 30 nm, better than about 20 nm, or better than about 10 nm, etc.

There are a variety of techniques able to determine or image the spatial positions of entities optically, e.g., using fluorescence microscopy. In some cases, the spatial positions may be determined at super resolutions, or at resolutions better than the wavelength of light. Non-limiting examples include STORM (stochastic optical reconstruction microscopy), STED (stimulated emission depletion microscopy), NSOM (Near-field Scanning Optical Microscopy), 4Pi microscopy, SIM (Structured Illumination Microscopy), SMI (Spatially Modulated Illumination) microscopy, RESOLFT (Reversible Saturable Optically Linear Fluorescence Transition Microscopy), GSD (Ground State Depletion Microscopy), SSIM (Saturated Structured-Illumination Microscopy), SPDM (Spectral Precision Distance Microscopy), Photo-Activated Localization Microscopy (PALM), Fluorescence Photoactivation Localization Microscopy (FPALM), LIMON (3D Light Microscopical Nanosizing Microscopy), Super-resolution optical fluctuation imaging (SOFI), or the like. See, e.g., U.S. Pat. No. 7,838,302, issued Nov. 23, 2010, entitled "Sub-Diffraction Limit Image Resolution and Other Imaging Techniques," by Zhuang, et al.; U.S. Pat. No. 8,564,792, issued Oct. 22, 2013, entitled "Sub-diffraction Limit Image Resolution in Three Dimensions," by Zhuang, et al.; or Int. Pat. Apl. Pub. No. WO 2013/090360, published Jun. 20, 2013, entitled "High Resolution Dual-Objective Microscopy," by Zhuang, et al., each incorporated herein by reference in their entireties.

In addition, the signaling entity may be inactivated in some cases. For example, in some embodiments, a first secondary nucleic acid probe containing a signaling entity may be applied to a sample that can recognize a first read sequence, then the first secondary nucleic acid probe can be inactivated before a second secondary nucleic acid probe is applied to the sample. If multiple signaling entities are used, the same or different techniques may be used to inactivate the signaling entities, and some or all of the multiple signaling entities may be inactivated, e.g., sequentially or simultaneously.

Inactivation may be caused by removal of the signaling entity (e.g., from the sample, or from the nucleic acid probe, etc.), and/or by chemically altering the signaling entity in some fashion, e.g., by photobleaching the signaling entity, bleaching or chemically altering the structure of the signaling entity, etc.). For instance, in one set of embodiments, a fluorescent signaling entity may be inactivated by chemical or optical techniques such as oxidation, photobleaching, chemically bleaching, stringent washing or enzymatic digestion or reaction by exposure to an enzyme, dissociating the signaling entity from other components (e.g., a probe), chemical reaction of the signaling entity (e.g., to a reactant able to alter the structure of the signaling entity) or the like.

In some embodiments, various nucleic acid probes (including primary and/or secondary nucleic acid probes) may include one or more signaling entities. If more than one nucleic acid probe is used, the signaling entities may each by the same or different. In certain embodiments, a signaling entity is any entity able to emit light. For instance, in one embodiment, the signaling entity is fluorescent. In other embodiments, the signaling entity may be phosphorescent, radioactive, absorptive, etc. In some cases, the signaling entity is any entity that can be determined within a sample at relatively high resolutions, e.g., at resolutions better than the wavelength of visible light. The signaling entity may be, for example, a dye, a small molecule, a peptide or protein, or the like. The signaling entity may be a single molecule in some cases. If multiple secondary nucleic acid probes are used, the nucleic acid probes may comprise the same or different signaling entities.

Non-limiting examples of signaling entities include fluorescent entities (fluorophores) or phosphorescent entities, for example, cyanine dyes (e.g., Cy2, Cy3, Cy3B, Cy5, Cy5.5, Cy7, etc.), Alexa Fluor dyes, Atto dyes, photoswtichable dyes, photoactivatable dyes, fluorescent dyes, metal nanoparticles, semiconductor nanoparticles or "quantum dots", fluorescent proteins such as GFP (Green Fluorescent Protein), or photoactivabale fluorescent proteins, such as PAGFP, PSCFP, PSCFP2, Dendra, Dendra2, EosFP, tdEos, mEos2, mEos3, PAmCherry, PAtagRFP, mMaple, mMaple2, and mMaple3. Other suitable signaling entities are known to those of ordinary skill in the art. See, e.g., U.S. Pat. No. 7,838,302 or U.S. Pat. Apl. Ser. No. 61/979,436, each incorporated herein by reference in its entirety.

As used herein, the term "light" generally refers to electromagnetic radiation, having any suitable wavelength (or equivalently, frequency). For instance, in some embodiments, the light may include wavelengths in the optical or visual range (for example, having a wavelength of between about 400 nm and about 700 nm, i.e., "visible light"), infrared wavelengths (for example, having a wavelength of between about 300 micrometers and 700 nm), ultraviolet wavelengths (for example, having a wavelength of between about 400 nm and about 10 nm), or the like. In certain cases, as discussed in detail below, more than one entity may be used, i.e., entities that are chemically different or distinct, for example, structurally. However, in other cases, the entities may be chemically identical or at least substantially chemically identical.

In one set of embodiments, the signaling entity is "switchable," i.e., the entity can be switched between two or more states, at least one of which emits light having a desired wavelength. In the other state(s), the entity may emit no light, or emit light at a different wavelength. For instance, an entity may be "activated" to a first state able to produce light having a desired wavelength, and "deactivated" to a second state not able to emit light of the same wavelength. An entity is "photoactivatable" if it can be activated by incident light of a suitable wavelength. As a non-limiting example, Cy5, can be switched between a fluorescent and a dark state in a controlled and reversible manner by light of different wavelengths, i.e., 633 nm (or 642 nm, 647 nm, 656 nm) red light can switch or deactivate Cy5 to a stable dark state, while 405 nm green light can switch or activate the Cy5 back to the fluorescent state. In some cases, the entity can be reversibly switched between the two or more states, e.g., upon exposure to the proper stimuli. For example, a first stimuli (e.g., a first wavelength of light) may be used to activate the switchable entity, while a second stimuli (e.g., a second wavelength of light) may be used to deactivate the switchable entity, for instance, to a non-emitting state. Any suitable method may be used to activate the entity. For example, in one embodiment, incident light of a suitable wavelength may be used to activate the entity to emit light, i.e., the entity is "photoswitchable." Thus, the photoswitchable entity can be switched between different light-emitting or non-emitting states by incident light, e.g., of different wavelengths. The light may be monochromatic (e.g., produced using a laser) or polychromatic. In another embodiment, the entity may be activated upon stimulation by electric field and/or magnetic field. In other embodiments, the entity may be activated upon exposure to a suitable chemical environment, e.g., by adjusting the pH, or inducing a reversible chemical reaction involving the entity, etc. Similarly, any suitable method may be used to deactivate the entity, and the methods of activating and deactivating the entity need not be the same. For instance, the entity may be deactivated upon exposure to incident light of a suitable wavelength, or the entity may be deactivated by waiting a sufficient time.

Typically, a "switchable" entity can be identified by one of ordinary skill in the art by determining conditions under which an entity in a first state can emit light when exposed to an excitation wavelength, switching the entity from the first state to the second state, e.g., upon exposure to light of a switching wavelength, then showing that the entity, while in the second state can no longer emit light (or emits light at a much reduced intensity) when exposed to the excitation wavelength.

In one set of embodiments, as discussed, a switchable entity may be switched upon exposure to light. In some cases, the light used to activate the switchable entity may come from an external source, e.g., a light source such as a laser light source, another light-emitting entity proximate the switchable entity, etc. The second, light emitting entity, in some cases, may be a fluorescent entity, and in certain embodiments, the second, light-emitting entity may itself also be a switchable entity.

In some embodiments, the switchable entity includes a first, light-emitting portion (e.g., a fluorophore), and a second portion that activates or "switches" the first portion. For example, upon exposure to light, the second portion of the switchable entity may activate the first portion, causing the first portion to emit light. Examples of activator portions include, but are not limited to, Alexa Fluor 405 (Invitrogen), Alexa Fluor 488 (Invitrogen), Cy2 (GE Healthcare), Cy3 (GE Healthcare), Cy3B (GE Healthcare), Cy3.5 (GE Healthcare), or other suitable dyes. Examples of light-emitting portions include, but are not limited to, Cy5, Cy5.5 (GE Healthcare), Cy7 (GE Healthcare), Alexa Fluor 647 (Invitrogen), Alexa Fluor 680 (Invitrogen), Alexa Fluor 700 (Invitrogen), Alexa Fluor 750 (Invitrogen), Alexa Fluor 790 (Invitrogen), DiD, DiR, YOYO-3 (Invitrogen), YO-PRO-3 (Invitrogen), TOT-3 (Invitrogen), TO-PRO-3 (Invitrogen) or other suitable dyes. These may linked together, e.g., covalently, for example, directly, or through a linker, e.g., forming compounds such as, but not limited to, Cy5-Alexa Fluor 405, Cy5-Alexa Fluor 488, Cy5-Cy2, Cy5-Cy3, Cy5-Cy3.5, Cy5.5-Alexa Fluor 405, Cy5.5-Alexa Fluor 488, Cy5.5-Cy2, Cy5.5-Cy3, Cy5.5-Cy3.5, Cy7-Alexa Fluor 405, Cy7-Alexa Fluor 488, Cy7-Cy2, Cy7-Cy3, Cy7-Cy3.5, Alexa Fluor 647-Alexa Fluor 405, Alexa Fluor 647-Alexa Fluor 488, Alexa Fluor 647-Cy2, Alexa Fluor 647-Cy3, Alexa Fluor 647-Cy3.5, Alexa Fluor 750-Alexa Fluor 405, Alexa Fluor 750-Alexa Fluor 488, Alexa Fluor 750-Cy2, Alexa Fluor 750-Cy3, or Alexa Fluor 750-Cy3.5. Those of ordinary skill in the art will be aware of the structures of these and other compounds, many of which are available commercially. The portions may be linked via a covalent bond, or by a linker, such as those described in detail below. Other light-emitting or activator portions may include portions having two quaternized nitrogen atoms joined by a polymethine chain, where each nitrogen is independently part of a heteroaromatic moiety, such as pyrrole, imidazole, thiazole, pyridine, quinoine, indole, benzothiazole, etc., or part of a nonaromatic amine. In some cases, there may be 5, 6, 7, 8, 9, or more carbon atoms between the two nitrogen atoms.

In certain cases, the light-emitting portion and the activator portions, when isolated from each other, may each be fluorophores, i.e., entities that can emit light of a certain, emission wavelength when exposed to a stimulus, for example, an excitation wavelength. However, when a switchable entity is formed that comprises the first fluorophore and the second fluorophore, the first fluorophore forms a first, light-emitting portion and the second fluorophore forms an activator portion that switches that activates or "switches" the first portion in response to a stimulus. For example, the switchable entity may comprise a first fluorophore directly bonded to the second fluorophore, or the first and second entity may be connected via a linker or a common entity. Whether a pair of light-emitting portion and activator portion produces a suitable switchable entity can be tested by methods known to those of ordinary skills in the art. For example, light of various wavelength can be used to stimulate the pair and emission light from the light-emitting portion can be measured to determined wither the pair makes a suitable switch.

As a non-limiting example, Cy3 and Cy5 may be linked together to form such an entity. In this example, Cy3 is an activator portion that is able to activate Cy5, the light-emission portion. Thus, light at or near the absorption maximum (e.g., near 532 nm light for Cy3) of the activation or second portion of the entity may cause that portion to activate the first, light-emitting portion, thereby causing the first portion to emit light (e.g., near 647 nm for Cy5). See, e.g., U.S. Pat. No. 7,838,302, incorporated herein by reference in its entirety. In some cases, the first, light-emitting portion can subsequently be deactivated by any suitable technique (e.g., by directing 647 nm red light to the Cy5 portion of the molecule).

Other non-limiting examples of potentially suitable activator portions include 1,5 IAEDANS, 1,8-ANS, 4-Methylumbelliferone, 5-carboxy-2,7-dichlorofluorescein, 5-Carboxyfluorescein (5-FAM), 5-Carboxynapthofluorescein, 5-Carboxytetramethylrhodamine (5-TAMRA), 5-FAM (5-Carboxyfluorescein), 5-HAT (Hydroxy Tryptamine), 5-Hydroxy Tryptamine (HAT), 5-ROX (carboxy-X-rhodamine), 5-TAMRA (5-Carboxytetramethylrhodamine), 6-Carboxyrhodamine 6G, 6-CR 6G, 6-JOE, 7-Amino-4-methylcoumarin, 7-Aminoactinomycin D (7-AAD), 7-Hydroxy-4- methylcoumarin, 9-Amino-6-chloro-2-methoxyacridine, ABQ, Acid Fuchsin, ACMA (9-Amino-6-chloro-2-methoxyacridine), Acridine Orange, Acridine Red, Acridine Yellow, Acriflavin, Acriflavin Feulgen SITSA, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alizarin Complexon, Alizarin Red, AMC, AMCA-S, AMCA (Aminomethylcoumarin), AMCA-X, Aminoactinomycin D, Aminocoumarin, Aminomethylcoumarin (AMCA), Anilin Blue, Anthrocyl stearate, APTRA-BTC, APTS, Astrazon Brilliant Red 4G, Astrazon Orange R, Astrazon Red 6B, Astrazon Yellow 7 GLL, Atabrine, ATTO 390, ATTO 425, ATTO 465, ATTO 488, ATTO 495, ATTO 520, ATTO 532, ATTO 550, ATTO 565, ATTO 590, ATTO 594, ATTO 610, ATTO 611X, ATTO 620, ATTO 633, ATTO 635, ATTO 647, ATTO 647N, ATTO 655, ATTO 680, ATTO 700, ATTO 725, ATTO 740, ATTO-TAG CBQCA, ATTO-TAG FQ, Auramine, Aurophosphine G, Aurophosphine, BAO 9 (Bisaminophenyloxadiazole), BCECF (high pH), BCECF (low pH), Berberine Sulphate, Bimane, Bisbenzamide, Bisbenzimide (Hoechst), bis-BTC, Blancophor FFG, Blancophor SV, BOBO -1, BOBO -3, Bodipy 492/515, Bodipy 493/503, Bodipy 500/510, Bodipy 505/515, Bodipy 530/550, Bodipy 542/563, Bodipy 558/568, Bodipy 564/570, Bodipy 576/589, Bodipy 581/591, Bodipy 630/650-X, Bodipy 650/665-X, Bodipy 665/676, Bodipy Fl, Bodipy FL ATP, Bodipy Fl-Ceramide, Bodipy R6G, Bodipy TMR, Bodipy TMR-X conjugate, Bodipy TMR-X, SE, Bodipy TR, Bodipy TR ATP, Bodipy TR-X SE, BO-PRO-1, BO-PRO-3, Brilliant Sulphoflavin FF, BTC, BTC-5N, Calcein, Calcein Blue, Calcium Crimson, Calcium Green, Calcium Green-1 $Ca^{2+}$ Dye, Calcium Green-2 $Ca^{2+}$, Calcium Green-5N $Ca^{2+}$, Calcium Green-C18 $Ca^{2+}$, Calcium Orange, Calcofluor White, Carboxy-X-rhodamine (5-ROX), Cascade Blue, Cascade Yellow, Catecholamine, CCF2 (GeneBlazer), CFDA, Chromomycin A, Chromomycin A, CL-NERF, CMFDA, Coumarin Phalloidin, CPM Methylcoumarin, CTC, CTC Formazan, Cy2, Cy3.1 8, Cy3.5, Cy3, Cy5.1 8, cyclic AMP Fluorosensor (FiCRhR), Dabcyl, Dansyl, Dansyl Amine, Dansyl Cadaverine, Dansyl Chloride, Dansyl DHPE, Dansyl fluoride, DAPI, Dapoxyl, Dapoxyl 2, Dapoxyl 3' DCFDA, DCFH (Dichlorodihydrofluorescein Diacetate), DDAO, DHR (Dihydorhodamine 123), Di-4-ANEPPS, Di-8-ANEPPS (non-ratio), DiA (4-Di-16-ASP), Dichlorodihydrofluorescein Diacetate (DCFH), DiD-Lipophilic Tracer, DiD (DiIC18(5)), DIDS, Dihydrohodamine 123 (DHR), DiI (DiIC18(3)), Dinitrophenol, DiO (DiOC18(3)), DiR, DiR (DiIC18(7)), DM-NERF (high pH), DNP, Dopamine, DTAF, DY-630-NHS, DY-635-NHS, DyLight 405, DyLight 488, DyLight 549, DyLight 633, DyLight 649, DyLight 680, DyLight 800, ELF 97, Eosin, Erythrosin, Erythrosin ITC, Ethidium Bromide, Ethidium homodimer-1 (EthD-1), Euchrysin, EukoLight, Europium (III) chloride, Fast Blue, FDA, Feulgen (Pararosaniline), FIF (Formaldehyd Induced Fluorescence), FITC, Flazo Orange, Fluo-3, Fluo-4, Fluorescein (FITC), Fluorescein Diacetate, Fluoro-Emerald, Fluoro-Gold (Hydroxystilbamidine), Fluor-Ruby, FluorX, FM 1-43, FM 4-46, Fura Red (high pH), Fura Red/Fluo-3, Fura-2, Fura-2/BCECF, Genacryl Brilliant Red B, Genacryl Brilliant Yellow 10GF, Genacryl Pink 3G, Genacryl Yellow SGF, GeneBlazer (CCF2), Gloxalic Acid, Granular blue, Haematoporphyrin, Hoechst 33258, Hoechst 33342, Hoechst 34580, HPTS, Hydroxycoumarin, Hydroxystilbamidine (FluoroGold), Hydroxytryptamine, Indo-1, high calcium, Indo-1, low calcium, Indodicarbocyanine (DiD), Indotricarbocyanine (DiR), Intrawhite Cf, JC-1, JO-JO-1, JO-PRO-1, LaserPro, Laurodan, LDS 751 (DNA), LDS 751 (RNA), Leucophor PAF, Leucophor SF, Leucophor WS, Lissamine Rhodamine, Lissamine Rhodamine B, Calcein/Ethidium homodimer, LOLO-1, LO-PRO-1, Lucifer Yellow, Lyso Tracker Blue, Lyso Tracker Blue-White, Lyso Tracker Green, Lyso Tracker Red, Lyso Tracker Yellow, LysoSensor Blue, LysoSensor Green, LysoSensor Yellow/Blue, Mag Green, Magdala Red (Phloxin B), Mag-Fura Red, Mag-Fura-2, Mag-Fura-5, Mag-Indo-1, Magnesium Green, Magnesium Orange, Malachite Green, Marina Blue, Maxilon Brilliant Flavin 10 GFF, Maxilon Brilliant Flavin 8 GFF, Merocyanin, Methoxycoumarin, Mitotracker Green FM, Mitotracker Orange, Mitotracker Red, Mitramycin, Monobromobimane, Monobromobimane (mBBr-GSH), Monochlorobimane, MPS (Methyl Green Pyronine Stilbene), NBD, NBD Amine, Nile Red, Nitrobenzoxadidole, Noradrenaline, Nuclear Fast Red, Nuclear Yellow, Nylosan Brilliant lavin E8G, Oregon Green, Oregon Green 488-X, Oregon Green, Oregon Green 488, Oregon Green 500, Oregon Green 514, Pacific Blue, Pararosaniline (Feulgen), PBFI, Phloxin B (Magdala Red), Phorwite AR, Phorwite BKL, Phorwite Rev, Phorwite RPA, Phosphine 3R, PKH26 (Sigma), PKH67, PMIA, Pontochrome Blue Black, POPO-1, POPO-3, PO-PRO-1, PO-PRO-3, Primuline, Procion Yellow, Propidium Iodid (PI), PyMPO, Pyrene, Pyronine, Pyronine B, Pyrozal Brilliant Flavin 7GF, QSY 7, Quinacrine Mustard, Resorufin, RH 414, Rhod-2, Rhodamine, Rhodamine 110, Rhodamine 123, Rhodamine 5 GLD, Rhodamine 6G, Rhodamine B, Rhodamine B 200, Rhodamine B extra, Rhodamine BB, Rhodamine BG, Rhodamine Green, Rhodamine Phallicidine, Rhodamine Phalloidine, Rhodamine Red, Rhodamine WT, Rose Bengal, S65A, S65C, S65L, S65T, SBFI, Serotonin, Sevron Brilliant Red 2B, Sevron Brilliant Red 4G, Sevron Brilliant Red B, Sevron Orange, Sevron Yellow L, SITS, SITS (Primuline), SITS (Stilbene Isothiosulphonic Acid), SNAFL calcein, SNAFL-1, SNAFL-2, SNARF calcein, SNARF1, Sodium Green, SpectrumAqua, SpectrumGreen, SpectrumOrange, Spectrum Red, SPQ (6-methoxy-N-(3-sulfopropyl)quinolinium), Stilbene, Sulphorhodamine B can C, Sulphorhodamine Extra, SYTO 11, SYTO 12, SYTO 13, SYTO 14, SYTO 15, SYTO 16, SYTO 17, SYTO 18, SYTO 20, SYTO 21, SYTO 22, SYTO 23, SYTO 24, SYTO 25, SYTO 40, SYTO 41, SYTO 42, SYTO 43, SYTO 44, SYTO 45, SYTO 59, SYTO 60, SYTO 61, SYTO 62, SYTO 63, SYTO 64, SYTO 80, SYTO 81, SYTO 82, SYTO 83, SYTO 84, SYTO 85, SYTOX Blue, SYTOX Green, SYTOX Orange, Tetracycline, Tetramethylrhodamine (TAMRA), Texas Red, Texas Red-X conjugate, Thiadicarbocyanine (DiSC3), Thiazine Red R, Thiazole Orange, Thioflavin 5, Thioflavin S, Thioflavin TCN, Thiolyte, Thiozole Orange, Tinopol CBS (Calcofluor White), TMR, TO-PRO-1, TO-PRO-3, TO-PRO-5, TOTO-1, TOTO-3, TRITC (tetramethylrodamine isothiocyanate), True Blue, TruRed, Ultralite, Uranine B, Uvitex SFC, WW 781, X-Rhodamine, XRITC, Xylene Orange, Y66F, Y66H, Y66W, YO-PRO-1, YO-PRO-3, YOYO-1, YOYO-3, SYBR Green, Thiazole orange (interchelating dyes), or combinations thereof.

In some aspects, the nucleotides can be used to study a sample, such as a biological sample. For instance, the nucleotides may be used to determine nucleic acids within a cell or other sample. The sample may include a cell culture, a suspension of cells, a biological tissue, a biopsy, an organism, or the like. The sample may also be cell-free but nevertheless contain nucleic acids. If the sample contains a cell, the cell may be a human cell, or any other suitable cell, e.g., a mammalian cell, a fish cell, an insect cell, a plant cell, or the like. More than one cell may be present in some cases.

The nucleic acids to be determined may be, for example, DNA, RNA, or other nucleic acids that are present within a cell (or other sample). The nucleic acids may be endogenous to the cell, or added to the cell. For instance, the nucleic acid may be viral, or artificially created. In some cases, the nucleic acid to be determined may be expressed by the cell. The nucleic acid is RNA in some embodiments. The RNA may be coding and/or non-coding RNA. Non-limiting examples of RNA that may be studied within the cell include mRNA, siRNA, rRNA, miRNA, tRNA, lncRNA, snoRNAs, snRNAs, exRNAs, piRNAs, or the like. In some embodiments, for example, at least some of the plurality of oligonucleotides are complementary to a portion of a specific chromosome sequence, e.g., of a human chromosome.

In some cases, a significant portion of the nucleic acid within the cell may be studied. For instance, in some cases, enough of the RNA present within a cell may be determined so as to produce a partial or complete transcriptome of the cell. In some cases, at least 4 types of mRNAs are determined within a cell, and in some cases, at least 3, at least 4, at least 7, at least 8, at least 12, at least 14, at least 15, at least 16, at least 22, at least 30, at least 31, at least 32, at least 50, at least 63, at least 64, at least 72, at least 75, at least 100, at least 127, at least 128, at least 140, at least 255, at least 256, at least 500, at least 1,000, at least 1,500, at least 2,000, at least 2,500, at least 3,000, at least 4,000, at least 5,000, at least 7,500, at least 10,000, at least 12,000, at least 15,000, at least 20,000, at least 25,000, at least 30,000, at least 40,000, at least 50,000, at least 75,000, or at least 100,000 types of mRNAs may be determined within a cell.

In some cases, the transcriptome of a cell may be determined. It should be understood that the transriptome generally encompasses all RNA molecules produced within a cell, not just mRNA. Thus, for instance, the transcriptome may also include rRNA, tRNA, etc. In some embodiments, at least 5%, at least 10%, at least 15%, at least 20%, at least 25%, at least 30%, at least 40%, at least 50%, at least 60%, at least 70%, at least 80%, at least 90%, or 100% of the transcriptome of a cell may be determined.

The determination of one or more nucleic acids within the cell or other sample may be qualitative and/or quantitative. In addition, the determination may also be spatial, e.g., the position of the nucleic acid within the cell or other sample may be determined in two or three dimensions. In some embodiments, the positions, number, and/or concentrations of nucleic acids within the cell (or other sample) may be determined.

One non-limiting example of such as system may be found in U.S. Provisional Patent Application Ser. No. 62/031,062, filed Jul. 30, 2014, entitled "Systems and Methods for Determining Nucleic Acids," by Zhuang, et al. incorporated herein by reference in its entirety.

The following documents are each incorporated herein by reference in their entireties: U.S. Pat. No. 7,838,302, issued Nov. 23, 2010, entitled "Sub-Diffraction Limit Image Resolution and Other Imaging Techniques," by Zhuang, et al.; U.S. Pat. No. 8,564,792, issued Oct. 22, 2013, entitled "Sub-diffraction Limit Image Resolution in Three Dimensions," by Zhuang, et al.; and Int. Pat. Apl. Pub. No. WO 2013/090360, published Jun. 20, 2013, entitled "High Resolution Dual-Objective Microscopy," by Zhuang, et al. In addition, incorporated herein by reference in their entireties are U.S. Provisional Patent Application Ser. No. 62/031,062, filed Jul. 30, 2014, entitled "Systems and Methods for Determining Nucleic Acids," by Zhuang, et al.; U.S. Provisional Patent Application Ser. No. 62/050,636, filed Sep. 15, 2014, entitled "Probe Library Construction," by Zhuang, et al.; U.S. Provisional Patent Application Ser. No. 62/142,653, filed Apr. 3, 2015, entitled "Systems and Methods for Determining Nucleic Acids," by Zhuang, et al.; and a PCT application filed on even date herewith, entitled "Systems and Methods for Determining Nucleic Acids," by Zhuang, et al.

The following examples are intended to illustrate certain embodiments of the present invention, but do not exemplify the full scope of the invention.

EXAMPLE 1

This example illustrates high-throughput hybridization construction of DNA probes, according to certain embodiments of the invention.

Overview. This protocol uses complex libraries of oligonucleotides as templates for the enzymatic construction of large quantities of single-stranded DNA molecules that can be chemically labeled and which are designed to be hybridized to specific sets of nucleic acid targets that can vary significantly in complexity, i.e. the number of unique target sequences. The use of this protocol involves several basic steps: 1) computational design and optimization of a set of oligonucleotide sequences that will serve as the hybridization regions on the sample of interest; 2) computational design and optimization of a large set of short oligonucleotide sequences to serve as highly specific PCR primers; 3) computational construction of the template molecules; 4) synthesis of the template molecules to create the template library; 5) selection of a sub-set of in vitro template molecules from a template library via PCR; 6) in-vitro-transcription-based amplification of the in vitro template molecules into RNA, which serves as the final template for the hybridization probes; 7) reverse transcription of the RNA back into DNA using chemically-modified primers; 8) removal of the RNA via alkaline hydrolysis; and 9) purification of the chemically-modified ssDNA molecules, called probes in this example. These steps are discussed in detail below.

Construction of Probes. Selection of Hybridization Regions. The software OligoArray 2.0 was used to design a large set of potential hybridization regions in the *E. coli* transcriptome in this example. Briefly, this software selects hybridization regions that lie within user-specified ranges for length and melting temperature. This software also screens for off-target hybridization as well as potential secondary structure. This software was used to generate hybridization regions of 30-nt length, a melting-temperature range of 80-85° C., a GC content of between 50-60%, and a secondary structure melting threshold and cross-hybridization-melting temperature of 75° C. using all annotated, transcribed mRNAs in *E. coli* (K-12 mg1655; NC90013.2).

Design of Hundreds of Orthogonal Primers. The general hybridization probe set may require far fewer unique sequences than is provided in the complex sets of oligonucleotides typically generated by array-based synthesis— the oligopool. To exploit this disparity in complexity and significantly lower the cost per experiment, this example uses a method to embed a large number of unique template sets within a single oligopool. Briefly, each template molecule was flanked by a unique pair of PCR primers common only to the template molecules for all probes within a given set. To facilitate the embedding of hundreds of unique probe template sets within a single oligopool, a protocol was created for constructing hundreds of orthogonal PCR primers.

Specifically, the protocol starts by truncating the members of an existing library of 240,000, semi-orthogonal, 25-mer oligonucleotides to 20-nt length and selecting oligos on parameters optimal for PCR: a narrow range of predicted melting-temperature (65-70° C.) and GC content (50-60%); the absence of contiguous runs of the same base longer than 4, i.e. AAAA; and the presence of a 3' GC-clamp, i.e. 2-3 G/C within the final 5 nt. BLAST was then run with these optimized primers against all annotated RNAs in the *E. coli* transcriptome as well as the T7 promoter (TAATACGACT-CACTATAGGG) (SEQ ID NO. 1) and a common priming region (P9: CAGGCATCCGAGAGGTCTGG) (SEQ ID NO. 2) and potential primers with hits to the transcriptome with 12-nt or longer of homology, or with a hit of any length within 3-nt of the 3' end of the potential primer, were removed. Finally, the remaining primers were screened for homology to each other, again using BLAST. Any primer with longer than 11-nt of homology or with any homology within 3-nt of the 3' end of another primer was removed. These cuts reduced the original 240,000 oligos to 198 highly optimized primers for the E. coli transcriptome. The final set of 198 primers are listed in FIGS. 3A-3D.

If required, more primers could be generated using established techniques to create a larger set of initial oligonucleotides, or by relaxing the stringency of the cuts described above. Finally, by changing the transcriptome used to screen the primers, this approach can also be generalized to the generation of optimal index primers for any organism.

Template Construction. To design the template libraries used to create our probe sets, the desired RNA targets were first selected to be stained simultaneously. Individual template molecules were designed by concatenating the following sequences: i) the first of two unique primers for the appropriate mRNA group, ii) the common primer P9, iii) the site for the nicking enzyme Nb.BsmI, iv) the reverse complement of the hybridization region to the target, v) the reverse complement of the nicking enzyme Nb.BsrDI, and vi) the reverse complement of the second unique primer for the given mRNA group. FIG. 2 demonstrates this organization. Multiple probe template sets were combined into large oligopools and these pools were synthesized via Custom-Array.

FIG. 2 shows an example template sequence containing a probe the mRNA, acnB. Underlined at the beginning is the sequence of the first primer, not underlined is the common P9 priming site, then underlined is the Nb.BsmI site, not underlined is the reverse complement to the hybridization region for acnB, next underlined is the reverse complement of the Nb.BsrDI site, and the final not underlined portion is the second unique primer. This template is one of 736 used to create probes to stain all mRNAs expressed in the copy number range of 1-10 per cell transcribed from the E. coli genomic locus corresponding to base pairs 1-100 kb. See FIGS. 4A-4BV for the sequences of the 736 probes.

Index PCR. The template for specific probe sets were selected from the complex oligopool via limited-cycle PCR. 0.5 to 1 ng of the complex oligopool was combined with 0.5 micromolar of each primer. The forward primer matched the priming sequence for the desired sub set while the reverse primer was a 5'concatenation of this sequence with the T7 promoter. To avoid the generation of G-quadruplets, which can be difficult to synthesize, the terminal Gs required in the T7 promoter were generated from Gs located at the 5' of the priming region where appropriate. All primers were synthesized by IDT. A 50 microliter reaction volume was amplified either using the KAPA real-time library amplification kit (KAPA Biosystems; KK2701) or via a homemade qPCR mix which included 0.8X EvaGreen (Biotum; 31000-T) and the hot-start Phusion polymerase (New England Biolabs; M0535S). Amplification was followed in real time using Agilent's MX300P or Biorad's CFX Connect. Individual samples were removed before the plateau in amplification, often at concentrations about 10-fold lower than would correspond to this plateau, to minimize distortion of template abundance due to over-amplification. Individual templates were purified with columns according to the manufacturer's instructions (Zymo DNA Clean and Concentrator; D4003) and eluted in RNase-free deionized water.

Amplification via in vitro transcription. The template was then amplified via in vitro transcription. Briefly, 0.5 to 1 micrograms of template DNA was amplified into 100 to 200 micrograms of RNA in a single 20-30 microliter reaction with a high yield RNA polymerase (New England Biolabs; E2040S). Reactions were supplemented with 1× RNase inhibitor (Promega RNasin; N2611). Amplification was typically run for 2 to 4 hours at 37° C. to maximize the yield. The RNA was not purified after the reaction and was either stored at −80° C. or immediately converted into DNA as described below. Reverse Transcription. 1-2 nmol of fluorescently-labeled ssDNA probe was created from the above in vitro transcription reactions using the reverse transcriptase Maxima H− (Thermo Scientific; EP0751). This enzyme was used because of its higher processivity and temperature resistance, which allowed the conversion of large quantities of RNA into DNA within small volumes at temperatures that disfavor secondary structure formation. The unpurified RNA created above was supplemented with 1.6 mM of each dNPT, 1-2 nmol of fluorescently labeled P9 primer, 300 units of Maxima H−, 60 units of RNasin, and a final 1× concentration of the Maxima RT buffer. The final 75 microliter volume was incubated at 50° C. for 60 minutes.

Strand Selection and Purification. The template RNA in the reaction above was then removed from the DNA via alkaline hydrolysis. 75 microliters of a solution of 0.25 M EDTA and 0.5 N NaOH was added to each reverse transcription reaction, and the sample was incubated at 95° C. for 10 minutes. The reaction was immediately neutralized by purifying the ssDNA probe with a modified version of the Zymo Oligo Clean and Concentrator protocol. Specifically, the 5-microgram capacity column was replaced with a 100-microgram capacity DNA column as appropriate. The remainder of the protocol was run according to the manufacturer's instructions. Probe was eluted in 100 microliter RNase-free deionized water and evaporated in a vacuum concentrator. The final pellet was resuspend in 10 microliter RNase-free water and stored at −20° C. Denaturing polyacrylimid gel electrophoresis and absorption spectroscopy revealed that this protocol typically produces 90-100% incorporate of the fluorescent primer into full length probe and 60-75% recovery of the total fluorescent probe. Thus, without exceeding a 150-microliter reaction volume, this protocol can be used to create ~2 nmol of fluorescent probe. The small reaction volumes were conducive to the use of high-throughput fluid handling techniques and significantly lower the cost of this reaction as compared to alternative approaches. Thus, 24-96 probes could be constructed in parallel, with minimal hands-on time, across two days, for a final cost of ~$14 per 2 nmol of each probe set.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method of producing DNA by amplifying a plurality of oligonucleotides, comprising:
   amplifying, without substantial selective amplification, at least some of a plurality of oligonucleotides contained in a common liquid using real-time PCR to produce amplified oligonucleotides;
   transcribing in vitro at least some of the amplified oligonucleotides to produce RNA;
   reverse transcribing the RNA to produce transcribed DNA; and
   selectively degrading the RNA relative to the transcribed DNA.

2. The method of claim 1, wherein the plurality of oligonucleotides have an average length of between 10 and 200 nucleotides.

3. The method of claim 1, wherein the plurality of oligonucleotides includes at least 10 unique oligonucleotide sequences.

4. The method of claim 1, wherein the unique oligonucleotide sequences each comprise a first region that is identical in the unique oligonucleotide sequences, and a second region that is not identical in the unique oligonucleotide sequences.

5. The method of claim 1, wherein amplifying at least some of the plurality of oligonucleotides comprises exposing a least some of the plurality of oligonucleotides to primer-containing sequences.

6. The method of claim 1, wherein at least some of the amplified oligonucleotides contain a promoter.

7. The method of claim 1, wherein at least some of the plurality of oligonucleotides comprise at least a first set of oligonucleotides having a first common index region, and a second set of oligonucleotides having a second common index region distinguishable from the first common index region.

8. The method of claim 7, comprising amplifying the first set of oligonucleotides but not the second set of oligonucleotides.

9. The method of claim 7, wherein the plurality of oligonucleotides comprises at least 2 sets of oligonucleotides having distinguishable common index regions.

10. The method of claim 1, wherein transcribing at least some of the amplified oligonucleotides comprises a mass of RNA that is at least 100-fold greater than the mass of amplified oligonucleotides.

11. The method of claim 1, wherein transcribing at least some of the amplified oligonucleotides comprises exposing the amplified oligonucleotides to an RNA polymerase.

12. The method of claim 1, wherein transcribing at least some of amplified oligonucleotides to produce RNA comprises producing, on average, at least 10 RNA copies of each of the amplified oligonucleotides.

13. The method of claim 1, wherein reverse transcribing the RNA comprises exposing the RNA to a reverse transcriptase.

14. The method of claim 1, wherein reverse transcribing the RNA to produce transcribed DNA occurs without first purifying the RNA from components used to produce the RNA.

15. The method of claim 1, further comprising purifying the RNA from components used to produce the RNA prior to reverse transcribing the RNA to produce transcribed DNA.

16. The method of claim 1, wherein reverse transcribing the RNA to produce transcribed DNA comprises reverse transcribing the RNA to produce transcribed DNA using a sequence containing a transcription primer.

17. The method of claim 16, wherein the sequence containing a transcription primer is incorporated into the transcribed DNA.

18. The method of claim 1, wherein selectively degrading the RNA relative to the transcribed DNA comprises chemically reducing the RNA.

19. The method of claim 1, wherein the transcribed DNA is substantially single-stranded.

20. The method of claim 1, wherein each oligonucleotide of a subset of the oligonucleotides comprises an index portion that is identical.

21. The method of claim 1, wherein the plurality of oligonucleotides has a distribution of lengths such that no more than 10% of the oligonucleotides has a length that is less than 80% or greater than 120% of the overall average length of the plurality of nucleotides.

* * * * *

SEQUENCE LISTING

<160> NUMBER OF SEQ ID NOS: 937

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
taatacgact cactataggg                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 2

```
caggcatccg agaggtctgg                                              20

<210> SEQ ID NO 3
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 3
acaaccgcgt gttacaaggc caggcatccg agaggtctgg gaatgccagc agctctacaa    60
gtgcggccat ttggttcatt gcgcttctcc ggaaacatta gc                     102

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 4
cggtaggacc ctacacatcc                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
tgtggcgcct aaccatacac                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 6
gacaccgagc tagaattcgg                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7
tgtcttgggt cctcttacgg                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 8
tatcacgtga ggctccgtgt                                              20

<210> SEQ ID NO 9
```

-continued

```
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 9
gtctacggat ccttgcgtgt                                                  20

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
acgggtacat tggatccact                                                  20

<210> SEQ ID NO 11
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 11
aagacgtggt ccaccctgat                                                  20

<210> SEQ ID NO 12
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 12
tgccaggtcc actacttggg                                                  20

<210> SEQ ID NO 13
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 13
gacccgaagg agaatgcaaa                                                  20

<210> SEQ ID NO 14
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 14
atgtcgtctc tcagggcttt                                                  20

<210> SEQ ID NO 15
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 15
```
aagggcggaa gcactctctt                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 16
tggtcccgca tttgtacctt                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 17
aagtccgtct gctaagccat                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 18
cttccagagt cctggcatga                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 19
tctaacgagc tccgtggttg                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 20
cctgggcagg aaacaacact                                               20

<210> SEQ ID NO 21
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 21
gcgcacacct tagtcatagc                                               20

<210> SEQ ID NO 22
<211> LENGTH: 20
<212> TYPE: DNA

```
<213> ORGANISM: Artificial Sequence
<220> FEATURE:
<223> OTHER INFORMATION: Synthetic Polynucleotide

<400> SEQUENCE: 22
gtgcgattgt cacatgtgct                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 23
ggcttgtcct caattatccg                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 24
cccacgtgac ttgacttctc                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 25
cctctacatg ctccggatcc                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 26
gaatagtaac ccggtcgcaa                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 27
tgggccacta gtcttcgcta                                               20

<210> SEQ ID NO 28
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 28
cggcacgtac cctttacagg                                               20
```

<210> SEQ ID NO 29
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 29
gatcagtgag cctcaccaag                                             20

<210> SEQ ID NO 30
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 30
tggtatgtga gctctttggg                                             20

<210> SEQ ID NO 31
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 31
agagtcacgc atacttggga                                             20

<210> SEQ ID NO 32
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 32
gggtcaggcg tcatagattg                                             20

<210> SEQ ID NO 33
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 33
agaatgtgga ggacatgtgg                                             20

<210> SEQ ID NO 34
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 34
tcggactgtg agacatttcc                                             20

<210> SEQ ID NO 35
<211> LENGTH: 20
<212> TYPE: DNA
<213> ORGANISM: Artificial Sequence
<220> FEATURE:

<223> OTHER INFORMATION: Synthetic Polynucleotide

<400> SEQUENCE: 35
atcaaatgcc tcggtcgttg                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 36
gcaatgctat gctgggacaa                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 37
atggaggccg ttctctgaca                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 38
gcagatgggt gcattcattc                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 39
tatgcactct gcggatgacc                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 40
gacccgggag ttatgatacg                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 41
ctcgggtagg ctatctccaa                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 42
ctgcaggtgc tctagatgga                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 43
gtccaggctc gtcttctcga                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 44
cttacctgag cgcagttcga                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 45
gttgttcgat ccctccacca                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 46
cggcagagga taatcctagc                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 47
gggagtccgg atgttagtgc                                              20

<210> SEQ ID NO 48
<211> LENGTH: 20
<212> TYPE: DNA
<213> ORGANISM: Artificial Sequence
<220> FEATURE:
<223> OTHER INFORMATION: Synthetic Polynucleotide

```
<400> SEQUENCE: 48
cgcatctatg ctccgcttac                                              20

<210> SEQ ID NO 49
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 49
aacgcgctac ccaattctag                                              20

<210> SEQ ID NO 50
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 50
tactggacga ttcccgactg                                              20

<210> SEQ ID NO 51
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 51
agcgtcgtac ccagttaagc                                              20

<210> SEQ ID NO 52
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 52
gagattcacg ccctcatgag                                              20

<210> SEQ ID NO 53
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 53
ccgctagcgt tacctctacc                                              20

<210> SEQ ID NO 54
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 54
ccacaccgta tgcatttctg                                              20

<210> SEQ ID NO 55
<211> LENGTH: 20
```

-continued

```
<212> TYPE: DNA
<213> ORGANISM: Artificial Sequence
<220> FEATURE:
<223> OTHER INFORMATION: Synthetic Polynucleotide

<400> SEQUENCE: 55
ccttagcgca caaagagacg                                               20

<210> SEQ ID NO 56
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 56
gtcctgatgg ctttctcacg                                               20

<210> SEQ ID NO 57
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 57
ggtcgtcggt agatcattgc                                               20

<210> SEQ ID NO 58
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 58
agagccggta tgatccatcg                                               20

<210> SEQ ID NO 59
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 59
ccggacgaag gttgatatcc                                               20

<210> SEQ ID NO 60
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 60
acccggtacc tgttatcacg                                               20

<210> SEQ ID NO 61
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 61
```

```
atcccgtctc gttctatggg                                              20

<210> SEQ ID NO 62
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 62
caggtgaggg tctctccttc                                              20

<210> SEQ ID NO 63
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 63
ccttatggaa acgtgatgcc                                              20

<210> SEQ ID NO 64
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 64
ggctgggcat acatagacct                                              20

<210> SEQ ID NO 65
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 65
agtggcggct attaccggat                                              20

<210> SEQ ID NO 66
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 66
tgataacgtc cgctcgttga                                              20

<210> SEQ ID NO 67
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 67
tacatcgttg aggcccgttt                                              20

<210> SEQ ID NO 68
<211> LENGTH: 20
<212> TYPE: DNA
<213> ORGANISM: Artificial Sequence
```

```
<220> FEATURE:
<223> OTHER INFORMATION: Synthetic Polynucleotide

<400> SEQUENCE: 68
cgttgtggca tcagctagag                                                   20

<210> SEQ ID NO 69
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 69
actggcccac acacttacct                                                   20

<210> SEQ ID NO 70
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 70
atcgggtcac ggaatatgac                                                   20

<210> SEQ ID NO 71
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 71
cgtaggttca cagatttgcg                                                   20

<210> SEQ ID NO 72
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 72
tagggcacga gaaggtatcc                                                   20

<210> SEQ ID NO 73
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 73
actagcttgt atcgccggat                                                   20

<210> SEQ ID NO 74
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 74
cggcggtttg atattcgaag                                                   20
```

```
<210> SEQ ID NO 75
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 75
gccgagtgtt tatgagcaag                                                       20

<210> SEQ ID NO 76
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 76
tctccgaaga tccgatatcg                                                       20

<210> SEQ ID NO 77
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 77
gatgcagggc ctaattaacg                                                       20

<210> SEQ ID NO 78
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 78
tgacgcggct aaatactgac                                                       20

<210> SEQ ID NO 79
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 79
gcaatgcacg ctctcctagt                                                       20

<210> SEQ ID NO 80
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 80
tggcgtcaga tggattagga                                                       20

<210> SEQ ID NO 81
<211> LENGTH: 20
<212> TYPE: DNA
<213> ORGANISM: Artificial Sequence
<220> FEATURE:
<223> OTHER INFORMATION: Synthetic Polynucleotide
```

```
<400> SEQUENCE: 81
gttggcggga gactaagaag                                                20

<210> SEQ ID NO 82
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 82
tcgcgtctcg tccttctacc                                                20

<210> SEQ ID NO 83
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 83
cggtcacgtc ggaaataacc                                                20

<210> SEQ ID NO 84
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 84
attaacgggc caggttactg                                                20

<210> SEQ ID NO 85
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 85
attgtatgga ggcgccctat                                                20

<210> SEQ ID NO 86
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 86
gccagctttc caagattcag                                                20

<210> SEQ ID NO 87
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 87
acaaccgcgt gttacaaggc                                                20

<210> SEQ ID NO 88
```

```
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 88
gctaatgttt ccggagaagc                                                 20

<210> SEQ ID NO 89
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 89
gaagtatccg gcatcacagc                                                 20

<210> SEQ ID NO 90
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 90
tcgttacgga ctttcacgac                                                 20

<210> SEQ ID NO 91
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 91
gccattctga catacccaga                                                 20

<210> SEQ ID NO 92
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 92
gtatttgaac cggccagctg                                                 20

<210> SEQ ID NO 93
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 93
ggttgtgggc catatccaat                                                 20

<210> SEQ ID NO 94
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 94
```
ggcgttccat cgaaactcta                                              20

<210> SEQ ID NO 95
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 95
ggccatcgac ttagattcca                                              20

<210> SEQ ID NO 96
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 96
ggtgctcctg ccattatagg                                              20

<210> SEQ ID NO 97
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 97
tgtcgacgtg cggaaagtag                                              20

<210> SEQ ID NO 98
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 98
gccgcacgag tatgctactg                                              20

<210> SEQ ID NO 99
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 99
tgctgccgct tactactgct                                              20

<210> SEQ ID NO 100
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 100
tagcactctt ctggccatcg                                              20

<210> SEQ ID NO 101
<211> LENGTH: 20
<212> TYPE: DNA

<213> ORGANISM: Artificial Sequence
<220> FEATURE:
<223> OTHER INFORMATION: Synthetic Polynucleotide

<400> SEQUENCE: 101
cggtaatcgg ttcaccagtg                                               20

<210> SEQ ID NO 102
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 102
tttagtgcct ggctccgttg                                               20

<210> SEQ ID NO 103
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 103
ggagttacag ccactttcgg                                               20

<210> SEQ ID NO 104
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 104
gtgtggacgg aacctgacaa                                               20

<210> SEQ ID NO 105
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 105
cacacgtgga attgttctgc                                               20

<210> SEQ ID NO 106
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 106
cttgtacatg gagggcgact                                               20

<210> SEQ ID NO 107
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 107
aatccggtgt acaggttccc                                               20

<210> SEQ ID NO 108
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 108
aggtgcgacg atatacacca                                               20

<210> SEQ ID NO 109
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 109
actgcatatg accgctgcaa                                               20

<210> SEQ ID NO 110
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 110
ccttccatta gccgagatca                                               20

<210> SEQ ID NO 111
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 111
gacgcgagga gtgatcgact                                               20

<210> SEQ ID NO 112
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 112
cgaccctcac acatttgggt                                               20

<210> SEQ ID NO 113
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 113
cgctcccgta ttcttctgtg                                               20

<210> SEQ ID NO 114
<211> LENGTH: 20
<212> TYPE: DNA
<213> ORGANISM: Artificial Sequence
<220> FEATURE:

<223> OTHER INFORMATION: Synthetic Polynucleotide

<400> SEQUENCE: 114
cagggatagt caggccagtg                                               20

<210> SEQ ID NO 115
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 115
cgtaatgagt gcttcgccat                                               20

<210> SEQ ID NO 116
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 116
ctcgtctcgt ggaacacatg                                               20

<210> SEQ ID NO 117
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 117
tatgctgggc agtaatcagg                                               20

<210> SEQ ID NO 118
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 118
gcatctcgta gcatcctgct                                               20

<210> SEQ ID NO 119
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 119
agtatggtac cgggaacagc                                               20

<210> SEQ ID NO 120
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 120
accattctcg caactcgcta                                               20

```
<210> SEQ ID NO 121
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 121
cgtgggcgaa gtacttggtc                                                   20

<210> SEQ ID NO 122
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 122
ccggacgtct tcgataatgc                                                   20

<210> SEQ ID NO 123
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 123
tgatgctctt tgcagttcgg                                                   20

<210> SEQ ID NO 124
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 124
atgccggtca taacagtgtc                                                   20

<210> SEQ ID NO 125
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 125
tggtggctcg ttatcacaag                                                   20

<210> SEQ ID NO 126
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 126
tctgaagcgt ggccattacc                                                   20

<210> SEQ ID NO 127
<211> LENGTH: 20
<212> TYPE: DNA
<213> ORGANISM: Artificial Sequence
<220> FEATURE:
<223> OTHER INFORMATION: Synthetic Polynucleotide
```

```
<400> SEQUENCE: 127
catatgccgg acattcagct                                              20

<210> SEQ ID NO 128
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 128
actaatggtc ctgcggcata                                              20

<210> SEQ ID NO 129
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 129
ggtgccgtgt tgcatgtaag                                              20

<210> SEQ ID NO 130
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 130
aagcggtcgt ggtttatacc                                              20

<210> SEQ ID NO 131
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 131
gccaccttgt atggtatcga                                              20

<210> SEQ ID NO 132
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 132
taatgcttag gcccgtcggt                                              20

<210> SEQ ID NO 133
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 133
gacgcgacgg attatttagg                                              20

<210> SEQ ID NO 134
<211> LENGTH: 20
```

```
<212> TYPE: DNA
<213> ORGANISM: Artificial Sequence
<220> FEATURE:
<223> OTHER INFORMATION: Synthetic Polynucleotide

<400> SEQUENCE: 134
ggtcgcgccc atatataagg                                           20

<210> SEQ ID NO 135
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 135
tgactacggt tgggtgcatc                                           20

<210> SEQ ID NO 136
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 136
tcaggcgctc attgtatgtc                                           20

<210> SEQ ID NO 137
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 137
gtagatactc ccggcccgaa                                           20

<210> SEQ ID NO 138
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 138
gcagcactta gggcagcatc                                           20

<210> SEQ ID NO 139
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 139
cgcgggaacc atattaggaa                                           20

<210> SEQ ID NO 140
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 140
```

```
gatccatggc cagttcgtat                                              20

<210> SEQ ID NO 141
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 141
gtgcgccaaa ggacttagtg                                              20

<210> SEQ ID NO 142
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 142
gatcccgcta ttcaccgatt                                              20

<210> SEQ ID NO 143
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 143
gcatagatgg ttcacccgta                                              20

<210> SEQ ID NO 144
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 144
gtctataagc cgcgctgcaa                                              20

<210> SEQ ID NO 145
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 145
gcggagtatg ccatcatgag                                              20

<210> SEQ ID NO 146
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 146
tgccgcgatc atctactatg                                              20

<210> SEQ ID NO 147
<211> LENGTH: 20
<212> TYPE: DNA
<213> ORGANISM: Artificial Sequence
```

```
<220> FEATURE:
<223> OTHER INFORMATION: Synthetic Polynucleotide

<400> SEQUENCE: 147
gaccgggtat tcgacgtcat                                                 20

<210> SEQ ID NO 148
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 148
gcagtgcggg tagatacgct                                                 20

<210> SEQ ID NO 149
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 149
aggcgtgggt agcaacgtat                                                 20

<210> SEQ ID NO 150
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 150
gctcattgga ctttctccca                                                 20

<210> SEQ ID NO 151
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 151
aaggaccacg tatctgcatg                                                 20

<210> SEQ ID NO 152
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 152
atctgatagt gccgcgacgt                                                 20

<210> SEQ ID NO 153
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 153
tgacctgcac ggatagtagg                                                 20
```

```
<210> SEQ ID NO 154
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 154
gttattcgca gtccttgggt                                                  20

<210> SEQ ID NO 155
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 155
gtgcagtgtg cttaaatccg                                                  20

<210> SEQ ID NO 156
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 156
cgcgggtgtt aaataaggac                                                  20

<210> SEQ ID NO 157
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 157
gcgaggcgtg gtaatagtca                                                  20

<210> SEQ ID NO 158
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 158
caaggcgcaa acatagacag                                                  20

<210> SEQ ID NO 159
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 159
ggaacaaggg cgtctatgtc                                                  20

<210> SEQ ID NO 160
<211> LENGTH: 20
<212> TYPE: DNA
<213> ORGANISM: Artificial Sequence
<220> FEATURE:
<223> OTHER INFORMATION: Synthetic Polynucleotide
```

<400> SEQUENCE: 160
gcagtgcgga taagctacac                                          20

<210> SEQ ID NO 161
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 161
agagatgcgt gtaggcgatt                                          20

<210> SEQ ID NO 162
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 162
ccctttcgag ctaagtttgg                                          20

<210> SEQ ID NO 163
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 163
ccttaagcaa cccgtcgatg                                          20

<210> SEQ ID NO 164
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 164
ttgctcgtga ctgaacaacg                                          20

<210> SEQ ID NO 165
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 165
ggtcgtgcgt ataagcctca                                          20

<210> SEQ ID NO 166
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 166
cggatggtct tcgtttaacc                                          20

<210> SEQ ID NO 167

```
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 167
ggcacggtgg ctagtaacga                                              20

<210> SEQ ID NO 168
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 168
gccggcccaa ctgatagtag                                              20

<210> SEQ ID NO 169
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 169
tcgacttcgg tcacctttcc                                              20

<210> SEQ ID NO 170
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 170
cgggtcgata ctttcctcgt                                              20

<210> SEQ ID NO 171
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 171
gtgccgtgtg taatatccga                                              20

<210> SEQ ID NO 172
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 172
cgcgcctgga ataactccta                                              20

<210> SEQ ID NO 173
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 173
```
gtcagggaac cgtttcttca                                                20

<210> SEQ ID NO 174
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 174
cttgtcatgt acccgaatgg                                                20

<210> SEQ ID NO 175
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 175
cgacctggct acgtagaacc                                                20

<210> SEQ ID NO 176
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 176
ctagctaaag ggccgtgcgt                                                20

<210> SEQ ID NO 177
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 177
aagtattagc gcggcaacgt                                                20

<210> SEQ ID NO 178
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 178
ggttgcgtgc cacttaaagc                                                20

<210> SEQ ID NO 179
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 179
ggaggttcgg ttgtactgca                                                20

<210> SEQ ID NO 180
<211> LENGTH: 20
<212> TYPE: DNA

```
<213> ORGANISM: Artificial Sequence
<220> FEATURE:
<223> OTHER INFORMATION: Synthetic Polynucleotide

<400> SEQUENCE: 180
gttgtcgtcc tccatcggtt                                                    20

<210> SEQ ID NO 181
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 181
gggacggaac tacacatgtg                                                    20

<210> SEQ ID NO 182
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 182
gatccatcct gattgagggt                                                    20

<210> SEQ ID NO 183
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 183
cttcatggta ccggttgaga                                                    20

<210> SEQ ID NO 184
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 184
tcggtcggct gtaaggatac                                                    20

<210> SEQ ID NO 185
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 185
attgcacgag gtcagagtcg                                                    20

<210> SEQ ID NO 186
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 186
gcttagatcc gctcgctacg                                                    20
```

<210> SEQ ID NO 187
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 187
cggctggcct actgtagaga                                              20

<210> SEQ ID NO 188
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 188
gcaacatgac ctgtcatcgc                                              20

<210> SEQ ID NO 189
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 189
ggccgcacga tatatttgac                                              20

<210> SEQ ID NO 190
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 190
cagccgggcc ataatagttg                                              20

<210> SEQ ID NO 191
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 191
tgcggtggac ctattatcct                                              20

<210> SEQ ID NO 192
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 192
cctgcgttag gcaatccatc                                              20

<210> SEQ ID NO 193
<211> LENGTH: 20
<212> TYPE: DNA
<213> ORGANISM: Artificial Sequence
<220> FEATURE:

<223> OTHER INFORMATION: Synthetic Polynucleotide

<400> SEQUENCE: 193
gtgggctctt cgaagtaacc                                               20

<210> SEQ ID NO 194
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 194
gccgtggacc actaaagttc                                               20

<210> SEQ ID NO 195
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 195
gcttaagtca tgggcgcatc                                               20

<210> SEQ ID NO 196
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 196
acaggttagt tccgcgcact                                               20

<210> SEQ ID NO 197
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 197
ggcgtggcat ttagactacc                                               20

<210> SEQ ID NO 198
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 198
actacggcca acaaccaaca                                               20

<210> SEQ ID NO 199
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 199
gttgacaagg ctctgtacgg                                               20

```
<210> SEQ ID NO 200
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 200
ttgttctctt gccggtcgat                                                    20

<210> SEQ ID NO 201
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 201
gttgatcgta gccaattcgg                                                    20

<210> SEQ ID NO 202
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 202
acaaccgcgt gttacaaggc caggcatccg agaggtctgg gaatgccagc agctctacaa        60
gtgcggccat ttggttcatt gcgcttctcc ggaaacatta gc                          102

<210> SEQ ID NO 203
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 203
acaaccgcgt gttacaaggc caggcatccg agaggtctgg gaatgccttt cgcgatagca        60
gccaggaagc ctgcttcatt gcgcttctcc ggaaacatta gc                          102

<210> SEQ ID NO 204
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 204
acaaccgcgt gttacaaggc caggcatccg agaggtctgg gaatgcccag cgggaaacct        60
ttctgttgca gagcttcatt gcgcttctcc ggaaacatta gc                          102

<210> SEQ ID NO 205
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 205
acaaccgcgt gttacaaggc caggcatccg agaggtctgg gaatgccgcc agttccgcag        60
aagccaggaa gacattcatt gcgcttctcc ggaaacatta gc                          102
```

<210> SEQ ID NO 206
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 206
acaaccgcgt gttacaaggc caggcatccg agaggtctgg gaatgccggt gtggcagaaa    60
gactgcatca ccaggtcatt gcgcttctcc ggaaacatta gc    102

<210> SEQ ID NO 207
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 207
acaaccgcgt gttacaaggc caggcatccg agaggtctgg gaatgccgcc gcgtttgttc    60
ggcacatgtg gaatatcatt gcgcttctcc ggaaacatta gc    102

<210> SEQ ID NO 208
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 208
acaaccgcgt gttacaaggc caggcatccg agaggtctgg gaatgcggtg cgtgttcacg    60
tcaactggct tcggatcatt gcgcttctcc ggaaacatta gc    102

<210> SEQ ID NO 209
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 209
acaaccgcgt gttacaaggc caggcatccg agaggtctgg gaatgccatc tgcatcggct    60
tccagcagct caggatcatt gcgcttctcc ggaaacatta gc    102

<210> SEQ ID NO 210
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 210
acaaccgcgt gttacaaggc caggcatccg agaggtctgg gaatgccgca gcacggaagt    60
gaccgatgtt ggtcatcatt gcgcttctcc ggaaacatta gc    102

<210> SEQ ID NO 211
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 211

```
acaaccgcgt gttacaaggc caggcatccg agaggtctgg gaatgccatc cgggtcgttc    60
ggagcacaca ggattgcatt gcgcttctcc ggaaacatta gc                      102

<210> SEQ ID NO 212
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 212
acaaccgcgt gttacaaggc caggcatccg agaggtctgg gaatgcatac gcgcaccact    60
cttaccgaag acgctgcatt gcgcttctcc ggaaacatta gc                      102

<210> SEQ ID NO 213
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 213
acaaccgcgt gttacaaggc caggcatccg agaggtctgg gaatgcatcg gctttctcgg    60
tgtactgaga aagctgcatt gcgcttctcc ggaaacatta gc                      102

<210> SEQ ID NO 214
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 214
acaaccgcgt gttacaaggc caggcatccg agaggtctgg gaatgccagt acccagacgg    60
ttcgggaagt tacgggcatt gcgcttctcc ggaaacatta gc                      102

<210> SEQ ID NO 215
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 215
acaaccgcgt gttacaaggc caggcatccg agaggtctgg gaatgccttt gttcagcttg    60
atggtacaac cagcggcatt gcgcttctcc ggaaacatta gc                      102

<210> SEQ ID NO 216
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 216
acaaccgcgt gttacaaggc caggcatccg agaggtctgg gaatgccatc cgcccaggac    60
tgcataacct gcttcgcatt gcgcttctcc ggaaacatta gc                      102

<210> SEQ ID NO 217
<211> LENGTH: 102
<212> TYPE: DNA
```

```
<213> ORGANISM: Artificial Sequence
<220> FEATURE:
<223> OTHER INFORMATION: Synthetic Polynucleotide

<400> SEQUENCE: 217
acaaccgcgt gttacaaggc caggcatccg agaggtctgg gaatgcccca taaaccacag      60
aacggagtta gtggcgcatt gcgcttctcc ggaaacatta gc                        102

<210> SEQ ID NO 218
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 218
acaaccgcgt gttacaaggc caggcatccg agaggtctgg gaatgctcgt tgcctgcttt      60
cgctttctct tctacgcatt gcgcttctcc ggaaacatta gc                        102

<210> SEQ ID NO 219
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 219
acaaccgcgt gttacaaggc caggcatccg agaggtctgg gaatgcccgg tgccggagaa      60
aggtcatcgg tgttagcatt gcgcttctcc ggaaacatta gc                        102

<210> SEQ ID NO 220
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 220
acaaccgcgt gttacaaggc caggcatccg agaggtctgg gaatgcaccg ccacggttca      60
taatgaagtc cggcagcatt gcgcttctcc ggaaacatta gc                        102

<210> SEQ ID NO 221
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 221
acaaccgcgt gttacaaggc caggcatccg agaggtctgg gaatgcggtc ggcaactgac      60
ctttatgcgc atccagcatt gcgcttctcc ggaaacatta gc                        102

<210> SEQ ID NO 222
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 222
acaaccgcgt gttacaaggc caggcatccg agaggtctgg gaatgccagt tcgccggttt      60
cgtggttacg cacttccatt gcgcttctcc ggaaacatta gc                        102
```

<210> SEQ ID NO 223
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 223
acaaccgcgt gttacaaggc caggcatccg agaggtctgg gaatgctcgc cgtaaccttc    60
cgcgatcatc cacttccatt gcgcttctcc ggaaacatta gc    102

<210> SEQ ID NO 224
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 224
acaaccgcgt gttacaaggc caggcatccg agaggtctgg gaatgccttg atcggaccaa    60
caacaccagg ctggtccatt gcgcttctcc ggaaacatta gc    102

<210> SEQ ID NO 225
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 225
acaaccgcgt gttacaaggc caggcatccg agaggtctgg gaatgcccgg tggtgtcctg    60
ggaacctaca gaagtccatt gcgcttctcc ggaaacatta gc    102

<210> SEQ ID NO 226
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 226
acaaccgcgt gttacaaggc caggcatccg agaggtctgg gaatgcggac gcatcggtta    60
gctcaaaggc ctgctccatt gcgcttctcc ggaaacatta gc    102

<210> SEQ ID NO 227
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 227
acaaccgcgt gttacaaggc caggcatccg agaggtctgg gaatgcatct acctgcgcca    60
cgtaggtctg gtactccatt gcgcttctcc ggaaacatta gc    102

<210> SEQ ID NO 228
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 228
acaaccgcgt gttacaaggc caggcatccg agaggtctgg gaatgcatac ggccaccagc    60
acgcacttca tcaatccatt gcgcttctcc ggaaacatta gc                     102

<210> SEQ ID NO 229
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 229
acaaccgcgt gttacaaggc caggcatccg agaggtctgg gaatgcatcg aacatcagca    60
gcgtgtgaga aagtgccatt gcgcttctcc ggaaacatta gc                     102

<210> SEQ ID NO 230
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 230
acaaccgcgt gttacaaggc caggcatccg agaggtctgg gaatgcaata tccgccagat    60
cgatgtcgat cactgccatt gcgcttctcc ggaaacatta gc                     102

<210> SEQ ID NO 231
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 231
acaaccgcgt gttacaaggc caggcatccg agaggtctgg gaatgcaaca cttcgtcgat    60
cttctcaccc tgtacccatt gcgcttctcc ggaaacatta gc                     102

<210> SEQ ID NO 232
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 232
acaaccgcgt gttacaaggc caggcatccg agaggtctgg gaatgccttg cctttcttct    60
caacggtcag cagacccatt gcgcttctcc ggaaacatta gc                     102

<210> SEQ ID NO 233
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 233
acaaccgcgt gttacaaggc caggcatccg agaggtctgg gaatgcccat gccctgaata    60
cgacgttcca gggtaccatt gcgcttctcc ggaaacatta gc                     102

<210> SEQ ID NO 234
<211> LENGTH: 102

```
<212> TYPE: DNA
<213> ORGANISM: Artificial Sequence
<220> FEATURE:
<223> OTHER INFORMATION: Synthetic Polynucleotide

<400> SEQUENCE: 234
acaaccgcgt gttacaaggc caggcatccg agaggtctgg gaatgcggaa acgggtatgg    60
gagtcaccac cggtaccatt gcgcttctcc ggaaacatta gc                      102

<210> SEQ ID NO 235
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 235
acaaccgcgt gttacaaggc caggcatccg agaggtctgg gaatgccgaa gaacccgtac    60
ccacaacgtc accgaccatt gcgcttctcc ggaaacatta gc                      102

<210> SEQ ID NO 236
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 236
acaaccgcgt gttacaaggc caggcatccg agaggtctgg gaatgcacgt caatcacgtc    60
gcccatgttc aggttacatt gcgcttctcc ggaaacatta gc                      102

<210> SEQ ID NO 237
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 237
acaaccgcgt gttacaaggc caggcatccg agaggtctgg gaatgcacca gaccagaacc    60
cgccgggaaa gagatacatt gcgcttctcc ggaaacatta gc                      102

<210> SEQ ID NO 238
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 238
acaaccgcgt gttacaaggc caggcatccg agaggtctgg gaatgcttga agcgcaccag    60
aacggattcc ggcatacatt gcgcttctcc ggaaacatta gc                      102

<210> SEQ ID NO 239
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 239
acaaccgcgt gttacaaggc caggcatccg agaggtctgg gaatgccctt cttcggtcaa    60
```
ctgtgcggcg tccatacatt gcgcttctcc ggaaacatta gc                    102

<210> SEQ ID NO 240
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 240
acaaccgcgt gttacaaggc caggcatccg agaggtctgg gaatgcggtt acccatacac    60
agggaacagc cagggacatt gcgcttctcc ggaaacatta gc                    102

<210> SEQ ID NO 241
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 241
acaaccgcgt gttacaaggc caggcatccg agaggtctgg gaatgctcag atccggcaga    60
ccttcaattt ccaggacatt gcgcttctcc ggaaacatta gc                    102

<210> SEQ ID NO 242
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 242
acaaccgcgt gttacaaggc caggcatccg agaggtctgg gaatgcccag tttggcatca    60
tccagcgcgt cgatcacatt gcgcttctcc ggaaacatta gc                    102

<210> SEQ ID NO 243
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 243
acaaccgcgt gttacaaggc caggcatccg agaggtctgg gaatgcccca ggcacgccag    60
gtctttcagt tcatcacatt gcgcttctcc ggaaacatta gc                    102

<210> SEQ ID NO 244
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 244
acaaccgcgt gttacaaggc caggcatccg agaggtctgg gaatgccttt ggtggtcagg    60
ccacgcccga taatcacatt gcgcttctcc ggaaacatta gc                    102

<210> SEQ ID NO 245
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 245
acaaccgcgt gttacaaggc caggcatccg agaggtctgg aatgctgat cgcatacagc    60 ggaatagcgt gtaccacatt gcgcttctcc ggaaacatta gc    102

<210> SEQ ID NO 246
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 246
acaaccgcgt gttacaaggc caggcatccg agaggtctgg aatgcgcag tgcacccgcg    60 tcttccatcg tgttaacatt gcgcttctcc ggaaacatta gc    102

<210> SEQ ID NO 247
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 247
acaaccgcgt gttacaaggc caggcatccg agaggtctgg aatgcgcag cagcatacgg    60 ttcagccagg agtgaacatt gcgcttctcc ggaaacatta gc    102

<210> SEQ ID NO 248
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 248
acaaccgcgt gttacaaggc caggcatccg agaggtctgg aatgcgctc tcagcgacat    60 ctttcgcctg acggaacatt gcgcttctcc ggaaacatta gc    102

<210> SEQ ID NO 249
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 249
acaaccgcgt gttacaaggc caggcatccg agaggtctgg aatgcggtt tcaaggtcgc    60 ccgccagttt ctgtttcatt gcgcttctcc ggaaacatta gc    102

<210> SEQ ID NO 250
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 250
acaaccgcgt gttacaaggc caggcatccg agaggtctgg aatgccacg gtgctggaac    60 caccggcata gaagttcatt gcgcttctcc ggaaacatta gc    102

<210> SEQ ID NO 251

```
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 251
acaaccgcgt gttacaaggc caggcatccg agaggtctgg gaatgcggtc ccgttgatac      60
caacagcata acctgtcatt gcgcttctcc ggaaacatta gc                        102

<210> SEQ ID NO 252
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 252
acaaccgcgt gttacaaggc caggcatccg agaggtctgg gaatgctgaa acgggcataa      60
ccgcgatcca gatagtcatt gcgcttctcc ggaaacatta gc                        102

<210> SEQ ID NO 253
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 253
acaaccgcgt gttacaaggc caggcatccg agaggtctgg gaatgccgga acacgttggg      60
tatcggtatc gacagtcatt gcgcttctcc ggaaacatta gc                        102

<210> SEQ ID NO 254
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 254
acaaccgcgt gttacaaggc caggcatccg agaggtctgg gaatgcacgg tgaagtacgg      60
gttggttacc gacagtcatt gcgcttctcc ggaaacatta gc                        102

<210> SEQ ID NO 255
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 255
acaaccgcgt gttacaaggc caggcatccg agaggtctgg gaatgcacag ctcacccggc      60
tcgatcttag tcagctcatt gcgcttctcc ggaaacatta gc                        102

<210> SEQ ID NO 256
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 256
acaaccgcgt gttacaaggc caggcatccg agaggtctgg gaatgctgtt ggtatagtcg      60
```

```
gacaggtcgg cgtcatcatt gcgcttctcc ggaaacatta gc                        102

<210> SEQ ID NO 257
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 257
acaaccgcgt gttacaaggc caggcatccg agaggtctgg gaatgcggcg acacgctgaa     60
ggccttcgaa atgaatcatt gcgcttctcc ggaaacatta gc                       102

<210> SEQ ID NO 258
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 258
acaaccgcgt gttacaaggc caggcatccg agaggtctgg gaatgctgga aatgagagat     60
cagttcgtcg gtggtgcatt gcgcttctcc ggaaacatta gc                       102

<210> SEQ ID NO 259
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 259
acaaccgcgt gttacaaggc caggcatccg agaggtctgg gaatgcttgc tggatttcag     60
ctgacacacc ttcctgcatt gcgcttctcc ggaaacatta gc                       102

<210> SEQ ID NO 260
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 260
acaaccgcgt gttacaaggc caggcatccg agaggtctgg gaatgcgtcg gcatcgttaa     60
tttcgggcat cgactgcatt gcgcttctcc ggaaacatta gc                       102

<210> SEQ ID NO 261
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 261
acaaccgcgt gttacaaggc caggcatccg agaggtctgg gaatgcactg ctttcggacc     60
aatggtattg gactggcatt gcgcttctcc ggaaacatta gc                       102

<210> SEQ ID NO 262
<211> LENGTH: 102
<212> TYPE: DNA
<213> ORGANISM: Artificial Sequence
<220> FEATURE:
```

<223> OTHER INFORMATION: Synthetic Polynucleotide

<400> SEQUENCE: 262
acaaccgcgt gttacaaggc caggcatccg agaggtctgg gaatgcacct tgtagacgac    60
atcaacctgg tccgggcatt gcgcttctcc ggaaacatta gc    102

<210> SEQ ID NO 263
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 263
acaaccgcgt gttacaaggc caggcatccg agaggtctgg gaatgctatc cgatccagga    60
atggtcactt taccggcatt gcgcttctcc ggaaacatta gc    102

<210> SEQ ID NO 264
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 264
acaaccgcgt gttacaaggc caggcatccg agaggtctgg gaatgctcac tacgaaccct    60
tcagcaccgt atacggcatt gcgcttctcc ggaaacatta gc    102

<210> SEQ ID NO 265
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 265
acaaccgcgt gttacaaggc caggcatccg agaggtctgg gaatgcagcc atgcaccttc    60
catctgacgc atttcgcatt gcgcttctcc ggaaacatta gc    102

<210> SEQ ID NO 266
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 266
acaaccgcgt gttacaaggc caggcatccg agaggtctgg gaatgcccca gacctgcacg    60
cagcgagtta tattcgcatt gcgcttctcc ggaaacatta gc    102

<210> SEQ ID NO 267
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 267
acaaccgcgt gttacaaggc caggcatccg agaggtctgg gaatgcaact ggaactgttc    60
tgccttgtct ccatcgcatt gcgcttctcc ggaaacatta gc    102

<210> SEQ ID NO 268
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 268
acaaccgcgt gttacaaggc caggcatccg agaggtctgg gaatgcatct tcatcattaa    60
ccgtgtcgcc tgtgcgcatt gcgcttctcc ggaaacatta gc                      102

<210> SEQ ID NO 269
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 269
acaaccgcgt gttacaaggc caggcatccg agaggtctgg gaatgctcca accatagttg    60
aacgtgaagt cgtccgcatt gcgcttctcc ggaaacatta gc                      102

<210> SEQ ID NO 270
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 270
acaaccgcgt gttacaaggc caggcatccg agaggtctgg gaatgcccat tgtaatgcga    60
tacccgcaga catacgcatt gcgcttctcc ggaaacatta gc                      102

<210> SEQ ID NO 271
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 271
acaaccgcgt gttacaaggc caggcatccg agaggtctgg gaatgcattt acgatcgcct    60
accacgttcc accacgcatt gcgcttctcc ggaaacatta gc                      102

<210> SEQ ID NO 272
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 272
acaaccgcgt gttacaaggc caggcatccg agaggtctgg gaatgctggc tggaatccca    60
gtttgtatcc caaacgcatt gcgcttctcc ggaaacatta gc                      102

<210> SEQ ID NO 273
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 273
acaaccgcgt gttacaaggc caggcatccg agaggtctgg gaatgcacgc tggcgctata    60
tttaccgacg ctgtagcatt gcgcttctcc ggaaacatta gc    102

<210> SEQ ID NO 274
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 274
acaaccgcgt gttacaaggc caggcatccg agaggtctgg gaatgcaccg cctacagcat    60
catccgattt acacagcatt gcgcttctcc ggaaacatta gc    102

<210> SEQ ID NO 275
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 275
acaaccgcgt gttacaaggc caggcatccg agaggtctgg gaatgcatct ggcgtcagac    60
tgacctgggt agagtccatt gcgcttctcc ggaaacatta gc    102

<210> SEQ ID NO 276
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 276
acaaccgcgt gttacaaggc caggcatccg agaggtctgg gaatgccgcg ccgtcctgag    60
tcgcacattc gtaatccatt gcgcttctcc ggaaacatta gc    102

<210> SEQ ID NO 277
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 277
acaaccgcgt gttacaaggc caggcatccg agaggtctgg gaatgcacaa cccatttgtg    60
atcgtcatcg atcggccatt gcgcttctcc ggaaacatta gc    102

<210> SEQ ID NO 278
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 278
acaaccgcgt gttacaaggc caggcatccg agaggtctgg gaatgcaccc atagagtaca    60
gataacgcca catcgccatt gcgcttctcc ggaaacatta gc    102

<210> SEQ ID NO 279
<211> LENGTH: 102
<212> TYPE: DNA
<213> ORGANISM: Artificial Sequence

```
<220> FEATURE:
<223> OTHER INFORMATION: Synthetic Polynucleotide

<400> SEQUENCE: 279
acaaccgcgt gttacaaggc caggcatccg agaggtctgg aatgcatac caaagttgaa    60 gctaccggtg ttgcgccatt gcgcttctcc ggaaacatta gc                     102

<210> SEQ ID NO 280
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 280
acaaccgcgt gttacaaggc caggcatccg agaggtctgg aatgctata gaagagacga    60 ccaccgaggc ttacgccatt gcgcttctcc ggaaacatta gc                     102

<210> SEQ ID NO 281
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 281
acaaccgcgt gttacaaggc caggcatccg agaggtctgg aatgcgtca tcttccatct    60 tggtcacttt ggtgcccatt gcgcttctcc ggaaacatta gc                     102

<210> SEQ ID NO 282
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 282
acaaccgcgt gttacaaggc caggcatccg agaggtctgg aatgccgga tcttacgcac    60 gtagaaacgg ttaccccatt gcgcttctcc ggaaacatta gc                     102

<210> SEQ ID NO 283
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 283
acaaccgcgt gttacaaggc caggcatccg agaggtctgg aatgccagg acggcatctt    60 tcgaggtatc gttacccatt gcgcttctcc ggaaacatta gc                     102

<210> SEQ ID NO 284
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 284
acaaccgcgt gttacaaggc caggcatccg agaggtctgg aatgcagaa gcccagacga    60 ttcagacgct ccttaccatt gcgcttctcc ggaaacatta gc                     102
```

<210> SEQ ID NO 285
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 285
acaaccgcgt gttacaaggc caggcatccg agaggtctgg gaatgctgac acgtgaacca    60
tctgtcggga agtaaccatt gcgcttctcc ggaaacatta gc                      102

<210> SEQ ID NO 286
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 286
acaaccgcgt gttacaaggc caggcatccg agaggtctgg gaatgcctgc taaacagcag    60
cgacgctatg agcaaccatt gcgcttctcc ggaaacatta gc                      102

<210> SEQ ID NO 287
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 287
acaaccgcgt gttacaaggc caggcatccg agaggtctgg gaatgcgagg ctgcatgttg    60
gacagggagt tatgtacatt gcgcttctcc ggaaacatta gc                      102

<210> SEQ ID NO 288
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 288
acaaccgcgt gttacaaggc caggcatccg agaggtctgg gaatgccggg aagcccaacg    60
tcacgtctgt accatacatt gcgcttctcc ggaaacatta gc                      102

<210> SEQ ID NO 289
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 289
acaaccgcgt gttacaaggc caggcatccg agaggtctgg gaatgcccgg atcataatta    60
ctggcctgat gcgggacatt gcgcttctcc ggaaacatta gc                      102

<210> SEQ ID NO 290
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 290
acaaccgcgt gttacaaggc caggcatccg agaggtctgg aatgcaagc tgttatcctg    60 atcagaggtg ctcggacatt gcgcttctcc ggaaacatta gc                     102

<210> SEQ ID NO 291
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 291
acaaccgcgt gttacaaggc caggcatccg agaggtctgg aatgcacct gaaccagaag    60 ggtatcacca tcacgacatt gcgcttctcc ggaaacatta gc                     102

<210> SEQ ID NO 292
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 292
acaaccgcgt gttacaaggc caggcatccg agaggtctgg aatgcggca tctctttgcc    60 gcctaaacca tcaccacatt gcgcttctcc ggaaacatta gc                     102

<210> SEQ ID NO 293
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 293
acaaccgcgt gttacaaggc caggcatccg agaggtctgg aatgcccag ttatcctgct    60 gcacaccagc ctggaacatt gcgcttctcc ggaaacatta gc                     102

<210> SEQ ID NO 294
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 294
acaaccgcgt gttacaaggc caggcatccg agaggtctgg aatgcgcgg ataggcataa    60 ccatagcgac cgagaacatt gcgcttctcc ggaaacatta gc                     102

<210> SEQ ID NO 295
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 295
acaaccgcgt gttacaaggc caggcatccg agaggtctgg aatgccaag gttgccgctc    60 acttcaacgc cagaaacatt gcgcttctcc ggaaacatta gc                     102

<210> SEQ ID NO 296
<211> LENGTH: 102
<212> TYPE: DNA

```
<213> ORGANISM: Artificial Sequence
<220> FEATURE:
<223> OTHER INFORMATION: Synthetic Polynucleotide

<400> SEQUENCE: 296
acaaccgcgt gttacaaggc caggcatccg agaggtctgg gaatgcgcga acatcctcaa    60
agttgccggt agcaaacatt gcgcttctcc ggaaacatta gc                      102

<210> SEQ ID NO 297
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 297
acaaccgcgt gttacaaggc caggcatccg agaggtctgg gaatgcacgt gggcttgcac    60
gttcaaacca gtcactcatt gcgcttctcc ggaaacatta gc                      102

<210> SEQ ID NO 298
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 298
acaaccgcgt gttacaaggc caggcatccg agaggtctgg gaatgccctg tgaaagcgca    60
ttacagagct gttgtgcatt gcgcttctcc ggaaacatta gc                      102

<210> SEQ ID NO 299
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 299
acaaccgcgt gttacaaggc caggcatccg agaggtctgg gaatgcttgc gctttcaatt    60
gcgcgtactg atccagcatt gcgcttctcc ggaaacatta gc                      102

<210> SEQ ID NO 300
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 300
acaaccgcgt gttacaaggc caggcatccg agaggtctgg gaatgcgcgc ttgtggagga    60
tagtcggaat agctgccatt gcgcttctcc ggaaacatta gc                      102

<210> SEQ ID NO 301
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 301
acaaccgcgt gttacaaggc caggcatccg agaggtctgg gaatgcagga atttggtccg    60
gtccgcctgt aatgaccatt gcgcttctcc ggaaacatta gc                      102
```

<210> SEQ ID NO 302
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 302
acaaccgcgt gttacaaggc caggcatccg agaggtctgg gaatgccgag cgtgctaaca    60
cctgttcgcg gctaaccatt gcgcttctcc ggaaacatta gc                      102

<210> SEQ ID NO 303
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 303
acaaccgcgt gttacaaggc caggcatccg agaggtctgg gaatgcgcat tacctccacg    60
ccaggcaatc accagacatt gcgcttctcc ggaaacatta gc                      102

<210> SEQ ID NO 304
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 304
acaaccgcgt gttacaaggc caggcatccg agaggtctgg gaatgcgcaa aggcaagttc    60
agtgttggcg ggagaacatt gcgcttctcc ggaaacatta gc                      102

<210> SEQ ID NO 305
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 305
acaaccgcgt gttacaaggc caggcatccg agaggtctgg gaatgcgata tcgcggatat    60
gcagcagcca gttgttcatt gcgcttctcc ggaaacatta gc                      102

<210> SEQ ID NO 306
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 306
acaaccgcgt gttacaaggc caggcatccg agaggtctgg gaatgcgcag ttcaggtcag    60
tgtgaatgac caggttcatt gcgcttctcc ggaaacatta gc                      102

<210> SEQ ID NO 307
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 307
acaaccgcgt gttacaaggc caggcatccg agaggtctgg gaatgccatt acggtgaaca    60
aagagttcgc ccggctcatt gcgcttctcc ggaaacatta gc                      102

<210> SEQ ID NO 308
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 308
acaaccgcgt gttacaaggc caggcatccg agaggtctgg gaatgcttgt ggttggcgtg    60
tttcagcttg aggttgcatt gcgcttctcc ggaaacatta gc                      102

<210> SEQ ID NO 309
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 309
acaaccgcgt gttacaaggc caggcatccg agaggtctgg gaatgcccgg ttaaacgttc    60
tgcaggaacg cgactgcatt gcgcttctcc ggaaacatta gc                      102

<210> SEQ ID NO 310
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 310
acaaccgcgt gttacaaggc caggcatccg agaggtctgg gaatgccctg ttccatgacg    60
ttcagttcac acaaggcatt gcgcttctcc ggaaacatta gc                      102

<210> SEQ ID NO 311
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 311
acaaccgcgt gttacaaggc caggcatccg agaggtctgg gaatgctcga gtacatccac    60
tgcatactga accacgcatt gcgcttctcc ggaaacatta gc                      102

<210> SEQ ID NO 312
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 312
acaaccgcgt gttacaaggc caggcatccg agaggtctgg gaatgccgtt tccacgctga    60
ttgcataatg gtggagcatt gcgcttctcc ggaaacatta gc                      102

<210> SEQ ID NO 313
<211> LENGTH: 102

```
<212> TYPE: DNA
<213> ORGANISM: Artificial Sequence
<220> FEATURE:
<223> OTHER INFORMATION: Synthetic Polynucleotide

<400> SEQUENCE: 313
acaaccgcgt gttacaaggc caggcatccg agaggtctgg gaatgccccg tgacggtaac    60
gttgctcaag ggtttccatt gcgcttctcc ggaaacatta gc                      102

<210> SEQ ID NO 314
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 314
acaaccgcgt gttacaaggc caggcatccg agaggtctgg gaatgcccgc cgcaaccgta    60
gtggccacag ataatacatt gcgcttctcc ggaaacatta gc                      102

<210> SEQ ID NO 315
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 315
acaaccgcgt gttacaaggc caggcatccg agaggtctgg gaatgcggtg gcggtaacat    60
ccagatcacg cagcaacatt gcgcttctcc ggaaacatta gc                      102

<210> SEQ ID NO 316
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 316
acaaccgcgt gttacaaggc caggcatccg agaggtctgg gaatgctaat gattctcgtc    60
atagtgccag gcccgtcatt gcgcttctcc ggaaacatta gc                      102

<210> SEQ ID NO 317
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 317
acaaccgcgt gttacaaggc caggcatccg agaggtctgg gaatgccaga aacaacgccg    60
cgatgacgac gggtatcatt gcgcttctcc ggaaacatta gc                      102

<210> SEQ ID NO 318
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 318
acaaccgcgt gttacaaggc caggcatccg agaggtctgg gaatgcgcca gcatgcagac    60
```
caccagcgtt acaatgcatt gcgcttctcc ggaaacatta gc                     102

<210> SEQ ID NO 319
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 319
acaaccgcgt gttacaaggc caggcatccg agaggtctgg gaatgcagag ttacgccaga    60
ttgctgcgga acctggcatt gcgcttctcc ggaaacatta gc                     102

<210> SEQ ID NO 320
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 320
acaaccgcgt gttacaaggc caggcatccg agaggtctgg gaatgccgaa gcccaaagtg    60
agatttcaac cagcggcatt gcgcttctcc ggaaacatta gc                     102

<210> SEQ ID NO 321
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 321
acaaccgcgt gttacaaggc caggcatccg agaggtctgg gaatgcgtaa caacaagcaa    60
gcaaagaccg gtaccgcatt gcgcttctcc ggaaacatta gc                     102

<210> SEQ ID NO 322
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 322
acaaccgcgt gttacaaggc caggcatccg agaggtctgg gaatgcggat catgacatag    60
agcagccata ttgcgccatt gcgcttctcc ggaaacatta gc                     102

<210> SEQ ID NO 323
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 323
acaaccgcgt gttacaaggc caggcatccg agaggtctgg gaatgctacc accgtgtcct    60
ggaattaaat gaccgccatt gcgcttctcc ggaaacatta gc                     102

<210> SEQ ID NO 324
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 324
acaaccgcgt gttacaaggc caggcatccg agaggtctgg gaatgctttg ccaaacatat    60
atgcgccgga gtcagccatt gcgcttctcc ggaaacatta gc    102

<210> SEQ ID NO 325
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 325
acaaccgcgt gttacaaggc caggcatccg agaggtctgg gaatgcccgc tgcagtagcg    60
agtccaccga taaagccatt gcgcttctcc ggaaacatta gc    102

<210> SEQ ID NO 326
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 326
acaaccgcgt gttacaaggc caggcatccg agaggtctgg gaatgcacgc ttaaacatac    60
tctcggtcag atcgcccatt gcgcttctcc ggaaacatta gc    102

<210> SEQ ID NO 327
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 327
acaaccgcgt gttacaaggc caggcatccg agaggtctgg gaatgcgcat cagcgccaac    60
aataacccgc ataacacatt gcgcttctcc ggaaacatta gc    102

<210> SEQ ID NO 328
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 328
acaaccgcgt gttacaaggc caggcatccg agaggtctgg gaatgcgcga cgtcgagatt    60
cgcccacatg ccataacatt gcgcttctcc ggaaacatta gc    102

<210> SEQ ID NO 329
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 329
acaaccgcgt gttacaaggc caggcatccg agaggtctgg gaatgcagca ccagcaatag    60
cgcgacaatc caccaacatt gcgcttctcc ggaaacatta gc    102

<210> SEQ ID NO 330

```
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 330
acaaccgcgt gttacaaggc caggcatccg agaggtctgg gaatgcctga ggctaacgct    60
gcgacaatag agcaaacatt gcgcttctcc ggaaacatta gc                      102

<210> SEQ ID NO 331
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 331
acaaccgcgt gttacaaggc caggcatccg agaggtctgg gaatgcgaac gcgaccgtag    60
tggatttcgc cggtttcatt gcgcttctcc ggaaacatta gc                      102

<210> SEQ ID NO 332
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 332
acaaccgcgt gttacaaggc caggcatccg agaggtctgg gaatgcccgg aatccagcag    60
ggcgatcacc tgatttcatt gcgcttctcc ggaaacatta gc                      102

<210> SEQ ID NO 333
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 333
acaaccgcgt gttacaaggc caggcatccg agaggtctgg gaatgcgtgc cttcatcaac    60
atatgcgccg atgttgcatt gcgcttctcc ggaaacatta gc                      102

<210> SEQ ID NO 334
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 334
acaaccgcgt gttacaaggc caggcatccg agaggtctgg gaatgccaac cactgatgcg    60
tcacccactg accgtccatt gcgcttctcc ggaaacatta gc                      102

<210> SEQ ID NO 335
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 335
acaaccgcgt gttacaaggc caggcatccg agaggtctgg gaatgcgtaa cggtgtctgc    60
```
attggctggc gtgatccatt gcgcttctcc ggaaacatta gc                              102

<210> SEQ ID NO 336
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 336
acaaccgcgt gttacaaggc caggcatccg agaggtctgg gaatgcaacc gcacagtaga     60
ggctgtattt gccatccatt gcgcttctcc ggaaacatta gc                        102

<210> SEQ ID NO 337
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 337
acaaccgcgt gttacaaggc caggcatccg agaggtctgg gaatgcagtc gatggtacgc     60
agcagttcgt taatgccatt gcgcttctcc ggaaacatta gc                        102

<210> SEQ ID NO 338
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 338
acaaccgcgt gttacaaggc caggcatccg agaggtctgg gaatgcaata cgggtgctct     60
gaccaatgta tacgcccatt gcgcttctcc ggaaacatta gc                        102

<210> SEQ ID NO 339
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 339
acaaccgcgt gttacaaggc caggcatccg agaggtctgg gaatgcactt cagagcgcgc     60
gccgatgaag caattacatt gcgcttctcc ggaaacatta gc                        102

<210> SEQ ID NO 340
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 340
acaaccgcgt gttacaaggc caggcatccg agaggtctgg gaatgcgacg gcatcagcac     60
ggtgttacgg gcaatacatt gcgcttctcc ggaaacatta gc                        102

<210> SEQ ID NO 341
<211> LENGTH: 102
<212> TYPE: DNA
<213> ORGANISM: Artificial Sequence
<220> FEATURE:

<223> OTHER INFORMATION: Synthetic Polynucleotide

<400> SEQUENCE: 341
acaaccgcgt gttacaaggc caggcatccg agaggtctgg gaatgccttc gtcgtagtcg    60
gcgaatttca tcggcacatt gcgcttctcc ggaaacatta gc    102

<210> SEQ ID NO 342
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 342
acaaccgcgt gttacaaggc caggcatccg agaggtctgg gaatgctggc acaacgcgga    60
agccttcttt ctggaacatt gcgcttctcc ggaaacatta gc    102

<210> SEQ ID NO 343
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 343
acaaccgcgt gttacaaggc caggcatccg agaggtctgg gaatgccaca agaaccgacg    60
gtcgcccagg tatcaacatt gcgcttctcc ggaaacatta gc    102

<210> SEQ ID NO 344
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 344
acaaccgcgt gttacaaggc caggcatccg agaggtctgg gaatgcccgg taaaccggca    60
ccttgccata gaagttcatt gcgcttctcc ggaaacatta gc    102

<210> SEQ ID NO 345
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 345
acaaccgcgt gttacaaggc caggcatccg agaggtctgg gaatgcggtc gacaggatac    60
gcgtcaatac cgccttcatt gcgcttctcc ggaaacatta gc    102

<210> SEQ ID NO 346
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 346
acaaccgcgt gttacaaggc caggcatccg agaggtctgg gaatgcgctg tggctggtca    60
tacccggtga ggtattcatt gcgcttctcc ggaaacatta gc    102

<210> SEQ ID NO 347
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 347
acaaccgcgt gttacaaggc caggcatccg agaggtctgg gaatgcctgt ccatcgctgt      60
ccagcataac gtcaatcatt gcgcttctcc ggaaacatta gc                        102

<210> SEQ ID NO 348
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 348
acaaccgcgt gttacaaggc caggcatccg agaggtctgg gaatgctcgc ctcataatca      60
tagaaggttc cggacgcatt gcgcttctcc ggaaacatta gc                        102

<210> SEQ ID NO 349
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 349
acaaccgcgt gttacaaggc caggcatccg agaggtctgg gaatgccctt tgcaacctaa      60
cgtcgtccat gctttccatt gcgcttctcc ggaaacatta gc                        102

<210> SEQ ID NO 350
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 350
acaaccgcgt gttacaaggc caggcatccg agaggtctgg gaatgcccgc gaccgtgtag      60
cgcgataaac actttccatt gcgcttctcc ggaaacatta gc                        102

<210> SEQ ID NO 351
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 351
acaaccgcgt gttacaaggc caggcatccg agaggtctgg gaatgcgaca ttcccacact      60
ggaaccttcg cggctccatt gcgcttctcc ggaaacatta gc                        102

<210> SEQ ID NO 352
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 352
acaaccgcgt gttacaaggc caggcatccg agaggtctgg gaatgcttct tcaccgagta    60
tcgcaaccgt gaactccatt gcgcttctcc ggaaacatta gc    102

<210> SEQ ID NO 353
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 353
acaaccgcgt gttacaaggc caggcatccg agaggtctgg gaatgcaacc ggcaaaccca    60
gagcagaaat ttctgccatt gcgcttctcc ggaaacatta gc    102

<210> SEQ ID NO 354
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 354
acaaccgcgt gttacaaggc caggcatccg agaggtctgg gaatgctaat gcctgcaaat    60
tggcctcttg tgacgccatt gcgcttctcc ggaaacatta gc    102

<210> SEQ ID NO 355
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 355
acaaccgcgt gttacaaggc caggcatccg agaggtctgg gaatgcatcc attgaaagcg    60
cagatgccat cactcccatt gcgcttctcc ggaaacatta gc    102

<210> SEQ ID NO 356
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 356
acaaccgcgt gttacaaggc caggcatccg agaggtctgg gaatgctagt ccgccagttc    60
cagaattcgt actacccatt gcgcttctcc ggaaacatta gc    102

<210> SEQ ID NO 357
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 357
acaaccgcgt gttacaaggc caggcatccg agaggtctgg gaatgcgccc atcgacttca    60
gttgcgtcac gtcgaccatt gcgcttctcc ggaaacatta gc    102

<210> SEQ ID NO 358
<211> LENGTH: 102
<212> TYPE: DNA
<213> ORGANISM: Artificial Sequence

```
<220> FEATURE:
<223> OTHER INFORMATION: Synthetic Polynucleotide

<400> SEQUENCE: 358
acaaccgcgt gttacaaggc caggcatccg agaggtctgg aatgcggct aacaccgctg     60 cgccagaatt cagagacatt gcgcttctcc ggaaacatta gc                      102

<210> SEQ ID NO 359
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 359
acaaccgcgt gttacaaggc caggcatccg agaggtctgg aatgccggt ataaggcaag     60 cccatcagct cgagcacatt gcgcttctcc ggaaacatta gc                      102

<210> SEQ ID NO 360
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 360
acaaccgcgt gttacaaggc caggcatccg agaggtctgg aatgccacg ttgttcacta    60 ccacgccctg atctttcatt gcgcttctcc ggaaacatta gc                      102

<210> SEQ ID NO 361
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 361
acaaccgcgt gttacaaggc caggcatccg agaggtctgg aatgcgttc aggttaacca    60 gcgcaccacc ggagttcatt gcgcttctcc ggaaacatta gc                      102

<210> SEQ ID NO 362
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 362
acaaccgcgt gttacaaggc caggcatccg agaggtctgg aatgcctgc agttccaggt    60 tcacgttaac ctgcttcatt gcgcttctcc ggaaacatta gc                      102

<210> SEQ ID NO 363
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 363
acaaccgcgt gttacaaggc caggcatccg agaggtctgg aatgcgcag cggaggaatt    60 aggcagaacc tggcttcatt gcgcttctcc ggaaacatta gc                      102
```

<210> SEQ ID NO 364
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 364
acaaccgcgt gttacaaggc caggcatccg agaggtctgg gaatgcactc agagccagtg    60
cactcagtgc taatgtcatt gcgcttctcc ggaaacatta gc    102

<210> SEQ ID NO 365
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 365
acaaccgcgt gttacaaggc caggcatccg agaggtctgg gaatgctgtt gctcatctca    60
gcgccttcaa tgccgtcatt gcgcttctcc ggaaacatta gc    102

<210> SEQ ID NO 366
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 366
acaaccgcgt gttacaaggc caggcatccg agaggtctgg gaatgctgaa tgttgagtgc    60
cagcacagac ggtttgcatt gcgcttctcc ggaaacatta gc    102

<210> SEQ ID NO 367
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 367
acaaccgcgt gttacaaggc caggcatccg agaggtctgg gaatgcgccg gaacccagcg    60
ccatgaattt ctgttgcatt gcgcttctcc ggaaacatta gc    102

<210> SEQ ID NO 368
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 368
acaaccgcgt gttacaaggc caggcatccg agaggtctgg gaatgcatgg agctggaatc    60
aacctgattc tggctgcatt gcgcttctcc ggaaacatta gc    102

<210> SEQ ID NO 369
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 369

```
acaaccgcgt gttacaaggc caggcatccg agaggtctgg aatgcataa tacccagctc    60 accgcgtttc acctggcatt gcgcttctcc ggaaacatta gc                     102

<210> SEQ ID NO 370
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 370
acaaccgcgt gttacaaggc caggcatccg agaggtctgg aatgcggca aagctgctga    60 tcggcttacc gttcagcatt gcgcttctcc ggaaacatta gc                     102

<210> SEQ ID NO 371
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 371
acaaccgcgt gttacaaggc caggcatccg agaggtctgg aatgcctgg gcgtcaactt    60 tcatcgcttt cgccagcatt gcgcttctcc ggaaacatta gc                     102

<210> SEQ ID NO 372
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 372
acaaccgcgt gttacaaggc caggcatccg agaggtctgg aatgcgcat ctgctgggct    60 gtcgttgctg aagaagcatt gcgcttctcc ggaaacatta gc                     102

<210> SEQ ID NO 373
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 373
acaaccgcgt gttacaaggc caggcatccg agaggtctgg aatgcagcg cagagacaat    60 cccggaagtt accgtccatt gcgcttctcc ggaaacatta gc                     102

<210> SEQ ID NO 374
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 374
acaaccgcgt gttacaaggc caggcatccg agaggtctgg aatgccggg ttctggattt    60 ggatcagcgc gatatccatt gcgcttctcc ggaaacatta gc                     102

<210> SEQ ID NO 375
<211> LENGTH: 102
<212> TYPE: DNA
```

<213> ORGANISM: Artificial Sequence
<220> FEATURE:
<223> OTHER INFORMATION: Synthetic Polynucleotide

<400> SEQUENCE: 375
acaaccgcgt gttacaaggc caggcatccg agaggtctgg gaatgcggtg cgaggatcgc    60
ggtgttgata ccgatccatt gcgcttctcc ggaaacatta gc    102

<210> SEQ ID NO 376
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 376
acaaccgcgt gttacaaggc caggcatccg agaggtctgg gaatgcactg cattaacagg    60
tagatggtgc tgtcgccatt gcgcttctcc ggaaacatta gc    102

<210> SEQ ID NO 377
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 377
acaaccgcgt gttacaaggc caggcatccg agaggtctgg gaatgccaac aacgtggttg    60
ttggtgacga catagccatt gcgcttctcc ggaaacatta gc    102

<210> SEQ ID NO 378
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 378
acaaccgcgt gttacaaggc caggcatccg agaggtctgg gaatgccggc catcgctcag    60
ttgaacttta atgacccatt gcgcttctcc ggaaacatta gc    102

<210> SEQ ID NO 379
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 379
acaaccgcgt gttacaaggc caggcatccg agaggtctgg gaatgcacgt taatgctgac    60
cactgaaggc atcacccatt gcgcttctcc ggaaacatta gc    102

<210> SEQ ID NO 380
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 380
acaaccgcgt gttacaaggc caggcatccg agaggtctgg gaatgccact gcctgctggt    60
tcgcgccaat aatcaccatt gcgcttctcc ggaaacatta gc    102

<210> SEQ ID NO 381
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 381

```
acaaccgcgt gttacaaggc caggcatccg agaggtctgg gaatgcacgc gcagtgcatc    60
agaatccgcc atcttacatt gcgcttctcc ggaaacatta gc                      102
```

<210> SEQ ID NO 382
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 382

```
acaaccgcgt gttacaaggc caggcatccg agaggtctgg gaatgcacca aacgggttac    60
caatcgctac ggtgtacatt gcgcttctcc ggaaacatta gc                      102
```

<210> SEQ ID NO 383
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 383

```
acaaccgcgt gttacaaggc caggcatccg agaggtctgg gaatgcggca tacgcggcgt    60
attaacggtt gtgctacatt gcgcttctcc ggaaacatta gc                      102
```

<210> SEQ ID NO 384
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 384

```
acaaccgcgt gttacaaggc caggcatccg agaggtctgg gaatgcgcag taagcccagg    60
gtcagtttgc tgcctacatt gcgcttctcc ggaaacatta gc                      102
```

<210> SEQ ID NO 385
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 385

```
acaaccgcgt gttacaaggc caggcatccg agaggtctgg gaatgcgcgg atctttgcca    60
accatcttcg cgtcgacatt gcgcttctcc ggaaacatta gc                      102
```

<210> SEQ ID NO 386
<211> LENGTH: 102
<212> TYPE: DNA
<213> ORGANISM: Artificial Sequence
<220> FEATURE:
<223> OTHER INFORMATION: Synthetic Polynucleotide

```
<400> SEQUENCE: 386
acaaccgcgt gttacaaggc caggcatccg agaggtctgg gaatgctggc agaacggaga    60
gctctggaac ggagaacatt gcgcttctcc ggaaacatta gc                      102

<210> SEQ ID NO 387
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 387
acaaccgcgt gttacaaggc caggcatccg agaggtctgg gaatgcctgg cagaacggag    60
aatcatcacc gaagaacatt gcgcttctcc ggaaacatta gc                      102

<210> SEQ ID NO 388
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 388
acaaccgcgt gttacaaggc caggcatccg agaggtctgg gaatgcgccg ttgcagagag    60
cggagataac gccaaacatt gcgcttctcc ggaaacatta gc                      102

<210> SEQ ID NO 389
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 389
acaaccgcgt gttacaaggc caggcatccg agaggtctgg gaatgccgat ggtcatatcg    60
ccttcgttca cctgatcatt gcgcttctcc ggaaacatta gc                      102

<210> SEQ ID NO 390
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 390
acaaccgcgt gttacaaggc caggcatccg agaggtctgg gaatgcagat tcgggttatc    60
ttcgtcagcg atcaggcatt gcgcttctcc ggaaacatta gc                      102

<210> SEQ ID NO 391
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 391
acaaccgcgt gttacaaggc caggcatccg agaggtctgg gaatgcagat actaaaggaa    60
gaaccgcaac cgcaggcatt gcgcttctcc ggaaacatta gc                      102

<210> SEQ ID NO 392
<211> LENGTH: 102
```

```
<212> TYPE: DNA
<213> ORGANISM: Artificial Sequence
<220> FEATURE:
<223> OTHER INFORMATION: Synthetic Polynucleotide

<400> SEQUENCE: 392
acaaccgcgt gttacaaggc caggcatccg agaggtctgg gaatgcaact ttgttggctg      60
ctgcgtcggt aaactccatt gcgcttctcc ggaaacatta gc                         102

<210> SEQ ID NO 393
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 393
acaaccgcgt gttacaaggc caggcatccg agaggtctgg gaatgcacct tcggtataat      60
caacggaacc gccgaccatt gcgcttctcc ggaaacatta gc                         102

<210> SEQ ID NO 394
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 394
acaaccgcgt gttacaaggc caggcatccg agaggtctgg gaatgccgcg ttcgggttgg      60
tcacgatgaa acgagacatt gcgcttctcc ggaaacatta gc                         102

<210> SEQ ID NO 395
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 395
acaaccgcgt gttacaaggc caggcatccg agaggtctgg gaatgcaagg tgaaaccata      60
ctggaagccg ctgcaacatt gcgcttctcc ggaaacatta gc                         102

<210> SEQ ID NO 396
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 396
acaaccgcgt gttacaaggc caggcatccg agaggtctgg gaatgcgccc tgcaacttca      60
ggccattcag atagttcatt gcgcttctcc ggaaacatta gc                         102

<210> SEQ ID NO 397
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 397
acaaccgcgt gttacaaggc caggcatccg agaggtctgg gaatgccagt ctggaacagg      60
```

```
ctgtcagtac cggcttcatt gcgcttctcc ggaaacatta gc                      102
```

<210> SEQ ID NO 398
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 398

```
acaaccgcgt gttacaaggc caggcatccg agaggtctgg gaatgcgctg accatattca   60
acaggccgcc aggactcatt gcgcttctcc ggaaacatta gc                      102
```

<210> SEQ ID NO 399
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 399

```
acaaccgcgt gttacaaggc caggcatccg agaggtctgg gaatgccacc accacgccag   60
gtaaactgtt tgtcatcatt gcgcttctcc ggaaacatta gc                      102
```

<210> SEQ ID NO 400
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 400

```
acaaccgcgt gttacaaggc caggcatccg agaggtctgg gaatgccgtc gtaaccaaac   60
caggcgttga tgtcatcatt gcgcttctcc ggaaacatta gc                      102
```

<210> SEQ ID NO 401
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 401

```
acaaccgcgt gttacaaggc caggcatccg agaggtctgg gaatgcgtaa agcacggaaa   60
ccgggccacg cataatcatt gcgcttctcc ggaaacatta gc                      102
```

<210> SEQ ID NO 402
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 402

```
acaaccgcgt gttacaaggc caggcatccg agaggtctgg gaatgccggt agcagactgt   60
cgcgccgcaa tagttgcatt gcgcttctcc ggaaacatta gc                      102
```

<210> SEQ ID NO 403
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 403
acaaccgcgt gttacaaggc caggcatccg agaggtctgg gaatgccgtc ccggcaacgc    60
ggttaagaga ttcttgcatt gcgcttctcc ggaaacatta gc    102

<210> SEQ ID NO 404
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 404
acaaccgcgt gttacaaggc caggcatccg agaggtctgg gaatgcccgc tttcgcttcg    60
atttctacgc cacgtgcatt gcgcttctcc ggaaacatta gc    102

<210> SEQ ID NO 405
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 405
acaaccgcgt gttacaaggc caggcatccg agaggtctgg gaatgcgtcg atatcgccag    60
tggcaaactt gctctgcatt gcgcttctcc ggaaacatta gc    102

<210> SEQ ID NO 406
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 406
acaaccgcgt gttacaaggc caggcatccg agaggtctgg gaatgctacg tgccagataa    60
tggcctttat ccgctgcatt gcgcttctcc ggaaacatta gc    102

<210> SEQ ID NO 407
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 407
acaaccgcgt gttacaaggc caggcatccg agaggtctgg gaatgctcgg agcagacgcc    60
gtaaccataa acgctgcatt gcgcttctcc ggaaacatta gc    102

<210> SEQ ID NO 408
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 408
acaaccgcgt gttacaaggc caggcatccg agaggtctgg gaatgcaggt agtatcggtg    60
gtgtattccg catcggcatt gcgcttctcc ggaaacatta gc    102

<210> SEQ ID NO 409

```
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 409
acaaccgcgt gttacaaggc caggcatccg agaggtctgg gaatgcatac gcataaagtc    60
gacaccggtc agcaggcatt gcgcttctcc ggaaacatta gc                      102

<210> SEQ ID NO 410
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 410
acaaccgcgt gttacaaggc caggcatccg agaggtctgg gaatgcgact tcggctgatg    60
cagcgccatc tcttcgcatt gcgcttctcc ggaaacatta gc                      102

<210> SEQ ID NO 411
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 411
acaaccgcgt gttacaaggc caggcatccg agaggtctgg gaatgcgccg gatctttggc    60
attgaagtcg aaatcgcatt gcgcttctcc ggaaacatta gc                      102

<210> SEQ ID NO 412
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 412
acaaccgcgt gttacaaggc caggcatccg agaggtctgg gaatgccacg atcgaacagg    60
ttgttaacat gcagcgcatt gcgcttctcc ggaaacatta gc                      102

<210> SEQ ID NO 413
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 413
acaaccgcgt gttacaaggc caggcatccg agaggtctgg gaatgctcat taaagtctgt    60
cggcagacgc ttaccgcatt gcgcttctcc ggaaacatta gc                      102

<210> SEQ ID NO 414
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 414
acaaccgcgt gttacaaggc caggcatccg agaggtctgg gaatgccgcg ttccagcata    60
```
tacgggtcaa tgaccgcatt gcgcttctcc ggaaacatta gc                                102

<210> SEQ ID NO 415
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 415
acaaccgcgt gttacaaggc caggcatccg agaggtctgg gaatgcatac acggcaccag    60
taactacaat cggacgcatt gcgcttctcc ggaaacatta gc                       102

<210> SEQ ID NO 416
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 416
acaaccgcgt gttacaaggc caggcatccg agaggtctgg gaatgcccag tcataacgac    60
cgcctagggt gaccagcatt gcgcttctcc ggaaacatta gc                       102

<210> SEQ ID NO 417
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 417
acaaccgcgt gttacaaggc caggcatccg agaggtctgg gaatgcacca tccttcccaa    60
cttgcgaaga aggttccatt gcgcttctcc ggaaacatta gc                       102

<210> SEQ ID NO 418
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 418
acaaccgcgt gttacaaggc caggcatccg agaggtctgg gaatgccgca ggtgcagcgg    60
taacggtgat agtgtccatt gcgcttctcc ggaaacatta gc                       102

<210> SEQ ID NO 419
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 419
acaaccgcgt gttacaaggc caggcatccg agaggtctgg gaatgcaatt cgtgatcgaa    60
gctgtagccg accatccatt gcgcttctcc ggaaacatta gc                       102

<210> SEQ ID NO 420
<211> LENGTH: 102
<212> TYPE: DNA
<213> ORGANISM: Artificial Sequence
<220> FEATURE:

```
<223> OTHER INFORMATION: Synthetic Polynucleotide

<400> SEQUENCE: 420
acaaccgcgt gttacaaggc caggcatccg agaggtctgg gaatgcgaag cagccataag      60
tgttaaagca gctggccatt gcgcttctcc ggaaacatta gc                        102

<210> SEQ ID NO 421
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 421
acaaccgcgt gttacaaggc caggcatccg agaggtctgg gaatgctccc actttaaagg      60
agttagccgg atcacccatt gcgcttctcc ggaaacatta gc                        102

<210> SEQ ID NO 422
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 422
acaaccgcgt gttacaaggc caggcatccg agaggtctgg gaatgcttag aaacggaagg      60
ttgcggttgc aacgaccatt gcgcttctcc ggaaacatta gc                        102

<210> SEQ ID NO 423
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 423
acaaccgcgt gttacaaggc caggcatccg agaggtctgg gaatgccacc ggattgtaca      60
gattgagcag tggcaccatt gcgcttctcc ggaaacatta gc                        102

<210> SEQ ID NO 424
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 424
acaaccgcgt gttacaaggc caggcatccg agaggtctgg gaatgcgcca ggtgaacgcc      60
ggtgcaatag cataaccatt gcgcttctcc ggaaacatta gc                        102

<210> SEQ ID NO 425
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 425
acaaccgcgt gttacaaggc caggcatccg agaggtctgg gaatgccgca agaccggtca      60
ggcgataaga gtaaaccatt gcgcttctcc ggaaacatta gc                        102
```

```
<210> SEQ ID NO 426
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 426
acaaccgcgt gttacaaggc caggcatccg agaggtctgg aatgcatcc cactgcgcct      60 gatcctgaac ataaaccatt gcgcttctcc ggaaacatta gc                        102

<210> SEQ ID NO 427
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 427
acaaccgcgt gttacaaggc caggcatccg agaggtctgg aatgcccat gccgactcgc      60 gccagatcat aacgtacatt gcgcttctcc ggaaacatta gc                        102

<210> SEQ ID NO 428
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 428
acaaccgcgt gttacaaggc caggcatccg agaggtctgg aatgcgtac caacagagac      60 acccggcgtg tagctacatt gcgcttctcc ggaaacatta gc                        102

<210> SEQ ID NO 429
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 429
acaaccgcgt gttacaaggc caggcatccg agaggtctgg aatgccgca aagccgcgaa      60 tgatcaggtg gtcatacatt gcgcttctcc ggaaacatta gc                        102

<210> SEQ ID NO 430
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 430
acaaccgcgt gttacaaggc caggcatccg agaggtctgg aatgctgaa cttctttcag      60 cggttcggtg gtcggacatt gcgcttctcc ggaaacatta gc                        102

<210> SEQ ID NO 431
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 431
```
acaaccgcgt gttacaaggc caggcatccg agaggtctgg gaatgccgct aaccgctgtg    60
gctactacaa ctgcgacatt gcgcttctcc ggaaacatta gc    102

<210> SEQ ID NO 432
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 432
acaaccgcgt gttacaaggc caggcatccg agaggtctgg gaatgccggt tcaaccgctg    60
cctgtgcata aacagacatt gcgcttctcc ggaaacatta gc    102

<210> SEQ ID NO 433
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 433
acaaccgcgt gttacaaggc caggcatccg agaggtctgg gaatgcaccg gtttccggct    60
cgttctggaa gtaagacatt gcgcttctcc ggaaacatta gc    102

<210> SEQ ID NO 434
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 434
acaaccgcgt gttacaaggc caggcatccg agaggtctgg gaatgctctt ctgacccttt    60
ctgctgggca ttggcacatt gcgcttctcc ggaaacatta gc    102

<210> SEQ ID NO 435
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 435
acaaccgcgt gttacaaggc caggcatccg agaggtctgg gaatgccagc aaagcgcagg    60
ttctgacgca cagtaacatt gcgcttctcc ggaaacatta gc    102

<210> SEQ ID NO 436
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 436
acaaccgcgt gttacaaggc caggcatccg agaggtctgg gaatgcatct cgccaccttc    60
aaccgagaag aaggaacatt gcgcttctcc ggaaacatta gc    102

<210> SEQ ID NO 437
<211> LENGTH: 102
<212> TYPE: DNA
<213> ORGANISM: Artificial Sequence

```
<220> FEATURE:
<223> OTHER INFORMATION: Synthetic Polynucleotide

<400> SEQUENCE: 437
acaaccgcgt gttacaaggc caggcatccg agaggtctgg gaatgccagc gtcagacctg      60
aaagcggacc gtcaaacatt gcgcttctcc ggaaacatta gc                          102

<210> SEQ ID NO 438
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 438
acaaccgcgt gttacaaggc caggcatccg agaggtctgg gaatgcgagg aagctgctgc      60
ggcaaataag ccacttcatt gcgcttctcc ggaaacatta gc                          102

<210> SEQ ID NO 439
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 439
acaaccgcgt gttacaaggc caggcatccg agaggtctgg gaatgcgcga cagcacatca      60
acctggtggg cgatatcatt gcgcttctcc ggaaacatta gc                          102

<210> SEQ ID NO 440
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 440
acaaccgcgt gttacaaggc caggcatccg agaggtctgg gaatgcgagc agagtggatt      60
taccagaacc gttgtgcatt gcgcttctcc ggaaacatta gc                          102

<210> SEQ ID NO 441
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 441
acaaccgcgt gttacaaggc caggcatccg agaggtctgg gaatgcccca tcgggatgcc      60
ataaatcatt tcgaggcatt gcgcttctcc ggaaacatta gc                          102

<210> SEQ ID NO 442
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 442
acaaccgcgt gttacaaggc caggcatccg agaggtctgg gaatgccaaa cgctttgctg      60
ctccagcttt ccagcgcatt gcgcttctcc ggaaacatta gc                          102
```

<210> SEQ ID NO 443
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 443
acaaccgcgt gttacaaggc caggcatccg agaggtctgg gaatgcccgc gcagggcgac    60
cagataatca cagtagcatt gcgcttctcc ggaaacatta gc    102

<210> SEQ ID NO 444
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 444
acaaccgcgt gttacaaggc caggcatccg agaggtctgg gaatgcccac gggtaacgac    60
caatcgccac cagttccatt gcgcttctcc ggaaacatta gc    102

<210> SEQ ID NO 445
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 445
acaaccgcgt gttacaaggc caggcatccg agaggtctgg gaatgcccga ggtcggttcg    60
tcgagcaaca gacaaccatt gcgcttctcc ggaaacatta gc    102

<210> SEQ ID NO 446
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 446
acaaccgcgt gttacaaggc caggcatccg agaggtctgg gaatgcgacc ggtcactttc    60
ccggcaggaa aggttacatt gcgcttctcc ggaaacatta gc    102

<210> SEQ ID NO 447
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 447
acaaccgcgt gttacaaggc caggcatccg agaggtctgg gaatgccaat gaccgtcagg    60
ccacgctcct gacttacatt gcgcttctcc ggaaacatta gc    102

<210> SEQ ID NO 448
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 448

```
acaaccgcgt gttacaaggc caggcatccg agaggtctgg gaatgcgtgc gcccgggcac    60
acgaaaggag atattacatt gcgcttctcc ggaaacatta gc                      102

<210> SEQ ID NO 449
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 449
acaaccgcgt gttacaaggc caggcatccg agaggtctgg gaatgcgacg ttcgccgcca    60
gagagactat cgaccacatt gcgcttctcc ggaaacatta gc                      102

<210> SEQ ID NO 450
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 450
acaaccgcgt gttacaaggc caggcatccg agaggtctgg gaatgcgcat aatttccgca    60
ggcgttccct gagcaacatt gcgcttctcc ggaaacatta gc                      102

<210> SEQ ID NO 451
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 451
acaaccgcgt gttacaaggc caggcatccg agaggtctgg gaatgctagt gcggaacggt    60
caggcgttca gtatttcatt gcgcttctcc ggaaacatta gc                      102

<210> SEQ ID NO 452
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 452
acaaccgcgt gttacaaggc caggcatccg agaggtctgg gaatgccgga gaggccagat    60
tgctgcctat ggcaatcatt gcgcttctcc ggaaacatta gc                      102

<210> SEQ ID NO 453
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 453
acaaccgcgt gttacaaggc caggcatccg agaggtctgg gaatgctacc aaacagcatg    60
atgtcgagat ccagcgcatt gcgcttctcc ggaaacatta gc                      102

<210> SEQ ID NO 454
<211> LENGTH: 102
<212> TYPE: DNA
```

```
<213> ORGANISM: Artificial Sequence
<220> FEATURE:
<223> OTHER INFORMATION: Synthetic Polynucleotide

<400> SEQUENCE: 454
acaaccgcgt gttacaaggc caggcatccg agaggtctgg gaatgcatca ggaaacacca      60
actccggcgc gatttccatt gcgcttctcc ggaaacatta gc                         102

<210> SEQ ID NO 455
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 455
acaaccgcgt gttacaaggc caggcatccg agaggtctgg gaatgccacg gctgcgttta      60
agtaatcggg ttgatccatt gcgcttctcc ggaaacatta gc                         102

<210> SEQ ID NO 456
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 456
acaaccgcgt gttacaaggc caggcatccg agaggtctgg gaatgccggt aagaatgtgg      60
ctttcaggga tatcgccatt gcgcttctcc ggaaacatta gc                         102

<210> SEQ ID NO 457
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 457
acaaccgcgt gttacaaggc caggcatccg agaggtctgg gaatgcagta gctcttcagg      60
tgcaagagag gtttcccatt gcgcttctcc ggaaacatta gc                         102

<210> SEQ ID NO 458
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 458
acaaccgcgt gttacaaggc caggcatccg agaggtctgg gaatgcgcgg ccacagcata      60
aatccacgat tcttcacatt gcgcttctcc ggaaacatta gc                         102

<210> SEQ ID NO 459
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 459
acaaccgcgt gttacaaggc caggcatccg agaggtctgg gaatgccttt gcggacgcga      60
ccttgctgca attcaacatt gcgcttctcc ggaaacatta gc                         102
```

<210> SEQ ID NO 460
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 460
acaaccgcgt gttacaaggc caggcatccg agaggtctgg gaatgcgctc gatcacctct    60
gccagtgtct gacgttcatt gcgcttctcc ggaaacatta gc                      102

<210> SEQ ID NO 461
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 461
acaaccgcgt gttacaaggc caggcatccg agaggtctgg gaatgccacc gatatcgacg    60
acgcagacac ccagttcatt gcgcttctcc ggaaacatta gc                      102

<210> SEQ ID NO 462
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 462
acaaccgcgt gttacaaggc caggcatccg agaggtctgg gaatgccggc gtgccaaagg    60
cgtaagcgat atcactcatt gcgcttctcc ggaaacatta gc                      102

<210> SEQ ID NO 463
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 463
acaaccgcgt gttacaaggc caggcatccg agaggtctgg gaatgctact aaagcggcaa    60
ccttcgcggt accaatcatt gcgcttctcc ggaaacatta gc                      102

<210> SEQ ID NO 464
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 464
acaaccgcgt gttacaaggc caggcatccg agaggtctgg gaatgccgca cgcccgaaag    60
tcctaccgga ttcttgcatt gcgcttctcc ggaaacatta gc                      102

<210> SEQ ID NO 465
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 465
acaaccgcgt gttacaaggc caggcatccg agaggtctgg gaatgccgcc atatcgttgt 60
gacatgtgat caggtgcatt gcgcttctcc ggaaacatta gc 102

<210> SEQ ID NO 466
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 466
acaaccgcgt gttacaaggc caggcatccg agaggtctgg gaatgcggca ccataccaat 60
ttcattctgg cagctgcatt gcgcttctcc ggaaacatta gc 102

<210> SEQ ID NO 467
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 467
acaaccgcgt gttacaaggc caggcatccg agaggtctgg gaatgccctt tatccatacc 60
acgcgacggg cagctgcatt gcgcttctcc ggaaacatta gc 102

<210> SEQ ID NO 468
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 468
acaaccgcgt gttacaaggc caggcatccg agaggtctgg gaatgctcct gatagtcaat 60
cgcatactct tgcgggcatt gcgcttctcc ggaaacatta gc 102

<210> SEQ ID NO 469
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 469
acaaccgcgt gttacaaggc caggcatccg agaggtctgg gaatgcgcca gcataaggaa 60
ttaccttagt gtggcgcatt gcgcttctcc ggaaacatta gc 102

<210> SEQ ID NO 470
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 470
acaaccgcgt gttacaaggc caggcatccg agaggtctgg gaatgcactc tttcccatag 60
tgaagcaatc ccaccgcatt gcgcttctcc ggaaacatta gc 102

<210> SEQ ID NO 471
<211> LENGTH: 102

```
<212> TYPE: DNA
<213> ORGANISM: Artificial Sequence
<220> FEATURE:
<223> OTHER INFORMATION: Synthetic Polynucleotide

<400> SEQUENCE: 471
acaaccgcgt gttacaaggc caggcatccg agaggtctgg gaatgctacg gctcctgagc      60
ataatccgtt aaaccgcatt gcgcttctcc ggaaacatta gc                        102

<210> SEQ ID NO 472
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 472
acaaccgcgt gttacaaggc caggcatccg agaggtctgg gaatgcgcca atgatattga      60
ccataccgtc gggcagcatt gcgcttctcc ggaaacatta gc                        102

<210> SEQ ID NO 473
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 473
acaaccgcgt gttacaaggc caggcatccg agaggtctgg gaatgccagt tggtcaactt      60
tcagcccaca acgttccatt gcgcttctcc ggaaacatta gc                        102

<210> SEQ ID NO 474
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 474
acaaccgcgt gttacaaggc caggcatccg agaggtctgg gaatgcctga caatctgcca      60
tcaattctgc ctggtccatt gcgcttctcc ggaaacatta gc                        102

<210> SEQ ID NO 475
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 475
acaaccgcgt gttacaaggc caggcatccg agaggtctgg gaatgctatc tcttcgttga      60
ccaggttgag cagctccatt gcgcttctcc ggaaacatta gc                        102

<210> SEQ ID NO 476
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 476
acaaccgcgt gttacaaggc caggcatccg agaggtctgg gaatgcccca gcgcacaacc      60
```

```
gtggcgaact ttaatccatt gcgcttctcc ggaaacatta gc                       102
```

<210> SEQ ID NO 477
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 477

```
acaaccgcgt gttacaaggc caggcatccg agaggtctgg gaatgccaat accgaataac    60
ttgatgccag tccggccatt gcgcttctcc ggaaacatta gc                       102
```

<210> SEQ ID NO 478
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 478

```
acaaccgcgt gttacaaggc caggcatccg agaggtctgg gaatgcgcac ttgcgtatga    60
aacacgcgct gagcaccatt gcgcttctcc ggaaacatta gc                       102
```

<210> SEQ ID NO 479
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 479

```
acaaccgcgt gttacaaggc caggcatccg agaggtctgg gaatgccgca gccaactatt    60
gagtcgcttg atccaccatt gcgcttctcc ggaaacatta gc                       102
```

<210> SEQ ID NO 480
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 480

```
acaaccgcgt gttacaaggc caggcatccg agaggtctgg gaatgccttc gatctgcgct    60
gcgccaccgg ttaatacatt gcgcttctcc ggaaacatta gc                       102
```

<210> SEQ ID NO 481
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 481

```
acaaccgcgt gttacaaggc caggcatccg agaggtctgg gaatgccgcg ttgtacgcac    60
ttgaccacgg attcgacatt gcgcttctcc ggaaacatta gc                       102
```

<210> SEQ ID NO 482
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 482
acaaccgcgt gttacaaggc caggcatccg agaggtctgg gaatgccgtt ctggcggcac    60
gctgaaggta tttcctcatt gcgcttctcc ggaaacatta gc                      102

<210> SEQ ID NO 483
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 483
acaaccgcgt gttacaaggc caggcatccg agaggtctgg gaatgccttc cgggccatac    60
agcattggaa gcacctcatt gcgcttctcc ggaaacatta gc                      102

<210> SEQ ID NO 484
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 484
acaaccgcgt gttacaaggc caggcatccg agaggtctgg gaatgctttc gcgatagccc    60
tgcaacactt cattggcatt gcgcttctcc ggaaacatta gc                      102

<210> SEQ ID NO 485
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 485
acaaccgcgt gttacaaggc caggcatccg agaggtctgg gaatgcgttg ctgagtagat    60
tcctctggcg gcaaggcatt gcgcttctcc ggaaacatta gc                      102

<210> SEQ ID NO 486
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 486
acaaccgcgt gttacaaggc caggcatccg agaggtctgg gaatgcccca atgccaggat    60
cgactgccgg atatcgcatt gcgcttctcc ggaaacatta gc                      102

<210> SEQ ID NO 487
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 487
acaaccgcgt gttacaaggc caggcatccg agaggtctgg gaatgctaat ccacggcagg    60
cgttgttcta tttgcgcatt gcgcttctcc ggaaacatta gc                      102

<210> SEQ ID NO 488

<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 488
acaaccgcgt gttacaaggc caggcatccg agaggtctgg gaatgctgtt gacatcctgg    60
gtcataaagg tacccgcatt gcgcttctcc ggaaacatta gc    102

<210> SEQ ID NO 489
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 489
acaaccgcgt gttacaaggc caggcatccg agaggtctgg gaatgcatcg ttattcagcg    60
tcaactgcca ggaacgcatt gcgcttctcc ggaaacatta gc    102

<210> SEQ ID NO 490
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 490
acaaccgcgt gttacaaggc caggcatccg agaggtctgg gaatgcccag acgcgttcca    60
ttattgcggc gagaagcatt gcgcttctcc ggaaacatta gc    102

<210> SEQ ID NO 491
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 491
acaaccgcgt gttacaaggc caggcatccg agaggtctgg gaatgccggt catcgccgct    60
tccttcagag taaatccatt gcgcttctcc ggaaacatta gc    102

<210> SEQ ID NO 492
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 492
acaaccgcgt gttacaaggc caggcatccg agaggtctgg gaatgcacgt agctaatccg    60
tttgccatcg gtttgccatt gcgcttctcc ggaaacatta gc    102

<210> SEQ ID NO 493
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 493
acaaccgcgt gttacaaggc caggcatccg agaggtctgg gaatgcgtct accatatgtt    60
gatcattcca ccgcgccatt gcgcttctcc ggaaacatta gc        102

<210> SEQ ID NO 494
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 494
acaaccgcgt gttacaaggc caggcatccg agaggtctgg gaatgctcaa ttcatcaggc    60
cactgctttc tgacgccatt gcgcttctcc ggaaacatta gc                     102

<210> SEQ ID NO 495
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 495
acaaccgcgt gttacaaggc caggcatccg agaggtctgg gaatgccagc ctactgccgc    60
tccagagtca taacgccatt gcgcttctcc ggaaacatta gc                     102

<210> SEQ ID NO 496
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 496
acaaccgcgt gttacaaggc caggcatccg agaggtctgg gaatgcacgt gtgtaatggc    60
gttcaccggt caacaccatt gcgcttctcc ggaaacatta gc                     102

<210> SEQ ID NO 497
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 497
acaaccgcgt gttacaaggc caggcatccg agaggtctgg gaatgctctt cttcgctgtt    60
tcgcgtgttc agagcacatt gcgcttctcc ggaaacatta gc                     102

<210> SEQ ID NO 498
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 498
acaaccgcgt gttacaaggc caggcatccg agaggtctgg gaatgcagca aatgcacgga    60
tggtgttacc taccgtcatt gcgcttctcc ggaaacatta gc                     102

<210> SEQ ID NO 499
<211> LENGTH: 102
<212> TYPE: DNA
<213> ORGANISM: Artificial Sequence
<220> FEATURE:

<223> OTHER INFORMATION: Synthetic Polynucleotide

<400> SEQUENCE: 499
acaaccgcgt gttacaaggc caggcatccg agaggtctgg gaatgctgca cagcgccttt      60
cagtacatcg ttcgctcatt gcgcttctcc ggaaacatta gc                         102

<210> SEQ ID NO 500
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 500
acaaccgcgt gttacaaggc caggcatccg agaggtctgg gaatgcagag aagtaccgat      60
aaccacagtc gcgttgcatt gcgcttctcc ggaaacatta gc                         102

<210> SEQ ID NO 501
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 501
acaaccgcgt gttacaaggc caggcatccg agaggtctgg gaatgctgct gaacctgctt      60
attggtcacc agagtgcatt gcgcttctcc ggaaacatta gc                         102

<210> SEQ ID NO 502
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 502
acaaccgcgt gttacaaggc caggcatccg agaggtctgg gaatgccggt tacgcgcagc      60
tcgtcattca tatccgcatt gcgcttctcc ggaaacatta gc                         102

<210> SEQ ID NO 503
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 503
acaaccgcgt gttacaaggc caggcatccg agaggtctgg gaatgccagg gagataccgc      60
ggcccagaac tttcagcatt gcgcttctcc ggaaacatta gc                         102

<210> SEQ ID NO 504
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 504
acaaccgcgt gttacaaggc caggcatccg agaggtctgg gaatgccgcg ccagacaggt      60
cgatatcttc cagcagcatt gcgcttctcc ggaaacatta gc                         102

<210> SEQ ID NO 505
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 505
acaaccgcgt gttacaaggc caggcatccg agaggtctgg gaatgccagg tcgaagcccg    60
ccgtgatgtt aaccagcatt gcgcttctcc ggaaacatta gc                      102

<210> SEQ ID NO 506
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 506
acaaccgcgt gttacaaggc caggcatccg agaggtctgg gaatgcagga cgtttgtcca    60
tgccgatacc tgtcgccatt gcgcttctcc ggaaacatta gc                      102

<210> SEQ ID NO 507
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 507
acaaccgcgt gttacaaggc caggcatccg agaggtctgg gaatgcagag atagccattt    60
cagcagcttc ttccgccatt gcgcttctcc ggaaacatta gc                      102

<210> SEQ ID NO 508
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 508
acaaccgcgt gttacaaggc caggcatccg agaggtctgg gaatgcccac cacccatacc    60
cgcagcaata aagacccatt gcgcttctcc ggaaacatta gc                      102

<210> SEQ ID NO 509
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 509
acaaccgcgt gttacaaggc caggcatccg agaggtctgg gaatgccttc agcgacgact    60
ggtgctgcac ctgtaccatt gcgcttctcc ggaaacatta gc                      102

<210> SEQ ID NO 510
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 510

```
acaaccgcgt gttacaaggc caggcatccg agaggtctgg gaatgccagc gcccagtcct      60
ttggtgatac cgctaccatt gcgcttctcc ggaaacatta gc                         102
```

<210> SEQ ID NO 511
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 511

```
acaaccgcgt gttacaaggc caggcatccg agaggtctgg gaatgccgca gtttgcggcg      60
cattgtcatt cacgaccatt gcgcttctcc ggaaacatta gc                         102
```

<210> SEQ ID NO 512
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 512

```
acaaccgcgt gttacaaggc caggcatccg agaggtctgg gaatgccatt acggtgcgta      60
cgtctgcaaa gtccaccatt gcgcttctcc ggaaacatta gc                         102
```

<210> SEQ ID NO 513
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 513

```
acaaccgcgt gttacaaggc caggcatccg agaggtctgg gaatgctcaa acccggacga      60
gtaatcagtt cagcgacatt gcgcttctcc ggaaacatta gc                         102
```

<210> SEQ ID NO 514
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 514

```
acaaccgcgt gttacaaggc caggcatccg agaggtctgg gaatgctgaa aggcttagtg      60
acgacagcaa cggtcacatt gcgcttctcc ggaaacatta gc                         102
```

<210> SEQ ID NO 515
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 515

```
acaaccgcgt gttacaaggc caggcatccg agaggtctgg gaatgcccga cgccgatgac      60
tttaatcacc gcgtcacatt gcgcttctcc ggaaacatta gc                         102
```

<210> SEQ ID NO 516
<211> LENGTH: 102
<212> TYPE: DNA
<213> ORGANISM: Artificial Sequence

```
<220> FEATURE:
<223> OTHER INFORMATION: Synthetic Polynucleotide

<400> SEQUENCE: 516
acaaccgcgt gttacaaggc caggcatccg agaggtctgg aatgcccat cccatgctgc       60 tggtagcgat ccatcacatt gcgcttctcc ggaaacatta gc                        102

<210> SEQ ID NO 517
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 517
acaaccgcgt gttacaaggc caggcatccg agaggtctgg aatgctgtc gttcgggata      60 gtgatcagag agtccacatt gcgcttctcc ggaaacatta gc                        102

<210> SEQ ID NO 518
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 518
acaaccgcgt gttacaaggc caggcatccg agaggtctgg aatgccagc gcttgtgcat      60 cggtatttac cgcgaacatt gcgcttctcc ggaaacatta gc                        102

<210> SEQ ID NO 519
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 519
acaaccgcgt gttacaaggc caggcatccg agaggtctgg aatgccttc aatgcgctcg      60 cgcaccatgt gttcaacatt gcgcttctcc ggaaacatta gc                        102

<210> SEQ ID NO 520
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 520
acaaccgcgt gttacaaggc caggcatccg agaggtctgg aatgcgacc cggtttggtg      60 tctggcatat tgctttcatt gcgcttctcc ggaaacatta gc                        102

<210> SEQ ID NO 521
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 521
acaaccgcgt gttacaaggc caggcatccg agaggtctgg aatgccatc acttccggcg      60 aagcggtttc tgctttcatt gcgcttctcc ggaaacatta gc                        102
```

<210> SEQ ID NO 522
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 522
acaaccgcgt gttacaaggc caggcatccg agaggtctgg gaatgctggt gcccaggagt    60
ttggcgagtt aaaggtcatt gcgcttctcc ggaaacatta gc    102

<210> SEQ ID NO 523
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 523
acaaccgcgt gttacaaggc caggcatccg agaggtctgg gaatgccatg ataagagaca    60
ccacggcagg ttacgtcatt gcgcttctcc ggaaacatta gc    102

<210> SEQ ID NO 524
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 524
acaaccgcgt gttacaaggc caggcatccg agaggtctgg gaatgctgtg ttcgtcagac    60
gggattgcgt tcggatcatt gcgcttctcc ggaaacatta gc    102

<210> SEQ ID NO 525
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 525
acaaccgcgt gttacaaggc caggcatccg agaggtctgg gaatgcccgg aaccaccagt    60
tcgccattac gacgatcatt gcgcttctcc ggaaacatta gc    102

<210> SEQ ID NO 526
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 526
acaaccgcgt gttacaaggc caggcatccg agaggtctgg gaatgccacc gctaatcagc    60
agtgcgacca ccagtgcatt gcgcttctcc ggaaacatta gc    102

<210> SEQ ID NO 527
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 527

```
acaaccgcgt gttacaaggc caggcatccg agaggtctgg gaatgccgcc ggagcgtaaa    60
taactggcac tttctgcatt gcgcttctcc ggaaacatta gc                      102
```

<210> SEQ ID NO 528
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 528

```
acaaccgcgt gttacaaggc caggcatccg agaggtctgg gaatgccgcc cactttaatc    60
ggcgtcactt cattggcatt gcgcttctcc ggaaacatta gc                      102
```

<210> SEQ ID NO 529
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 529

```
acaaccgcgt gttacaaggc caggcatccg agaggtctgg gaatgctgct ggctgtttac    60
atggcagacc aaatggcatt gcgcttctcc ggaaacatta gc                      102
```

<210> SEQ ID NO 530
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 530

```
acaaccgcgt gttacaaggc caggcatccg agaggtctgg gaatgcaatc gcaatcagtc    60
gaccatcatt gaccggcatt gcgcttctcc ggaaacatta gc                      102
```

<210> SEQ ID NO 531
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 531

```
acaaccgcgt gttacaaggc caggcatccg agaggtctgg gaatgcttga gcacgccttt    60
attggcgaag gtttcgcatt gcgcttctcc ggaaacatta gc                      102
```

<210> SEQ ID NO 532
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 532

```
acaaccgcgt gttacaaggc caggcatccg agaggtctgg gaatgcacat atccgcaccg    60
ctcaaatctt tcgtcgcatt gcgcttctcc ggaaacatta gc                      102
```

<210> SEQ ID NO 533
<211> LENGTH: 102
<212> TYPE: DNA

<213> ORGANISM: Artificial Sequence
<220> FEATURE:
<223> OTHER INFORMATION: Synthetic Polynucleotide

<400> SEQUENCE: 533
acaaccgcgt gttacaaggc caggcatccg agaggtctgg gaatgccgtt atcggcgtta    60
atttgtttca gcggcgcatt gcgcttctcc ggaaacatta gc                       102

<210> SEQ ID NO 534
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 534
acaaccgcgt gttacaaggc caggcatccg agaggtctgg gaatgcgggc tgttagcgtg    60
acgagtaatc gtcgcgcatt gcgcttctcc ggaaacatta gc                       102

<210> SEQ ID NO 535
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 535
acaaccgcgt gttacaaggc caggcatccg agaggtctgg gaatgctagt cgcccatctt    60
cgtaccaaat gaaccgcatt gcgcttctcc ggaaacatta gc                       102

<210> SEQ ID NO 536
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 536
acaaccgcgt gttacaaggc caggcatccg agaggtctgg gaatgcccga gcatcacaag    60
gccagcgata gggtagcatt gcgcttctcc ggaaacatta gc                       102

<210> SEQ ID NO 537
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 537
acaaccgcgt gttacaaggc caggcatccg agaggtctgg gaatgcctgc ggatcgttaa    60
atccggccca ggtcagcatt gcgcttctcc ggaaacatta gc                       102

<210> SEQ ID NO 538
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 538
acaaccgcgt gttacaaggc caggcatccg agaggtctgg gaatgccagg cgctggtgag    60
cggtacacag gtaaagcatt gcgcttctcc ggaaacatta gc                       102

<210> SEQ ID NO 539
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 539
acaaccgcgt gttacaaggc caggcatccg agaggtctgg gaatgcgtta cccgggaaga     60
ccagcgtacc ctgttccatt gcgcttctcc ggaaacatta gc                      102

<210> SEQ ID NO 540
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 540
acaaccgcgt gttacaaggc caggcatccg agaggtctgg gaatgcatcg gtgataatcg     60
gtggcgaagt cggttccatt gcgcttctcc ggaaacatta gc                      102

<210> SEQ ID NO 541
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 541
acaaccgcgt gttacaaggc caggcatccg agaggtctgg gaatgcctgt gccggaagat     60
ccatgtccca caggtccatt gcgcttctcc ggaaacatta gc                      102

<210> SEQ ID NO 542
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 542
acaaccgcgt gttacaaggc caggcatccg agaggtctgg gaatgcggtc acgcccatcg     60
gcagatagac cagatccatt gcgcttctcc ggaaacatta gc                      102

<210> SEQ ID NO 543
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 543
acaaccgcgt gttacaaggc caggcatccg agaggtctgg gaatgccagg atcgtaatgc     60
catttctctt tgccgccatt gcgcttctcc ggaaacatta gc                      102

<210> SEQ ID NO 544
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 544
acaaccgcgt gttacaaggc caggcatccg agaggtctgg gaatgcttac ttcacatcat    60
ccggcagcgc ataagccatt gcgcttctcc ggaaacatta gc    102

<210> SEQ ID NO 545
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 545
acaaccgcgt gttacaaggc caggcatccg agaggtctgg gaatgcgaac ggtctggtag    60
ctccacgcca gtttcccatt gcgcttctcc ggaaacatta gc    102

<210> SEQ ID NO 546
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 546
acaaccgcgt gttacaaggc caggcatccg agaggtctgg gaatgcgcct gcggagatca    60
ccacatactg cttacccatt gcgcttctcc ggaaacatta gc    102

<210> SEQ ID NO 547
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 547
acaaccgcgt gttacaaggc caggcatccg agaggtctgg gaatgcctgc cgtagcggcg    60
ataaacagca cgttaccatt gcgcttctcc ggaaacatta gc    102

<210> SEQ ID NO 548
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 548
acaaccgcgt gttacaaggc caggcatccg agaggtctgg gaatgccttc ataggtcatt    60
ggcgtagcct gaccaccatt gcgcttctcc ggaaacatta gc    102

<210> SEQ ID NO 549
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 549
acaaccgcgt gttacaaggc caggcatccg agaggtctgg gaatgcggca atcgccactt    60
cacgatttgg atcaaccatt gcgcttctcc ggaaacatta gc    102

<210> SEQ ID NO 550
<211> LENGTH: 102

<212> TYPE: DNA
<213> ORGANISM: Artificial Sequence
<220> FEATURE:
<223> OTHER INFORMATION: Synthetic Polynucleotide

<400> SEQUENCE: 550
acaaccgcgt gttacaaggc caggcatccg agaggtctgg gaatgccgga gtcagcgccc    60
agaagtcgaa accaaccatt gcgcttctcc ggaaacatta gc                      102

<210> SEQ ID NO 551
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 551
acaaccgcgt gttacaaggc caggcatccg agaggtctgg gaatgcggaa cgggttgagc    60
gtgacaccat acggtacatt gcgcttctcc ggaaacatta gc                      102

<210> SEQ ID NO 552
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 552
acaaccgcgt gttacaaggc caggcatccg agaggtctgg gaatgcaccg ttgctcatgt    60
tgtaagcgcg caggtacatt gcgcttctcc ggaaacatta gc                      102

<210> SEQ ID NO 553
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 553
acaaccgcgt gttacaaggc caggcatccg agaggtctgg gaatgcggat cgttcggctg    60
cttcacatcg ccagtacatt gcgcttctcc ggaaacatta gc                      102

<210> SEQ ID NO 554
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 554
acaaccgcgt gttacaaggc caggcatccg agaggtctgg gaatgcgacc agccagcctc    60
cgccaatgag tagatacatt gcgcttctcc ggaaacatta gc                      102

<210> SEQ ID NO 555
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 555
acaaccgcgt gttacaaggc caggcatccg agaggtctgg gaatgctgcc ttcatagcgc    60
atctggtgga acatcacatt gcgcttctcc ggaaacatta gc    102

<210> SEQ ID NO 556
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 556
acaaccgcgt gttacaaggc caggcatccg agaggtctgg gaatgccgtt gaccttcctg    60
attacgacca taggcacatt gcgcttctcc ggaaacatta gc    102

<210> SEQ ID NO 557
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 557
acaaccgcgt gttacaaggc caggcatccg agaggtctgg gaatgccctg cggcgtacca    60
atacgtttct tccacacatt gcgcttctcc ggaaacatta gc    102

<210> SEQ ID NO 558
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 558
acaaccgcgt gttacaaggc caggcatccg agaggtctgg gaatgcccag gaccacgcgg    60
gatcagtttc gaaacacatt gcgcttctcc ggaaacatta gc    102

<210> SEQ ID NO 559
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 559
acaaccgcgt gttacaaggc caggcatccg agaggtctgg gaatgccccg cccagcatcg    60
gcatacccat attgaacatt gcgcttctcc ggaaacatta gc    102

<210> SEQ ID NO 560
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 560
acaaccgcgt gttacaaggc caggcatccg agaggtctgg gaatgcgaca aacggcagga    60
tcagccagat gccgaacatt gcgcttctcc ggaaacatta gc    102

<210> SEQ ID NO 561
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 561
acaaccgcgt gttacaaggc caggcatccg agaggtctgg gaatgcgatc acgccagacg    60
tttcgcgggt tgagaacatt gcgcttctcc ggaaacatta gc                       102

<210> SEQ ID NO 562
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 562
acaaccgcgt gttacaaggc caggcatccg agaggtctgg gaatgccacg ccggaccagc    60
tctgacctga atgtttcatt gcgcttctcc ggaaacatta gc                       102

<210> SEQ ID NO 563
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 563
acaaccgcgt gttacaaggc caggcatccg agaggtctgg gaatgcgcgc tttcgcaacg    60
aactgcacga agtgttcatt gcgcttctcc ggaaacatta gc                       102

<210> SEQ ID NO 564
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 564
acaaccgcgt gttacaaggc caggcatccg agaggtctgg gaatgctgtg cctacggtgt    60
ccatatttgc ggcgatcatt gcgcttctcc ggaaacatta gc                       102

<210> SEQ ID NO 565
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 565
acaaccgcgt gttacaaggc caggcatccg agaggtctgg gaatgccacc agtcactacg    60
ttaccagcac aaatggcatt gcgcttctcc ggaaacatta gc                       102

<210> SEQ ID NO 566
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 566
acaaccgcgt gttacaaggc caggcatccg agaggtctgg gaatgccaaa cgaagtttaa    60
tgccgggttc aggtcgcatt gcgcttctcc ggaaacatta gc                       102

<210> SEQ ID NO 567

```
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 567
acaaccgcgt gttacaaggc caggcatccg agaggtctgg gaatgcaaat ttctcgccgt      60
tctcctcaac gatgcgcatt gcgcttctcc ggaaacatta gc                        102

<210> SEQ ID NO 568
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 568
acaaccgcgt gttacaaggc caggcatccg agaggtctgg gaatgcagag tggagcgttt      60
agggcggatg agaacgcatt gcgcttctcc ggaaacatta gc                        102

<210> SEQ ID NO 569
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 569
acaaccgcgt gttacaaggc caggcatccg agaggtctgg gaatgctggt gcagccacca      60
tcgctgacga tcattccatt gcgcttctcc ggaaacatta gc                        102

<210> SEQ ID NO 570
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 570
acaaccgcgt gttacaaggc caggcatccg agaggtctgg gaatgcaacg atatcggcac      60
ctgagaggat aagctccatt gcgcttctcc ggaaacatta gc                        102

<210> SEQ ID NO 571
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 571
acaaccgcgt gttacaaggc caggcatccg agaggtctgg gaatgccttg ttcctgcaca      60
cgaataaacg tggtgccatt gcgcttctcc ggaaacatta gc                        102

<210> SEQ ID NO 572
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 572
acaaccgcgt gttacaaggc caggcatccg agaggtctgg gaatgcattg acgttccagt      60
```
tcaacatcgg aacggccatt gcgcttctcc ggaaacatta gc 102

<210> SEQ ID NO 573
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 573
acaaccgcgt gttacaaggc caggcatccg agaggtctgg aatgcgacg cgagttgtac 60 aaacagaacc tgggcccatt gcgcttctcc ggaaacatta gc 102

<210> SEQ ID NO 574
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 574
acaaccgcgt gttacaaggc caggcatccg agaggtctgg aatgcgcca acgtgacgtt 60 tcatcgcaga ctcggacatt gcgcttctcc ggaaacatta gc 102

<210> SEQ ID NO 575
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 575
acaaccgcgt gttacaaggc caggcatccg agaggtctgg aatgccgca gcatcggcac 60 attcgattac cgcagacatt gcgcttctcc ggaaacatta gc 102

<210> SEQ ID NO 576
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 576
acaaccgcgt gttacaaggc caggcatccg agaggtctgg aatgccgaa atccgcatca 60 gacgtaccgg tagaaacatt gcgcttctcc ggaaacatta gc 102

<210> SEQ ID NO 577
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 577
acaaccgcgt gttacaaggc caggcatccg agaggtctgg aatgcggca gtcagcgtga 60 ccatggtaac acccttcatt gcgcttctcc ggaaacatta gc 102

<210> SEQ ID NO 578
<211> LENGTH: 102
<212> TYPE: DNA
<213> ORGANISM: Artificial Sequence
<220> FEATURE:

<223> OTHER INFORMATION: Synthetic Polynucleotide

<400> SEQUENCE: 578
acaaccgcgt gttacaaggc caggcatccg agaggtctgg gaatgccacc atatccatgg    60
tcgggaccag ttcggtcatt gcgcttctcc ggaaacatta gc    102

<210> SEQ ID NO 579
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 579
acaaccgcgt gttacaaggc caggcatccg agaggtctgg gaatgcgctt cttctgccgc    60
ttccagcaga ccttctcatt gcgcttctcc ggaaacatta gc    102

<210> SEQ ID NO 580
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 580
acaaccgcgt gttacaaggc caggcatccg agaggtctgg gaatgccact tccatttcgg    60
ttggtgcacc aaagctcatt gcgcttctcc ggaaacatta gc    102

<210> SEQ ID NO 581
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 581
acaaccgcgt gttacaaggc caggcatccg agaggtctgg gaatgcgaac tctggcagcg    60
gcggaacaca gttcatcatt gcgcttctcc ggaaacatta gc    102

<210> SEQ ID NO 582
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 582
acaaccgcgt gttacaaggc caggcatccg agaggtctgg gaatgcacgt gttgtcagct    60
catccagcgt ttcgtgcatt gcgcttctcc ggaaacatta gc    102

<210> SEQ ID NO 583
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 583
acaaccgcgt gttacaaggc caggcatccg agaggtctgg gaatgctatt gatatcttcc    60
atgctgtgcg ccacggcatt gcgcttctcc ggaaacatta gc    102

<210> SEQ ID NO 584
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 584
acaaccgcgt gttacaaggc caggcatccg agaggtctgg gaatgcgcta cgcggaaacc    60
ggtcatcact tcatcgcatt gcgcttctcc ggaaacatta gc    102

<210> SEQ ID NO 585
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 585
acaaccgcgt gttacaaggc caggcatccg agaggtctgg gaatgcttgc catcaacatc    60
gtacagataa gcgccgcatt gcgcttctcc ggaaacatta gc    102

<210> SEQ ID NO 586
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 586
acaaccgcgt gttacaaggc caggcatccg agaggtctgg gaatgcccga ggcaggttaa    60
atctggcact acgccgcatt gcgcttctcc ggaaacatta gc    102

<210> SEQ ID NO 587
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 587
acaaccgcgt gttacaaggc caggcatccg agaggtctgg gaatgcctca aatgcggcgc    60
gtacagaagc cagatccatt gcgcttctcc ggaaacatta gc    102

<210> SEQ ID NO 588
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 588
acaaccgcgt gttacaaggc caggcatccg agaggtctgg gaatgccaac ttcgcaaaca    60
cccgacgtgc agcatccatt gcgcttctcc ggaaacatta gc    102

<210> SEQ ID NO 589
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 589
acaaccgcgt gttacaaggc caggcatccg agaggtctgg gaatgccgct taaagcgttc      60
cacgtcacag gccatccatt gcgcttctcc ggaaacatta gc      102

<210> SEQ ID NO 590
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 590
acaaccgcgt gttacaaggc caggcatccg agaggtctgg gaatgcaggt atatttggcg      60
aaatctgccg gaacgccatt gcgcttctcc ggaaacatta gc      102

<210> SEQ ID NO 591
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 591
acaaccgcgt gttacaaggc caggcatccg agaggtctgg gaatgcctca tggtcgcttc      60
agtgccggag ttcacccatt gcgcttctcc ggaaacatta gc      102

<210> SEQ ID NO 592
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 592
acaaccgcgt gttacaaggc caggcatccg agaggtctgg gaatgcccag cgcatccatt      60
acatcacgac gaccaccatt gcgcttctcc ggaaacatta gc      102

<210> SEQ ID NO 593
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 593
acaaccgcgt gttacaaggc caggcatccg agaggtctgg gaatgccgct tcaaacgctg      60
acggtgccag gtaaaccatt gcgcttctcc ggaaacatta gc      102

<210> SEQ ID NO 594
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 594
acaaccgcgt gttacaaggc caggcatccg agaggtctgg gaatgcgctg cgcgacttca      60
ttcagacagg cgaaaccatt gcgcttctcc ggaaacatta gc      102

<210> SEQ ID NO 595
<211> LENGTH: 102
<212> TYPE: DNA
<213> ORGANISM: Artificial Sequence

```
<220> FEATURE:
<223> OTHER INFORMATION: Synthetic Polynucleotide

<400> SEQUENCE: 595
acaaccgcgt gttacaaggc caggcatccg agaggtctgg gaatgcgcca tcgcaatcgg      60
gttaccggaa agcgtacatt gcgcttctcc ggaaacatta gc                        102

<210> SEQ ID NO 596
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 596
acaaccgcgt gttacaaggc caggcatccg agaggtctgg gaatgctacc gaacatgccg      60
ccaacgtggt taacgacatt gcgcttctcc ggaaacatta gc                        102

<210> SEQ ID NO 597
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 597
acaaccgcgt gttacaaggc caggcatccg agaggtctgg gaatgcctaa cgtgagtgcg      60
ccagaaccgg ctttcacatt gcgcttctcc ggaaacatta gc                        102

<210> SEQ ID NO 598
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 598
acaaccgcgt gttacaaggc caggcatccg agaggtctgg gaatgcctgc caccggctcg      60
acgataatac aggcaacatt gcgcttctcc ggaaacatta gc                        102

<210> SEQ ID NO 599
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 599
acaaccgcgt gttacaaggc caggcatccg agaggtctgg gaatgcccga tatacggcag      60
atgacggtaa cgctgtcatt gcgcttctcc ggaaacatta gc                        102

<210> SEQ ID NO 600
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 600
acaaccgcgt gttacaaggc caggcatccg agaggtctgg gaatgcccat atcgctgccg      60
ctgtctttgt aacgctcatt gcgcttctcc ggaaacatta gc                        102
```

<210> SEQ ID NO 601
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 601
acaaccgcgt gttacaaggc caggcatccg agaggtctgg gaatgcggtt cgcgcaggct      60
taagatctca cgcactcatt gcgcttctcc ggaaacatta gc                        102

<210> SEQ ID NO 602
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 602
acaaccgcgt gttacaaggc caggcatccg agaggtctgg gaatgctcat gagatacctg      60
aacttcacgg cacaggcatt gcgcttctcc ggaaacatta gc                        102

<210> SEQ ID NO 603
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 603
acaaccgcgt gttacaaggc caggcatccg agaggtctgg gaatgcgttt atccagcagc      60
gtacaaatcg ccagcgcatt gcgcttctcc ggaaacatta gc                        102

<210> SEQ ID NO 604
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 604
acaaccgcgt gttacaaggc caggcatccg agaggtctgg gaatgcaaat tctaccggga      60
cgttcacttc acgacgcatt gcgcttctcc ggaaacatta gc                        102

<210> SEQ ID NO 605
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 605
acaaccgcgt gttacaaggc caggcatccg agaggtctgg gaatgcatct tcaacaatca      60
gcacgtcctt gccacgcatt gcgcttctcc ggaaacatta gc                        102

<210> SEQ ID NO 606
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 606

```
acaaccgcgt gttacaaggc caggcatccg agaggtctgg gaatgcccgc taccgtagct    60
ggaggcggtc ataaagcatt gcgcttctcc ggaaacatta gc                      102

<210> SEQ ID NO 607
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 607
acaaccgcgt gttacaaggc caggcatccg agaggtctgg gaatgctcaa tgccgtaacc    60
caccacaaac tcatcccatt gcgcttctcc ggaaacatta gc                      102

<210> SEQ ID NO 608
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 608
acaaccgcgt gttacaaggc caggcatccg agaggtctgg gaatgcaaac ataaatgagc    60
cacgcagcag acccaccatt gcgcttctcc ggaaacatta gc                      102

<210> SEQ ID NO 609
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 609
acaaccgcgt gttacaaggc caggcatccg agaggtctgg gaatgcgacg acccagttcg    60
gcgatacgcg ctttaacatt gcgcttctcc ggaaacatta gc                      102

<210> SEQ ID NO 610
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 610
acaaccgcgt gttacaaggc caggcatccg agaggtctgg gaatgcggta ttcccggctg    60
ttagcgcttc agatttcatt gcgcttctcc ggaaacatta gc                      102

<210> SEQ ID NO 611
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 611
acaaccgcgt gttacaaggc caggcatccg agaggtctgg gaatgccgtt cttgcaaacg    60
cgagttaaag cgactgcatt gcgcttctcc ggaaacatta gc                      102

<210> SEQ ID NO 612
<211> LENGTH: 102
<212> TYPE: DNA
```

```
<213> ORGANISM: Artificial Sequence
<220> FEATURE:
<223> OTHER INFORMATION: Synthetic Polynucleotide

<400> SEQUENCE: 612
acaaccgcgt gttacaaggc caggcatccg agaggtctgg gaatgcgcca ataatacgca    60
gacgcacgtt atgtcgcatt gcgcttctcc ggaaacatta gc                      102

<210> SEQ ID NO 613
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 613
acaaccgcgt gttacaaggc caggcatccg agaggtctgg gaatgcaagg catacagcgt    60
taacgcctca ataccgcatt gcgcttctcc ggaaacatta gc                      102

<210> SEQ ID NO 614
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 614
acaaccgcgt gttacaaggc caggcatccg agaggtctgg gaatgcccac cgtagttcgc    60
cgcaatattc agcgtccatt gcgcttctcc ggaaacatta gc                      102

<210> SEQ ID NO 615
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 615
acaaccgcgt gttacaaggc caggcatccg agaggtctgg gaatgcatct gatctggttg    60
caggtttcct tgctgccatt gcgcttctcc ggaaacatta gc                      102

<210> SEQ ID NO 616
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 616
acaaccgcgt gttacaaggc caggcatccg agaggtctgg gaatgcggct ttatgcccaa    60
aggcacgaat cttcccatt gcgcttctcc ggaaacatta gc                       102

<210> SEQ ID NO 617
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 617
acaaccgcgt gttacaaggc caggcatccg agaggtctgg gaatgcccag ttgcctgact    60
ccctggacta tatccccatt gcgcttctcc ggaaacatta gc                      102
```

<210> SEQ ID NO 618
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 618
acaaccgcgt gttacaaggc caggcatccg agaggtctgg gaatgcgtct tgttcatcga    60
aatcgggcca gagaaccatt gcgcttctcc ggaaacatta gc    102

<210> SEQ ID NO 619
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 619
acaaccgcgt gttacaaggc caggcatccg agaggtctgg gaatgccgct atcgagcgcc    60
cacacaaaca gttccacatt gcgcttctcc ggaaacatta gc    102

<210> SEQ ID NO 620
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 620
acaaccgcgt gttacaaggc caggcatccg agaggtctgg gaatgcgccg ccgaaacgac    60
gctctcgatt agcaaacatt gcgcttctcc ggaaacatta gc    102

<210> SEQ ID NO 621
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 621
acaaccgcgt gttacaaggc caggcatccg agaggtctgg gaatgcccat gcgtagcgcc    60
aggtacaggc tttcttcatt gcgcttctcc ggaaacatta gc    102

<210> SEQ ID NO 622
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 622
acaaccgcgt gttacaaggc caggcatccg agaggtctgg gaatgcgagg caggcagaaa    60
ccgcgtgttg ttcattcatt gcgcttctcc ggaaacatta gc    102

<210> SEQ ID NO 623
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 623
acaaccgcgt gttacaaggc caggcatccg agaggtctgg gaatgccgag gtatcgccgt    60
ggaaaccatc tttgatcatt gcgcttctcc ggaaacatta gc    102

<210> SEQ ID NO 624
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 624
acaaccgcgt gttacaaggc caggcatccg agaggtctgg gaatgcttat cgtcgtgcg    60 agattatcgc cgggatcatt gcgcttctcc ggaaacatta gc    102

<210> SEQ ID NO 625
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 625
acaaccgcgt gttacaaggc caggcatccg agaggtctgg gaatgcgacg cccggtttaa    60
catacggttc gatcatcatt gcgcttctcc ggaaacatta gc    102

<210> SEQ ID NO 626
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 626
acaaccgcgt gttacaaggc caggcatccg agaggtctgg gaatgcagag atgcaaacgg    60
atttcggata gccgtgcatt gcgcttctcc ggaaacatta gc    102

<210> SEQ ID NO 627
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 627
acaaccgcgt gttacaaggc caggcatccg agaggtctgg gaatgctaat cattacagat    60
gcgatccagc tcgccgcatt gcgcttctcc ggaaacatta gc    102

<210> SEQ ID NO 628
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 628
acaaccgcgt gttacaaggc caggcatccg agaggtctgg gaatgcatcg ccatctttca    60
gcagcttagc atcgtccatt gcgcttctcc ggaaacatta gc    102

<210> SEQ ID NO 629
<211> LENGTH: 102

```
<212> TYPE: DNA
<213> ORGANISM: Artificial Sequence
<220> FEATURE:
<223> OTHER INFORMATION: Synthetic Polynucleotide

<400> SEQUENCE: 629
acaaccgcgt gttacaaggc caggcatccg agaggtctgg gaatgcgcgt tgaccattgg      60
ctcgatggtg aacgtccatt gcgcttctcc ggaaacatta gc                        102

<210> SEQ ID NO 630
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 630
acaaccgcgt gttacaaggc caggcatccg agaggtctgg gaatgcaccg tccagccatc      60
tttcatggtg cggatccatt gcgcttctcc ggaaacatta gc                        102

<210> SEQ ID NO 631
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 631
acaaccgcgt gttacaaggc caggcatccg agaggtctgg gaatgccatc cttgcgtagc      60
gtcagaattt cgcagccatt gcgcttctcc ggaaacatta gc                        102

<210> SEQ ID NO 632
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 632
acaaccgcgt gttacaaggc caggcatccg agaggtctgg gaatgctccg caatattcac      60
gaacgacgga gaagcccatt gcgcttctcc ggaaacatta gc                        102

<210> SEQ ID NO 633
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 633
acaaccgcgt gttacaaggc caggcatccg agaggtctgg gaatgctgcg gttcttcatg      60
gaagccgcga ccaatacatt gcgcttctcc ggaaacatta gc                        102

<210> SEQ ID NO 634
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 634
acaaccgcgt gttacaaggc caggcatccg agaggtctgg gaatgcaggt ttcagtacga      60
```
cgttggtttc acgggacatt gcgcttctcc ggaaacatta gc     102

<210> SEQ ID NO 635
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 635
acaaccgcgt gttacaaggc caggcatccg agaggtctgg gaatgccttc gacaaatttc     60
tgaatcgccg caccgacatt gcgcttctcc ggaaacatta gc     102

<210> SEQ ID NO 636
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 636
acaaccgcgt gttacaaggc caggcatccg agaggtctgg gaatgccgcc catgatggtc     60
ggcttaccga cgataacatt gcgcttctcc ggaaacatta gc     102

<210> SEQ ID NO 637
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 637
acaaccgcgt gttacaaggc caggcatccg agaggtctgg gaatgccgcc tgcgggaagc     60
tctgatacag cactttcatt gcgcttctcc ggaaacatta gc     102

<210> SEQ ID NO 638
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 638
acaaccgcgt gttacaaggc caggcatccg agaggtctgg gaatgcgctt acgcccttttg     60 cctttgccct taccttcatt gcgcttctcc ggaaacatta gc     102

<210> SEQ ID NO 639
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 639
acaaccgcgt gttacaaggc caggcatccg agaggtctgg gaatgccgca attggcgcat     60
ccgcaatcca cgtattcatt gcgcttctcc ggaaacatta gc     102

<210> SEQ ID NO 640
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 640
acaaccgcgt gttacaaggc caggcatccg agaggtctgg gaatgcagcg gacgggcact    60
caacatgtca tagagtcatt gcgcttctcc ggaaacatta gc    102

<210> SEQ ID NO 641
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 641
acaaccgcgt gttacaaggc caggcatccg agaggtctgg gaatgcggct tagctcttct    60
accgggcgac caaagtcatt gcgcttctcc ggaaacatta gc    102

<210> SEQ ID NO 642
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 642
acaaccgcgt gttacaaggc caggcatccg agaggtctgg gaatgcatga tcagcgccat    60
gtaagcttcg ttcgctcatt gcgcttctcc ggaaacatta gc    102

<210> SEQ ID NO 643
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 643
acaaccgcgt gttacaaggc caggcatccg agaggtctgg gaatgcccac cagcatcact    60
ctgccgcttt cgctatcatt gcgcttctcc ggaaacatta gc    102

<210> SEQ ID NO 644
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 644
acaaccgcgt gttacaaggc caggcatccg agaggtctgg gaatgcggat ttcgttgtcg    60
ccgctctgac cgagatcatt gcgcttctcc ggaaacatta gc    102

<210> SEQ ID NO 645
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 645
acaaccgcgt gttacaaggc caggcatccg agaggtctgg gaatgcctgg caccatacag    60
tttggtcggc tggttgcatt gcgcttctcc ggaaacatta gc    102

<210> SEQ ID NO 646

```
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 646
acaaccgcgt gttacaaggc caggcatccg agaggtctgg gaatgctttc accataccga      60
ctaacagcgc ctgctgcatt gcgcttctcc ggaaacatta gc                        102

<210> SEQ ID NO 647
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 647
acaaccgcgt gttacaaggc caggcatccg agaggtctgg gaatgcacgg acggcgaatc      60
atctcaatgc tgttggcatt gcgcttctcc ggaaacatta gc                        102

<210> SEQ ID NO 648
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 648
acaaccgcgt gttacaaggc caggcatccg agaggtctgg gaatgccggt catcattctg      60
cggtgaccag acctggcatt gcgcttctcc ggaaacatta gc                        102

<210> SEQ ID NO 649
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 649
acaaccgcgt gttacaaggc caggcatccg agaggtctgg gaatgcagat ttaccgtcgg      60
cacgttcatc gaacggcatt gcgcttctcc ggaaacatta gc                        102

<210> SEQ ID NO 650
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 650
acaaccgcgt gttacaaggc caggcatccg agaggtctgg gaatgcggtc atgtctggct      60
caagattgac cattcgcatt gcgcttctcc ggaaacatta gc                        102

<210> SEQ ID NO 651
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 651
acaaccgcgt gttacaaggc caggcatccg agaggtctgg gaatgccaaa ctgcggctca      60
```

```
gaacctccga ccatcgcatt gcgcttctcc ggaaacatta gc                          102

<210> SEQ ID NO 652
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 652
acaaccgcgt gttacaaggc caggcatccg agaggtctgg gaatgcgctc aagaatacgg        60
tctttgctgt aacgcgcatt gcgcttctcc ggaaacatta gc                          102

<210> SEQ ID NO 653
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 653
acaaccgcgt gttacaaggc caggcatccg agaggtctgg gaatgcaaca tatccttgat        60
ccaaccggct acaccgcatt gcgcttctcc ggaaacatta gc                          102

<210> SEQ ID NO 654
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 654
acaaccgcgt gttacaaggc caggcatccg agaggtctgg gaatgcccag taagaacgct        60
cgctggagag gaacagcatt gcgcttctcc ggaaacatta gc                          102

<210> SEQ ID NO 655
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 655
acaaccgcgt gttacaaggc caggcatccg agaggtctgg gaatgcatgg tgatcagacg        60
cggatcaaga cggaagcatt gcgcttctcc ggaaacatta gc                          102

<210> SEQ ID NO 656
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 656
acaaccgcgt gttacaaggc caggcatccg agaggtctgg gaatgccaaa cagacgctgc        60
tcaccgtttg gcgaagcatt gcgcttctcc ggaaacatta gc                          102

<210> SEQ ID NO 657
<211> LENGTH: 102
<212> TYPE: DNA
<213> ORGANISM: Artificial Sequence
<220> FEATURE:
```

<223> OTHER INFORMATION: Synthetic Polynucleotide

<400> SEQUENCE: 657
acaaccgcgt gttacaaggc caggcatccg agaggtctgg gaatgcgtcg cctccagcag    60
cttcaccatc tcgttccatt gcgcttctcc ggaaacatta gc    102

<210> SEQ ID NO 658
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 658
acaaccgcgt gttacaaggc caggcatccg agaggtctgg gaatgccgtc ggtttccctt    60
tgcgtccaat tggctccatt gcgcttctcc ggaaacatta gc    102

<210> SEQ ID NO 659
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 659
acaaccgcgt gttacaaggc caggcatccg agaggtctgg gaatgccggc tgttgctgcg    60
gctgagaaga ctgatccatt gcgcttctcc ggaaacatta gc    102

<210> SEQ ID NO 660
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 660
acaaccgcgt gttacaaggc caggcatccg agaggtctgg gaatgcacgg ttgttctcca    60
tattgacgat cgtcgccatt gcgcttctcc ggaaacatta gc    102

<210> SEQ ID NO 661
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 661
acaaccgcgt gttacaaggc caggcatccg agaggtctgg gaatgccggc tggcttaagg    60
ccgtcagata agtcgccatt gcgcttctcc ggaaacatta gc    102

<210> SEQ ID NO 662
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 662
acaaccgcgt gttacaaggc caggcatccg agaggtctgg gaatgctcga gataaacgcc    60
gtaaatggcg atcagccatt gcgcttctcc ggaaacatta gc    102

<210> SEQ ID NO 663
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 663
acaaccgcgt gttacaaggc caggcatccg agaggtctgg gaatgcataa tctgttgctg    60
ttgcagcaga cgcagccatt gcgcttctcc ggaaacatta gc                      102

<210> SEQ ID NO 664
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 664
acaaccgcgt gttacaaggc caggcatccg agaggtctgg gaatgctgac ggtcttctgt    60
cgccagcaaa gtatcccatt gcgcttctcc ggaaacatta gc                      102

<210> SEQ ID NO 665
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 665
acaaccgcgt gttacaaggc caggcatccg agaggtctgg gaatgctcgc tcaacttacg    60
ctgtttcttc agtgcccatt gcgcttctcc ggaaacatta gc                      102

<210> SEQ ID NO 666
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 666
acaaccgcgt gttacaaggc caggcatccg agaggtctgg gaatgcctgt tgcgtcagcg    60
tactcgcacc ctgtaccatt gcgcttctcc ggaaacatta gc                      102

<210> SEQ ID NO 667
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 667
acaaccgcgt gttacaaggc caggcatccg agaggtctgg gaatgcacaa gattcagcgg    60
cgttggcgtc tggttacatt gcgcttctcc ggaaacatta gc                      102

<210> SEQ ID NO 668
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 668
acaaccgcgt gttacaaggc caggcatccg agaggtctgg gaatgcgttt gccagcaccg    60
cacgtccgat tgagtacatt gcgcttctcc ggaaacatta gc                       102

<210> SEQ ID NO 669
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 669
acaaccgcgt gttacaaggc caggcatccg agaggtctgg gaatgctgcc gtcaatgccc    60
gcaaaccagg tatctacatt gcgcttctcc ggaaacatta gc                       102

<210> SEQ ID NO 670
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 670
acaaccgcgt gttacaaggc caggcatccg agaggtctgg gaatgccgcg ttgtaccacc    60
tgctgcatgg tccatacatt gcgcttctcc ggaaacatta gc                       102

<210> SEQ ID NO 671
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 671
acaaccgcgt gttacaaggc caggcatccg agaggtctgg gaatgcgcag gcagttgcca    60
gaccttgcca tcaatacatt gcgcttctcc ggaaacatta gc                       102

<210> SEQ ID NO 672
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 672
acaaccgcgt gttacaaggc caggcatccg agaggtctgg gaatgcccgt cgtagtccac    60
gcccatatct gcaatacatt gcgcttctcc ggaaacatta gc                       102

<210> SEQ ID NO 673
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 673
acaaccgcgt gttacaaggc caggcatccg agaggtctgg gaatgcactt caccactaaa    60
gcggtcgacg accacacatt gcgcttctcc ggaaacatta gc                       102

<210> SEQ ID NO 674
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 674
acaaccgcgt gttacaaggc caggcatccg agaggtctgg gaatgcgtac gcccagttta    60
atccaggtct ccgtaacatt gcgcttctcc ggaaacatta gc    102

<210> SEQ ID NO 675
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 675
acaaccgcgt gttacaaggc caggcatccg agaggtctgg gaatgccctg cagctcctga    60
cgcaccagtt gcataacatt gcgcttctcc ggaaacatta gc    102

<210> SEQ ID NO 676
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 676
acaaccgcgt gttacaaggc caggcatccg agaggtctgg gaatgcgtcc tgggccaccg    60
agtcaaaggt agtgaacatt gcgcttctcc ggaaacatta gc    102

<210> SEQ ID NO 677
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 677
acaaccgcgt gttacaaggc caggcatccg agaggtctgg gaatgcgcgc acctgtcctt    60
ctttactgtc cgggaacatt gcgcttctcc ggaaacatta gc    102

<210> SEQ ID NO 678
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 678
acaaccgcgt gttacaaggc caggcatccg agaggtctgg gaatgcgcaa gatacgcatg    60
ccaccgctgc aaacaacatt gcgcttctcc ggaaacatta gc    102

<210> SEQ ID NO 679
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 679
acaaccgcgt gttacaaggc caggcatccg agaggtctgg gaatgcttcg tccgagacaa    60
cgatatcgcc cactttcatt gcgcttctcc ggaaacatta gc    102

<210> SEQ ID NO 680
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 680
acaaccgcgt gttacaaggc caggcatccg agaggtctgg gaatgcctgc cggacagcct    60
ggtaactgac cgtattcatt gcgcttctcc ggaaacatta gc    102

<210> SEQ ID NO 681
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 681
acaaccgcgt gttacaaggc caggcatccg agaggtctgg gaatgccagg cctcagcggc    60
agcgatcagt ttatcgcatt gcgcttctcc ggaaacatta gc    102

<210> SEQ ID NO 682
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 682
acaaccgcgt gttacaaggc caggcatccg agaggtctgg gaatgcttcg caaccgccga    60
gactgatagt ttgacgcatt gcgcttctcc ggaaacatta gc    102

<210> SEQ ID NO 683
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 683
acaaccgcgt gttacaaggc caggcatccg agaggtctgg gaatgccatc aggctggact    60
gtttagcggc aacagccatt gcgcttctcc ggaaacatta gc    102

<210> SEQ ID NO 684
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 684
acaaccgcgt gttacaaggc caggcatccg agaggtctgg gaatgcatca catctggctt    60
gcagtgttcc aacagccatt gcgcttctcc ggaaacatta gc    102

<210> SEQ ID NO 685
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 685
acaaccgcgt gttacaaggc caggcatccg agaggtctgg gaatgccgcc agaccaacag    60
aaccgttgat gaaagccatt gcgcttctcc ggaaacatta gc                       102

<210> SEQ ID NO 686
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 686
acaaccgcgt gttacaaggc caggcatccg agaggtctgg gaatgctcga agctaagatg    60
agactgttga tcggcccatt gcgcttctcc ggaaacatta gc                       102

<210> SEQ ID NO 687
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 687
acaaccgcgt gttacaaggc caggcatccg agaggtctgg gaatgctagc catgtgcaag    60
tttctgcacc agtgaccatt gcgcttctcc ggaaacatta gc                       102

<210> SEQ ID NO 688
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 688
acaaccgcgt gttacaaggc caggcatccg agaggtctgg gaatgcggag atggcgcgta    60
cgacaacaaa cgggaccatt gcgcttctcc ggaaacatta gc                       102

<210> SEQ ID NO 689
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 689
acaaccgcgt gttacaaggc caggcatccg agaggtctgg gaatgcgcaa cctcggttcc    60
attcagttgg ccggtacatt gcgcttctcc ggaaacatta gc                       102

<210> SEQ ID NO 690
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 690
acaaccgcgt gttacaaggc caggcatccg agaggtctgg gaatgccatg ggcgattgcc    60
gtcgcttcca tctctacatt gcgcttctcc ggaaacatta gc                       102

<210> SEQ ID NO 691
<211> LENGTH: 102
<212> TYPE: DNA

<213> ORGANISM: Artificial Sequence
<220> FEATURE:
<223> OTHER INFORMATION: Synthetic Polynucleotide

<400> SEQUENCE: 691
acaaccgcgt gttacaaggc caggcatccg agaggtctgg gaatgcccgc agcgactta       60 ccgatgcccg atttcacatt gcgcttctcc ggaaacatta gc                          102

<210> SEQ ID NO 692
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 692
acaaccgcgt gttacaaggc caggcatccg agaggtctgg gaatgccgct aacaatcagg       60
ccacgtacag cgttaacatt gcgcttctcc ggaaacatta gc                          102

<210> SEQ ID NO 693
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 693
acaaccgcgt gttacaaggc caggcatccg agaggtctgg gaatgcccaa atgccgtgac       60
atccgcgtcg tgataacatt gcgcttctcc ggaaacatta gc                          102

<210> SEQ ID NO 694
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 694
acaaccgcgt gttacaaggc caggcatccg agaggtctgg gaatgccctc cggagtttgc       60
ggcttcagtt tgatttcatt gcgcttctcc ggaaacatta gc                          102

<210> SEQ ID NO 695
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 695
acaaccgcgt gttacaaggc caggcatccg agaggtctgg gaatgcggaa tacgcgcttc       60
atgagcggcg acaattcatt gcgcttctcc ggaaacatta gc                          102

<210> SEQ ID NO 696
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 696
acaaccgcgt gttacaaggc caggcatccg agaggtctgg gaatgccttt aatggtggcg       60
tccacttccg tcgggtcatt gcgcttctcc ggaaacatta gc                          102

<210> SEQ ID NO 697
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 697
acaaccgcgt gttacaaggc caggcatccg agaggtctgg gaatgcctcg cggtaacaat    60
tcgcggatca ccggatcatt gcgcttctcc ggaaacatta gc                      102

<210> SEQ ID NO 698
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 698
acaaccgcgt gttacaaggc caggcatccg agaggtctgg gaatgctcgg catcttcgct    60
gaagccgtaa gtcgtgcatt gcgcttctcc ggaaacatta gc                      102

<210> SEQ ID NO 699
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 699
acaaccgcgt gttacaaggc caggcatccg agaggtctgg gaatgcggtg acaatcgcca    60
ccatcggttg cagatgcatt gcgcttctcc ggaaacatta gc                      102

<210> SEQ ID NO 700
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 700
acaaccgcgt gttacaaggc caggcatccg agaggtctgg gaatgcttct caaagtcgcc    60
ctggtaggta tccatgcatt gcgcttctcc ggaaacatta gc                      102

<210> SEQ ID NO 701
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 701
acaaccgcgt gttacaaggc caggcatccg agaggtctgg gaatgcgctt ctgcgtagat    60
gctggaaacc atcgcgcatt gcgcttctcc ggaaacatta gc                      102

<210> SEQ ID NO 702
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 702
acaaccgcgt gttacaaggc caggcatccg agaggtctgg gaatgctagc ctcgtcgtca    60
atgccctctt ccgtagcatt gcgcttctcc ggaaacatta gc    102

<210> SEQ ID NO 703
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 703
acaaccgcgt gttacaaggc caggcatccg agaggtctgg gaatgcttca ttaactgctg    60
cgtgaccgga tttggccatt gcgcttctcc ggaaacatta gc    102

<210> SEQ ID NO 704
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 704
acaaccgcgt gttacaaggc caggcatccg agaggtctgg gaatgcctga taaccttcat    60
tggccagaac ttcggccatt gcgcttctcc ggaaacatta gc    102

<210> SEQ ID NO 705
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 705
acaaccgcgt gttacaaggc caggcatccg agaggtctgg gaatgcacca ttcactggct    60
ccagcgggaa ttcacccatt gcgcttctcc ggaaacatta gc    102

<210> SEQ ID NO 706
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 706
acaaccgcgt gttacaaggc caggcatccg agaggtctgg gaatgcccgg gcgatggttg    60
aaataaatcg tcgcaccatt gcgcttctcc ggaaacatta gc    102

<210> SEQ ID NO 707
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 707
acaaccgcgt gttacaaggc caggcatccg agaggtctgg gaatgcgcgg gccaatctgc    60
tgataatctt ctacaccatt gcgcttctcc ggaaacatta gc    102

<210> SEQ ID NO 708
<211> LENGTH: 102

```
<212> TYPE: DNA
<213> ORGANISM: Artificial Sequence
<220> FEATURE:
<223> OTHER INFORMATION: Synthetic Polynucleotide

<400> SEQUENCE: 708
acaaccgcgt gttacaaggc caggcatccg agaggtctgg gaatgccacg tccacgaatt    60
gtgcgacaca gcgaaccatt gcgcttctcc ggaaacatta gc                      102

<210> SEQ ID NO 709
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 709
acaaccgcgt gttacaaggc caggcatccg agaggtctgg gaatgcgtta tcggcagaaa    60
tcgcgctgga aacaaccatt gcgcttctcc ggaaacatta gc                      102

<210> SEQ ID NO 710
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 710
acaaccgcgt gttacaaggc caggcatccg agaggtctgg gaatgccggt taataccggt    60
gccagcatct cggctacatt gcgcttctcc ggaaacatta gc                      102

<210> SEQ ID NO 711
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 711
acaaccgcgt gttacaaggc caggcatccg agaggtctgg gaatgccgca ttaactcagc    60
cagcatttcg gcacgacatt gcgcttctcc ggaaacatta gc                      102

<210> SEQ ID NO 712
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 712
acaaccgcgt gttacaaggc caggcatccg agaggtctgg gaatgccttc gccagccgga    60
tacacttcca gcatcacatt gcgcttctcc ggaaacatta gc                      102

<210> SEQ ID NO 713
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 713
acaaccgcgt gttacaaggc caggcatccg agaggtctgg gaatgcacga tgcatcactc    60
```
tcatctgctt cggcaacatt gcgcttctcc ggaaacatta gc    102

<210> SEQ ID NO 714
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 714
acaaccgcgt gttacaaggc caggcatccg agaggtctgg gaatgcgtat caacctgcgt    60
cagcacattg gcgaaacatt gcgcttctcc ggaaacatta gc    102

<210> SEQ ID NO 715
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 715
acaaccgcgt gttacaaggc caggcatccg agaggtctgg gaatgccatc acgaggatct    60
gcccgtcagt gacgttcatt gcgcttctcc ggaaacatta gc    102

<210> SEQ ID NO 716
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 716
acaaccgcgt gttacaaggc caggcatccg agaggtctgg gaatgccaat gccaataacc    60
gggatcgcca gtgcttcatt gcgcttctcc ggaaacatta gc    102

<210> SEQ ID NO 717
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 717
acaaccgcgt gttacaaggc caggcatccg agaggtctgg gaatgcgacc atgttagcac    60
cggcacgcat aaccgtcatt gcgcttctcc ggaaacatta gc    102

<210> SEQ ID NO 718
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 718
acaaccgcgt gttacaaggc caggcatccg agaggtctgg gaatgctggc gaagctatag    60
tcataagcgg tgatggcatt gcgcttctcc ggaaacatta gc    102

<210> SEQ ID NO 719
<211> LENGTH: 102
<212> TYPE: DNA
<213> ORGANISM: Artificial Sequence
<220> FEATURE:
<223> OTHER INFORMATION: Synthetic Polynucleotide

```
<400> SEQUENCE: 719
acaaccgcgt gttacaaggc caggcatccg agaggtctgg gaatgctagg aatgtgaccg      60
ccggtaatac caaaggcatt gcgcttctcc ggaaacatta gc                        102

<210> SEQ ID NO 720
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 720
acaaccgcgt gttacaaggc caggcatccg agaggtctgg gaatgctgta cttctgcagt      60
aaggagatgg tggtcgcatt gcgcttctcc ggaaacatta gc                        102

<210> SEQ ID NO 721
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 721
acaaccgcgt gttacaaggc caggcatccg agaggtctgg gaatgctgga aactgtgttc      60
ttcgcccgga taaacgcatt gcgcttctcc ggaaacatta gc                        102

<210> SEQ ID NO 722
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 722
acaaccgcgt gttacaaggc caggcatccg agaggtctgg gaatgcagca gcttctaagg      60
ctaatgcatc gctgagcatt gcgcttctcc ggaaacatta gc                        102

<210> SEQ ID NO 723
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 723
acaaccgcgt gttacaaggc caggcatccg agaggtctgg gaatgcctcc acttcagcca      60
tatactgccg cacagccatt gcgcttctcc ggaaacatta gc                        102

<210> SEQ ID NO 724
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 724
acaaccgcgt gttacaaggc caggcatccg agaggtctgg gaatgcaacc taagtgacca      60
catacaggaa cggcaccatt gcgcttctcc ggaaacatta gc                        102

<210> SEQ ID NO 725
```

```
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 725
acaaccgcgt gttacaaggc caggcatccg agaggtctgg gaatgcgtca gcatttgtac    60
ggtttctacc agccaccatt gcgcttctcc ggaaacatta gc                      102

<210> SEQ ID NO 726
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 726
acaaccgcgt gttacaaggc caggcatccg agaggtctgg gaatgcgcag tgtggtaggc    60
gatatcggca acgtacatt gcgcttctcc ggaaacatta gc                       102

<210> SEQ ID NO 727
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 727
acaaccgcgt gttacaaggc caggcatccg agaggtctgg gaatgccata cgccataaac    60
ggcaggtcag ccagcacatt gcgcttctcc ggaaacatta gc                      102

<210> SEQ ID NO 728
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 728
acaaccgcgt gttacaaggc caggcatccg agaggtctgg gaatgcccag cgaatcgccc    60
accagcatga cgttaacatt gcgcttctcc ggaaacatta gc                      102

<210> SEQ ID NO 729
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 729
acaaccgcgt gttacaaggc caggcatccg agaggtctgg gaatgcccag gcggctacca    60
gaattactgc ccgtttcatt gcgcttctcc ggaaacatta gc                      102

<210> SEQ ID NO 730
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 730
acaaccgcgt gttacaaggc caggcatccg agaggtctgg gaatgcgatg tccggctgga    60
```

```
ccaggttgaa cagcttcatt gcgcttctcc ggaaacatta gc                      102

<210> SEQ ID NO 731
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 731
acaaccgcgt gttacaaggc caggcatccg agaggtctgg gaatgccttg ccttccatac    60
gcaggcggcg aatttgcatt gcgcttctcc ggaaacatta gc                      102

<210> SEQ ID NO 732
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 732
acaaccgcgt gttacaaggc caggcatccg agaggtctgg gaatgcacgt ttgtttagct    60
tctcgcagtc ctcctgcatt gcgcttctcc ggaaacatta gc                      102

<210> SEQ ID NO 733
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 733
acaaccgcgt gttacaaggc caggcatccg agaggtctgg gaatgcacgt aagtgtgggt    60
ttcagtaccg ttcgggcatt gcgcttctcc ggaaacatta gc                      102

<210> SEQ ID NO 734
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 734
acaaccgcgt gttacaaggc caggcatccg agaggtctgg gaatgcgcgt tgttccgccg    60
tcagataacc gttacgcatt gcgcttctcc ggaaacatta gc                      102

<210> SEQ ID NO 735
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 735
acaaccgcgt gttacaaggc caggcatccg agaggtctgg gaatgcatcg tgcaggttac    60
ccatggtagg caccagcatt gcgcttctcc ggaaacatta gc                      102

<210> SEQ ID NO 736
<211> LENGTH: 102
<212> TYPE: DNA
<213> ORGANISM: Artificial Sequence
<220> FEATURE:
```

<223> OTHER INFORMATION: Synthetic Polynucleotide

<400> SEQUENCE: 736
acaaccgcgt gttacaaggc caggcatccg agaggtctgg gaatgccaga ccgtctttgg    60
cgcgcataat tggcaccatt gcgcttctcc ggaaacatta gc                      102

<210> SEQ ID NO 737
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 737
acaaccgcgt gttacaaggc caggcatccg agaggtctgg gaatgccggg ctttggcttc    60
gtcgaccagc ttcatacatt gcgcttctcc ggaaacatta gc                      102

<210> SEQ ID NO 738
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 738
acaaccgcgt gttacaaggc caggcatccg agaggtctgg gaatgcgcag cagcggcagg    60
gtttcgataa ttaacacatt gcgcttctcc ggaaacatta gc                      102

<210> SEQ ID NO 739
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 739
acaaccgcgt gttacaaggc caggcatccg agaggtctgg gaatgccacc ttccagcatg    60
gtcgaaaggc caggaacatt gcgcttctcc ggaaacatta gc                      102

<210> SEQ ID NO 740
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 740
acaaccgcgt gttacaaggc caggcatccg agaggtctgg gaatgcccgc atgagtcact    60
ttcacgcggt ggagttcatt gcgcttctcc ggaaacatta gc                      102

<210> SEQ ID NO 741
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 741
acaaccgcgt gttacaaggc caggcatccg agaggtctgg gaatgcccag gtgcgagctt    60
cttcatctgg catggtcatt gcgcttctcc ggaaacatta gc                      102

<210> SEQ ID NO 742
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 742
acaaccgcgt gttacaaggc caggcatccg agaggtctgg aatgcgccg cgatggcata    60 agtggagaaa cgcttgcatt gcgcttctcc ggaaacatta gc                    102

<210> SEQ ID NO 743
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 743
acaaccgcgt gttacaaggc caggcatccg agaggtctgg aatgctcct ggtcaatggc    60 gcaagaacct tcatagcatt gcgcttctcc ggaaacatta gc                    102

<210> SEQ ID NO 744
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 744
acaaccgcgt gttacaaggc caggcatccg agaggtctgg aatgctcaa gcaacctgta    60 ccggaatcgc tttcgccatt gcgcttctcc ggaaacatta gc                    102

<210> SEQ ID NO 745
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 745
acaaccgcgt gttacaaggc caggcatccg agaggtctgg aatgcagct ggcgatgatg    60 acaatatcgc cgacaccatt gcgcttctcc ggaaacatta gc                    102

<210> SEQ ID NO 746
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 746
acaaccgcgt gttacaaggc caggcatccg agaggtctgg aatgccagt gggccgccgc    60 accgttaaca gaaatacatt gcgcttctcc ggaaacatta gc                    102

<210> SEQ ID NO 747
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 747
acaaccgcgt gttacaaggc caggcatccg agaggtctgg gaatgccgaa agcgtcgtga    60
taggtcaggc cgctttcatt gcgcttctcc ggaaacatta gc    102

<210> SEQ ID NO 748
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 748
acaaccgcgt gttacaaggc caggcatccg agaggtctgg gaatgcggtt tccgggctga    60
tgcgcatacc caatttcatt gcgcttctcc ggaaacatta gc    102

<210> SEQ ID NO 749
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 749
acaaccgcgt gttacaaggc caggcatccg agaggtctgg gaatgcctgc aactgccaga    60
tatcgcgggt taatgtcatt gcgcttctcc ggaaacatta gc    102

<210> SEQ ID NO 750
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 750
acaaccgcgt gttacaaggc caggcatccg agaggtctgg gaatgcggaa cgccgggttc    60
acgcgcatat cgttatcatt gcgcttctcc ggaaacatta gc    102

<210> SEQ ID NO 751
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 751
acaaccgcgt gttacaaggc caggcatccg agaggtctgg gaatgccgcg gtgacggttc    60
ttcatccagc tcgttgcatt gcgcttctcc ggaaacatta gc    102

<210> SEQ ID NO 752
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 752
acaaccgcgt gttacaaggc caggcatccg agaggtctgg gaatgcgccg tctccagcag    60
tgggtaccag aacatgcatt gcgcttctcc ggaaacatta gc    102

<210> SEQ ID NO 753
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 753
acaaccgcgt gttacaaggc caggcatccg agaggtctgg gaatgcatac aggctgttga    60
tagtgaaatc gcggcgcatt gcgcttctcc ggaaacatta gc                      102

<210> SEQ ID NO 754
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 754
acaaccgcgt gttacaaggc caggcatccg agaggtctgg gaatgcgttt aagcgattct    60
tcaaacaggc gtgccgcatt gcgcttctcc ggaaacatta gc                      102

<210> SEQ ID NO 755
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 755
acaaccgcgt gttacaaggc caggcatccg agaggtctgg gaatgcacag cttataggtt    60
tcgtaaccgt agcccgcatt gcgcttctcc ggaaacatta gc                      102

<210> SEQ ID NO 756
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 756
acaaccgcgt gttacaaggc caggcatccg agaggtctgg gaatgcgcag ttacggaaca    60
gtttgcgcac ctgctccatt gcgcttctcc ggaaacatta gc                      102

<210> SEQ ID NO 757
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 757
acaaccgcgt gttacaaggc caggcatccg agaggtctgg gaatgctttc cgggttacca    60
atcagacgga taacgccatt gcgcttctcc ggaaacatta gc                      102

<210> SEQ ID NO 758
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 758
acaaccgcgt gttacaaggc caggcatccg agaggtctgg gaatgctcat aagccgcacg    60
gaacttagga tgctcccatt gcgcttctcc ggaaacatta gc                      102

<210> SEQ ID NO 759
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 759
acaaccgcgt gttacaaggc caggcatccg agaggtctgg gaatgctcag atccttcatg    60
ccgccaacgt aatcaccatt gcgcttctcc ggaaacatta gc                      102

<210> SEQ ID NO 760
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 760
acaaccgcgt gttacaaggc caggcatccg agaggtctgg gaatgcggtc gctgacgtta    60
ccttcgtggt gtccaccatt gcgcttctcc ggaaacatta gc                      102

<210> SEQ ID NO 761
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 761
acaaccgcgt gttacaaggc caggcatccg agaggtctgg gaatgcgtcg caacttcgat    60
aatctccggg ccaaaccatt gcgcttctcc ggaaacatta gc                      102

<210> SEQ ID NO 762
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 762
acaaccgcgt gttacaaggc caggcatccg agaggtctgg gaatgcccaa ccagccaggc    60
ttcgtatccc gctttacatt gcgcttctcc ggaaacatta gc                      102

<210> SEQ ID NO 763
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 763
acaaccgcgt gttacaaggc caggcatccg agaggtctgg gaatgcgcgc agcatacgta    60
ccggatcttc acggtacatt gcgcttctcc ggaaacatta gc                      102

<210> SEQ ID NO 764
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 764

```
acaaccgcgt gttacaaggc caggcatccg agaggtctgg gaatgccatg cgcgtttacc    60
ctgacgacgg gacatacatt gcgcttctcc ggaaacatta gc                      102

<210> SEQ ID NO 765
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 765
acaaccgcgt gttacaaggc caggcatccg agaggtctgg gaatgccgcg tatcggtatt    60
cttcagcacc tgttcacatt gcgcttctcc ggaaacatta gc                      102

<210> SEQ ID NO 766
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 766
acaaccgcgt gttacaaggc caggcatccg agaggtctgg gaatgccgtt acgctcaact    60
tcagctcgca aggccacatt gcgcttctcc ggaaacatta gc                      102

<210> SEQ ID NO 767
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 767
acaaccgcgt gttacaaggc caggcatccg agaggtctgg gaatgccgt gaagtagcgg     60 gtaatggtcg ggaacacatt gcgcttctcc ggaaacatta gc                      102

<210> SEQ ID NO 768
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 768
acaaccgcgt gttacaaggc caggcatccg agaggtctgg gaatgcccgg atcagcggta    60
aacacgccgt caacttcatt gcgcttctcc ggaaacatta gc                      102

<210> SEQ ID NO 769
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 769
acaaccgcgt gttacaaggc caggcatccg agaggtctgg gaatgcgcaa caggctgata    60
gcttctgccc agctgtcatt gcgcttctcc ggaaacatta gc                      102

<210> SEQ ID NO 770
<211> LENGTH: 102
<212> TYPE: DNA
```

```
<213> ORGANISM: Artificial Sequence
<220> FEATURE:
<223> OTHER INFORMATION: Synthetic Polynucleotide

<400> SEQUENCE: 770
acaaccgcgt gttacaaggc caggcatccg agaggtctgg gaatgcccag cacttcgctg      60
taagtcagtt gctcgtcatt gcgcttctcc ggaaacatta gc                        102

<210> SEQ ID NO 771
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 771
acaaccgcgt gttacaaggc caggcatccg agaggtctgg gaatgcgctt tcagcaccac      60
atcggcttca atttcgcatt gcgcttctcc ggaaacatta gc                        102

<210> SEQ ID NO 772
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 772
acaaccgcgt gttacaaggc caggcatccg agaggtctgg gaatgcacca atcaccacac      60
caacctgaat acccagcatt gcgcttctcc ggaaacatta gc                        102

<210> SEQ ID NO 773
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 773
acaaccgcgt gttacaaggc caggcatccg agaggtctgg gaatgcttcc tgagccatac      60
gatccagtat gcttgccatt gcgcttctcc ggaaacatta gc                        102

<210> SEQ ID NO 774
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 774
acaaccgcgt gttacaaggc caggcatccg agaggtctgg gaatgccgaa tcggtaattt      60
atggtcacga gccagccatt gcgcttctcc ggaaacatta gc                        102

<210> SEQ ID NO 775
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 775
acaaccgcgt gttacaaggc caggcatccg agaggtctgg gaatgctcgc acacgccatt      60
caatggaata gcggaccatt gcgcttctcc ggaaacatta gc                        102
```

<210> SEQ ID NO 776
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 776
acaaccgcgt gttacaaggc caggcatccg agaggtctgg gaatgcgtgc cctgcagagc     60
ttcgccactc aacttacatt gcgcttctcc ggaaacatta gc                       102

<210> SEQ ID NO 777
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 777
acaaccgcgt gttacaaggc caggcatccg agaggtctgg gaatgcgcag gcaagctgct     60
gagtcggtgg taaagacatt gcgcttctcc ggaaacatta gc                       102

<210> SEQ ID NO 778
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 778
acaaccgcgt gttacaaggc caggcatccg agaggtctgg gaatgcttac ctgtaccggc     60
ggagaggatc accacacatt gcgcttctcc ggaaacatta gc                       102

<210> SEQ ID NO 779
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 779
acaaccgcgt gttacaaggc caggcatccg agaggtctgg gaatgcccat cgactttaac     60
gatcctgtcg cctgctcatt gcgcttctcc ggaaacatta gc                       102

<210> SEQ ID NO 780
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 780
acaaccgcgt gttacaaggc caggcatccg agaggtctgg gaatgccttc gacgatggcg     60
ttgaacggcc catactcatt gcgcttctcc ggaaacatta gc                       102

<210> SEQ ID NO 781
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 781
acaaccgcgt gttacaaggc caggcatccg agaggtctgg gaatgcttgg cgatagagat    60
cggcccactg aggttgcatt gcgcttctcc ggaaacatta gc    102

<210> SEQ ID NO 782
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 782
acaaccgcgt gttacaaggc caggcatccg agaggtctgg gaatgcacgt aaatcgagct    60
ttacatcccg ccgttgcatt gcgcttctcc ggaaacatta gc    102

<210> SEQ ID NO 783
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 783
acaaccgcgt gttacaaggc caggcatccg agaggtctgg gaatgcccgg gcaacccaga    60
aatgaccaaa ttcatgcatt gcgcttctcc ggaaacatta gc    102

<210> SEQ ID NO 784
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 784
acaaccgcgt gttacaaggc caggcatccg agaggtctgg gaatgcgcat cacaaaggtc    60
acccactgcg ttaaggcatt gcgcttctcc ggaaacatta gc    102

<210> SEQ ID NO 785
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 785
acaaccgcgt gttacaaggc caggcatccg agaggtctgg gaatgctatt attgaaggca    60
tggtggcgga gttccgcatt gcgcttctcc ggaaacatta gc    102

<210> SEQ ID NO 786
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 786
acaaccgcgt gttacaaggc caggcatccg agaggtctgg gaatgctcgc tttaccatta    60
cccggtttac tctccgcatt gcgcttctcc ggaaacatta gc    102

<210> SEQ ID NO 787
<211> LENGTH: 102

```
<212> TYPE: DNA
<213> ORGANISM: Artificial Sequence
<220> FEATURE:
<223> OTHER INFORMATION: Synthetic Polynucleotide

<400> SEQUENCE: 787
acaaccgcgt gttacaaggc caggcatccg agaggtctgg gaatgctaac gctaaggatt      60
tacccgggtt atcccgcatt gcgcttctcc ggaaacatta gc                        102

<210> SEQ ID NO 788
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 788
acaaccgcgt gttacaaggc caggcatccg agaggtctgg gaatgcccag tacaggttca      60
atttgcggcc cacgagcatt gcgcttctcc ggaaacatta gc                        102

<210> SEQ ID NO 789
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 789
acaaccgcgt gttacaaggc caggcatccg agaggtctgg gaatgcgttc acgctaataa      60
gcgcaagaaa cggcagcatt gcgcttctcc ggaaacatta gc                        102

<210> SEQ ID NO 790
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 790
acaaccgcgt gttacaaggc caggcatccg agaggtctgg gaatgcgccc aacgggatca      60
gggcgataac atattccatt gcgcttctcc ggaaacatta gc                        102

<210> SEQ ID NO 791
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 791
acaaccgcgt gttacaaggc caggcatccg agaggtctgg gaatgcctca tctggcaaag      60
gaatgacttt cggctccatt gcgcttctcc ggaaacatta gc                        102

<210> SEQ ID NO 792
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 792
acaaccgcgt gttacaaggc caggcatccg agaggtctgg gaatgcgacc aactgcaaac      60
```

```
gcacggcatc ccaatccatt gcgcttctcc ggaaacatta gc                     102
```

<210> SEQ ID NO 793
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 793

```
acaaccgcgt gttacaaggc caggcatccg agaggtctgg gaatgctgcc aaatggcgct    60
actgtaatgg tggtgccatt gcgcttctcc ggaaacatta gc                     102
```

<210> SEQ ID NO 794
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 794

```
acaaccgcgt gttacaaggc caggcatccg agaggtctgg gaatgcttaa cagcaccagc    60
agaatcgagc caatgccatt gcgcttctcc ggaaacatta gc                     102
```

<210> SEQ ID NO 795
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 795

```
acaaccgcgt gttacaaggc caggcatccg agaggtctgg gaatgcccca gcatactgac    60
cgtcagcttc atcagccatt gcgcttctcc ggaaacatta gc                     102
```

<210> SEQ ID NO 796
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 796

```
acaaccgcgt gttacaaggc caggcatccg agaggtctgg gaatgcaagt acacccagtg    60
caacgatgaa cgaagccatt gcgcttctcc ggaaacatta gc                     102
```

<210> SEQ ID NO 797
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 797

```
acaaccgcgt gttacaaggc caggcatccg agaggtctgg gaatgcagtt ccgtacctgg    60
tgcaatttgt gcttcccatt gcgcttctcc ggaaacatta gc                     102
```

<210> SEQ ID NO 798
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 798
acaaccgcgt gttacaaggc caggcatccg agaggtctgg gaatgcaccg gatcttcttt        60
atcaggctca aacgcccatt gcgcttctcc ggaaacatta gc                         102

<210> SEQ ID NO 799
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 799
acaaccgcgt gttacaaggc caggcatccg agaggtctgg gaatgcatcg aattggctgc        60
tatttcgcca accacccatt gcgcttctcc ggaaacatta gc                         102

<210> SEQ ID NO 800
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 800
acaaccgcgt gttacaaggc caggcatccg agaggtctgg gaatgcgctt atcagttcgc        60
cgccagagcg ccttaccatt gcgcttctcc ggaaacatta gc                         102

<210> SEQ ID NO 801
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 801
acaaccgcgt gttacaaggc caggcatccg agaggtctgg gaatgcccta ttgagaaacg        60
ctcaacgcga acaccacatt gcgcttctcc ggaaacatta gc                         102

<210> SEQ ID NO 802
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 802
acaaccgcgt gttacaaggc caggcatccg agaggtctgg gaatgctgaa gtttgcaacc        60
ggacctgcgg caataacatt gcgcttctcc ggaaacatta gc                         102

<210> SEQ ID NO 803
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 803
acaaccgcgt gttacaaggc caggcatccg agaggtctgg gaatgccgcc gttacgtggt        60
gcatcagcat gatgttcatt gcgcttctcc ggaaacatta gc                         102

<210> SEQ ID NO 804

```
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 804
acaaccgcgt gttacaaggc caggcatccg agaggtctgg gaatgccgtt ctggatctgc      60
acaccttctt tcgcttcatt gcgcttctcc ggaaacatta gc                        102

<210> SEQ ID NO 805
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 805
acaaccgcgt gttacaaggc caggcatccg agaggtctgg gaatgcccat ctccggttcc      60
atggcattga tgatgtcatt gcgcttctcc ggaaacatta gc                        102

<210> SEQ ID NO 806
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 806
acaaccgcgt gttacaaggc caggcatccg agaggtctgg gaatgccgtt ggcaatcgct      60
ttagtcaccc acgggtcatt gcgcttctcc ggaaacatta gc                        102

<210> SEQ ID NO 807
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 807
acaaccgcgt gttacaaggc caggcatccg agaggtctgg gaatgctacg catcagcgca      60
tcttccatcg acaggtcatt gcgcttctcc ggaaacatta gc                        102

<210> SEQ ID NO 808
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 808
acaaccgcgt gttacaaggc caggcatccg agaggtctgg gaatgccagg tgctctttcc      60
acagggagtc aagcgtcatt gcgcttctcc ggaaacatta gc                        102

<210> SEQ ID NO 809
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 809
acaaccgcgt gttacaaggc caggcatccg agaggtctgg gaatgccgct cacgcagcgt      60
```
ctcttcatgc agttctcatt gcgcttctcc ggaaacatta gc				102

<210> SEQ ID NO 810
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 810
acaaccgcgt gttacaaggc caggcatccg agaggtctgg gaatgcgacg accagaacga				60 ccgcgcaact ggttatcatt gcgcttctcc ggaaacatta gc				102

<210> SEQ ID NO 811
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 811
acaaccgcgt gttacaaggc caggcatccg agaggtctgg gaatgcctgc ctgccagcta				60 ccaccgagca caatatcatt gcgcttctcc ggaaacatta gc				102

<210> SEQ ID NO 812
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 812
acaaccgcgt gttacaaggc caggcatccg agaggtctgg gaatgcacgg gattcgtgac				60 gctcggtacc gatgatcatt gcgcttctcc ggaaacatta gc				102

<210> SEQ ID NO 813
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 813
acaaccgcgt gttacaaggc caggcatccg agaggtctgg gaatgccacg ggcaaggatc				60 gttacgtcct actttgcatt gcgcttctcc ggaaacatta gc				102

<210> SEQ ID NO 814
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 814
acaaccgcgt gttacaaggc caggcatccg agaggtctgg gaatgctatc ccacatttct				60 tccagcgact gtggtgcatt gcgcttctcc ggaaacatta gc				102

<210> SEQ ID NO 815
<211> LENGTH: 102
<212> TYPE: DNA
<213> ORGANISM: Artificial Sequence
<220> FEATURE:

<223> OTHER INFORMATION: Synthetic Polynucleotide

<400> SEQUENCE: 815
acaaccgcgt gttacaaggc caggcatccg agaggtctgg gaatgcggag tccacttcgt    60
ccaccagcgc atagtgcatt gcgcttctcc ggaaacatta gc    102

<210> SEQ ID NO 816
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 816
acaaccgcgt gttacaaggc caggcatccg agaggtctgg gaatgccata ccgccgagta    60
actgaacgtc gaagtgcatt gcgcttctcc ggaaacatta gc    102

<210> SEQ ID NO 817
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 817
acaaccgcgt gttacaaggc caggcatccg agaggtctgg gaatgcgatg gagatagtac    60
ccaccagcac cggctgcatt gcgcttctcc ggaaacatta gc    102

<210> SEQ ID NO 818
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 818
acaaccgcgt gttacaaggc caggcatccg agaggtctgg gaatgcttca acgactccag    60
catcgctgca aacatgcatt gcgcttctcc ggaaacatta gc    102

<210> SEQ ID NO 819
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 819
acaaccgcgt gttacaaggc caggcatccg agaggtctgg gaatgcttat acatttccga    60
gctgtcttct gccgggcatt gcgcttctcc ggaaacatta gc    102

<210> SEQ ID NO 820
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 820
acaaccgcgt gttacaaggc caggcatccg agaggtctgg gaatgctgca cgcctttacc    60
ggttagtgcg ttcaggcatt gcgcttctcc ggaaacatta gc    102

-continued

<210> SEQ ID NO 821
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 821
acaaccgcgt gttacaaggc caggcatccg agaggtctgg gaatgcctgt tgttccagct    60
cctcaacctc ttcaggcatt gcgcttctcc ggaaacatta gc                      102

<210> SEQ ID NO 822
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 822
acaaccgcgt gttacaaggc caggcatccg agaggtctgg gaatgcttgt cgcgcaggta    60
gtcaaagccg tattcgcatt gcgcttctcc ggaaacatta gc                      102

<210> SEQ ID NO 823
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 823
acaaccgcgt gttacaaggc caggcatccg agaggtctgg gaatgcacag acggaagtag    60
ttctggaagg tgatcgcatt gcgcttctcc ggaaacatta gc                      102

<210> SEQ ID NO 824
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 824
acaaccgcgt gttacaaggc caggcatccg agaggtctgg gaatgcttat ccagccactc    60
ggcaattggc aaatcgcatt gcgcttctcc ggaaacatta gc                      102

<210> SEQ ID NO 825
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 825
acaaccgcgt gttacaaggc caggcatccg agaggtctgg gaatgctacg ctgtacacgt    60
tcttcagggc tgaacgcatt gcgcttctcc ggaaacatta gc                      102

<210> SEQ ID NO 826
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 826
acaaccgcgt gttacaaggc caggcatccg agaggtctgg gaatgccgct tcgttggcgt    60
ggaatttggc gttcagcatt gcgcttctcc ggaaacatta gc    102

<210> SEQ ID NO 827
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 827
acaaccgcgt gttacaaggc caggcatccg agaggtctgg gaatgccatg cccggcaggt    60
tgataccgac agtcagcatt gcgcttctcc ggaaacatta gc    102

<210> SEQ ID NO 828
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 828
acaaccgcgt gttacaaggc caggcatccg agaggtctgg gaatgccgct tcagtcatgt    60
agaccaggtc cggcagcatt gcgcttctcc ggaaacatta gc    102

<210> SEQ ID NO 829
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 829
acaaccgcgt gttacaaggc caggcatccg agaggtctgg gaatgcttca tccatgatgc    60
cctctttcac cagcagcatt gcgcttctcc ggaaacatta gc    102

<210> SEQ ID NO 830
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 830
acaaccgcgt gttacaaggc caggcatccg agaggtctgg gaatgcaacg atgtagtcga    60
cgtcacgggt aaacagcatt gcgcttctcc ggaaacatta gc    102

<210> SEQ ID NO 831
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 831
acaaccgcgt gttacaaggc caggcatccg agaggtctgg gaatgccgag aagtggcctt    60
cgccctggaa ggtttccatt gcgcttctcc ggaaacatta gc    102

<210> SEQ ID NO 832
<211> LENGTH: 102
<212> TYPE: DNA
<213> ORGANISM: Artificial Sequence

```
<220> FEATURE:
<223> OTHER INFORMATION: Synthetic Polynucleotide

<400> SEQUENCE: 832
acaaccgcgt gttacaaggc caggcatccg agaggtctgg gaatgcccac gacccgccat      60
attggtcgcg atagtccatt gcgcttctcc ggaaacatta gc                        102

<210> SEQ ID NO 833
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 833
acaaccgcgt gttacaaggc caggcatccg agaggtctgg gaatgcaggt ggataccctg      60
acgcagatag tccatccatt gcgcttctcc ggaaacatta gc                        102

<210> SEQ ID NO 834
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 834
acaaccgcgt gttacaaggc caggcatccg agaggtctgg gaatgcgcag ttgcttacga      60
atgtcgaagt tacggccatt gcgcttctcc ggaaacatta gc                        102

<210> SEQ ID NO 835
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 835
acaaccgcgt gttacaaggc caggcatccg agaggtctgg gaatgcttta cgctgataca      60
cttcgatgga ctgcgccatt gcgcttctcc ggaaacatta gc                        102

<210> SEQ ID NO 836
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 836
acaaccgcgt gttacaaggc caggcatccg agaggtctgg gaatgcacag ttcgttacgc      60
tgggagtaaa tggcgccatt gcgcttctcc ggaaacatta gc                        102

<210> SEQ ID NO 837
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 837
acaaccgcgt gttacaaggc caggcatccg agaggtctgg gaatgcgctt cgcctggctt      60
catacccagt ttacgccatt gcgcttctcc ggaaacatta gc                        102
```

<210> SEQ ID NO 838
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 838
acaaccgcgt gttacaaggc caggcatccg agaggtctgg gaatgccgta ccgtaagtga    60
tgtcagctgc gtaagccatt gcgcttctcc ggaaacatta gc    102

<210> SEQ ID NO 839
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 839
acaaccgcgt gttacaaggc caggcatccg agaggtctgg gaatgccctg cttccagtac    60
cgcatcgtga cgtacccatt gcgcttctcc ggaaacatta gc    102

<210> SEQ ID NO 840
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 840
acaaccgcgt gttacaaggc caggcatccg agaggtctgg gaatgcatac cggctttggt    60
cagttcgttt gacacccatt gcgcttctcc ggaaacatta gc    102

<210> SEQ ID NO 841
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 841
acaaccgcgt gttacaaggc caggcatccg agaggtctgg gaatgcgctg ttaatggttt    60
cgctcacatc gctgaccatt gcgcttctcc ggaaacatta gc    102

<210> SEQ ID NO 842
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 842
acaaccgcgt gttacaaggc caggcatccg agaggtctgg gaatgcacga atcattggac    60
ggttggtcgg aacaaccatt gcgcttctcc ggaaacatta gc    102

<210> SEQ ID NO 843
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 843

```
acaaccgcgt gttacaaggc caggcatccg agaggtctgg gaatgcgtac gcatttcggc    60
gatgcagcgt tcgttacatt gcgcttctcc ggaaacatta gc                      102

<210> SEQ ID NO 844
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 844
acaaccgcgt gttacaaggc caggcatccg agaggtctgg gaatgctacc aaagacgcgc    60
ttacttgcct cacgtacatt gcgcttctcc ggaaacatta gc                      102

<210> SEQ ID NO 845
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 845
acaaccgcgt gttacaaggc caggcatccg agaggtctgg gaatgctgca tttgcgctaa    60
acgctcggct tccatacatt gcgcttctcc ggaaacatta gc                      102

<210> SEQ ID NO 846
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 846
acaaccgcgt gttacaaggc caggcatccg agaggtctgg gaatgcgcat gacgcctttc    60
tcgaagtgac gcatcacatt gcgcttctcc ggaaacatta gc                      102

<210> SEQ ID NO 847
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 847
acaaccgcgt gttacaaggc caggcatccg agaggtctgg gaatgccacg ttgcgccagg    60
tagtcgttga cggtaacatt gcgcttctcc ggaaacatta gc                      102

<210> SEQ ID NO 848
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 848
acaaccgcgt gttacaaggc caggcatccg agaggtctgg gaatgccggc tgcagagtcg    60
tcatcctgat ggctaacatt gcgcttctcc ggaaacatta gc                      102

<210> SEQ ID NO 849
<211> LENGTH: 102
<212> TYPE: DNA
```

```
<213> ORGANISM: Artificial Sequence
<220> FEATURE:
<223> OTHER INFORMATION: Synthetic Polynucleotide

<400> SEQUENCE: 849
acaaccgcgt gttacaaggc caggcatccg agaggtctgg gaatgccctg catggtacga      60
ccggtgtgtt cgtcaacatt gcgcttctcc ggaaacatta gc                        102

<210> SEQ ID NO 850
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 850
acaaccgcgt gttacaaggc caggcatccg agaggtctgg gaatgcacca tccctaataa      60
gagatgcggc cagaagcatt gcgcttctcc ggaaacatta gc                        102

<210> SEQ ID NO 851
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 851
acaaccgcgt gttacaaggc caggcatccg agaggtctgg gaatgccagc gcgctgagcg      60
tatccagtaa tgcaagcatt gcgcttctcc ggaaacatta gc                        102

<210> SEQ ID NO 852
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 852
acaaccgcgt gttacaaggc caggcatccg agaggtctgg gaatgcttcg cttccagcaa      60
ggccaattga ccaaagcatt gcgcttctcc ggaaacatta gc                        102

<210> SEQ ID NO 853
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 853
acaaccgcgt gttacaaggc caggcatccg agaggtctgg gaatgcgcgt tgctgagcgc      60
aggcaaacct aaactccatt gcgcttctcc ggaaacatta gc                        102

<210> SEQ ID NO 854
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 854
acaaccgcgt gttacaaggc caggcatccg agaggtctgg gaatgcaatc aacggaatag      60
ttcgaattcg ggcggccatt gcgcttctcc ggaaacatta gc                        102
```

<210> SEQ ID NO 855
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 855
acaaccgcgt gttacaaggc caggcatccg agaggtctgg gaatgcgcgc ctgaagaggc    60
aaagattctt cagcaacatt gcgcttctcc ggaaacatta gc                      102

<210> SEQ ID NO 856
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 856
acaaccgcgt gttacaaggc caggcatccg agaggtctgg gaatgcccag aatagtgacg    60
ctggcaccct gtggttcatt gcgcttctcc ggaaacatta gc                      102

<210> SEQ ID NO 857
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 857
acaaccgcgt gttacaaggc caggcatccg agaggtctgg gaatgcgcgg agaaatcacg    60
ccgcaggtag agacttcatt gcgcttctcc ggaaacatta gc                      102

<210> SEQ ID NO 858
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 858
acaaccgcgt gttacaaggc caggcatccg agaggtctgg gaatgccgct gtcggttaag    60
tcttccggtt tggtgtcatt gcgcttctcc ggaaacatta gc                      102

<210> SEQ ID NO 859
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 859
acaaccgcgt gttacaaggc caggcatccg agaggtctgg gaatgcttct ttccacagcg    60
cagcggtaat ttcctgcatt gcgcttctcc ggaaacatta gc                      102

<210> SEQ ID NO 860
<211> LENGTH: 102
<212> TYPE: DNA
<213> ORGANISM: Artificial Sequence
<220> FEATURE:
<223> OTHER INFORMATION: Synthetic Polynucleotide -continued

```
<400> SEQUENCE: 860
acaaccgcgt gttacaaggc caggcatccg agaggtctgg gaatgcgctg gcatattgcg      60
cccgtaataa atctcgcatt gcgcttctcc ggaaacatta gc                         102

<210> SEQ ID NO 861
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 861
acaaccgcgt gttacaaggc caggcatccg agaggtctgg gaatgcagac gttcacatcc      60
accatgtcat acagcgcatt gcgcttctcc ggaaacatta gc                         102

<210> SEQ ID NO 862
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 862
acaaccgcgt gttacaaggc caggcatccg agaggtctgg gaatgcacag gtttctgaca      60
ggatttcggt cagacgcatt gcgcttctcc ggaaacatta gc                         102

<210> SEQ ID NO 863
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 863
acaaccgcgt gttacaaggc caggcatccg agaggtctgg gaatgccggc gcggaaggta      60
cataaaccgc cttcagcatt gcgcttctcc ggaaacatta gc                         102

<210> SEQ ID NO 864
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 864
acaaccgcgt gttacaaggc caggcatccg agaggtctgg gaatgcatca agatgggcaa      60
cgaccgtttc tggcagcatt gcgcttctcc ggaaacatta gc                         102

<210> SEQ ID NO 865
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 865
acaaccgcgt gttacaaggc caggcatccg agaggtctgg gaatgcgtcg atgagtttcg      60
ggtcaaccgg ttcttccatt gcgcttctcc ggaaacatta gc                         102

<210> SEQ ID NO 866
<211> LENGTH: 102
```

```
<212> TYPE: DNA
<213> ORGANISM: Artificial Sequence
<220> FEATURE:
<223> OTHER INFORMATION: Synthetic Polynucleotide

<400> SEQUENCE: 866
acaaccgcgt gttacaaggc caggcatccg agaggtctgg gaatgcataa gcaatataac      60
cgtcgcgctc ttcggccatt gcgcttctcc ggaaacatta gc                        102

<210> SEQ ID NO 867
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 867
acaaccgcgt gttacaaggc caggcatccg agaggtctgg gaatgcctca agctggtgga      60
tcaggtaatt cagcgccatt gcgcttctcc ggaaacatta gc                        102

<210> SEQ ID NO 868
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 868
acaaccgcgt gttacaaggc caggcatccg agaggtctgg gaatgcccgc gcacgcgata      60
atcaatggtt acgatacatt gcgcttctcc ggaaacatta gc                        102

<210> SEQ ID NO 869
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 869
acaaccgcgt gttacaaggc caggcatccg agaggtctgg gaatgcgcca acgtcgctga      60
agtaatggct gagtttcatt gcgcttctcc ggaaacatta gc                        102

<210> SEQ ID NO 870
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 870
acaaccgcgt gttacaaggc caggcatccg agaggtctgg gaatgccgga tcgtcgtagc      60
taccggcgtt atggttcatt gcgcttctcc ggaaacatta gc                        102

<210> SEQ ID NO 871
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 871
acaaccgcgt gttacaaggc caggcatccg agaggtctgg gaatgctaga taaactcgtc      60
```

```
gcgctcggtg gtttgtcatt gcgcttctcc ggaaacatta gc                              102
```

<210> SEQ ID NO 872
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 872

```
acaaccgcgt gttacaaggc caggcatccg agaggtctgg gaatgcgggc cagtagcgga           60
acatgggtca tcatctcatt gcgcttctcc ggaaacatta gc                             102
```

<210> SEQ ID NO 873
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 873

```
acaaccgcgt gttacaaggc caggcatccg agaggtctgg gaatgcgccg ccgataatca           60
gcacatgttt cgcgtgcatt gcgcttctcc ggaaacatta gc                             102
```

<210> SEQ ID NO 874
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 874

```
acaaccgcgt gttacaaggc caggcatccg agaggtctgg gaatgcccga taggatcggt           60
gcagtcggag ataatgcatt gcgcttctcc ggaaacatta gc                             102
```

<210> SEQ ID NO 875
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 875

```
acaaccgcgt gttacaaggc caggcatccg agaggtctgg gaatgccgcg cctgaataat           60
ttcggttgag agatggcatt gcgcttctcc ggaaacatta gc                             102
```

<210> SEQ ID NO 876
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 876

```
acaaccgcgt gttacaaggc caggcatccg agaggtctgg gaatgcgccg tatggattgc           60
cggattgtaa taacggcatt gcgcttctcc ggaaacatta gc                             102
```

<210> SEQ ID NO 877
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 877
acaaccgcgt gttacaaggc caggcatccg agaggtctgg gaatgcgata ctgacggcag    60
aacgatacga cacccgcatt gcgcttctcc ggaaacatta gc    102

<210> SEQ ID NO 878
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 878
acaaccgcgt gttacaaggc caggcatccg agaggtctgg gaatgccatc cagcgccatt    60
acgcgaccaa atgcagcatt gcgcttctcc ggaaacatta gc    102

<210> SEQ ID NO 879
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 879
acaaccgcgt gttacaaggc caggcatccg agaggtctgg gaatgcaacg aaattgacgc    60
catcgtcgat caccagcatt gcgcttctcc ggaaacatta gc    102

<210> SEQ ID NO 880
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 880
acaaccgcgt gttacaaggc caggcatccg agaggtctgg gaatgcatct accgcaaagt    60
actgcccaaa ctggtccatt gcgcttctcc ggaaacatta gc    102

<210> SEQ ID NO 881
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 881
acaaccgcgt gttacaaggc caggcatccg agaggtctgg gaatgcgtca tgataccgcc    60
gtaataggtc gggatccatt gcgcttctcc ggaaacatta gc    102

<210> SEQ ID NO 882
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 882
acaaccgcgt gttacaaggc caggcatccg agaggtctgg gaatgcgtgc gacgaagata    60
ccgccaggat tcaggccatt gcgcttctcc ggaaacatta gc    102

<210> SEQ ID NO 883

```
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 883
acaaccgcgt gttacaaggc caggcatccg agaggtctgg gaatgcaagc cagtgcgtct    60
tgcagatact gaggtacatt gcgcttctcc ggaaacatta gc                      102

<210> SEQ ID NO 884
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 884
acaaccgcgt gttacaaggc caggcatccg agaggtctgg gaatgccaat gccgctgaga    60
tcgcggtagc tgtcttcatt gcgcttctcc ggaaacatta gc                      102

<210> SEQ ID NO 885
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 885
acaaccgcgt gttacaaggc caggcatccg agaggtctgg gaatgcctgc cgttaaatcg    60
gccatatctt cggcttcatt gcgcttctcc ggaaacatta gc                      102

<210> SEQ ID NO 886
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 886
acaaccgcgt gttacaaggc caggcatccg agaggtctgg gaatgccaga cggccatcag    60
gctgccgaat aacactcatt gcgcttctcc ggaaacatta gc                      102

<210> SEQ ID NO 887
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 887
acaaccgcgt gttacaaggc caggcatccg agaggtctgg gaatgcttga cgtaggcaag    60
caggcttaag gaatcgcatt gcgcttctcc ggaaacatta gc                      102

<210> SEQ ID NO 888
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 888
acaaccgcgt gttacaaggc caggcatccg agaggtctgg gaatgctgtc gaaggtgtcg    60
```
taattactga ggtccccatt gcgcttctcc ggaaacatta gc       102

<210> SEQ ID NO 889
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 889
acaaccgcgt gttacaaggc caggcatccg agaggtctgg gaatgcccag tgcgcgacga    60
atttgcccgt taggtacatt gcgcttctcc ggaaacatta gc       102

<210> SEQ ID NO 890
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 890
acaaccgcgt gttacaaggc caggcatccg agaggtctgg gaatgcccga ctggcgaatt    60
aaatccagca ccatggcatt gcgcttctcc ggaaacatta gc       102

<210> SEQ ID NO 891
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 891
acaaccgcgt gttacaaggc caggcatccg agaggtctgg gaatgctcac tgacattacg    60
gaagaaatgc agcgcgcatt gcgcttctcc ggaaacatta gc       102

<210> SEQ ID NO 892
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 892
acaaccgcgt gttacaaggc caggcatccg agaggtctgg gaatgcttag caacaggcca    60
gttcgaaatc cagacgcatt gcgcttctcc ggaaacatta gc       102

<210> SEQ ID NO 893
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 893
acaaccgcgt gttacaaggc caggcatccg agaggtctgg gaatgcttgc ggataaagct    60
gtgaatcgag cgacagcatt gcgcttctcc ggaaacatta gc       102

<210> SEQ ID NO 894
<211> LENGTH: 102
<212> TYPE: DNA
<213> ORGANISM: Artificial Sequence
<220> FEATURE:

<223> OTHER INFORMATION: Synthetic Polynucleotide

<400> SEQUENCE: 894
acaaccgcgt gttacaaggc caggcatccg agaggtctgg gaatgcacgc caatccaggt    60
ctggagttta cgttgccatt gcgcttctcc ggaaacatta gc                      102

<210> SEQ ID NO 895
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 895
acaaccgcgt gttacaaggc caggcatccg agaggtctgg gaatgcttaa tgcttcaata    60
cggctctggt ccacgccatt gcgcttctcc ggaaacatta gc                      102

<210> SEQ ID NO 896
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 896
acaaccgcgt gttacaaggc caggcatccg agaggtctgg gaatgctgta ggtaaatcaa    60
agctgcaaca gccgcccatt gcgcttctcc ggaaacatta gc                      102

<210> SEQ ID NO 897
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 897
acaaccgcgt gttacaaggc caggcatccg agaggtctgg gaatgcgtca agttctttca    60
acagctcagt gcggaccatt gcgcttctcc ggaaacatta gc                      102

<210> SEQ ID NO 898
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 898
acaaccgcgt gttacaaggc caggcatccg agaggtctgg gaatgcgaaa ttgcccgata    60
cgcggcgcgg aaattacatt gcgcttctcc ggaaacatta gc                      102

<210> SEQ ID NO 899
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 899
acaaccgcgt gttacaaggc caggcatccg agaggtctgg gaatgcgcgg gttcaggctg    60
gcaatccagg tttctacatt gcgcttctcc ggaaacatta gc                      102

<210> SEQ ID NO 900
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 900
acaaccgcgt gttacaaggc caggcatccg agaggtctgg gaatgcgctc agtcgctgac      60
gcaccagagc aatcaacatt gcgcttctcc ggaaacatta gc                        102

<210> SEQ ID NO 901
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 901
acaaccgcgt gttacaaggc caggcatccg agaggtctgg gaatgccccg caggttgggc      60
aattcaccgt aatagtcatt gcgcttctcc ggaaacatta gc                        102

<210> SEQ ID NO 902
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 902
acaaccgcgt gttacaaggc caggcatccg agaggtctgg gaatgctcac tgctttggtt      60
cttcgctcca gtcatccatt gcgcttctcc ggaaacatta gc                        102

<210> SEQ ID NO 903
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 903
acaaccgcgt gttacaaggc caggcatccg agaggtctgg gaatgccttc agcagcccat      60
tctccgaggt cgatcacatt gcgcttctcc ggaaacatta gc                        102

<210> SEQ ID NO 904
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 904
acaaccgcgt gttacaaggc caggcatccg agaggtctgg gaatgccctc aacgccgcat      60
agcgacaggc tttcttcatt gcgcttctcc ggaaacatta gc                        102

<210> SEQ ID NO 905
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 905

```
acaaccgcgt gttacaaggc caggcatccg agaggtctgg gaatgcccat cacctcttca        60
ccgtccatcc acagggcatt gcgcttctcc ggaaacatta gc                          102

<210> SEQ ID NO 906
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 906
acaaccgcgt gttacaaggc caggcatccg agaggtctgg gaatgcgcgc tgcttgttcc        60
acttcatcaa gcaaggcatt gcgcttctcc ggaaacatta gc                          102

<210> SEQ ID NO 907
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 907
acaaccgcgt gttacaaggc caggcatccg agaggtctgg gaatgcccgt tgccaggacc        60
gttcgctacc tttcagcatt gcgcttctcc ggaaacatta gc                          102

<210> SEQ ID NO 908
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 908
acaaccgcgt gttacaaggc caggcatccg agaggtctgg gaatgcttca tcgccagcga        60
attccagttg attggccatt gcgcttctcc ggaaacatta gc                          102

<210> SEQ ID NO 909
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 909
acaaccgcgt gttacaaggc caggcatccg agaggtctgg gaatgctact tctgctgcac        60
gaaattgcgg taagcccatt gcgcttctcc ggaaacatta gc                          102

<210> SEQ ID NO 910
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 910
acaaccgcgt gttacaaggc caggcatccg agaggtctgg gaatgcttca cctcttcatt        60
aaaccagtgc ccgacccatt gcgcttctcc ggaaacatta gc                          102

<210> SEQ ID NO 911
<211> LENGTH: 102
<212> TYPE: DNA
<213> ORGANISM: Artificial Sequence
```

```
<220> FEATURE:
<223> OTHER INFORMATION: Synthetic Polynucleotide

<400> SEQUENCE: 911
acaaccgcgt gttacaaggc caggcatccg agaggtctgg gaatgcatgg acatacgcac      60
ctttaccact ccggtacatt gcgcttctcc ggaaacatta gc                        102

<210> SEQ ID NO 912
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 912
acaaccgcgt gttacaaggc caggcatccg agaggtctgg gaatgcagtc gatactgata      60
gccatcgagc ttcggtcatt gcgcttctcc ggaaacatta gc                        102

<210> SEQ ID NO 913
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 913
acaaccgcgt gttacaaggc caggcatccg agaggtctgg gaatgcgcag cacttcaact      60
tccagcgtcg cggtatcatt gcgcttctcc ggaaacatta gc                        102

<210> SEQ ID NO 914
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 914
acaaccgcgt gttacaaggc caggcatccg agaggtctgg gaatgcgcat ttctgcttct      60
tccaggtagt gtgtggcatt gcgcttctcc ggaaacatta gc                        102

<210> SEQ ID NO 915
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 915
acaaccgcgt gttacaaggc caggcatccg agaggtctgg gaatgcacca gtgaaacaaa      60
cagctcttcc agacggcatt gcgcttctcc ggaaacatta gc                        102

<210> SEQ ID NO 916
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 916
acaaccgcgt gttacaaggc caggcatccg agaggtctgg gaatgcctgc ctgattcacc      60
acaatttgct gcacggcatt gcgcttctcc ggaaacatta gc                        102
```

<210> SEQ ID NO 917
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 917
acaaccgcgt gttacaaggc caggcatccg agaggtctgg gaatgcatcc cgccagataa    60
catacgcgca cgttcgcatt gcgcttctcc ggaaacatta gc                      102

<210> SEQ ID NO 918
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 918
acaaccgcgt gttacaaggc caggcatccg agaggtctgg gaatgccctg cggcaccagt    60
cccaactgac gtttagcatt gcgcttctcc ggaaacatta gc                      102

<210> SEQ ID NO 919
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 919
acaaccgcgt gttacaaggc caggcatccg agaggtctgg gaatgcgcat taacgcacgg    60
gcaatcatta aacggccatt gcgcttctcc ggaaacatta gc                      102

<210> SEQ ID NO 920
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 920
acaaccgcgt gttacaaggc caggcatccg agaggtctgg gaatgcacat tgagcggcga    60
agttcaatat ccacgccatt gcgcttctcc ggaaacatta gc                      102

<210> SEQ ID NO 921
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 921
acaaccgcgt gttacaaggc caggcatccg agaggtctgg gaatgctctc gagatcgtaa    60
ccaaatacgc tgaccccatt gcgcttctcc ggaaacatta gc                      102

<210> SEQ ID NO 922
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 922

```
acaaccgcgt gttacaaggc caggcatccg agaggtctgg gaatgcgatg tacgcttctt    60
tgcgctccac gccgtacatt gcgcttctcc ggaaacatta gc                       102

<210> SEQ ID NO 923
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 923
acaaccgcgt gttacaaggc caggcatccg agaggtctgg gaatgccggt gcgagatcga    60
gaataaaggt ttccgacatt gcgcttctcc ggaaacatta gc                       102

<210> SEQ ID NO 924
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 924
acaaccgcgt gttacaaggc caggcatccg agaggtctgg gaatgcccac cagctcaccg    60
tgttgaataa tgccgacatt gcgcttctcc ggaaacatta gc                       102

<210> SEQ ID NO 925
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 925
acaaccgcgt gttacaaggc caggcatccg agaggtctgg gaatgctcac ccgcttcgac    60
ctgcaaatct atcccacatt gcgcttctcc ggaaacatta gc                       102

<210> SEQ ID NO 926
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 926
acaaccgcgt gttacaaggc caggcatccg agaggtctgg gaatgctgat gacgcaacgt    60
tggcgtaggc attggtcatt gcgcttctcc ggaaacatta gc                       102

<210> SEQ ID NO 927
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 927
acaaccgcgt gttacaaggc caggcatccg agaggtctgg gaatgcttag ctacgcaaac    60
cacgtccacg ttggatcatt gcgcttctcc ggaaacatta gc                       102

<210> SEQ ID NO 928
<211> LENGTH: 102
<212> TYPE: DNA
```

<213> ORGANISM: Artificial Sequence
<220> FEATURE:
<223> OTHER INFORMATION: Synthetic Polynucleotide

<400> SEQUENCE: 928
acaaccgcgt gttacaaggc caggcatccg agaggtctgg gaatgcgcgt ctgcacccag      60
atacgcataa agcgatcatt gcgcttctcc ggaaacatta gc                        102

<210> SEQ ID NO 929
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 929
acaaccgcgt gttacaaggc caggcatccg agaggtctgg gaatgcaaag taaagggtca      60
tggtgatgac tggcggcatt gcgcttctcc ggaaacatta gc                        102

<210> SEQ ID NO 930
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 930
acaaccgcgt gttacaaggc caggcatccg agaggtctgg gaatgcggca aacacaccgt      60
tcagcaaacc cgcaagcatt gcgcttctcc ggaaacatta gc                        102

<210> SEQ ID NO 931
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 931
acaaccgcgt gttacaaggc caggcatccg agaggtctgg gaatgctacg tgagtggcgt      60
taacacaaag gttggccatt gcgcttctcc ggaaacatta gc                        102

<210> SEQ ID NO 932
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 932
acaaccgcgt gttacaaggc caggcatccg agaggtctgg gaatgcctgc atatagctga      60
agccatgcat atcgcccatt gcgcttctcc ggaaacatta gc                        102

<210> SEQ ID NO 933
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 933
acaaccgcgt gttacaaggc caggcatccg agaggtctgg gaatgctata acgattggg       60 ttcaggtgcg acagcccatt gcgcttctcc ggaaacatta gc                        102

```
<210> SEQ ID NO 934
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 934
acaaccgcgt gttacaaggc caggcatccg agaggtctgg gaatgctatc cggcaataat      60
gacgtgagtc ggaacccatt gcgcttctcc ggaaacatta gc                       102

<210> SEQ ID NO 935
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 935
acaaccgcgt gttacaaggc caggcatccg agaggtctgg gaatgcccgt gagcaccagc      60
gttaaggcaa cgaatacatt gcgcttctcc ggaaacatta gc                       102

<210> SEQ ID NO 936
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 936
acaaccgcgt gttacaaggc caggcatccg agaggtctgg gaatgctgac cagcggaaca      60
tcattgatac cgaggacatt gcgcttctcc ggaaacatta gc                       102

<210> SEQ ID NO 937
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 937
acaaccgcgt gttacaaggc caggcatccg agaggtctgg gaatgccgcc acaataaaga      60
ccaccagtac gccaaacatt gcgcttctcc ggaaacatta gc                       102
```

UNITED STATES PATENT AND TRADEMARK OFFICE
CERTIFICATE OF CORRECTION

PATENT NO. : 10,240,146 B2
APPLICATION NO. : 15/329651
DATED : March 26, 2019
INVENTOR(S) : Xiaowei Zhuang et al.

Page 1 of 1

It is certified that error appears in the above-identified patent and that said Letters Patent is hereby corrected as shown below:

In the Specification

Please replace the paragraph beginning at Column 1, Line 20, with the following paragraph:
--This invention was made with government support under grant GM096450 awarded by the National Institutes of Health (NIH). The government has certain rights to this invention.--

Signed and Sealed this
Fifth Day of May, 2020

Andrei Iancu
*Director of the United States Patent and Trademark Office*